US012759748B2

(12) United States Patent
Minarich et al.

(10) Patent No.: US 12,759,748 B2
(45) Date of Patent: Oct. 13, 2026

(54) AGRICULTURAL SAMPLE HANDLING SYSTEM AND RELATED METHODS

(71) Applicant: Precision Planting LLC, Tremont, IL (US)

(72) Inventors: Nicholas Minarich, Shorewood, IL (US); Todd Swanson, Morton, IL (US); Paul Wildermuth, Tremont, IL (US); Adam Vaccari, Tremont, IL (US); Joshua Seelye, Tremont, IL (US); Dale M. Koch, Tremont, IL (US)

(73) Assignee: Precision Planting LLC, Tremont, IL (US)

( * ) Notice: Subject to any disclaimer, the term of this patent is extended or adjusted under 35 U.S.C. 154(b) by 124 days.

(21) Appl. No.: 18/682,566

(22) PCT Filed: Sep. 7, 2022

(86) PCT No.: PCT/IB2022/058401

§ 371 (c)(1),
(2) Date: Feb. 9, 2024

(87) PCT Pub. No.: WO2023/042032

PCT Pub. Date: Mar. 23, 2023

(65) Prior Publication Data

US 2025/0136315 A1 May 1, 2025

Related U.S. Application Data

(60) Provisional application No. 63/370,072, filed on Aug. 1, 2022, provisional application No. 63/370,081, filed (Continued)

(51) Int. Cl.

*B01L 3/00* (2006.01)
*B65B 1/16* (2006.01)

(Continued)

(52) U.S. Cl.

CPC ............ *B01L 3/50825* (2013.01); *B65B 1/16* (2013.01); *B65B 37/06* (2013.01); *B65B 43/60* (2013.01);

(Continued)

(58) Field of Classification Search

CPC ........... B01L 3/50825; B01L 2300/045; B01L 2400/0478; B01L 2300/042;

(Continued)

(56) References Cited

U.S. PATENT DOCUMENTS

| | | |
|---|---|---|
| 1,109,446 A | 9/1914 | Melberg |
| 2,661,126 A | 12/1953 | Spencer |

(Continued)

FOREIGN PATENT DOCUMENTS

| | | |
|---|---|---|
| EP | 0606121 B1 | 4/1999 |
| EP | 1657183 A2 | 5/2006 |

(Continued)

OTHER PUBLICATIONS

Dale M. Koch, U.S. Appl. No. 18/350,847, filed Jul. 12, 2023, 268 pages.

(Continued)

*Primary Examiner* — David J Walczak

(57) ABSTRACT

An automated programmable processor-controlled system and related methods for packaging and handling an agricultural sample such as soil which may be tested for various chemical properties such as plant available nutrients. The packaging system includes a sample packaging apparatus which containerizes raw bulk sample material collected in the agricultural field. The apparatus may include a die block disposed between bulk material and sample collection chambers. A sample blade mechanism inserts a sample blade array through the bulk material chamber and extrudes the sample material through die slots in the die block, thereby forming (Continued)

plugs or blanks collected in the sample collection chamber coupled to the sample container. A cleaning blade mechanism inserts a cleaning blade array through the die slots after the extrusion for removing residual soil or debris. An unloading system uncaps and ejects the contents the filled containers for analysis. Samples are automatically tracked via a tracking system.

18 Claims, 128 Drawing Sheets

Related U.S. Application Data on Aug. 1, 2022, provisional application No. 63/370,077, filed on Aug. 1, 2022, provisional application No. 63/264,062, filed on Nov. 15, 2021, provisional application No. 63/264,065, filed on Nov. 15, 2021, provisional application No. 63/264,059, filed on Nov. 15, 2021, provisional application No. 63/245,278, filed on Sep. 17, 2021.

(51) Int. Cl.

| | |
|---|---|
| ***B65B 37/06*** | (2006.01) |
| ***B65B 43/60*** | (2006.01) |
| ***B65B 69/00*** | (2006.01) |
| ***G01N 1/00*** | (2006.01) |
| ***G01N 33/24*** | (2006.01) |
| ***G01N 35/00*** | (2006.01) |
| ***G01N 35/04*** | (2006.01) |

(52) U.S. Cl.

CPC ..... *B65B 69/0058* (2013.01); *G01N 35/0099* (2013.01); *G01N 35/04* (2013.01); *B01L 2300/042* (2013.01); *B01L 2300/045* (2013.01); *B01L 2400/0478* (2013.01); *G01N 2001/005* (2013.01); *G01N 33/24* (2013.01); *G01N 2035/0401* (2013.01); *G01N 2035/0405* (2013.01); *G01N 2035/0437* (2013.01); *G01N 2035/0465* (2013.01); *G01N 2035/0479* (2013.01)

(58) Field of Classification Search

CPC ....... B65B 69/0058; B65B 1/16; B65B 37/06; B65B 43/60; G01N 35/0099; G01N 35/04; G01N 2035/0437; G01N 2035/0465; G01N 2035/0479; G01N 33/24; G01N 2001/005; G01N 2035/0401; G01N 2035/0405

USPC ........ 222/386, 160, 164, 167, 329; 414/403, 414/405, 411, 419, 421

See application file for complete search history.

(56) References Cited

U.S. PATENT DOCUMENTS

| | | | | |
|---|---|---|---|---|
| 3,487,965 A | | 1/1970 | Gale | |
| 3,615,823 A | * | 10/1971 | Tuma | B65B 55/02 141/82 |
| 4,136,719 A | * | 1/1979 | Kronseder | B67C 3/001 134/169 C |
| 4,756,450 A | | 7/1988 | Negaty-Hindi et al. | |
| 5,421,663 A | | 6/1995 | Bravo | |
| 6,056,164 A | | 5/2000 | Wakayama | |
| 6,152,323 A | | 11/2000 | Immel | |
| 6,554,465 B2 | * | 4/2003 | Cruso | B28C 7/064 414/412 |
| 6,604,903 B2 | * | 8/2003 | Osborne | B67B 7/164 81/3.2 |
| 2010/0081166 A1 | | 4/2010 | Parker | |
| 2014/0157731 A1 | | 6/2014 | Perazzo et al. | |
| 2015/0166208 A1 | | 6/2015 | Miyauchi | |
| 2017/0106133 A1 | | 4/2017 | Brenneman et al. | |
| 2018/0124992 A1 | | 5/2018 | Koch et al. | |
| 2019/0033333 A1 | | 1/2019 | Tanaka et al. | |
| 2019/0331703 A1 | | 10/2019 | Olson et al. | |
| 2021/0208123 A1 | | 7/2021 | Swanson et al. | |
| 2021/0268456 A1 | | 9/2021 | Swanson et al. | |
| 2021/0341452 A1 | | 11/2021 | Swanson et al. | |
| 2022/0196628 A1 | | 6/2022 | Swanson et al. | |
| 2022/0252629 A1 | | 8/2022 | Situ et al. | |
| 2023/0133335 A1 | | 5/2023 | Swanson et al. | |
| 2023/0144670 A1 | | 5/2023 | Swanson et al. | |
| 2023/0151810 A1 | | 5/2023 | O'Neall et al. | |
| 2023/0173415 A1 | | 6/2023 | Swanson et al. | |

FOREIGN PATENT DOCUMENTS

| | | |
|---|---|---|
| WO | 1998032667 A1 | 7/1998 |
| WO | 2021171120 A1 | 9/2021 |
| WO | 2021171121 A1 | 9/2021 |
| WO | 2021220082 A1 | 11/2021 |
| WO | 2021220083 A1 | 11/2021 |
| WO | 2021220084 A1 | 11/2021 |
| WO | 2021220085 A1 | 11/2021 |
| WO | 2022243793 A1 | 11/2022 |
| WO | 2022243794 A1 | 11/2022 |
| WO | 2022243795 A1 | 11/2022 |
| WO | 2022243796 A1 | 11/2022 |
| WO | 2022243797 A1 | 11/2022 |
| WO | 2022243806 A1 | 11/2022 |
| WO | 2022243807 A1 | 11/2022 |
| WO | 2022243808 A1 | 11/2022 |
| WO | 2022243809 A1 | 11/2022 |
| WO | 2022259073 A1 | 12/2022 |
| WO | 2022269388 A1 | 12/2022 |
| WO | 2023031725 A1 | 3/2023 |
| WO | 2023031726 A1 | 3/2023 |
| WO | 2023031727 A1 | 3/2023 |
| WO | 2023042032 A1 | 3/2023 |
| WO | 2023042033 A1 | 3/2023 |
| WO | 2023042035 A1 | 3/2023 |
| WO | 2023042036 A1 | 3/2023 |
| WO | 2023042037 A1 | 3/2023 |
| WO | 2023042038 A1 | 3/2023 |
| WO | 2023042039 A1 | 3/2023 |
| WO | 2023161727 A1 | 8/2023 |
| WO | 2023161728 A1 | 8/2023 |
| WO | 2023170480 A1 | 9/2023 |
| WO | 2023170482 A1 | 9/2023 |
| WO | 2023227959 A1 | 11/2023 |
| WO | 2023227960 A1 | 11/2023 |
| WO | 2023248015 A1 | 12/2023 |
| WO | 2023248016 A1 | 12/2023 |
| WO | 2024023728 A1 | 2/2024 |
| WO | 2024023729 A1 | 2/2024 |

OTHER PUBLICATIONS

European Patent Office, Search Report for related PCT Application No. PCT/IB2022/058401 dated Jan. 3, 2023, 20 pages.

Alamy, "Plastic syringe with needle closed by protective cap . . . ", Alamy.com, [online], Available from: https://www.alamy.com/stockphoto-plastic-syringe-with-needle-closed-by-protective-cap-plasticsyringe-92510272.html [ Accessed May 19, 2022].

Corsair, "TM30 Performance Thermal Paste", Corsair.com, [online], Available from: https://www.corsair.com/us/en/Categories/Products/Accessories-%7 CParts/TM3 0-Performance-Thermal-Paste/p/CT-9010001-WW [Accessed May 19, 2022].

Amazon, "TEC Color Matched Caulk", Amazon.com, [online], Available from: https://www.amazon.com/Color-Matched-Caulk-Colorfast-Sanded/dp/B00X66X2GO?th=I [Accessed May 19, 2022].

* cited by examiner

AGRICULTURAL SAMPLE HANDLING SYSTEM AND RELATED METHODS

CROSS-REFERENCE TO RELATED APPLICATIONS

The present application is a national phase entry under 35 U.S.C. § 371 of International Patent Application PCT/IB2022/058401, filed Sep. 7, 2022 designating the United States of America and published in English as International Patent Publication WO 2023/042032 A1 on Mar. 23, 2023, which claims priority to U.S. Provisional Patent Application No. 63/245,278 filed 17 Sep. 2021; U.S. Provisional Patent Application No. 63/264,059 filed 15 Nov. 2021; U.S. Provisional Patent Application No. 63/264,062 filed 15 Nov. 2021; U.S. Provisional Patent Application No. 63/264,065 filed 15 Nov. 2021; U.S. Provisional Patent Application No. 63/370,072 filed 1 Aug. 2022: U.S. Provisional Patent Application No. 63/370,077 filed 1 Aug. 2022; and U.S. Provisional Patent Application No. 63/370,081 filed 1 Aug. 2022. The foregoing applications are incorporated herein by reference in their entireties.

BACKGROUND

The present disclosure relates generally to agricultural sampling and analysis, and more particularly to a system for packaging, tracking, and handling an agricultural sample such as without limitation soil for chemical analysis.

Periodic soil testing is an important aspect of the agricultural arts. Test results provide valuable information on the chemical makeup of the soil such as plant-available nutrients and other important properties (e.g., levels of nitrogen, magnesium, phosphorous, potassium, pH, etc.) so that various amendments may be added to the soil to maximize the quality and quantity of crop production.

In some existing soil sampling processes, collected bulk agricultural samples such as soil or other agricultural materials may require some form of packaging to facilitate transport and further preparation and processing for eventual chemical analysis. The packaging further protects the integrity of the samples until processed. In addition, a means for tracking where samples were collected from in the agricultural field is necessary to associate the chemical analysis results with a particular portion of the field. Furthermore, a system for unloading the packaged sample is necessary to allow further processing and analysis of the sample.

Improvements in agricultural sample handling are desired.

BRIEF SUMMARY

The present disclosure provides automated programmable processor-controlled agricultural sample packaging and handling systems, and related methods for containerizing an agricultural sample and then unloading a sample container. In some embodiments, the container may be a cylindrical sample tube capped at or near both ends. The sample may be a soil sample in some non-limiting embodiments, or other agricultural-related materials described further herein.

The packaging system may comprise a packaging apparatus which receives bulk soil sample material collected by an automated sample collection device/probe or manually, extracts portions of the material, and transfers the extracted portions to the sample container which may then be capped. The sample extraction and containerization process may be automatically controlled by a programmable system controller which communicates with multiple sensors which monitor the operation and position of the various components of the packaging equipment to control its operation. The system may include sample tracking comprising assigning a unique tracking ID to each sample which can be correlated to the location in the agricultural field or elsewhere where the sample was obtained. A machine-readable tracking tag may be affixed to the sample tube or its end caps for that purpose. In one embodiment, RFID (radio frequency identification) may be used. The tracking tag may therefore be an RFID tag readable by an RFID reader. In other embodiments, the tracking tag may be a bar code readable by a visual barcode scanner. Other forms of readable tracking tags and related systems may be used.

A sample container unloading system may be comprise a staging rack and sample container unloading apparatus operably coupled together. The staging rack is configured to receive and hold a plurality of the filled sample containers from the packaging system. A transfer mechanism may transfer and load the sample tubes from the rack sequentially into the unloading apparatus which operates to uncap the tubes and eject the sample contents for further processing. The sample tube staging, transfer mechanism, and sample unloading operation may be fully automated and controlled by the programmable controller.

In one aspect, an agricultural sample unloading system comprises: a sample staging rack comprising at least one inclined feed ramp configured for receiving an elongated sample tube configured for holding the sample, the sample tube including a first end cap and a second end cap; an unloading apparatus coupled to the staging rack, the unloading apparatus configured to receive the sample tube from the staging rack; and a transfer mechanism operable to transfer the sample tube from the staging rack to the unloading apparatus. The unloading apparatus comprises a rotatable carriage configured to hold and rotate the sample tube in opposing directions during the sample unloading process. The unloading apparatus further comprises a loading mechanism operable to load the sample tube into the carriage.

In another aspect, a method for unloading an agricultural sample container comprises: inserting a capped sample tube containing a sample into an unloading apparatus; rotating the sample tube a first time to an upright vertical position; uncapping the sample tube which creates an open top end; rotating the sample tube a second time to an inverted vertical position; and ejecting the sample from the sample tube. The unloading apparatus comprises a movable carriage including an elongated receptacle into which the sample tube is inserted and which performs the foregoing movements of the sample tube.

In another aspect, an agricultural sample container comprises: an elongated tubular body defining a longitudinal axis, a top end, a bottom end, and an internal cavity extending between the ends configured for holding the sample; a first cap detachably coupled to the top end; and a second cap slideably disposed in the cavity, the second cap being movable in opposing directions between the first and second ends. The second cap comprises a base and a plurality of longitudinally-extending retention protrusions extending downwards from the base. The body in some embodiments further comprises a plurality of circumferentially spaced apart retention slots configured to lockingly engage the retention protrusions.

Although the agricultural sample packaging system may be described herein with reference to containerizing soil samples which represents only a single category of use for the disclosed embodiments, it is to be understood that the same packaging systems including the apparatuses and related processes may further be used for processing other types of agricultural related samples including without limitation vegetation/plant, forage, manure, feed, milk, or other types of samples. The disclosure herein should therefore be considered broadly as an agricultural sample packaging system amenable for extracting and containerizing many different types of samples from bulk "as collected" sample material regardless of the method for collection. Accordingly, the present agricultural sample packaging system disclosed is expressly not limited to use of packaging soil samples alone for chemical analysis of properties of interest.

BRIEF DESCRIPTION OF THE DRAWINGS

The present disclosure will become more fully understood from the detailed description and the accompanying drawings, wherein like elements are labeled similarly and in which:

FIG. 117 is a second perspective view thereof;

FIG. 118 is a third perspective view thereof;

FIG. 119 is front view thereof;

FIG. 120 is a side view thereof;

FIG. 121 is a top view thereof;

FIG. 122 is a side view of an upper portion of the staging rack of FIG. 114 showing the upper sprocket of the chain drive;

FIG. 123 is a front perspective view of an alternative embodiment of a sample unloading system;

FIG. 124 is a rear perspective view thereof;

FIG. 125 is a front view thereof;

FIG. 126 is a rear view thereof;

FIG. 127 is a top view thereof;

FIG. 128 is a bottom view thereof;

Figure 123:
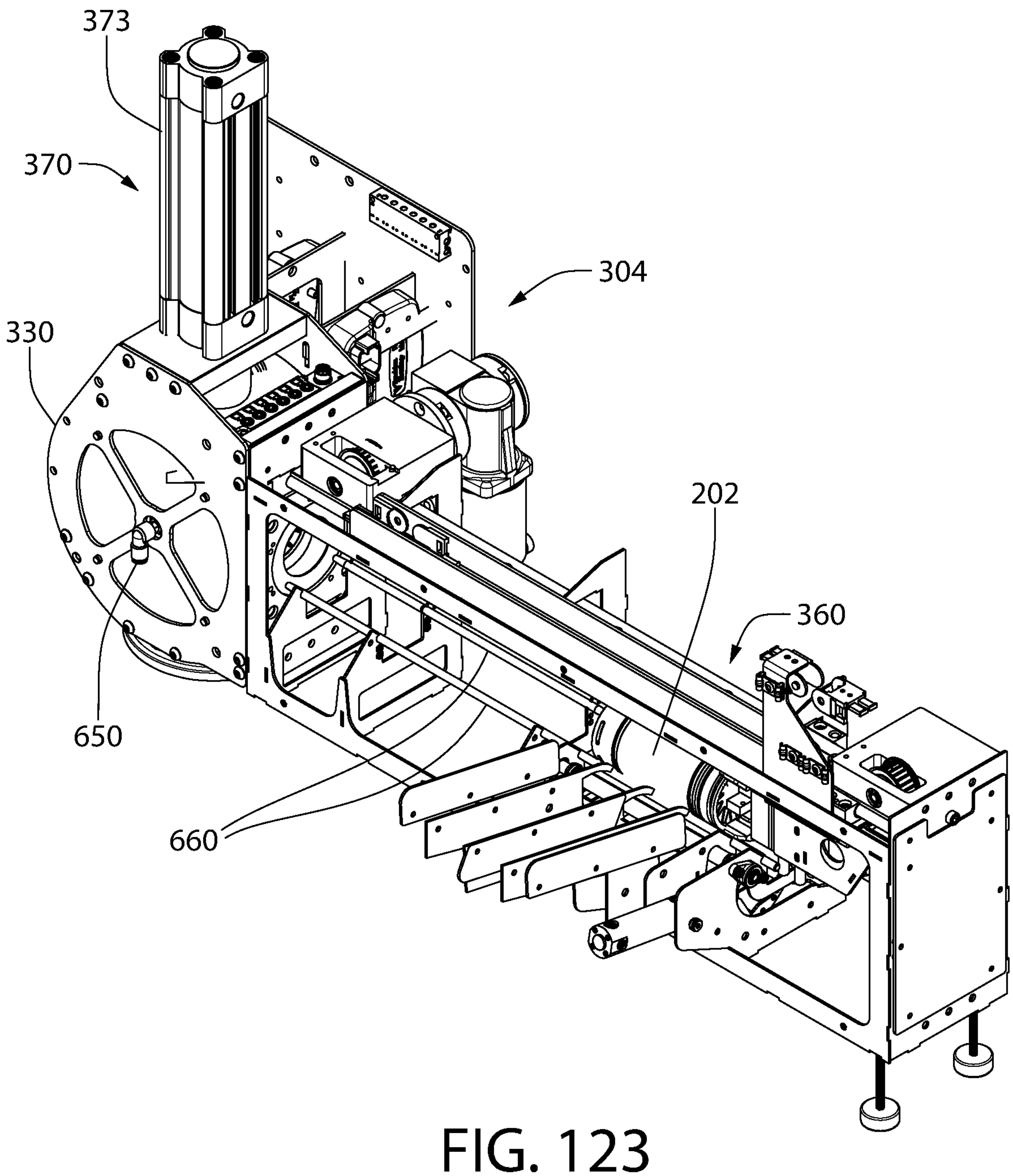
Figure 124:
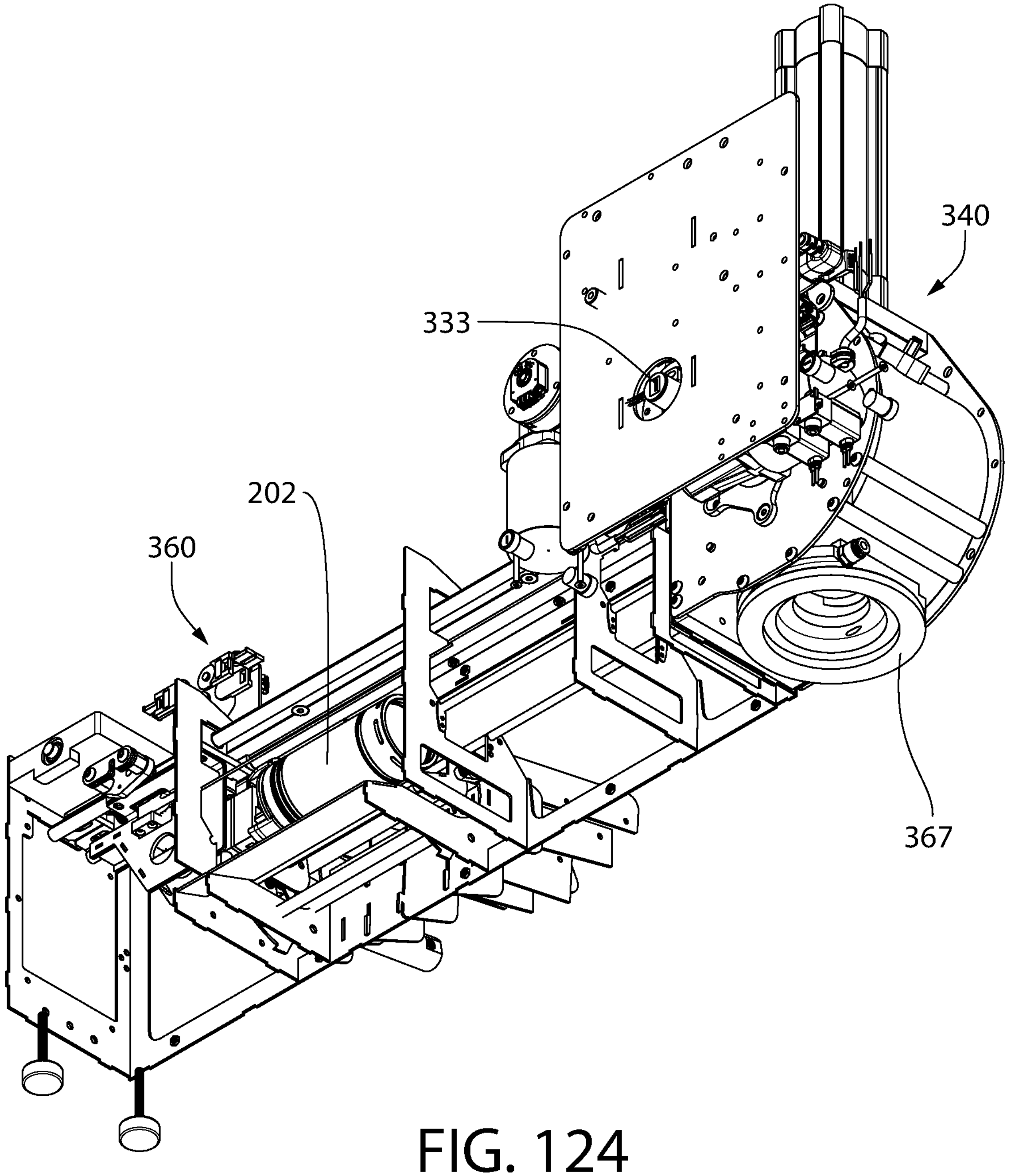
Figure 125:
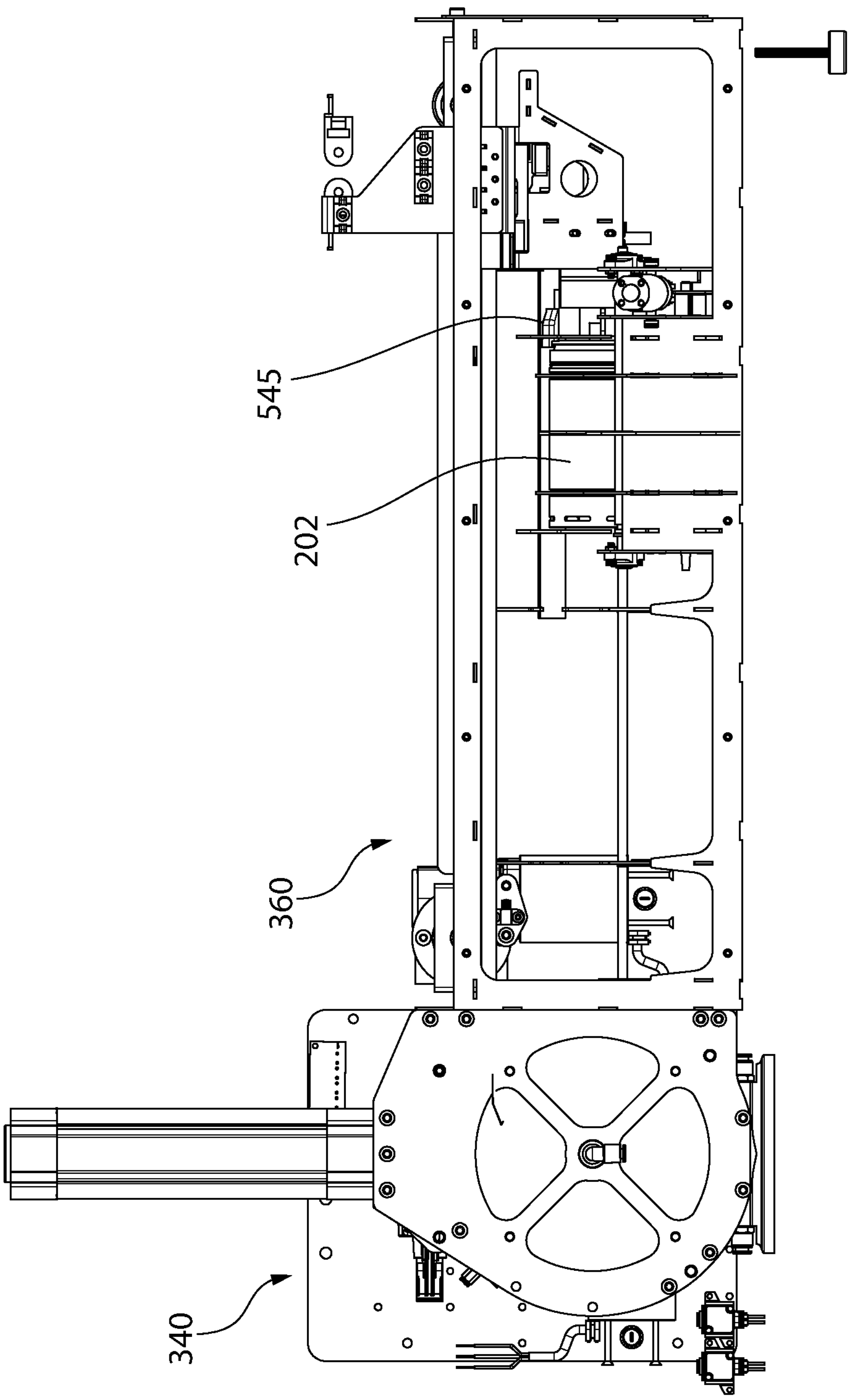
Figure 126:
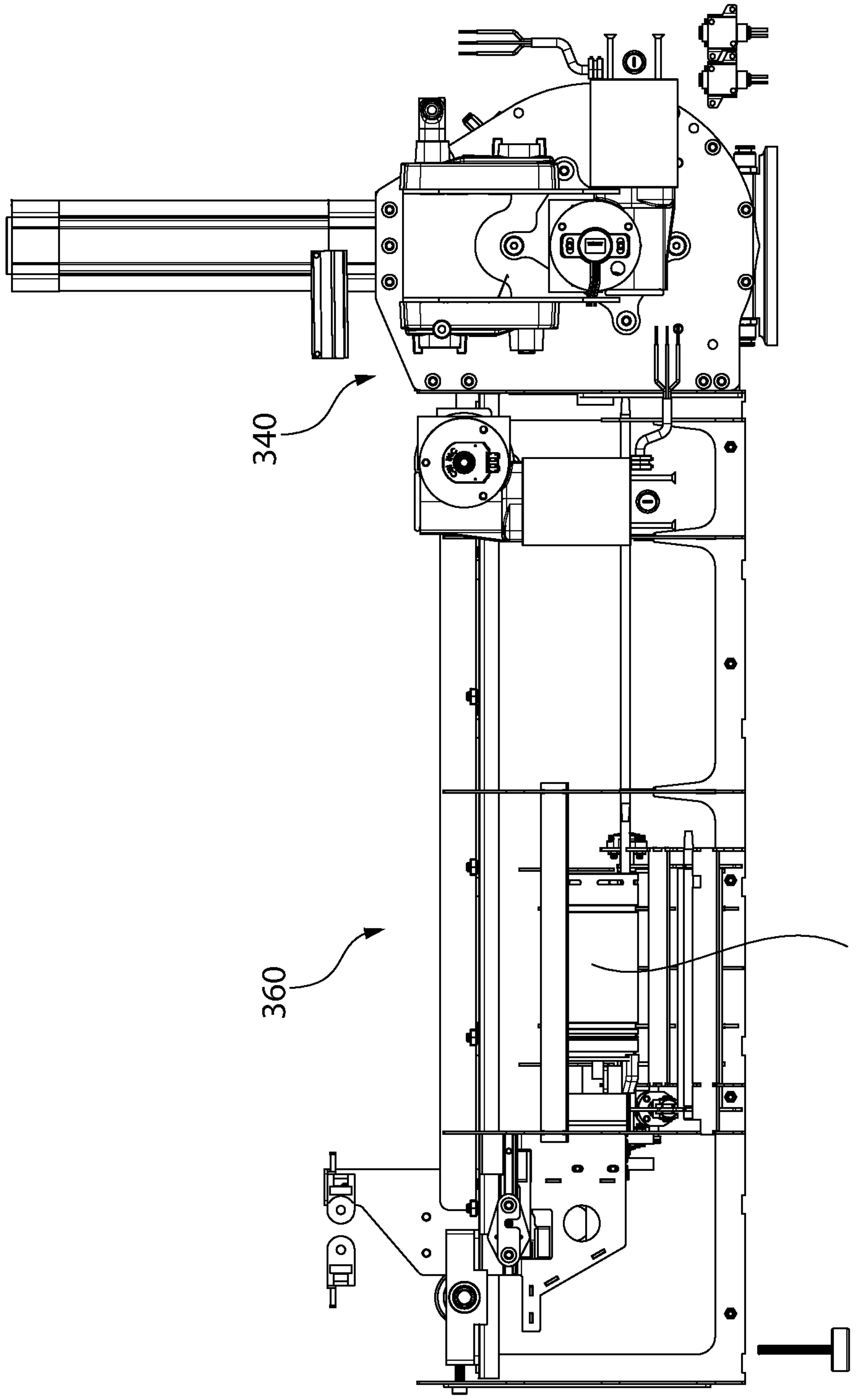
Figure 127:
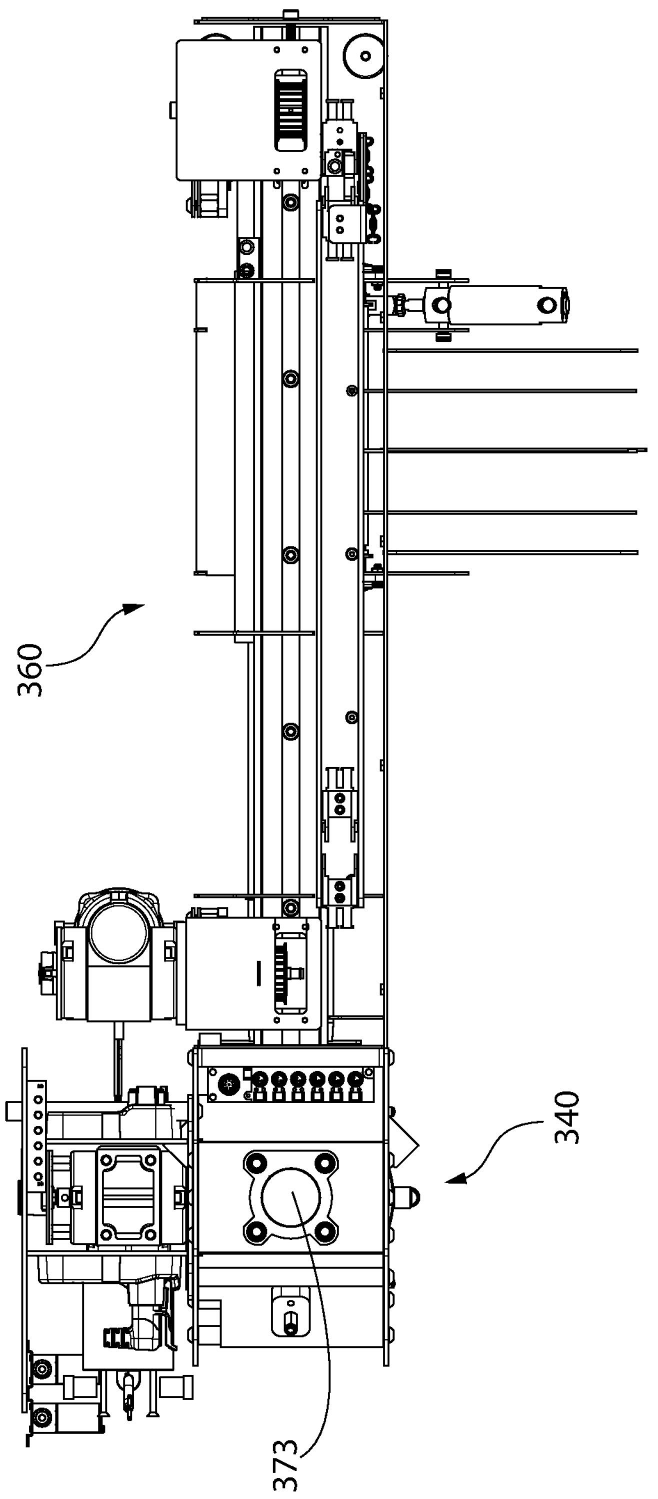
Figure 128:
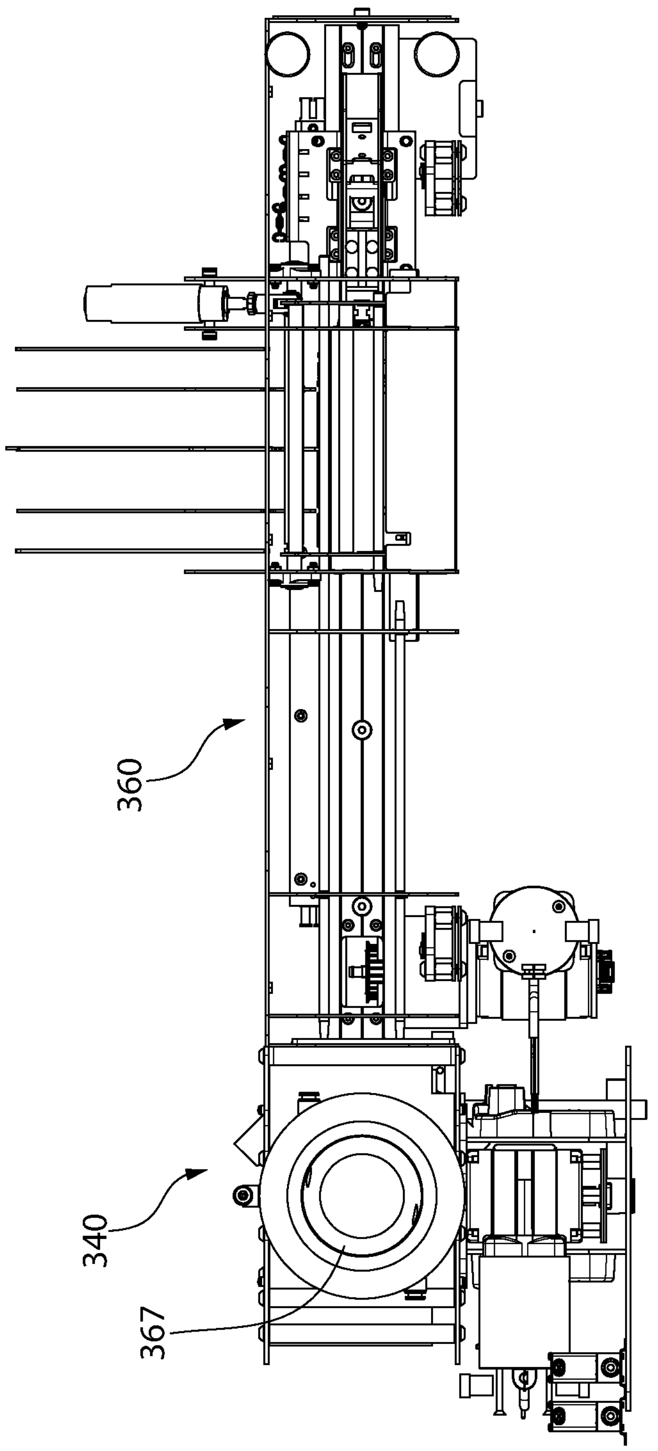
Figure 129:
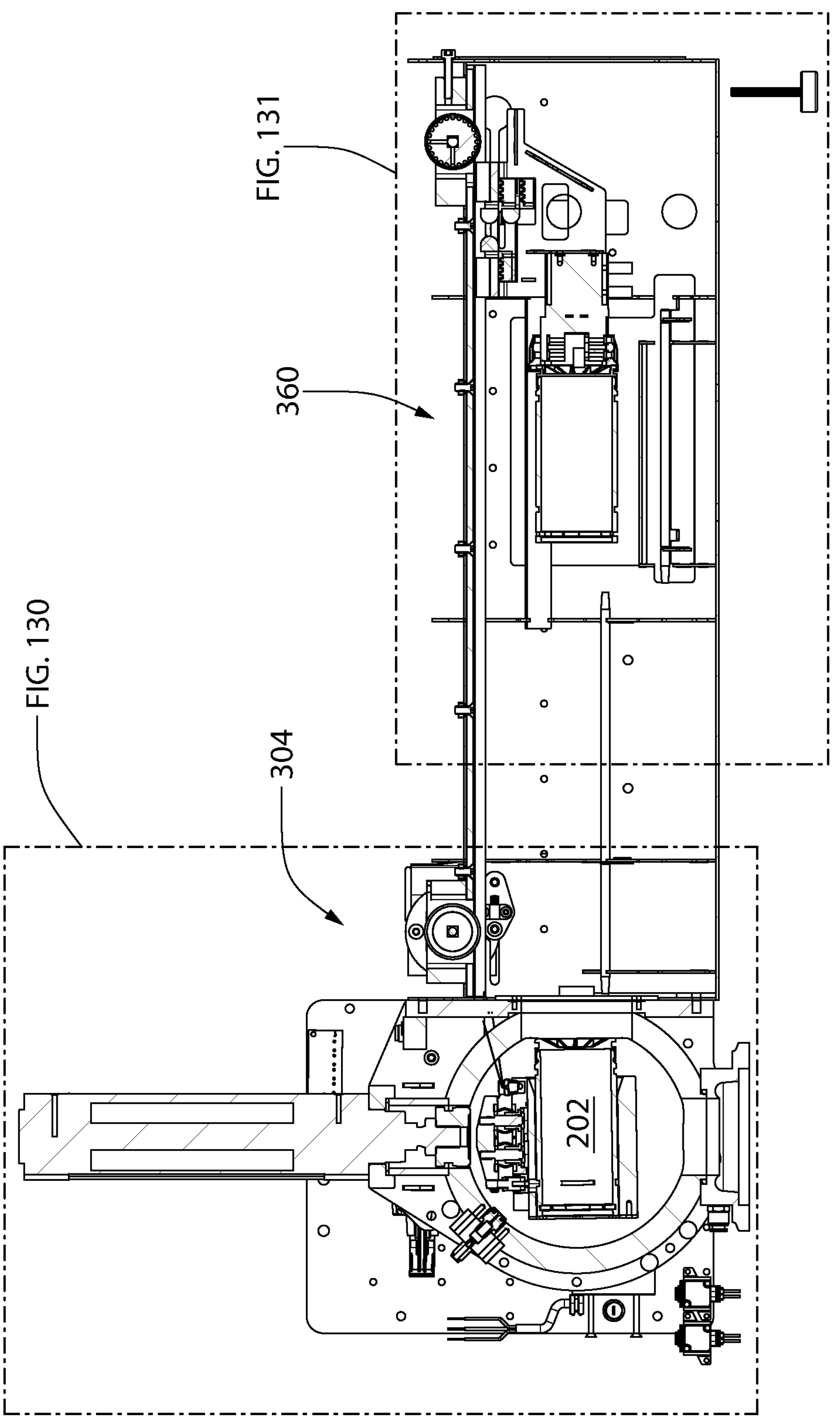
Figure 130:
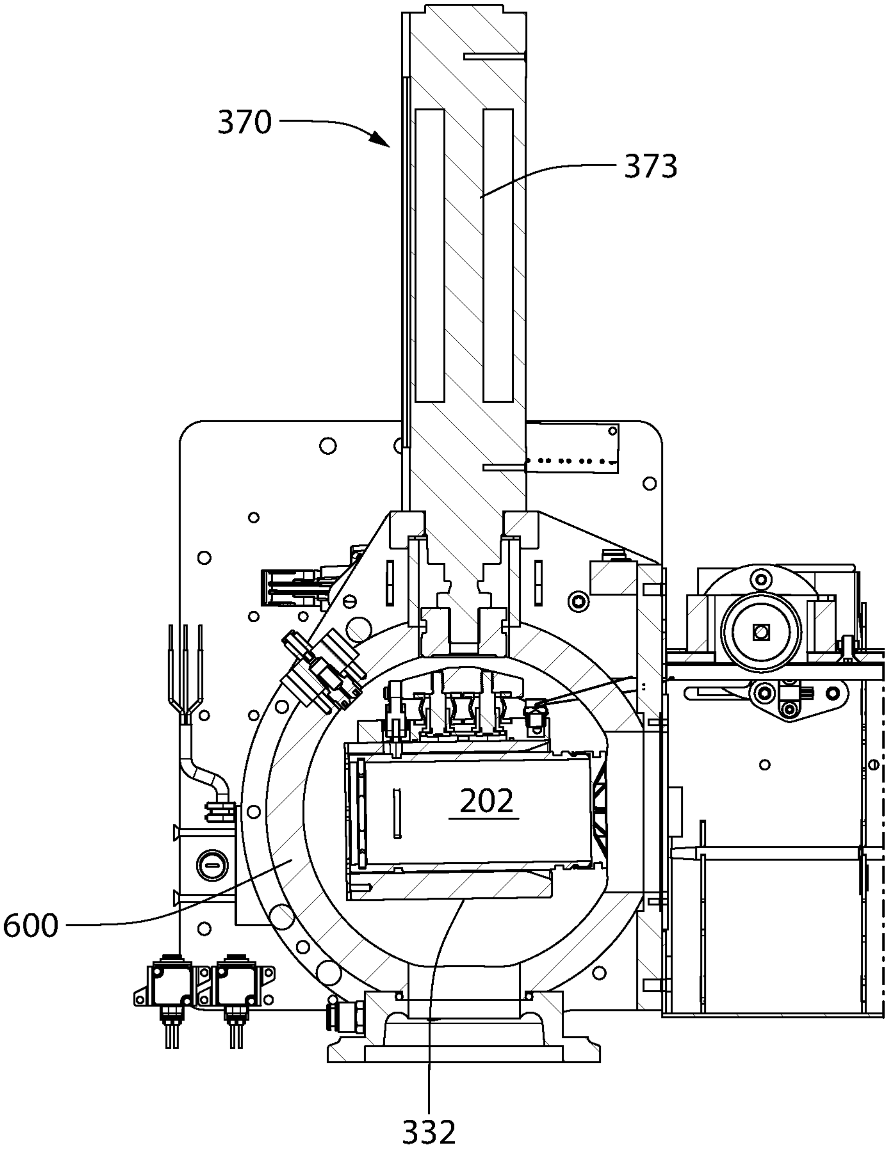
Figure 131:
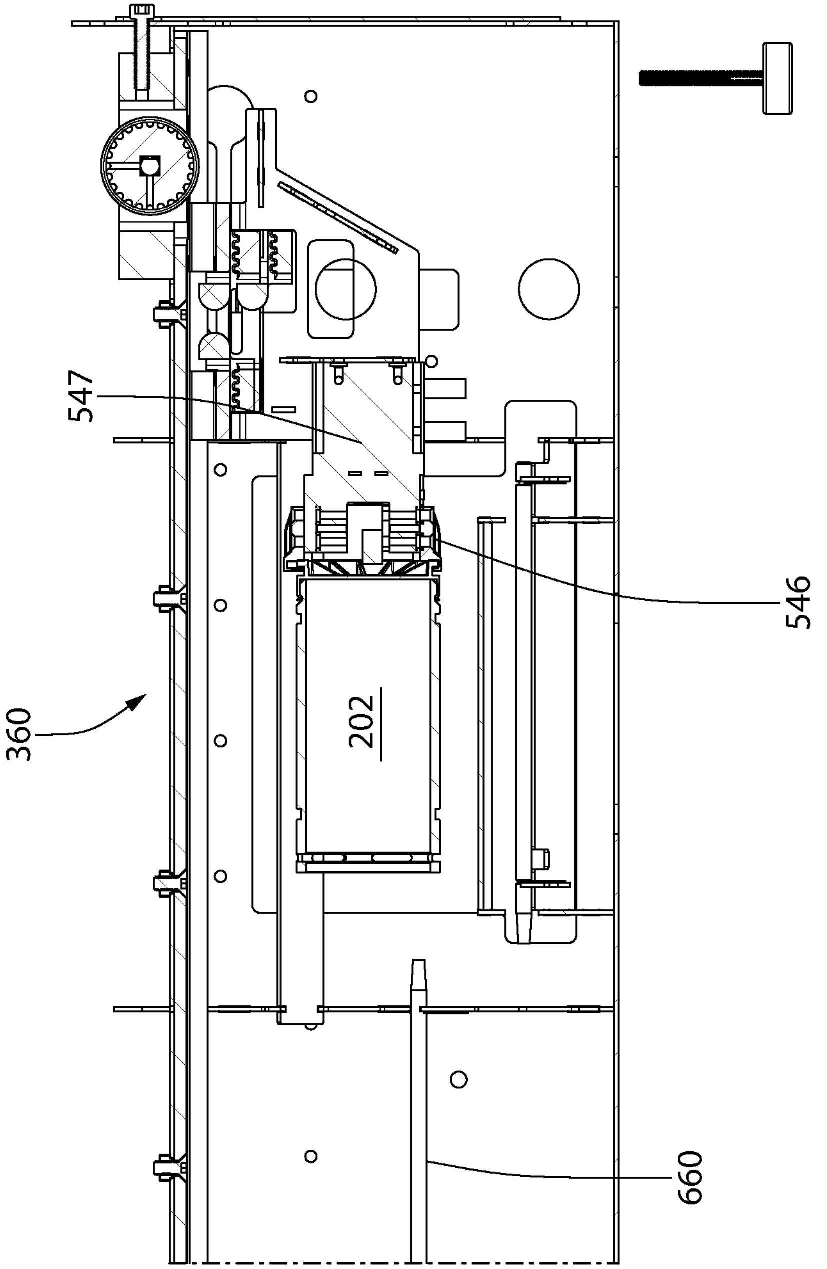
Figure 132:
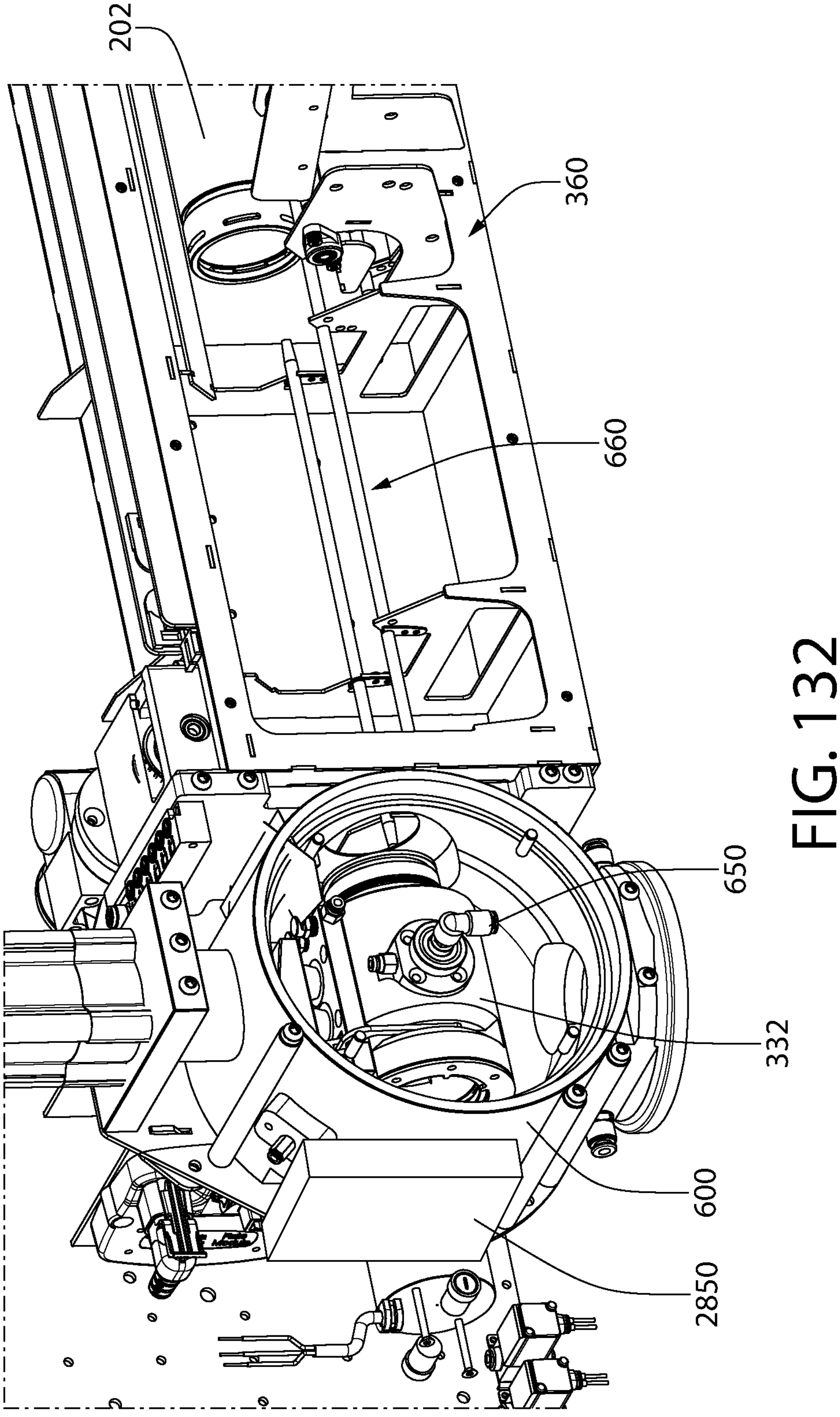
Figure 133:
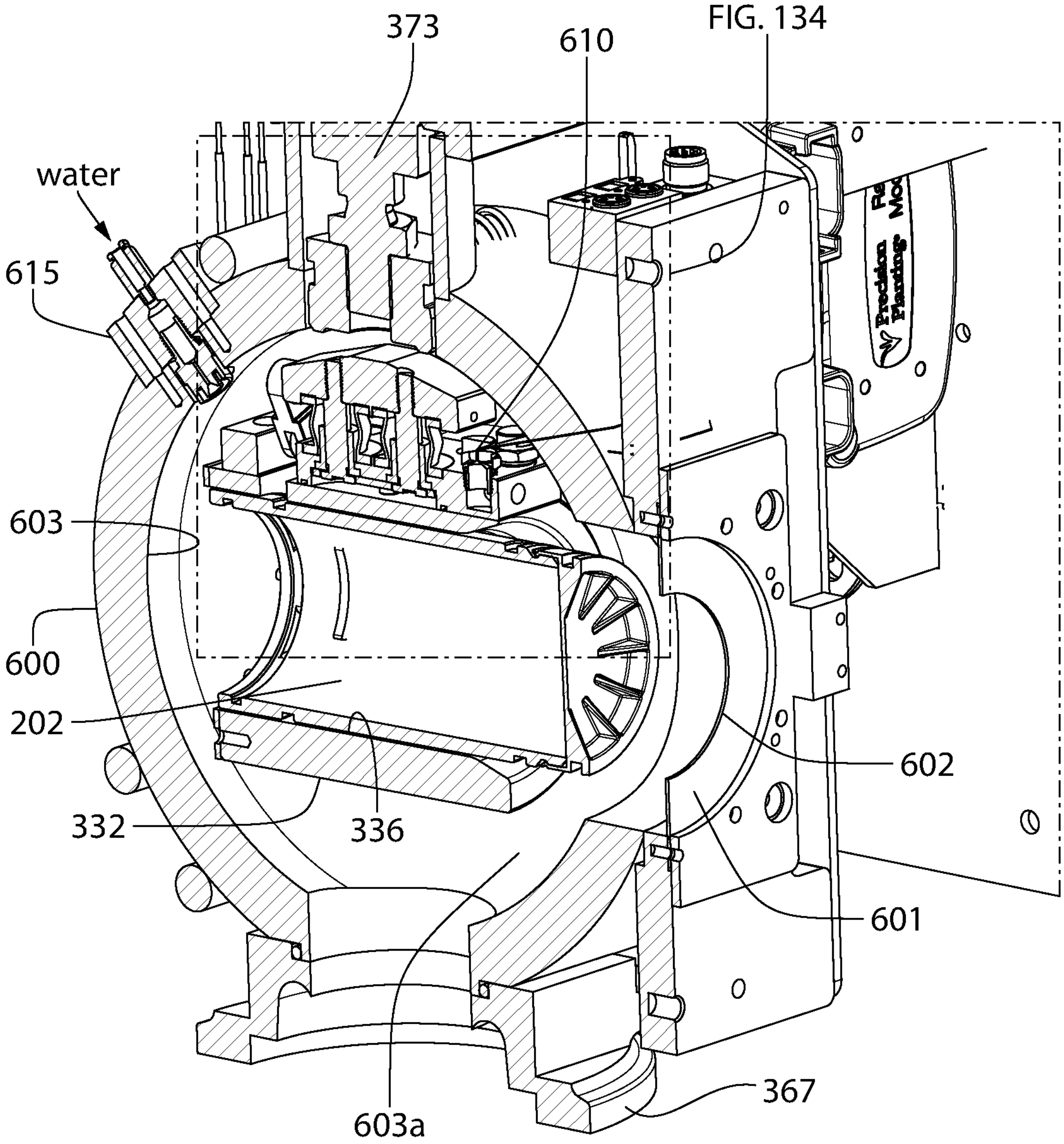
Figure 134:
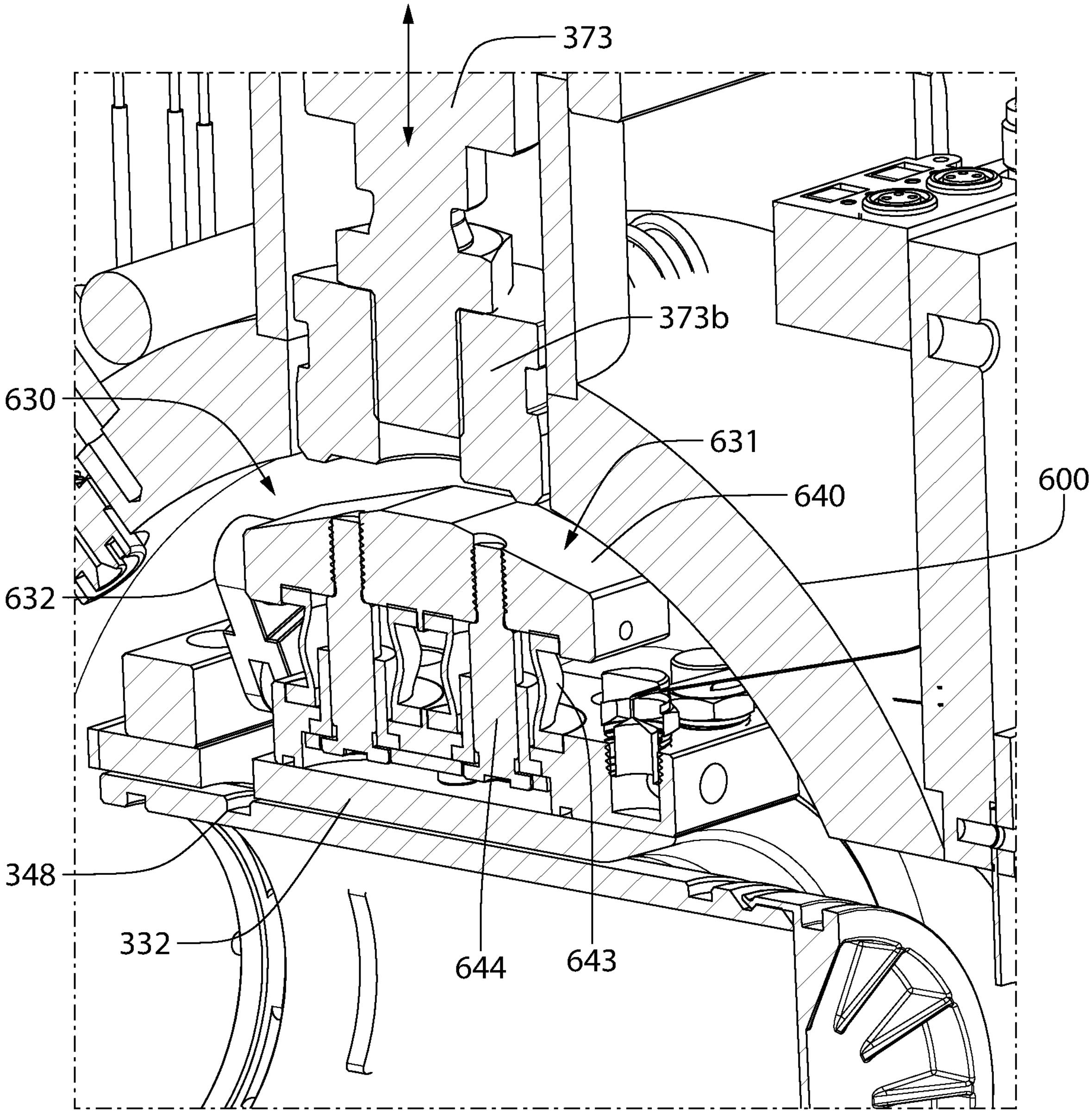
Figure 135:
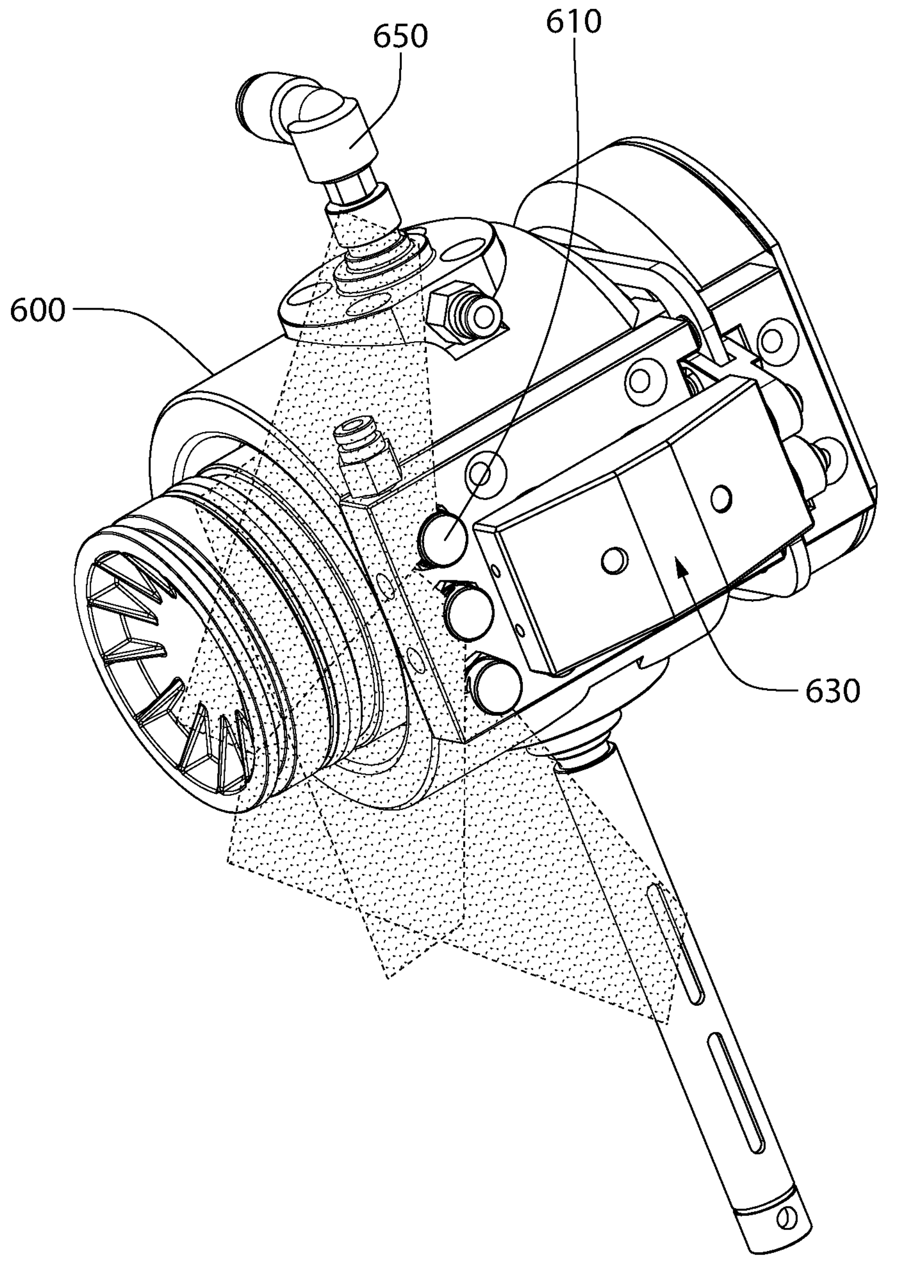
Figure 136:
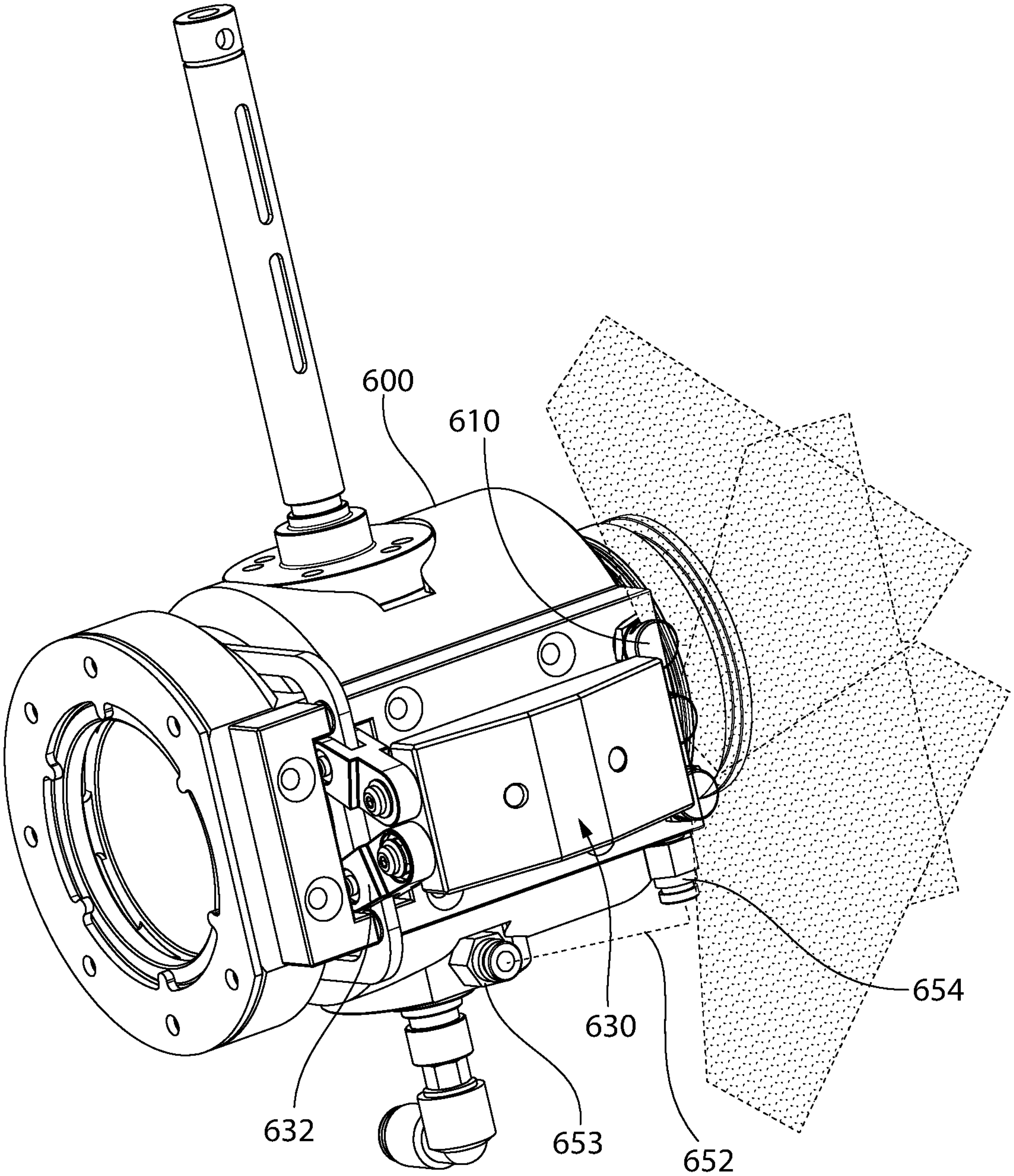
Figure 137:
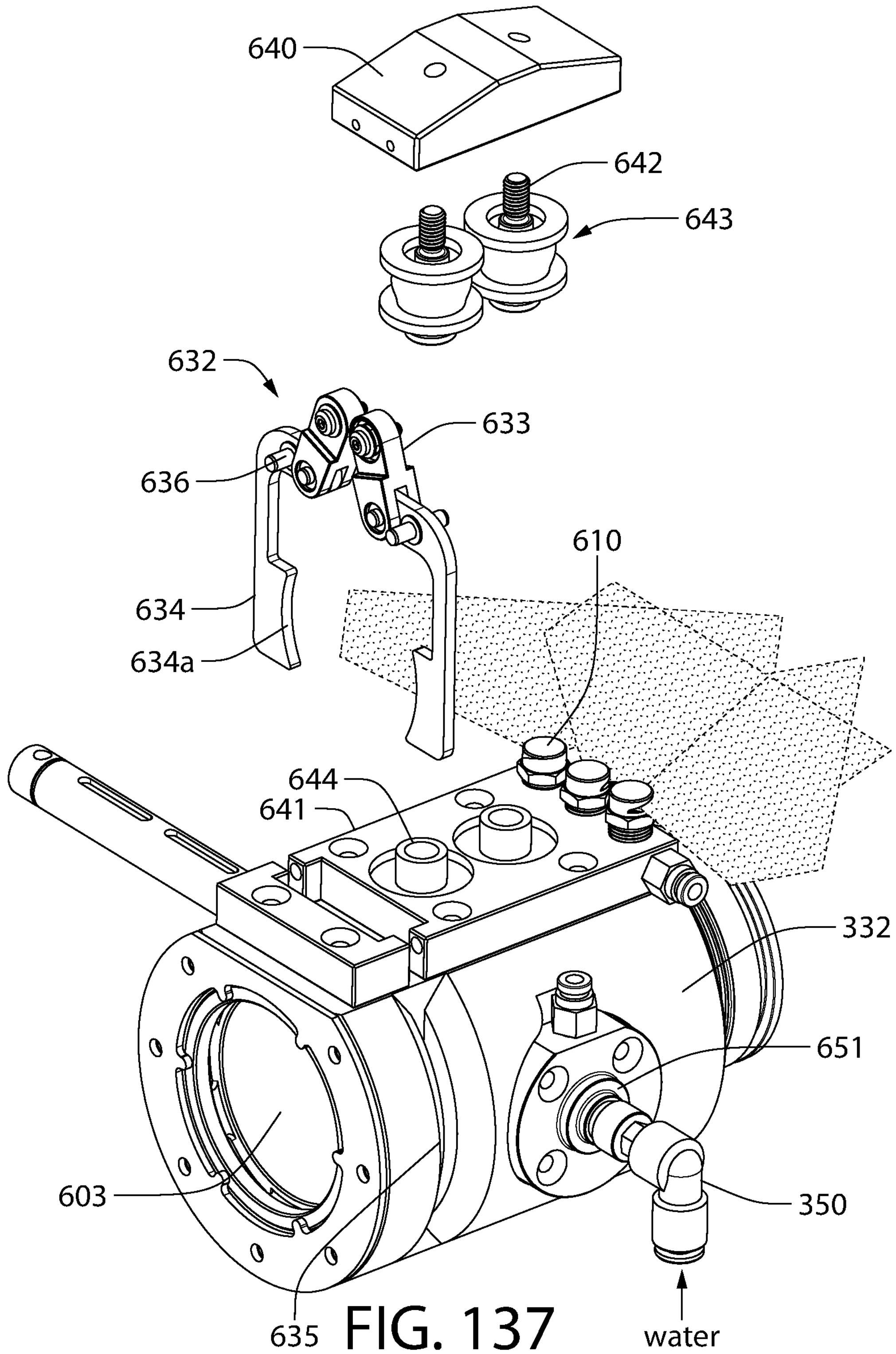
Figure 138:
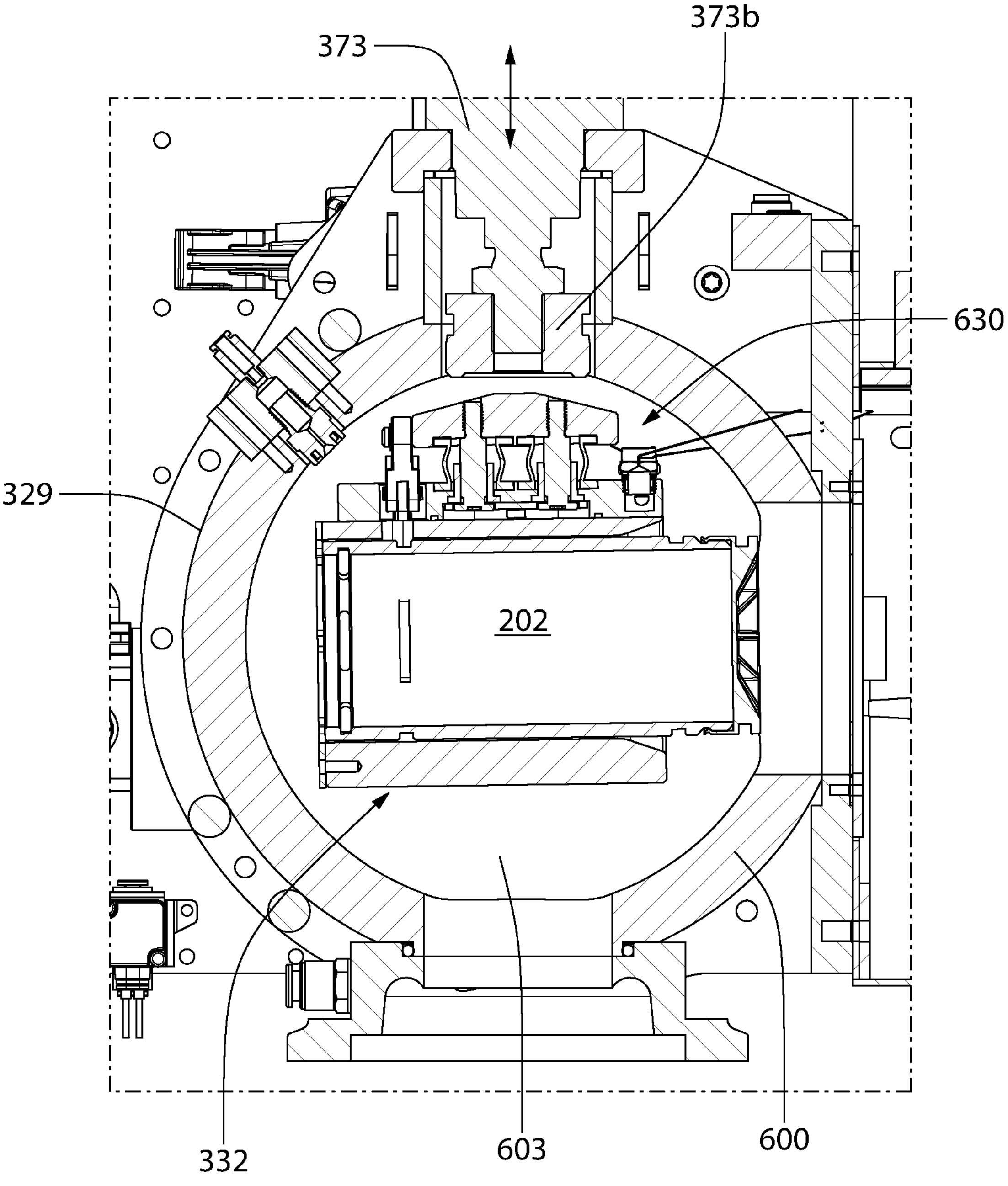
Figure 139:
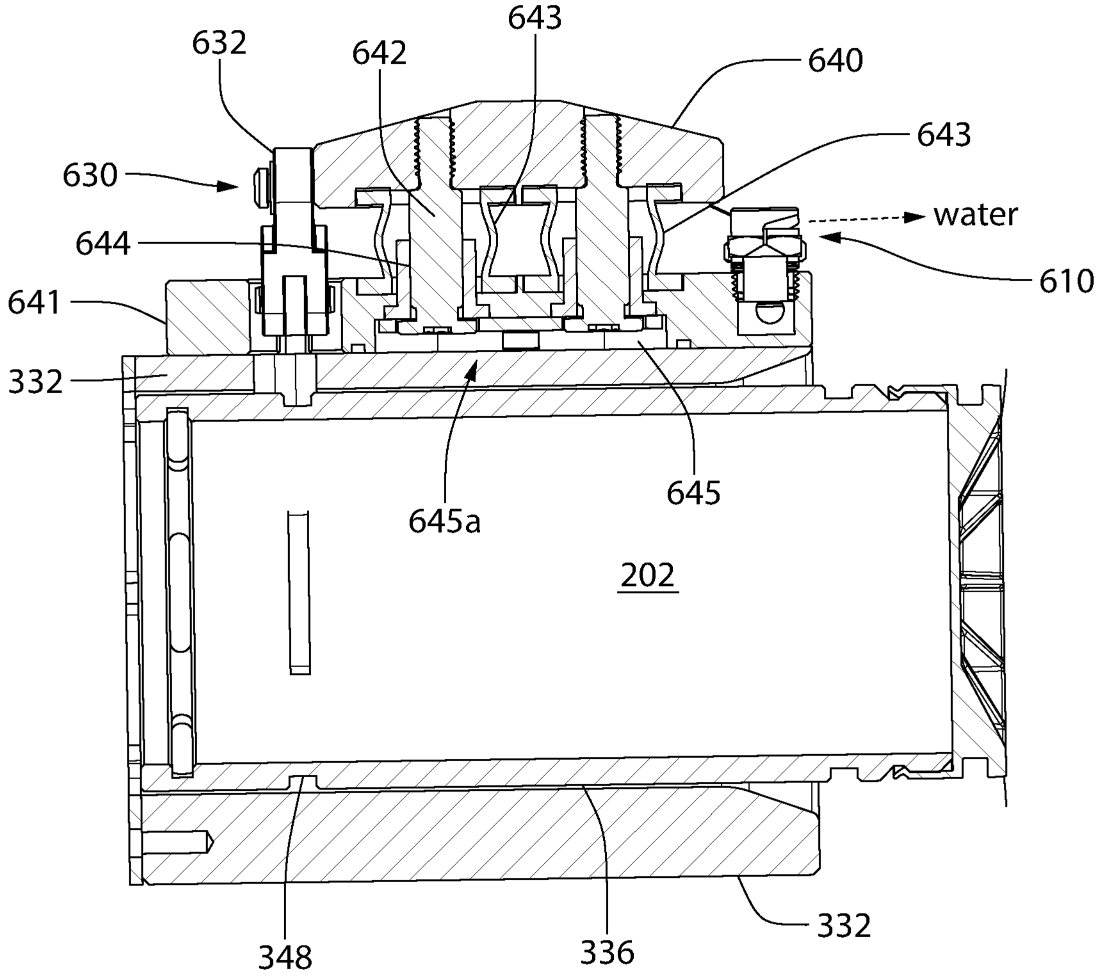
Figure 140:
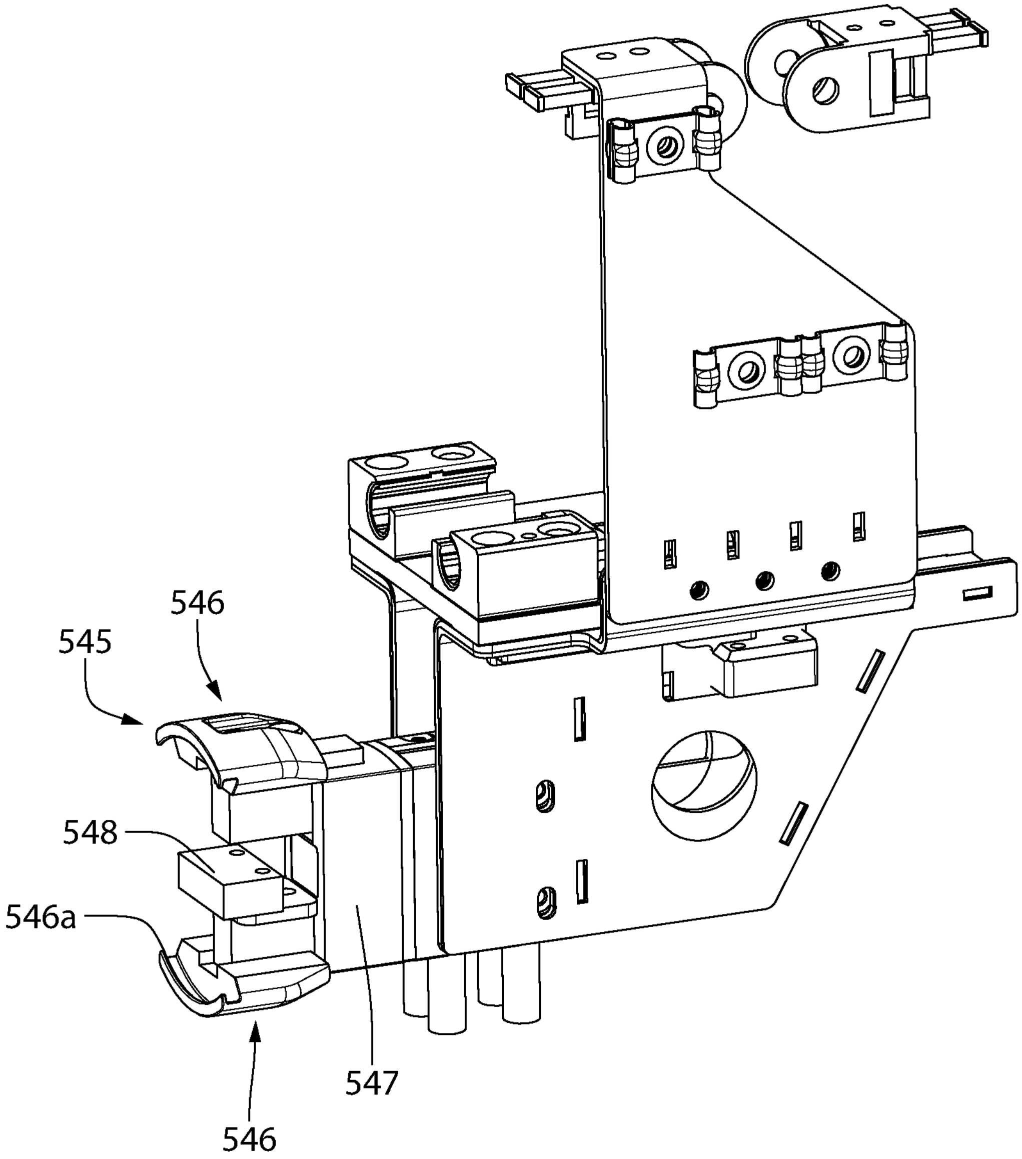
Figure 141:
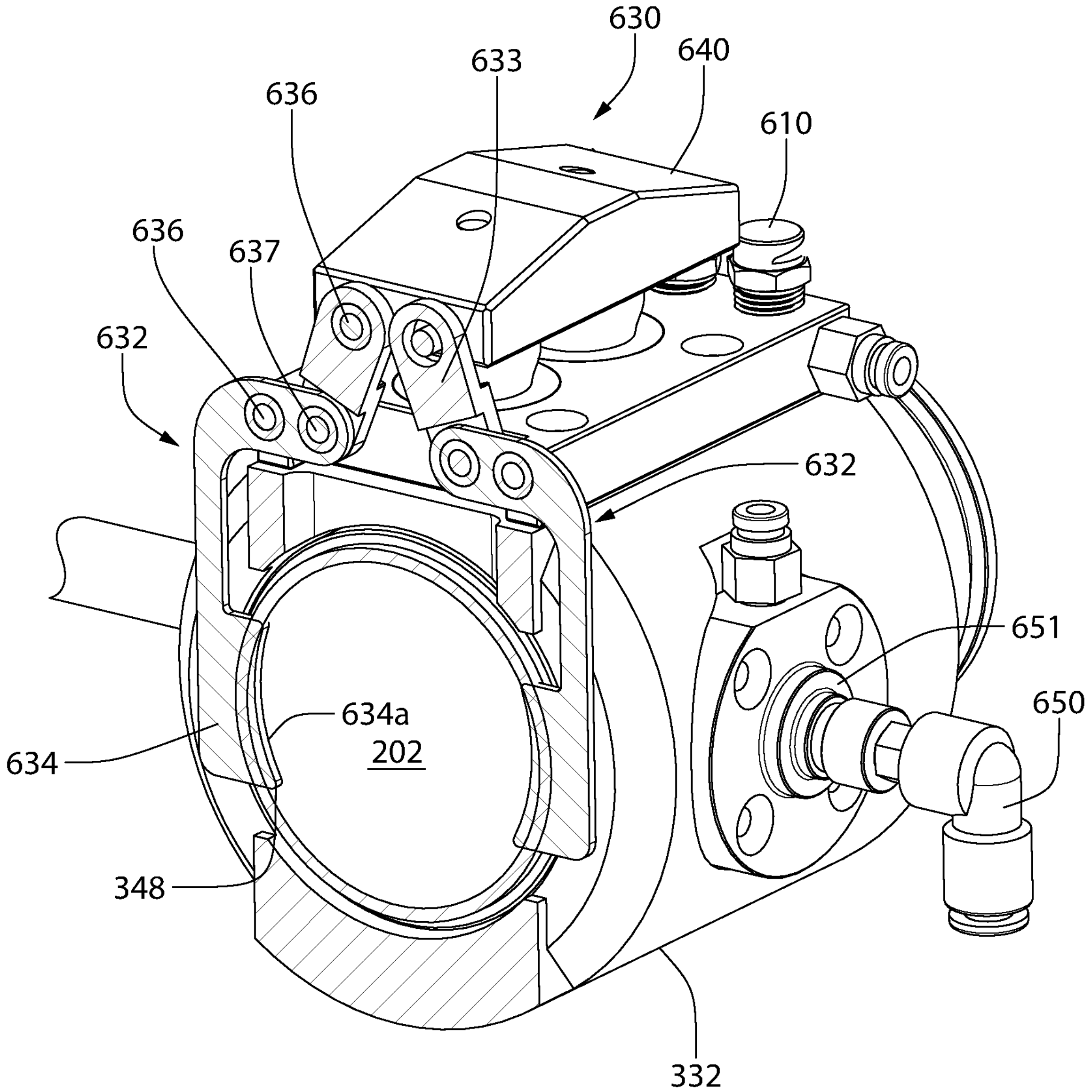
Figure 142:
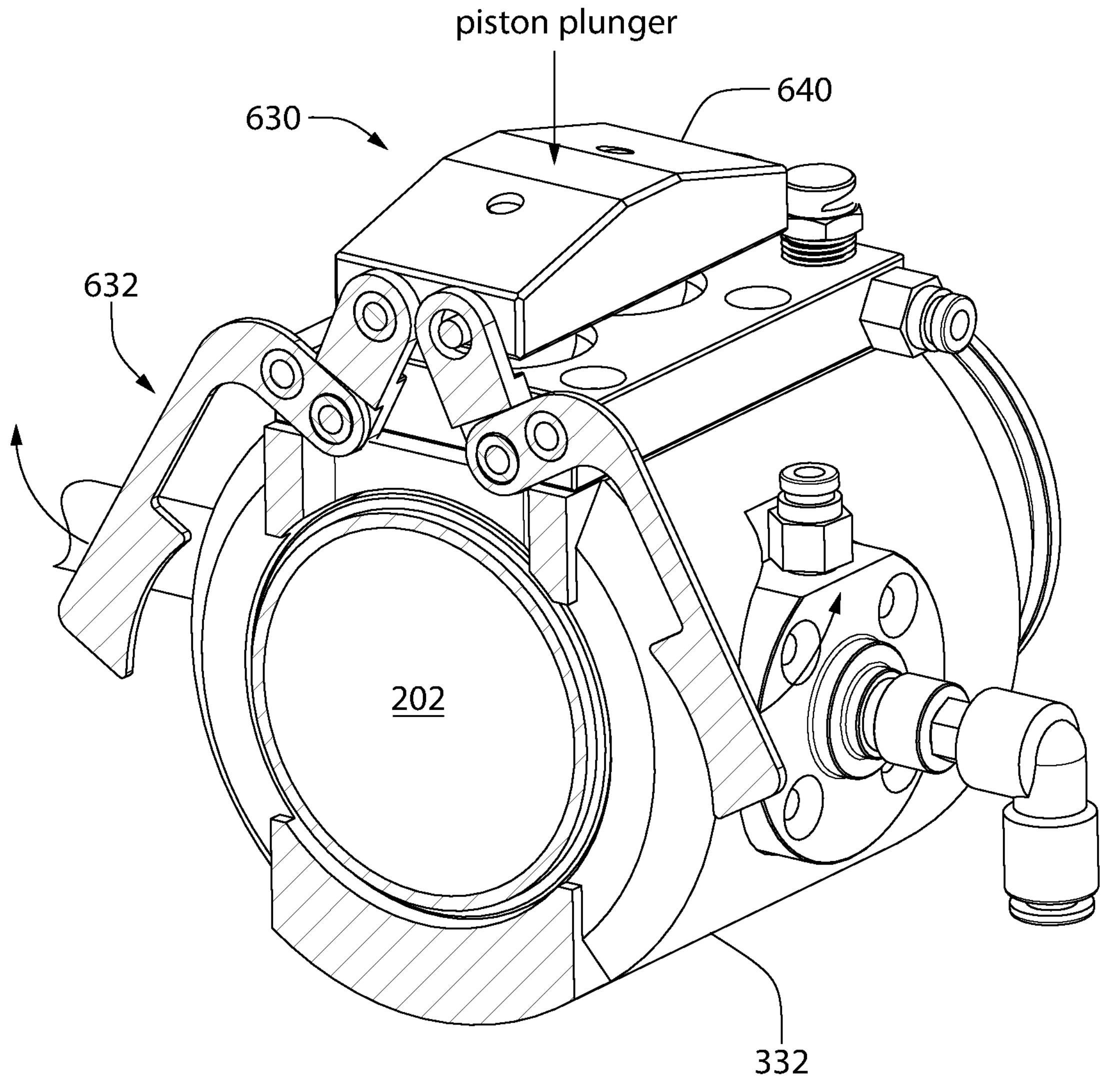

FIG. 129 is a front cross sectional view thereof;

FIG. 130 is a first detailed view taken from FIG. 129;

FIG. 131 is a second detailed view taken from FIG. 129;

FIG. 132 is a partial front perspective view of the unloading apparatus of FIG. 123;

FIG. 133 is an enlarged cross-sectional detailed perspective view of wash-down enclosure and sample tube carriage of the apparatus;

FIG. 134 is an enlarged view taken from FIG. 133;

FIG. 135 is a first perspective view of the wash-down enclosure showing spray nozzles of the wash-down system;

FIG. 136 is a second perspective view thereof;

FIG. 137 is a third perspective view thereof showing portions of the mechanical sample tube gripper mechanism in exploded detail;

FIG. 138 is a front cross sectional enlarged view of the wash-down enclosure and sample tube carriage of the sample unloading apparatus of FIG. 123;

FIG. 139 is a front cross-sectional enlarged view showing the sample tube carriage and components of the tube gripper mechanism;

FIG. 140 is a perspective view of a portion of the tube loading mechanism of the unloading apparatus showing an alternative embodiment of a sample tube decapper;

FIG. 141 is a first perspective view showing the tube gripper mechanism in an inward engaged position locking the sample tube in the rotatable carriage of the unloading apparatus; and FIG. 142 is a second perspective view thereof showing the tube gripper mechanism in an outward disengaged position unlocking the sample tube from the carriage.

All drawings are not necessarily to scale. Components numbered and appearing in one FIGURE but appearing un-numbered in other FIGURES are the same components unless expressly noted otherwise. Any reference herein to a figure by a whole figure number which may appear in multiple FIGURES bearing the same whole number but with different alphabetical suffixes shall be constructed as a general reference to all of those FIGURES unless expressly noted otherwise.

DETAILED DESCRIPTION

The features and benefits of the present disclosure are illustrated and described herein by reference to exemplary ("example") embodiments. This description of exemplary embodiments is intended to be read in connection with the accompanying drawings, which are to be considered part of the entire written description. Accordingly, the disclosure expressly should not be limited to such exemplary embodiments illustrating some possible non-limiting combination of features that may exist alone or in other combinations of features.

In the description of embodiments disclosed herein, any reference to direction or orientation is merely intended for convenience of description and is not intended in any way to limit the scope of the present disclosure. Relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise.

As used throughout, any ranges disclosed herein are used as shorthand for describing each and every value that is within the range. Any value within the range can be selected as the terminus of the range. In addition, all references cited herein to prior patents or patent applications are hereby incorporated by reference in their entireties. In the event of a conflict in a definition in the present disclosure and that of a cited reference, the present disclosure controls.

FIGS. 1-46 show one embodiment of an agricultural sample packaging system 100 and various components thereof according to the present disclosure. The packaging system may be used for and will be described for convenience with containerizing soil samples as an illustrative but not limiting use.

Packaging system 100 generally comprises agricultural sample packaging apparatus 110 defining a front 110*a*, rear 110*b*, right lateral side 110*c*, left lateral side 110*d*, top 110*e*, and bottom 110*f* for convenience of reference and not limitation. Apparatus 110 can be horizontally and laterally elongated in structure and defines a longitudinal axis LA extending horizontally through the right and left lateral sides and intersects the geometric centerline of the apparatus. An outer protective housing 116 of suitable configuration and material may be provided to protect a majority of the components of the packaging apparatus 110 including electronic components from dust, debris, direct rainfall, impacts, etc.

Packaging apparatus 110 includes a support frame 111 including an upper sub-frame 115 comprising a pair of laterally spaced apart vertical end supports 112 and one or more cross supports 113 spanning between and fixedly coupled to the end support members to form a self-supporting rigid frame structure. A lower base sub-frame 114 of the chassis 111 may be provided in some embodiments which is coupled to the upper sub-frame 115 and elevates and/or spaces the upper sub-frame above a support surface or object. Base sub-frame 114 may comprise an assemblage or weldment of plural structural members (e.g., tubes, rods, L-angles, I-beams, C-beams, etc.) configured to conform to and the mount the apparatus to a support surface or object. The support surface or object may be a stationary article or surface, or movable such as part of a self-powered or pulled wheeled vehicle (e.g., ATV, truck, trailer, etc.). Accordingly, numerous configurations of base sub-frames are possible depending on the mounting needs.

Upper sub-frame 115 of support frame 111 provides a mounting platform for and supports the functional and movable electronic and non-electronic components of the packaging apparatus 110. In one embodiment, the apparatus generally comprises a bulk material chamber 120, a sample transfer or collection chamber 180, a sample blade mechanism 130, a cleaning blade mechanism 140, a compaction piston-plunger 150, sample transfer piston-plunger 155, an optional container end cap actuator 160, funnel 170 with associated funnel door 171 and door actuator 172, and a rotatable container carousel 200 configured to removably hold the sample container 201 for the soil sample filling operation.

In the non-limiting illustrated embodiment, agricultural sample container 201 may be a hollow cylindrical sample tube 202 having a construction and customized features adapted for use with packaging apparatus 110 and unloading system 300 described below to containerize agricultural samples such as soil samples or others, and unload the containerized samples. Accordingly, sample tube 202 is distinguishable from ordinary tubes which may have capped ends.

Sample tube 202 has an elongated cylindrical tubular and hollow body defining cylindrical wall 202*a* terminated by a top end 203*a* and bottom end 203*b* closed and sealed by a pair of circular end caps 204. An internal cavity 207 extends between the ends along a longitudinal axis LA2 of the tube and holds the agricultural sample material. Caps 204 may be made of metallic or non-metallic (e.g., plastic or other) materials. In one embodiment, the tube body and caps 204 are formed of plastic. One end cap 204*a* may be a fixed or stationary cap configured for detachable coupling to top end 203*a* of the container 201 (i.e. top end cap 204*a*). The other remaining end cap may be a movable plunger-action "push" cap 204*b* which is slideably received inside the tube 202 adjacent to bottom end 203*b* of the tube. Push cap 204*b* is slideably moveable from bottom end 203*b* of the tube towards the other top end 203*a* and vice-versa during the tube fill and unloading operations. Bottom end 203*b* of tube 202 in some embodiments may include anti-rotation features to rotationally lock the tube in position when mounted to the packaging apparatus 110, as further described herein.

One unique aspect of sample tube 202 is push cap 204*b* which includes a disk-shaped circular base 208 and plurality of downwardly and outwardly projecting spring-action retention legs or protrusions 205 configured to slideably engage the interior walls of the sample tube 202. Retention protrusions 205 may be separately mounted to the perimeter and peripheral edge of base 208 of cap 204*b*, or may be integrally formed as part of a single monolithic unitary cap structure as illustrated herein. In one preferred but non-limiting embodiment, the push cap 204*b* including base 208 and retention protrusions 205 may be such a one-piece unitary molded structure made of a suitable semi-rigid but resiliently deformable plastic material having an elastic memory (e.g., polyethylene, polypropylene, etc.). Retention protrusions 205 in other embodiments, however, may be separate elements formed of spring metal or resilient deformable plastic elements affixed to cap 204*b*.

In one embodiment, retention protrusions 205 may each have a somewhat squared-off or U-shaped configuration as shown; however, other shaped retention protrusions may be used and the shape does not limit the invention. This gives the push cap 204*b* a somewhat castellated shape. The free terminal ends 205*a* of the retention protrusions may be outwardly flared forming outward protruding locking tabs 205*c* which can positively engage corresponding complementary configured arcuately curved and elongated retention slots 202*c* of sample tube 202. This gives the protrusions 205 a somewhat L-shaped configuration with the protrusions appearing as downwardly extending legs from base 208 of cap 204*b* with out-turned ends. Slots 202*c* are oriented crosswise in the tubular sample tube body perpendicularly to the length of its cylindrical wall 202*a*. The protrusions 205 may be circumferentially spaced apart as shown around the entire perimeter and periphery of the push cap 204*b*. Six retention protrusions 205 may be provided in one non-limiting embodiment; however, fewer or more protrusions may be provided. Retention protrusions 205 and particularly locking tabs 205*c* further slideably engage the interior surfaces of tube wall 202*a* when end cap 204*b* slides up and down inside tube cavity 207, as further described herein.

The circumferentially elongated retention slots 202*c* formed in the cylindrical walls 202*a* of the sample tube 202 are selectively engageable with retention protrusions 205*a* to lock or unlock the push cap 204*b* from the sample tube depending on the position of the cap inside the tube. Cap 204*b* therefore is sized in diameter to be fully inserted inside the internal cavity 207 of the sample tube whereas cap 204*a* is sized larger for affixation to the top end of the tube. Slots 202*c* may be through slots in one embodiment extending completely through the walls of the tube. Retention slots 202*c* are disposed proximate to bottom end 203*b* of sample tube 202 and spaced slightly upwardly and apart from the end of the tube. The opposite end of the tube receives fixed/stationary cap 204*a*. When sample tube 202 is placed in the carousel 200, the end of the tube with the retention slots 202*c* is preferably located at bottom for engagement with container end cap actuator 160 in some embodiments as further described herein.

Sample tube 202 may be formed of plastic, metal, or other suitable materials. In one preferred but non-limiting embodiments, the tube is made of plastic (e.g., polyethylene, polypropylene, etc.). The elongated tube body may be opaque or clear; the latter one allowing the sample to be visually inspected. Although the tube 202 is disclosed as being cylindrical in shape, other shapes and forms of sample containers may be used in other possible embodiments.

Bulk material chamber 120 and sample collection chamber 180 are each vertically-elongated hollow vessels located adjacent to each other and separated by an adjoining vertically-elongated die block 124 interspersed therebetween. Die block 124 forms a central division wall separating the chambers 120, 180 and comprises a set of vertically spaced apart die slots 124*a* extending completely therethrough and between the bulk material chamber and sample collection chamber. Slots 124*a* penetrate each of the chambers 120, 180 and are horizontally elongated in the front to rear direction. Die block 124 includes a flat wall side 124*b* which forms part of bulk material chamber 120 and opposite arcuately curved wall side 124*c* which forms part of sample collection chamber 180 as shown (see, e.g., FIGS. 42-43).

Figure 42:
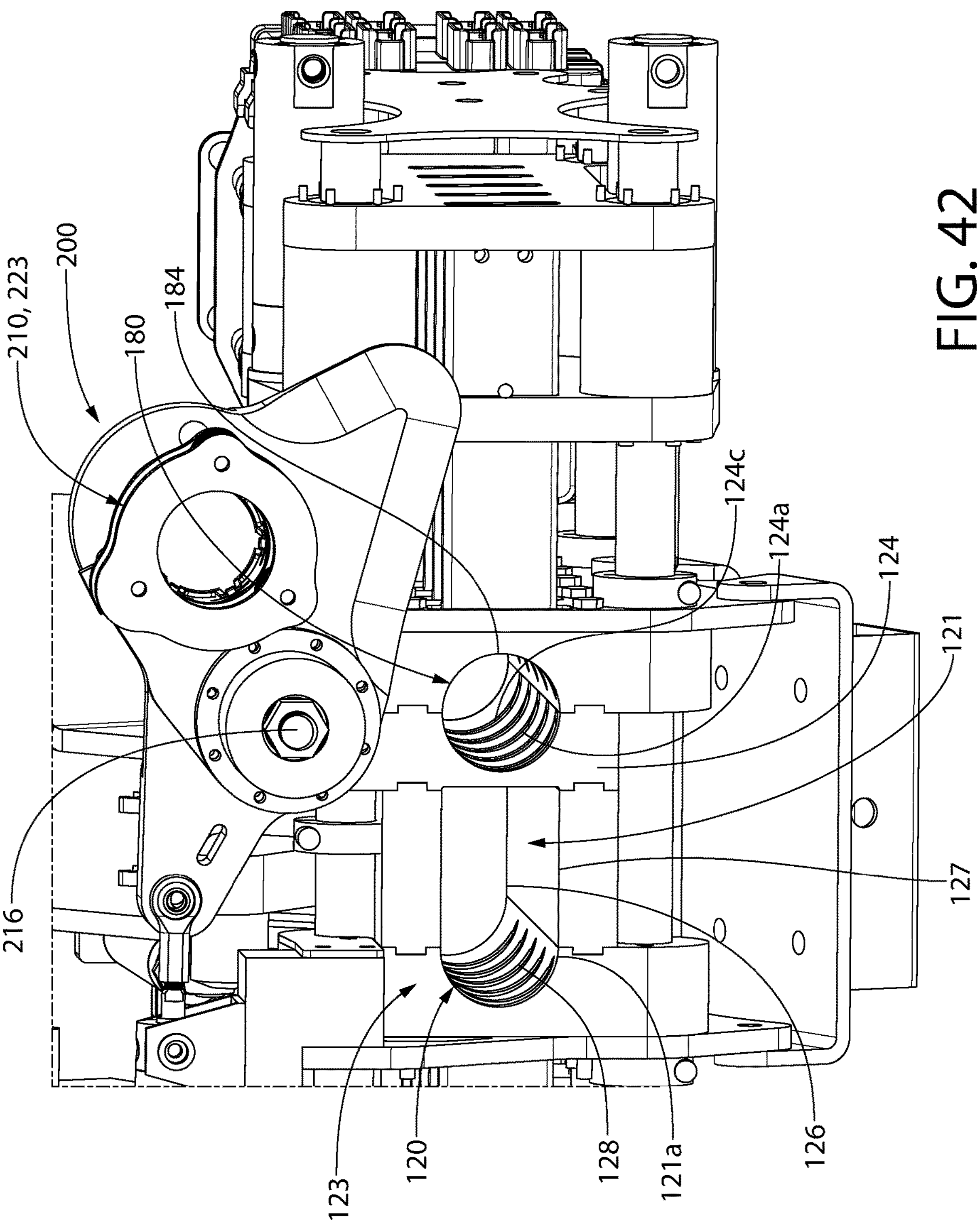
FIG. 42 is a first bottom perspective view thereof.
Figure 43:
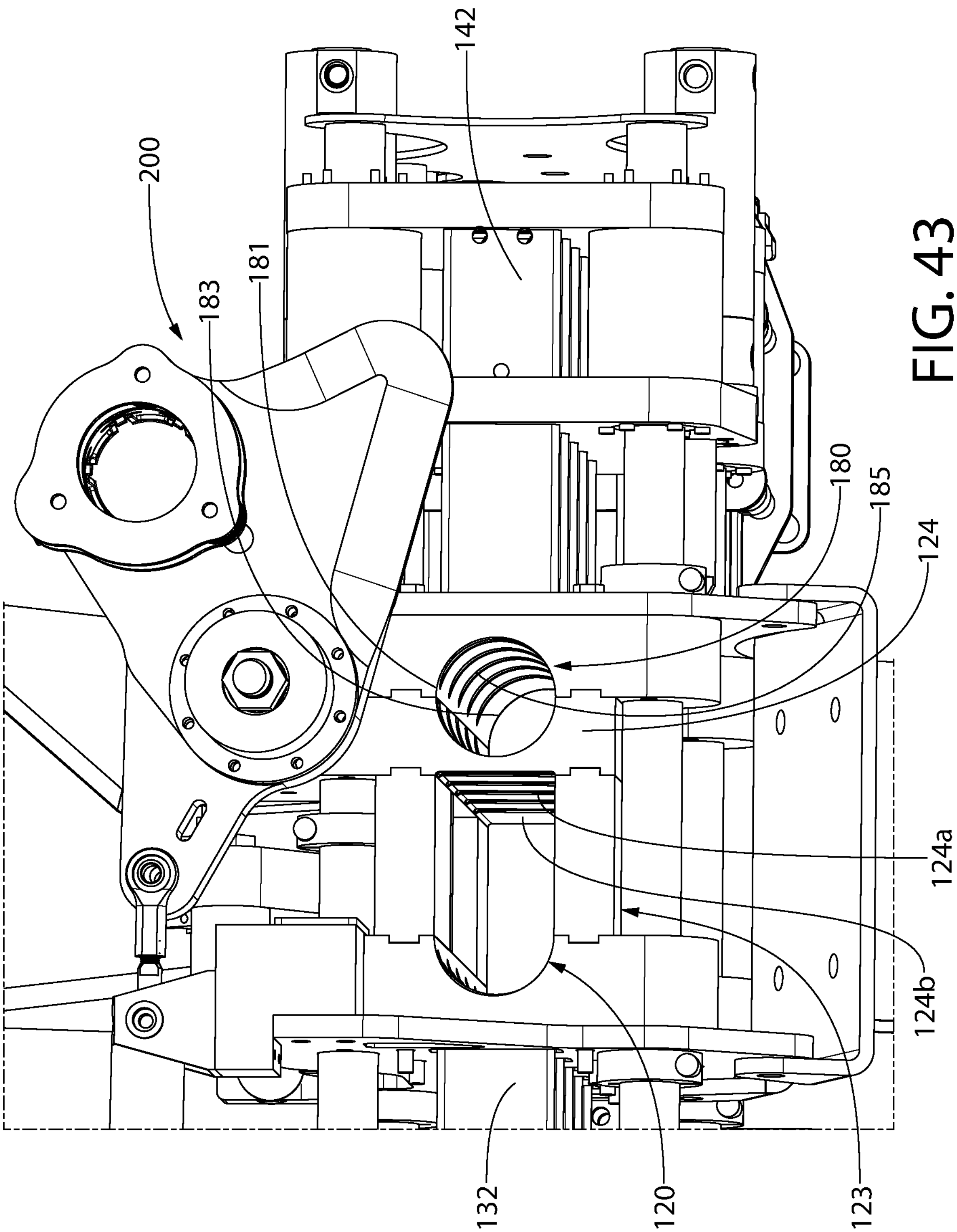
FIG. 43 is a second bottom perspective view thereof.
Figure 44:
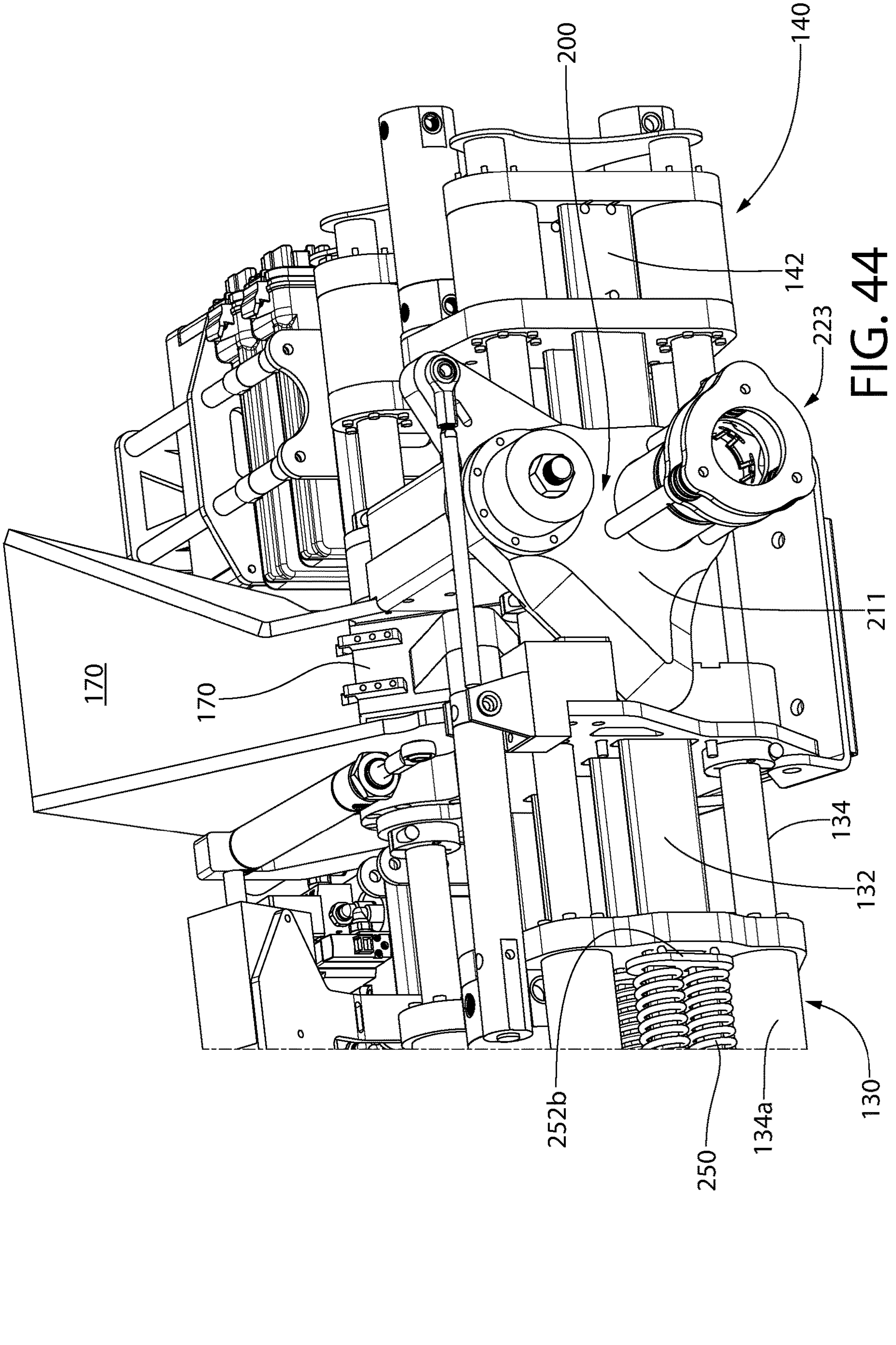
FIG. 44 is an enlarged bottom perspective view of the carousel of the apparatus.

Chambers 120, 180 may be formed in separate chamber blocks 123 in one embodiment comprising blocks of solid material coupled to opposite sides of die block 124 (see, e.g., FIGS. 42-43. This construction allows the sample and cleaning through slots in the chamber blocks associated with the chambers 120 and 180 to be pre-fabricated prior to coupling to the die block. Chamber 180 may be partially formed in part of die block 124 such that the curved right wall side 124*c* of the die block forms part of the chamber 180 walls (see, e.g., FIGS. 42-43). Chamber block 123 and die block 124 are supported by upper sub-frame 115 between the ends of the packaging apparatus 110 as shown.

Figure 24:
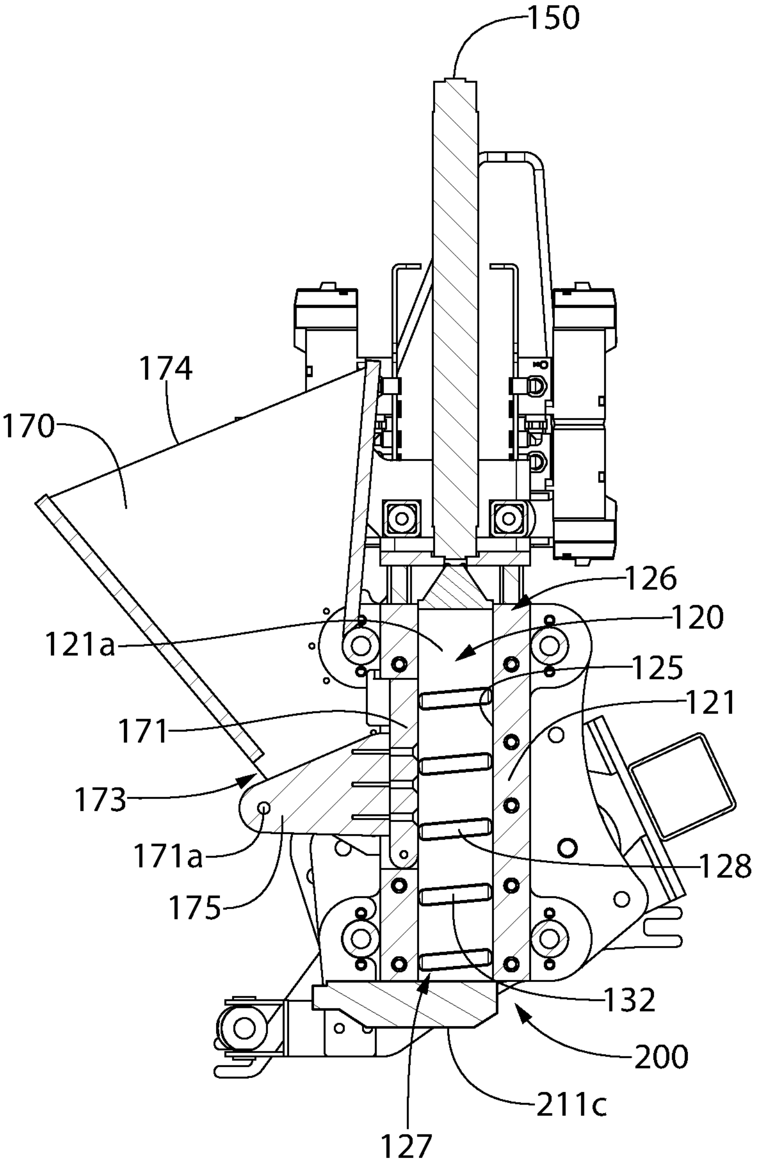
FIG. 24 is a side cross-sectional view of the apparatus showing the funnel door of the funnel in the closed position.
Figure 25:
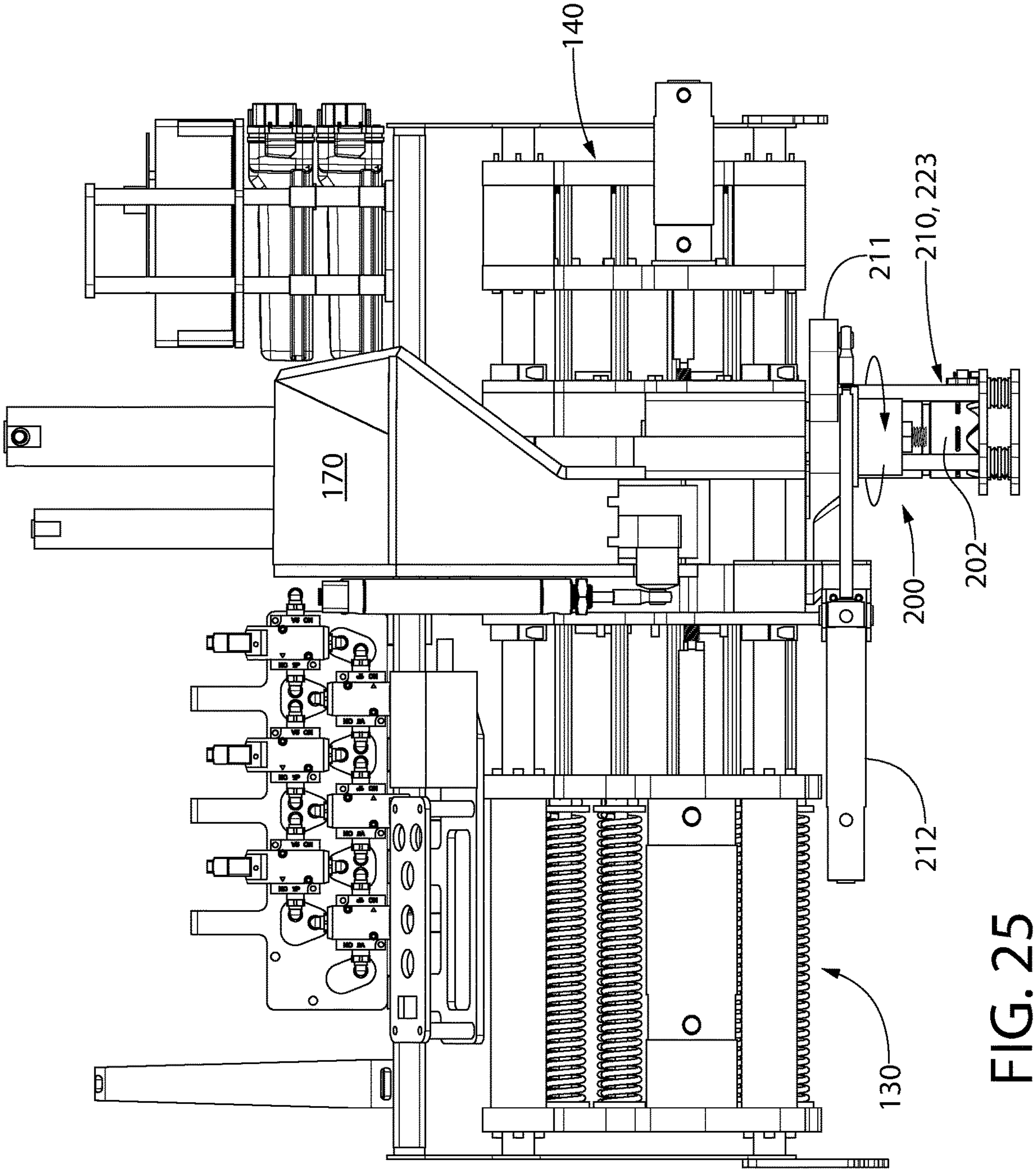
FIG. 25 is a front cross-sectional view of the apparatus showing the carousel and sample container rotated to the inward closed position ready for filling with the agricultural sample material.

Bulk material chamber 120 has a vertically-extending hollow body comprising sidewalls 121 defining an internal cavity 125, a top 126, and a bottom 127 (see, e.g., FIG. 24). The bottom 173 of funnel 170 is coupled to cavity 125 through the sidewalls 121 of chamber 120 to introduce the bulk soil sample material. In one embodiment, chamber 120 has an oblong transverse cross-sectional shape which is horizontally elongated in the axial longitudinal direction parallel to longitudinal axis LA (see, e.g., FIGS. 41-43). Sidewalls 121 may comprise an arcuately curved wall section 121*a* opposite the flat wall side 124*b* of die block 124 which forms part of the sidewalls of chamber 120. Wall section 121*a* comprises a set of vertically spaced apart blade slots 128 extending completely therethrough to slideably receive sample blades 131 of the sample blade mechanism 130. Slots 128 are positionally synchronized with and diametrically opposite die slots 124*b* such that each slot 128 is horizontally axially aligned with a corresponding die slot 124*a*.

Sample collection chamber 180 has a cylindrical configuration and vertically-extending hollow body comprising sidewalls 181 defining an internal cavity 182, a top 183, and a bottom 184. In one embodiment, chamber 180 has a circular transverse cross-sectional shape. Sidewalls 181 comprise a set of vertically spaced apart blade slots 185 extending completely therethrough to slideably receive cleaning blades 141 of the cleaning blade mechanism 140. Slots 185 are positionally synchronized with and diametrically opposite die slots 124*b* in curved wall side 124*c* of die block 124 such that each slot 185 is axially aligned with a corresponding die slot 124*b*.

Sample blade mechanism 130 comprises a chassis 131 and plurality of sample blades 132 fixedly coupled to the chassis in a vertically spaced apart array. Chassis 131 may include a pair of horizontally spaced apart right and left vertical end plates 133 at each end. Sample blades 132 may be slideably coupled to the left end plate 133*a* of the pair and slideably pass through complementary configured holes in a right end plate 133*b*. The right and left end plates are each rigidly connected together by horizontally oriented tubular guide rod sleeves 134*a* so that the chassis moves right and left as a single unit with the sample blades 132 and end plates 133.

Chassis 131 is slideably carried by a plurality of guide rods 134 each spanning laterally between and coupled to the vertical end supports 112 of frame 111 at one end and the chamber block 123 located therebetween at the other end of the rods. Guide rods 134 are slideably received inside the hollow tubular guide rod sleeves 134*a* of the chassis described above. Two sets of four guide rods 134 in each set may be provided in one embodiment which are vertically and horizontally spaced apart from each other top to bottom and front to rear as shown. One set is for slideably supporting the sample blade chassis 131 and the other is for slideably supporting sample transfer blade chassis 141. Each set of guide rods 134 may include a pair of upper and lower guide rods; each of which have an associated guide rod sleeve 134*a* of chassis 131 and guide rod sleeve 144*a* of chassis 141.

Sample blades 132 may each have a horizontally elongated bar-like body terminated by a concave terminal end 132*a* which passes through bulk material chamber 120 and die block 124 during the tube filling operation. End 132*a* has a radius of curvature (concave) which corresponds to the radius of curvature of the sample collection chamber 180 to form part of the walls of the chamber when inserted through die block 124, as further described herein. In some embodiments, the blade bodies may be arcuately curved from side to side between the longitudinal long sides of the blade 132. In other embodiments, the blade bodies may be flat. Sample blades 132 are axially and laterally moveable in the horizontal longitudinal direction between a retracted position withdrawn from bulk material chamber 120 and die block 124, and a projected position extending through the chamber 120 and die block 124. When projected, the blades extract and extrude/push soil sample material blanks or plugs from the bulk material chamber 120 through the die block 124 and into the sample collection chamber 180. In the retracted position, the concave ends 132*a* of blades 132 are flush with and form part of the arcuate curved wall section 121*a* of the bulk material chamber 120.

Sample blade mechanism 130 comprises an actuator 135 which linearly moves the chassis 131 and array of sample blades 132 supported thereby between the retracted and projected positions. Actuator 135 may be any suitable commercially-available electric linear rod actuator, pneumatic actuator, or hydraulic actuator with retractable/extendible operating rod 136 coupled to the chassis 131.

Sample blades 132 may be vertically stacked and spaced apart in one embodiment as shown. The chassis 131 to which they are mounted moves all the sample blades in unison between the retracted and projected positions.

According to one aspect of the sample blade mechanism 130, a spring-biased protection system may be provided to protect the sample blades 132 and mechanism from damage in the event one or more die slots 124*a* in die block 124 are plugged by foreign debris such as stones/rocks wedged into the die slots from a previous sample material extrusion run. In one embodiment, each sample blade 132 is mounted in a corresponding blade spring pack 253 comprising a pair of springs 250. Referring to FIGS. 20-23, the distal end portion of blades 132 (farthest from bulk material chamber 120) is bifurcated into a pair of longitudinally elongated legs 251; each of which captures a coiled compression spring 250 therearound. The proximal end of each spring 250 may be braced against and acts on an elongated proximal spring plate 252*a* slideably coupled to the blade 132 between its distal and proximal end. Proximal spring plate 252*a* abuttingly engages right end plate 133*b* of chassis 131 when mounted therein. The remaining distal end of each spring may be braced against a second elongated distal spring plate 252*b* which abuttingly engages the left end plate 133*a* of chassis 131. The bifurcated distal end of the blades 132 are projectible through corresponding openings in left distal spring plate 252*b* and left end plate 133*a* of the chassis in the event the blade encounters blockage of its respective die slot 124*a* in die block 124 when the sample blade mechanism 130 attempts to insert the blade through the slot. In operation, the remaining blades 132 whose paths are not blocked in die block 124 will continue to advance into the bulk material chamber 120 to extract soil sample material while the blocked blade will remain stationary as the chassis moves towards chamber 120 to the right. The springs associated with the blocked blade or blades 132 will be compressed and the blocked blade will not advance any farther towards the bulk material chamber. Advantageously, the sample blade mechanism will continue to function and extract samples even in the event one or more sample blade paths are blocked so that the soil sample material packaging operation is not interrupted.

The spring force (k) of springs 250 is selected to allow the sample blades 132 to be inserted through the die slots 124*a* of die block 124 with a reasonable maximum amount of force determined to prevent damage to the blades and cleaning blade mechanism 140. When this predetermined maximum force limit is exceeded as a blade encounters a blocked or plugged die slot, the springs 250 will compress to arrest progress of the blade and prevent damage to the blade and the mechanism.

Cleaning blade mechanism 140 may be generally similar to the sample blade mechanism 120 in construction and operation; however, the cleaning blades 142 enter the sample collection chamber 180 and die block 124 from the opposite direction to removed and clean residual soil deposits from the die block slots 124*a* in preparation for the next tube filling operation. Briefly, without undue repetition, cleaning blade mechanism 140 also comprises a chassis 141 supporting the plurality of cleaning blades 142 fixed coupled to the chassis in a spaced part array. Chassis 141 is slideably carried by the same type hollow tubular guide rod sleeves 144*a* which travel on guide rods 144 spanning laterally between and coupled to the vertical end supports 112 of frame 111 and chamber block 123. Chassis 141 also includes a pair of horizontally spaced apart vertical end plates 143. Cleaning blades 142 may be fixedly coupled to a right end plate 143*a* of the pair and slideably pass through complementary configured holes in a left end plate 143*b*. The blades may optionally be fixedly connected to the left end plate as well in some embodiments.

It bears noting that the cleaning blades 142 preferably do not include a spring protection mechanism like the sample blades 132. Since the function of the cleaning blades includes dislodging any debris (e.g., stones/rocks, hardened agricultural clumps, etc.) from the die block die slots 124*a*, it is preferred that the cleaning blades can be advance with full force through the die slots in a rigidly supported manner. It is therefore desirable in some embodiments for the cleaning blades 142 to not have the spring-operated relieving feature. If the cleaning blades are unable to forcefully dislodge an object obstructing one or more die slots 124*a*, the sample extraction cycle will stall (e.g., cleaning blade mechanism 140), which is detected by sample packaging machine controller 2811 via an appropriately configured sensor 2811*c* (see, e.g., FIG. 26) configured to detect that the sample blades have not fully advance and been inserted in the die slots. A positional or proximity sensors may be used for this purpose of the types similar to full tube sensor 220 described elsewhere herein, or other type sensors. The controller will electronically "time out" the cycle, indicating to the operator there is an internal problem. If a foreign object were allowed to stay lodged in the die block and the extraction cycle continues, damage will result to internal components of the apparatus mechanism. The controller 2811 communicates (e.g., visually and/or audibly) the "time out" condition to the human operator via an appropriate alarm signal so the operator is made aware of and can remedy the die block obstruction issue to restore normal operation.

Figure 20:
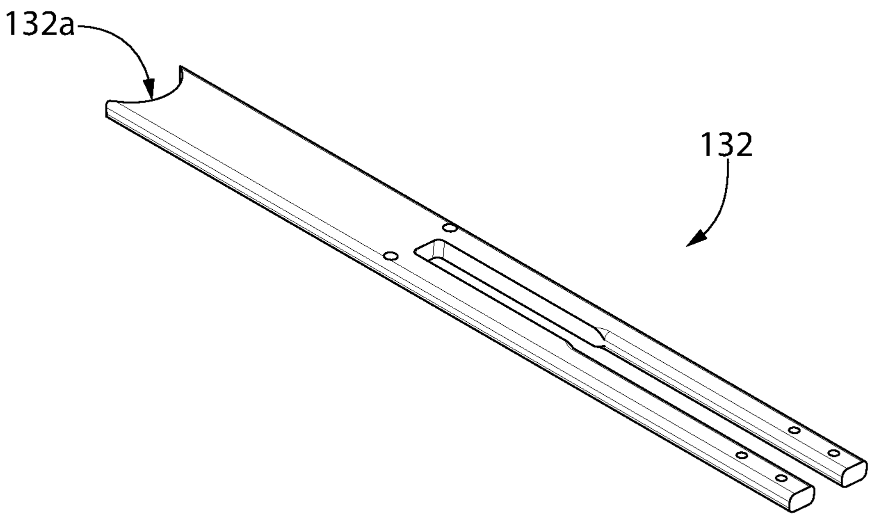
FIG. 20 is a top perspective view of a sample blade.
Figure 21:
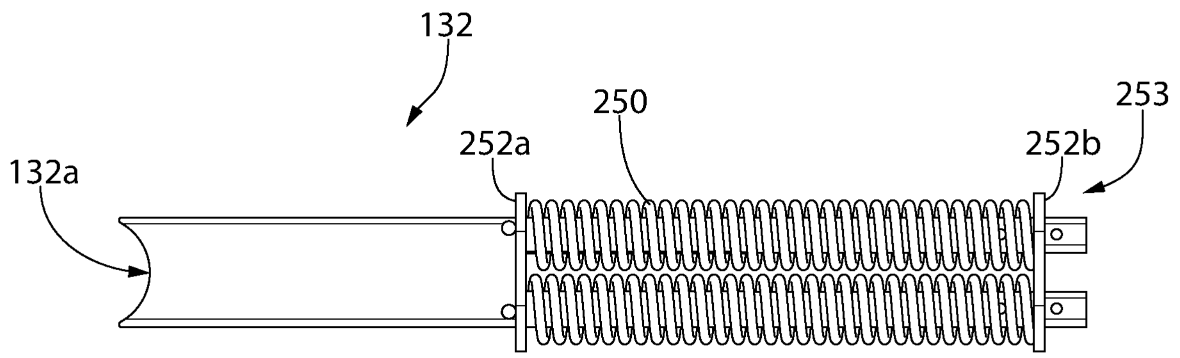
FIG. 21 is a top view of the sample blade showing a spring pack associated with the blade.

Cleaning blades 142 may have the same shape as sample blades 132 at least in cross section since they pass through the same horizontally elongated slots 124*a* in the die block 124 to remove residual soil therefrom, as further described herein. FIGS. 20 and 21 showing sample blades 132 may also represent cleaning blades 142 in shape and construction except the cleaning blade do not bifurcated ends because not spring protection mechanism is provided. Cleaning blades 142 also may each have a horizontally elongated bar-like body terminated by a concave terminal end 142*a* which passes through sample collection chamber 180 and die block 124 during the die cleaning operation. In some embodiments, the blade bodies may be arcuately curved between the longitudinal long sides. In other embodiments, the blade bodies may be flat. Cleaning blades 142 are axially and laterally moveable in the horizontal longitudinal direction between a retracted position withdrawn from chamber 180 and die block 124, and a projected position extending through the chamber 180 and die block 124. This pushes residual soil in slots 124*a* of die block 124 back into the bulk material chamber 120 from which they can be purged. In the retracted position, the concave ends 142*a* of blades 142 are flush with and form part of the arcuate curved sidewalls 181 of the sample collection chamber 180.

Cleaning blade mechanism 140 comprises an actuator 145 which linearly moves chassis 141 with the array of cleaning blades 142 supported thereby between the retracted and projected positions. Actuator 145 may be any suitable commercially available electric linear rod actuator, pneumatic actuator, or hydraulic actuator with retractable/extendible operating rod 146 coupled to the chassis 141.

Cleaning blades 142 may be vertically stacked and spaced apart in one embodiment as shown. The chassis 141 to which they are mounted moves all the cleaning blades in unison between the retracted and projected positions. The cleaning blades142 are positionally synchronized with the die slots 124*a* such that each blade is axially and horizontally aligned with a corresponding one of the die slots.

The sample and cleaning blades 132, 142 as well as the structural components of the sample and cleaning blade mechanisms 130, 140 (e.g., end plates, guide rods and sleeves, etc.) described above preferably are made of a suitably strong metallic material, such as steel or stainless steel in some embodiments. Other suitable materials may be used.

Compaction piston-plunger 150 and sample transfer piston-plunger 155 may each be any suitable type commercially available electric linear rod actuator, pneumatic cylinder, or hydraulic cylinder with retractable/extendible operating rod 151*a* and 151*b*. Rods 151*a*, 151*b* are terminated with a disk 152*a*, 152*b* respectively; each being configured to fit closely and conform to the shape and internal diameters of the bulk material chamber 120 and sample chamber 180 without any appreciable gaps between the disks and chamber walls. Disks 152*a*, 152*b* are sized such that the peripheral edges of the disks are located adjacent to their respective chamber walls to scrape any soil away from the walls as the disks slide upwards/downwards in their chambers. Disk 152*a* of compaction piston-plunger 150 has an oblong transverse cross-sectional shape which corresponds to the oblong cross-sectional shape of bulk material chamber 120. Disk 152*b* of sample transfer piston-plunger 155 has a circular transverse cross-sectional shape which corresponds to the circular cross-sectional shape of the sample collection chamber 180.

Piston-plungers 150, 155 are each vertically oriented in one embodiment and enter the open tops of chambers 120, 180. In operation, the piston-plungers are each linearly moveable from a retracted upward position withdrawn from chambers 120 or 180, or projected downward position extending to the bottom end of the chambers. The exposed bottom surfaces of each disk 152*a*, 152*b* may be substantially flush with the bottom end faces of the chambers 120, 180 to ensure all soil is purged from the chambers and to allow the lower disk faces to be scraped/wiped clean via operation of the carousel, as further described herein.

Funnel 170 provides a hopper-type vessel into which the bulk soil sample is filled for transfer to the bulk material chamber 120. Housing 116 includes an annular chute 170*a* positioned over and optionally detachably coupleable to and partially insertable into the top of the funnel for guiding the agricultural sample material (e.g., soil or other) into the funnel. Chute 170*a* may comprise sloping walls in some embodiments as shown to facilitate adding the sample material to the funnel. In certain embodiments, the sloping walls of funnel 170 and chute 170*a* may be comprised of a nonstick material such as UHMW-PE or similar, and/or be coated to encourage sample material to flow through and not adhere to the walls. This may be particularly beneficial when processing sticky type soils such as clay.

The funnel 170 may have any suitable configuration and gradually narrows in width from the open top 174 for adding the soil sample to the funnel to the bottom 173 under control of an openable/closeable funnel door 171 coupled to door actuator 172. In one embodiment, funnel 170 may be trapezoidal shaped as shown. Other funnel shapes including frustoconical shaped funnels may be used. Funnel door 171 is pivotably and hingedly mounted to the lower portion of the funnel via hinge pin 171*a* and coupled to an eccentric cam lever 175 operably coupled to actuator 172. Funnel door 171 is pivotably moveable via operation of actuator 172 between a closed position for filling the funnel 170 with the bulk soil sample material, and an open position for transferring the soil to bulk material chamber 120. The actuator 172 may be any suitable commercially available electric linear rod actuator, pneumatic actuator, or hydraulic actuator with retractable/extendible operating rod 176 coupled to the cam lever 175.

Container carousel 200 is configured to removably hold and rotatably move the sample container 201 inwards under the sample chamber 180 and outwards therefrom during the soil sample packaging operation. Carousel 200 is rotatably mounted about a vertical pivot axis PA under packaging apparatus 110 and positioned below and proximate to the bottom ends of the bulk material chamber 120 and sample chamber 180. The carousel generally includes a rotatable base member 211 supporting a container holder 210 and carousel actuator 212 coupled to the base member. The base member 211 in one embodiment may comprise a generally broad and flat plate-like monolithic structure having a compound configuration including outwardly extending eccentric cam arm 211*a*, container support arm 211*b*, and a solid closure arm 211*c*. Pivot axis PA is formed by a pivot pin 216 extending vertically through the base member 211 and offset from the geometric center of the plate. Base member 211 is rotatably movable about pivot axis PA in a horizontal reference plane defined by pivot pin 216 which mounts the base member to the support frame 111.

Solid closure arm 211*c* is rotatable underneath and adjacent to the normally open bottom end of bulk material chamber 120 to selectively close or open the bottom end of the chamber via rotation of base 211, as further described herein. The top surface of at least the closure arm 211*c* is preferably flat to form relatively tight closure of chamber 120 at bottom to prevent the bulk soil from falling through the chamber. Closure arm 211*c* slideably moves into and out of position against the bottom end of chamber 120. This advantageously helps clean and remove any soil residue at the bottom of the chamber 120 between tube filling cycles via a wiping/scraping type action across the bottom face of the chamber.

Container holder 210 may be a generally cup-shaped structure in one embodiment supported by base member 211. In one non-limiting embodiment, the holder includes a circular opening formed in the container support arm 211*b* of the base member to receive sample tube 202 and a circular support disk 213 suspended below support arm 211*b* in a vertically spaced apart manner by a plurality of vertically elongated spacer rods 214. The container holder 210 is configured via positioning of support disk 213 such that a majority of the height of the sample tube 202 is located below the base member 211 as shown. This ensures that the tube is held by the container holder in a stable manner both during the tube sample filling operation and during rotation of the tube with the base member 211. Other forms and configurations of container holder 210 are possible so long as the sample tube 202 can be removably held with the required degree of stability.

Sample tube 202 may be configured to be rotationally locked in position to support disk 213 to ensure the tube does not rotate and remains rotationally stable during the tube filling operation and movement of the base member 211 of carousel 200. In one embodiment, the bottom end 203*b* of the cylindrical walls 202*a* of tube 202 may have an arcuately undulating castellated configuration to form a rotational interlock with a mating arcuately undulating castellated feature on the support disk 213. Accordingly, the bottom end 203*b* of sample tube 202 adjacent to where retention slots 202*c* are formed in the tube may comprise anti-rotation protrusions 206*a* which lockingly engage a ring of mating anti-rotation protrusions 206*b* on the tube support disk 213. The protrusions 206*a*, 206*b* may have rounded ends with sloping sides in some embodiments as shown to help guide the sample tube 202 onto the castellated support disk 213. In other embodiments, the anti-rotations features may be omitted where it might not be necessary or desirable to rotationally lock the sample tube 202 into the packaging apparatus 110 during the filling operation.

Figure 46:
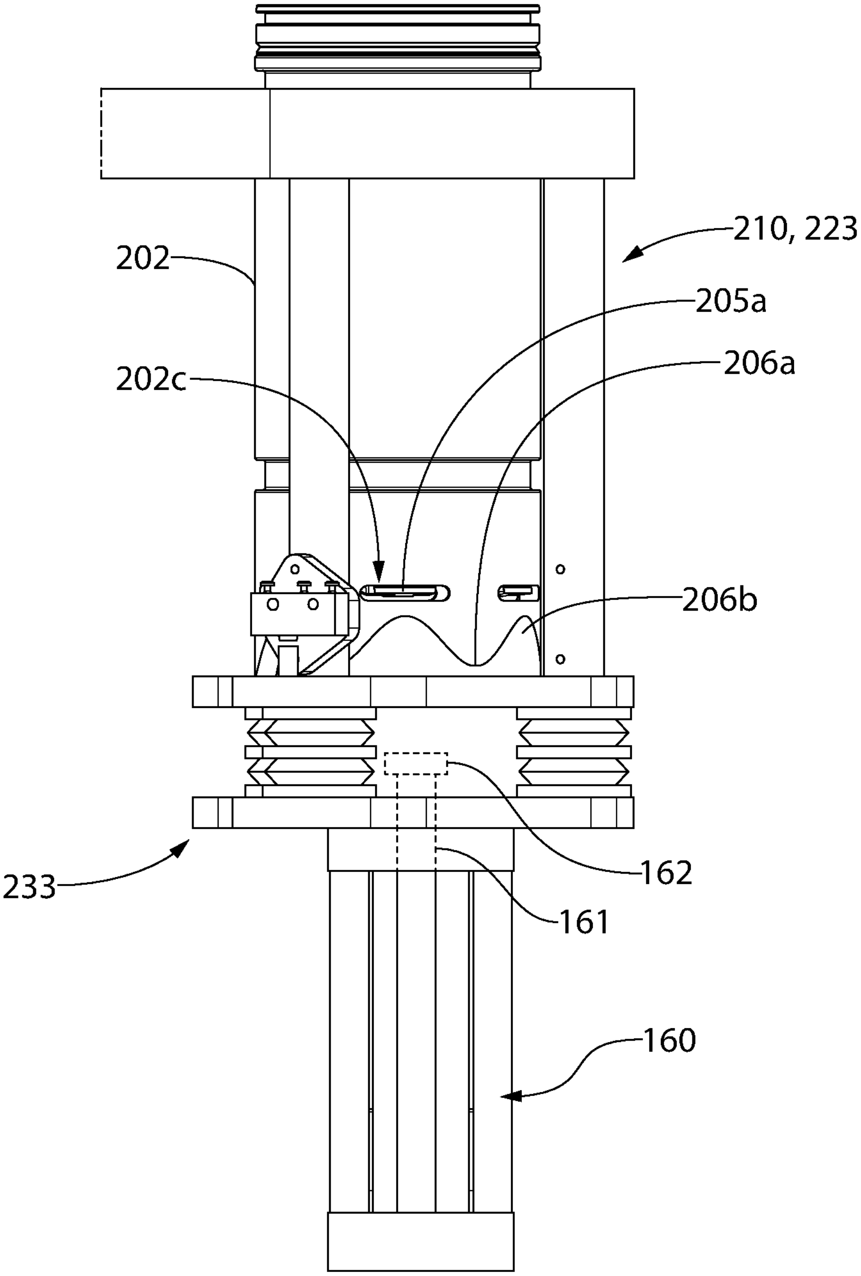
FIG. 46 is a side view of the collapsible embodiment of the cup hold of the carousel showing the push cap actuator.

In one embodiment, container end cap actuator 160 may be mounted to support disk 213 of container holder 210 (FIG. 19), or alternatively collapsible dual support plate assembly 233 of alternative container holder 223 (see, e.g., FIG. 46). Cap actuator 160 is therefore rotatable with base member 211 of carousel 200. The cap actuator 160 may be any suitable commercially available electric linear rod actuator, pneumatic actuator, or hydraulic actuator with retractable/extendible operating rod 161 which is projectable through a complementary configured opening in the support disk 213 to engage and activate the push cap 204*b*. Rod 161 may be terminated with a with a diametrically enlarged cylindrical disk 162 configured to engage push cap 204*b*. Actuator 160 is operable to disengage and unlock the push cap from retention slots 202*c* (i.e. retention protrusions 205*a*) so that the cap can be moved upwards in sample tube 202 for reasons associated with the sample tube filling operation, as further described herein.

Figure 26:
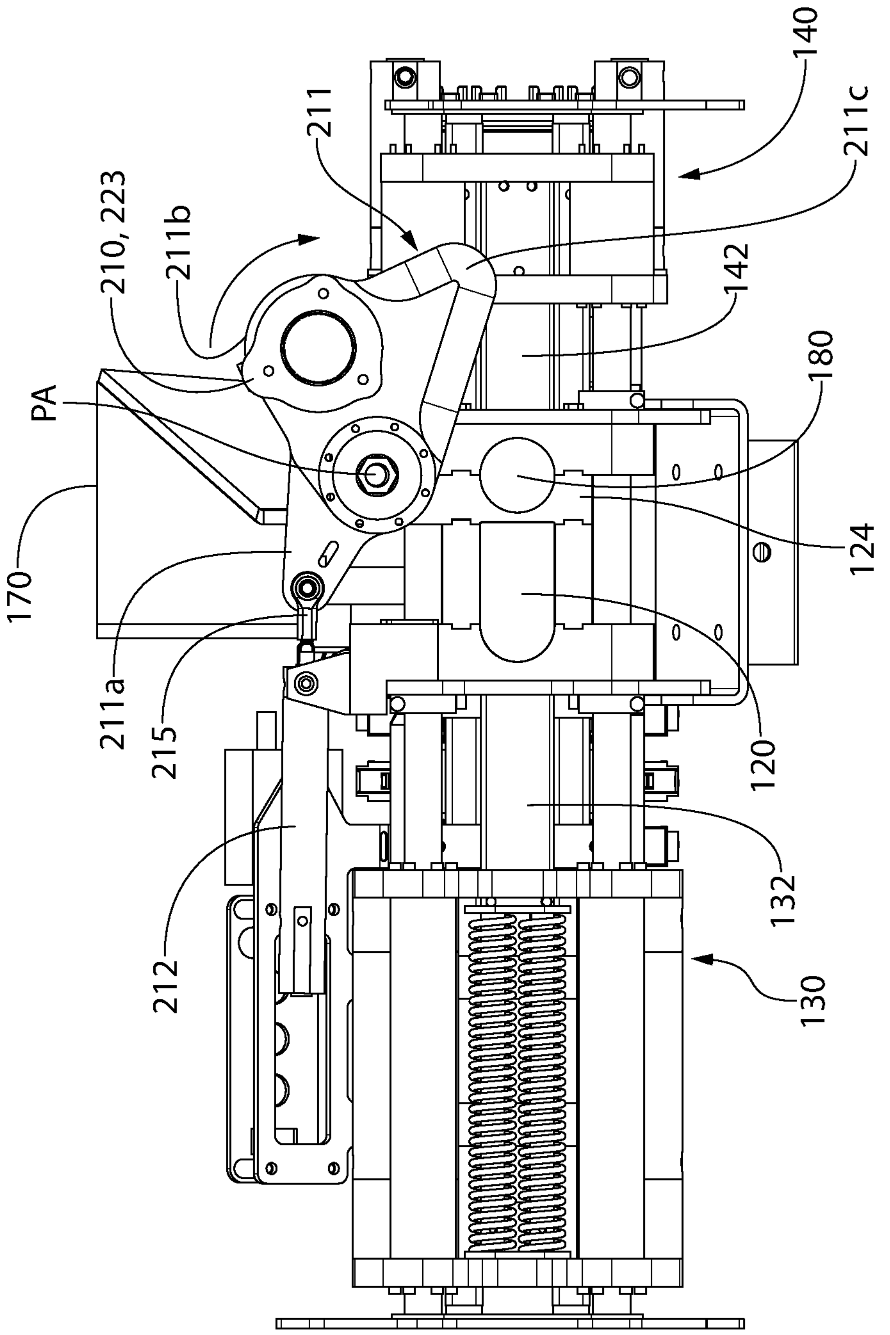
FIG. 26 is bottom view of the apparatus showing the carousel in the outward open position.
Figure 27:
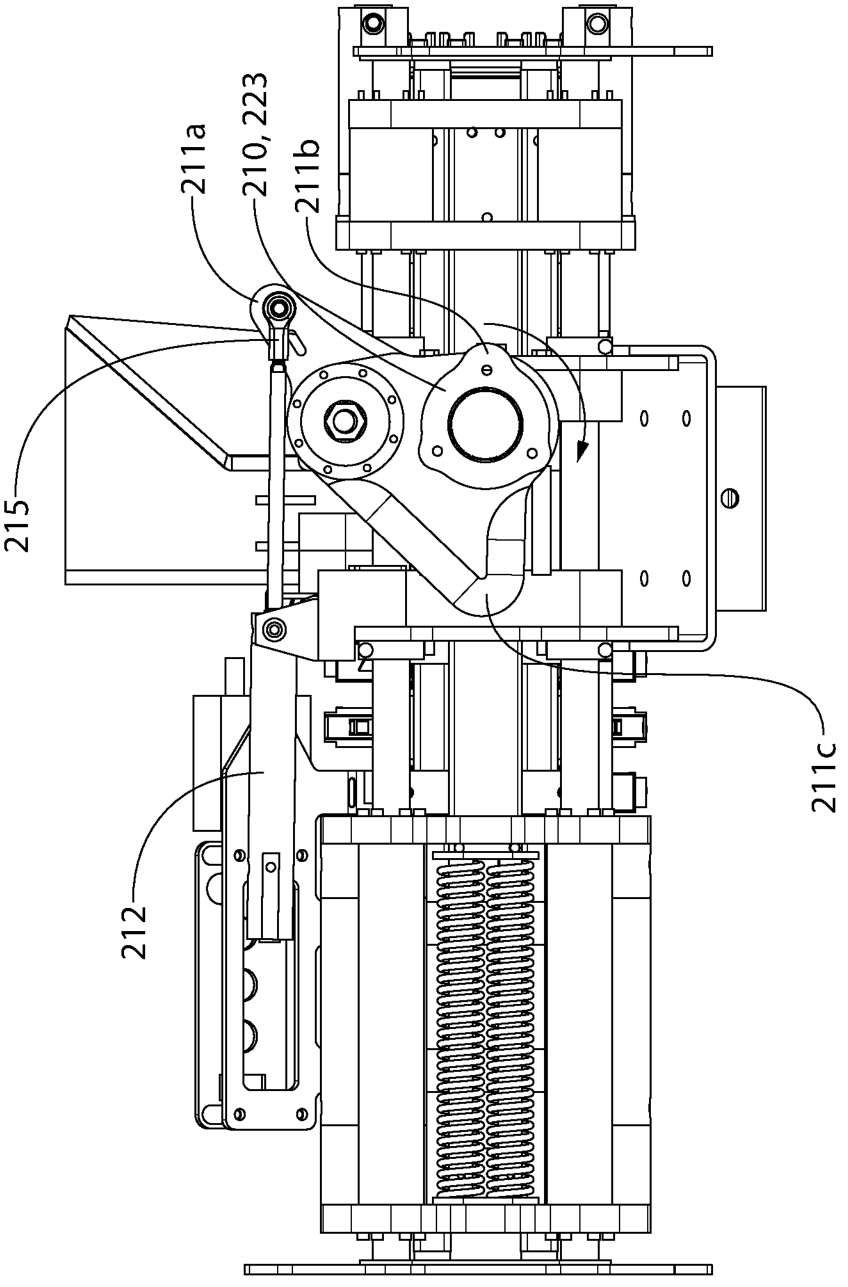
FIG. 27 is a bottom view of the apparatus showing the carousel in the inward closed position.

The actuator 212 coupled to cam arm 211*a* of base member 211 may be any suitable commercially available electric linear rod actuator, pneumatic actuator, or hydraulic actuator with retractable/extendible operating rod 215 coupled to the cam arm (see, e.g., FIG. 26). Actuator 212 is operable to rotate base member 211 about pivot axis PA to move the carousel between: (1) an inward closed position for tube filling in which sample tube 202 is positioned directly beneath and adjacent to the bottom end of sample chamber 180 and base member closure arm 211*c* is positioned directly beneath and adjacent to the bottom end of bulk material chamber 120 to close that chamber (see, e.g., FIG. 27); and (2) an outward open position in which sample tube 202 is not positioned beneath sample chamber 180 and base member closure arm 211*c* is not positioned beneath and adjacent to the bottom end of bulk material chamber 120 which is then downwardly open (see, e.g., FIG. 26). In the outward position, sample tubes 202 may be exchanged between tube filling cycles to remove filled tubes and mount new empty tubes.

Figure 1:
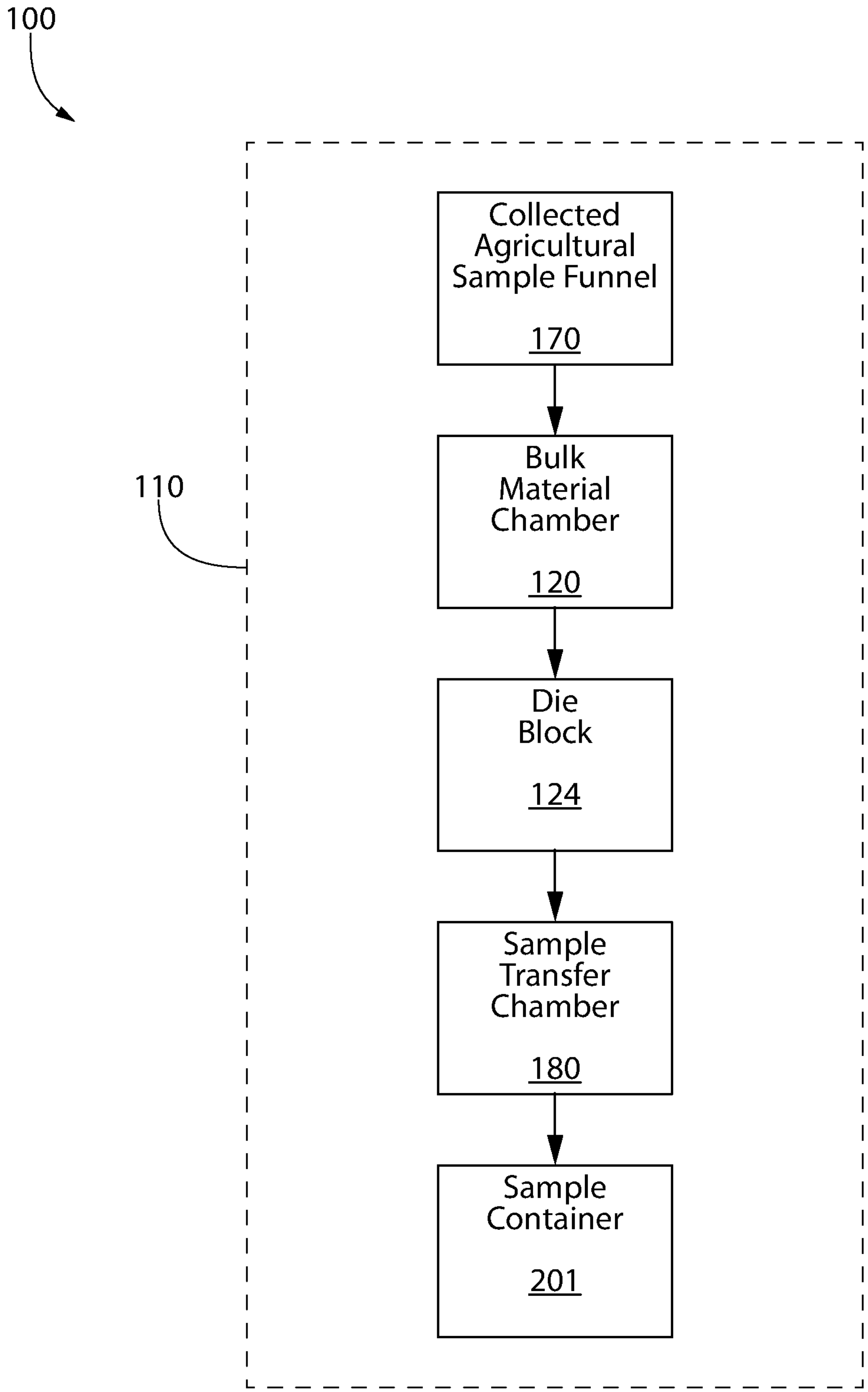
FIG. 1 is a high-level process flow chart providing a summary overview of the agricultural sample packaging process according to the present disclosure.

A method or process for packaging an agricultural sample will now be described. In one embodiment, the sample may be a soil sample which will be used for convenience and without limitation as a basis for describing the operation of agricultural sample packaging system 100 disclosed herein. FIG. 1 is a high-level process flow chart providing a summary overview of the packaging process. FIGS. 22-40 are sequential images showing one non-limiting embodiment the sample packaging operation and positional changes of the agricultural sample packaging apparatus 110 described herein. The sample material used in the process below may be soil for convenience of discussion and not limitation.

Figure 22:
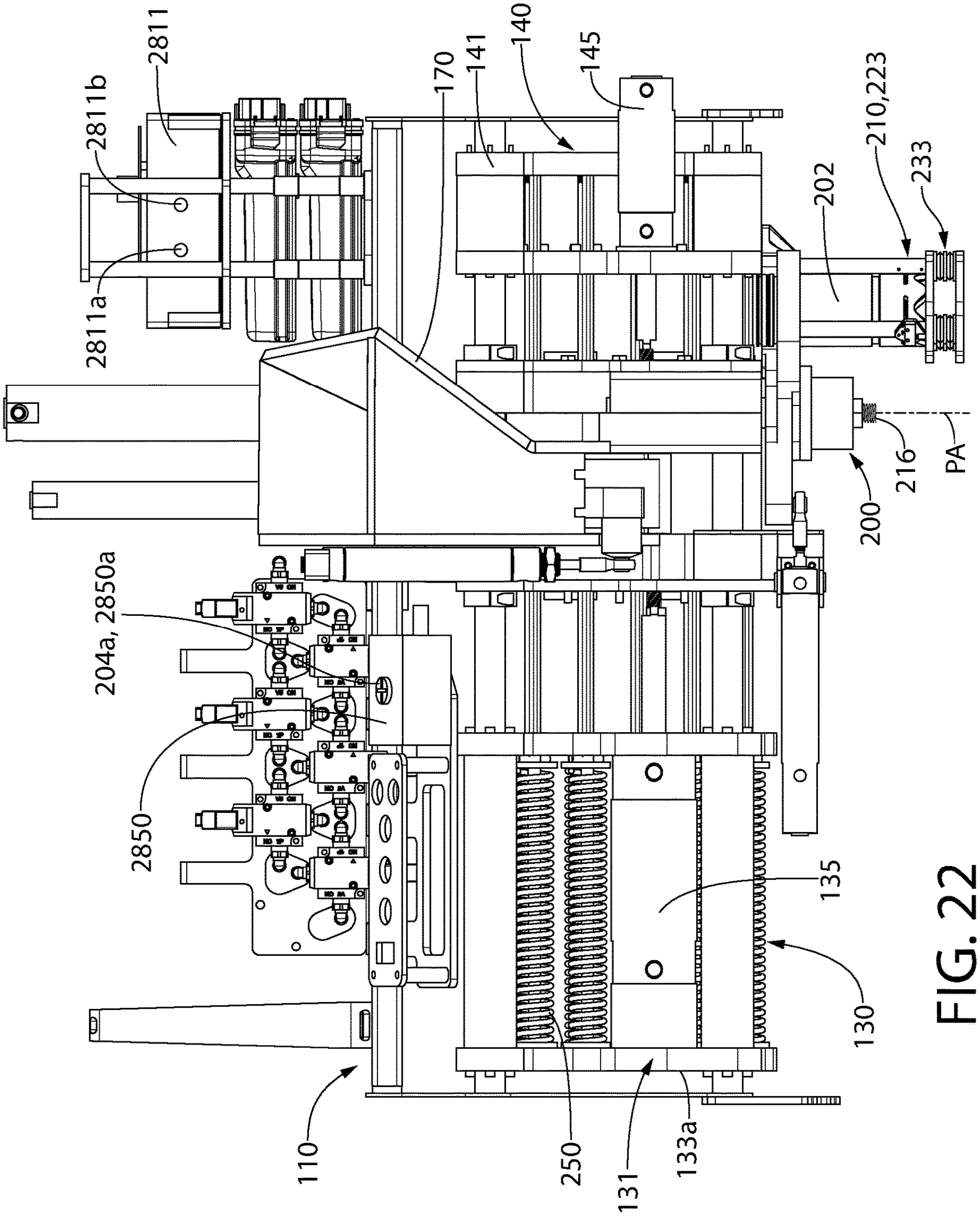
FIG. 22 is a front view of the sample packaging apparatus showing one operating position of the mechanism with sample funnel attached and the rotatable carousel with sample container supported thereby in the outward open position.

The method begins with the carousel 200 in the outward open position (see, e.g., FIG. 22). If the carousel is not outward and ready to accept the new empty sample tube 202, a carousel may be rotated outwards by actuating an actuator 2811*b* such as a button, toggle, or other type switch (FIG. 22) in some embodiment which is operably coupled to packaging machine controller 2811 (see, e.g., FIGS. 25-27). This may arbitrarily be referred to as the "Load Tube" switch or by another name. In other embodiments, the step may be actuated via a personal electronic device 2851 operably coupled to controller 2811 which initiates outward rotation of the carousel (see, e.g., FIG. 2). In either control scenario, rotating the carousel outward enables the operator to manually insert sample tube 202 into the container holder 210 or 223 of the carousel 200.

Figure 23:
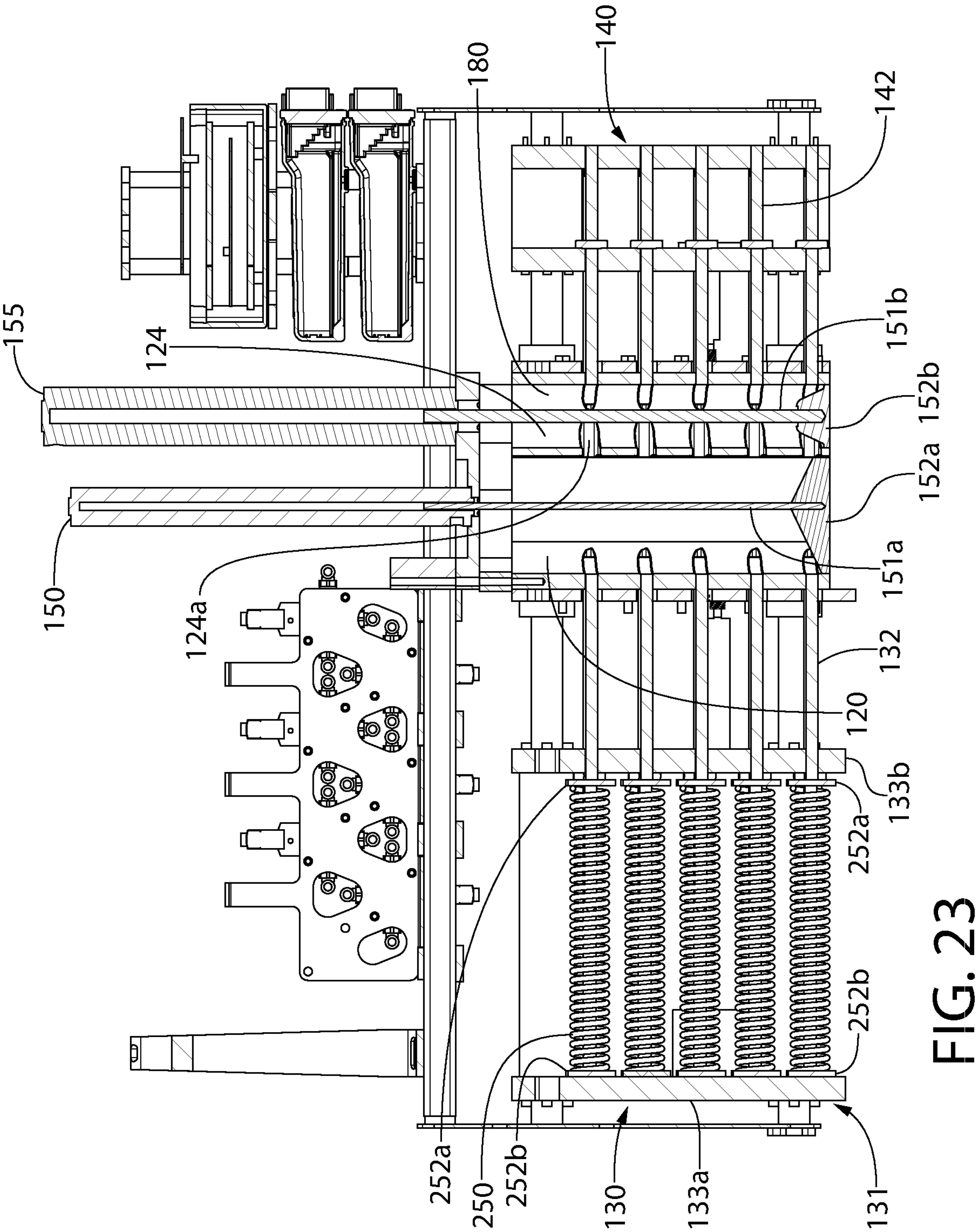
FIG. 23 is a front cross-sectional view thereof.

At the start of the packaging operation, the piston-plungers 150 and 155 are preferably in their downward extended/projected position shown in FIG. 23 from either the previous container packaging operation or in preparation to start the first packaging operation.

An empty sample container 201 such as sample tube 202 is first vertically inserted into and placed in the container holder 210 of the carousel A castellated and rotationally interlocked interface is formed between the bottom end 203*b* of the tube and support disk 213 of the holder 210, as previously described herein. The top end cap 204*a* of sample tube 202 may contain a tracking tag such as RFID tag 2850*a* in one non-limiting embodiment which is placed on RFID reader 2850. Packaging machine controller 2811 and/or main system controller 2820 automatically reads the tag and begins tracking the sample including all relevant data such as geolocation via GPS sensor 2854, time of day, etc. The RFID tag could alternatively be contained within the plunger cap 204*b* or cylindrical wall 202*a* of the sample tube and read automatically when the sample tube is loaded into the carousel 200. Additionally, if the RFID tag is within any portion of the tube or plunger cap that is loaded into container holder 210, the reader may be attached to container holder 210, enabling the capability to read the tube when it is loaded and not requiring a separate station for RFID reading.

At this point in the method/process, the funnel door 171 is in the closed position (see, e.g., FIG. 24). This prevents the soil sample material if loaded into the funnel 170 from entering and falling out of the still open bottom of the bulk material chamber 120 if loaded into the funnel before the sample tube 202 is rotated beneath chamber 120.

Carousel 200 is then rotated to the inward closed position via operation of carousel actuator 212. In some embodiments, this step may be initiated by actuating an actuator 2811*a* such as a button, toggle, or other type switch (FIG. 22) operably coupled to packaging machine controller 2811 (see, e.g., FIGS. 25-27). This may arbitrarily be referred to as the “Fill Tube” actuator or by another name. In other embodiments, the step may be actuated via a personal electronic device 2851 operably coupled to controller 2811 which initiates rotation of the carousel (see, e.g., FIG. 2). In either control scenario, rotating the carousel inwards positions sample tube 202 under sample collection chamber 180. The base member 211 (i.e. closure arm 211*c*) closes the bottom end of previously open bulk material chamber 120.

With the piston-plungers 150, 155 still in their downward position, it bears noting that the closure arm 211*c* of the carousel 200 will scrape any residue away from the bottom faces of the plunger disks 152*a*, 152*b* as the closure arm rotates inwards which may remain from the last container packaging operation.

The soil sample material may be added to funnel 170 after rotating the carousel inwards or at any point before that so long as the funnel door 171 remains closed up to this point in the process.

Next, the push cap 204*b* is unlocked/unclipped from the sample tube 202 by actuating end cap actuator 160 for those embodiments including the actuator. The actuator disengages the retention protrusions 205 of push cap 204*b* from the retention slots 202*c* in tube 202 and slideably pushes the cap vertically upwards inside the tube. Cap 204*b* is therefore no longer locked near the bottom end 203*b* of sample tube 202, but at some preselected position between the ends of the tubes. The protrusions 205 have a radially outwards directed spring force sufficient to positively engage the inside surface of cylindrical sample tube wall 202*a* to retain the position of the push cap 204*b*.

Alternatively, if the alternative container holder 223 embodiment without actuator 160 is used as further described below and shown in FIG. 22 et al., the push cap remains at its lower locked position in sample tube 202.

Figure 28:
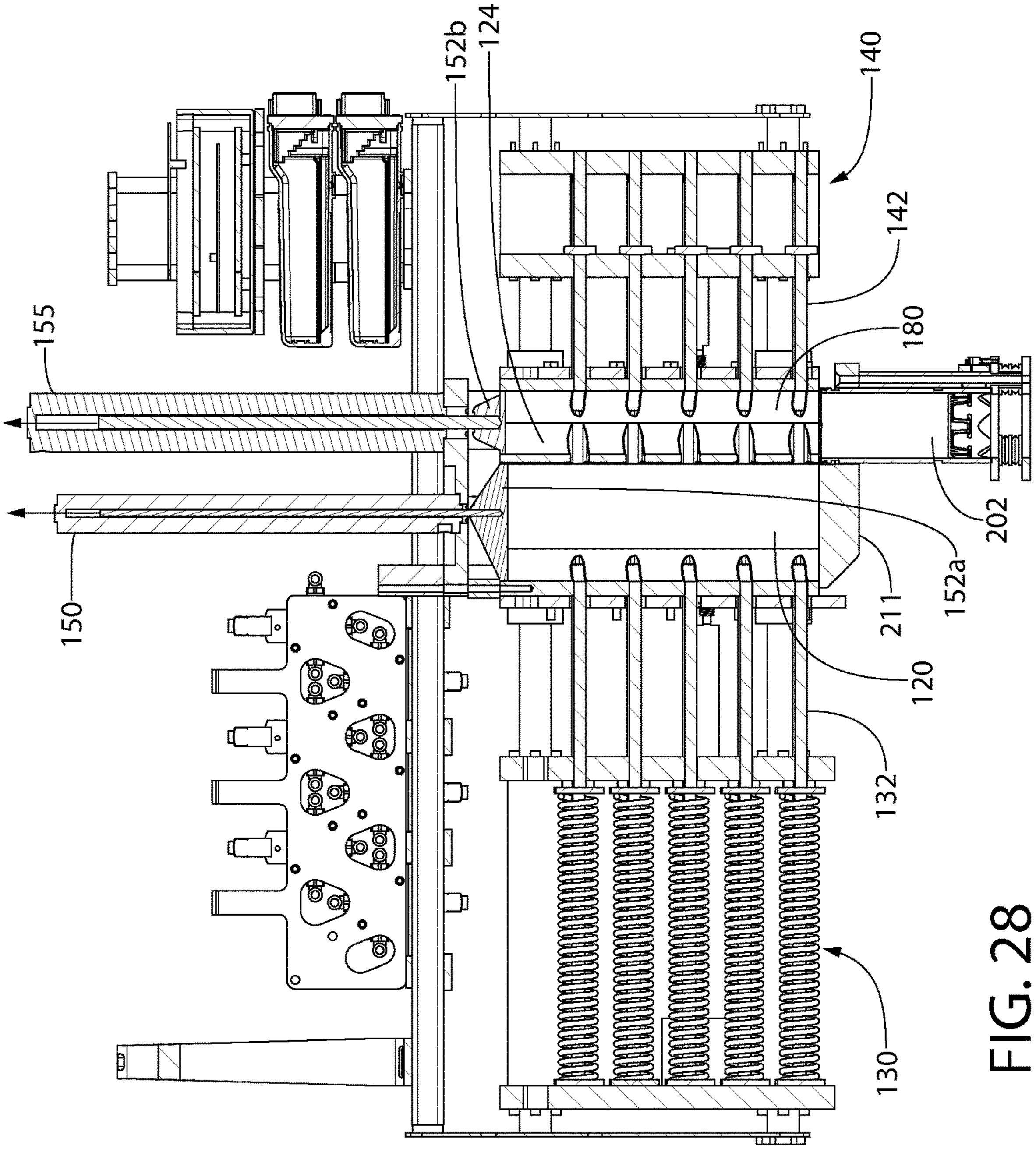
FIG. 28 is a front cross-sectional view of the apparatus showing the sample and cleaning blades of the apparatus in their retracted positions.

As shown in FIG. 28, the piston-plungers 150, 155 are retracted from the bulk material chamber 120 and sample collection chamber 180 (see, e.g., FIG. 28) if not previously retracted.

Figure 29:
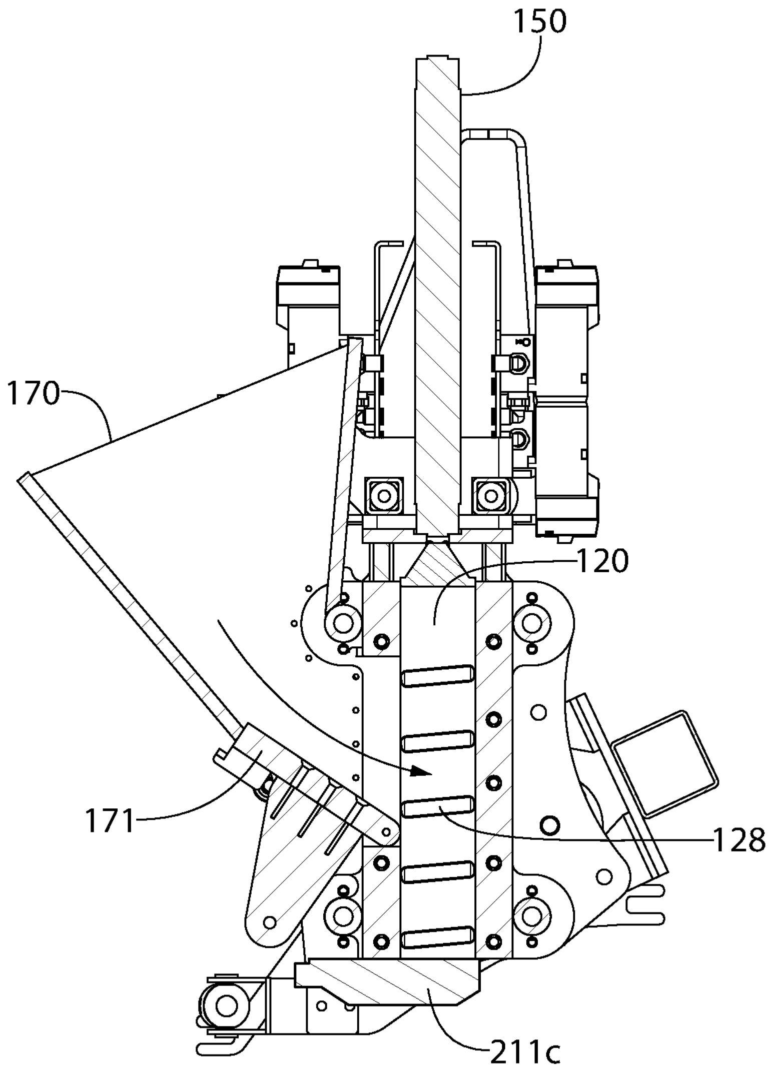
FIG. 29 is a side cross-sectional view of the apparatus showing the funnel door in the open position to admit sample material into the bulk material chamber as indicated by the directional arrow.
Figure 30:
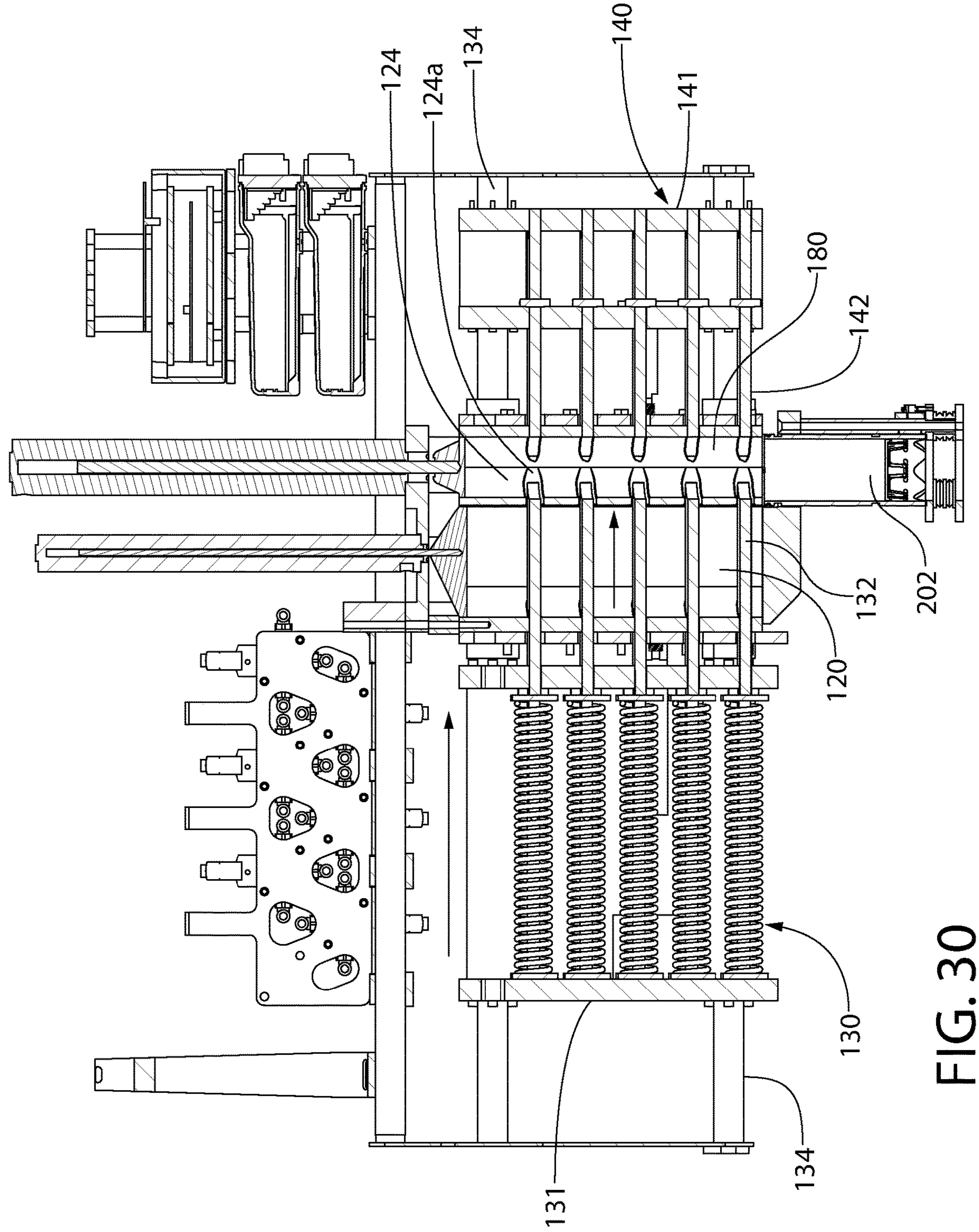
FIG. 30 is a front cross-sectional view of the apparatus showing the sample blades in their projected positions inserted through the bulk material chamber and die block.

Once the carousel is set up as described above and piston-plungers 150, 155 are retracted, the soil sample extraction process is ready to begin. The funnel door 171 is opened via operation of actuator 172. The bulk soil sample material is transferred to and enters the bulk material chamber 120 (FIG. 29). Door 171 may then be shut, which compacts any slight overfill of the chamber and prevents any remaining soil in the funnel from working its way into the chamber.

The method continues with activation of the sample blade mechanism 130. Actuator 135 slideably moves the sample blade chassis 131 along guide rods 134 and sample blades 132 are inserted through bulk material chamber 120 and die block 124. The blades 132 move from the initial retracted position to the projected position previously described herein (e.g., towards the right in FIG. 30—see directional arrows). The sample blades 132 each extrude or force a portion of soil from the bulk material sample through a respective die slot 124*a* in die block 124. The extruded/extracted soil, which comprises multiple plugs or blanks of soil are deposited in sample collection chamber 180 by the advancing blades 132). The extracted soil plugs fall downward into open sample tube 202 waiting below chamber 180.

Figure 31:
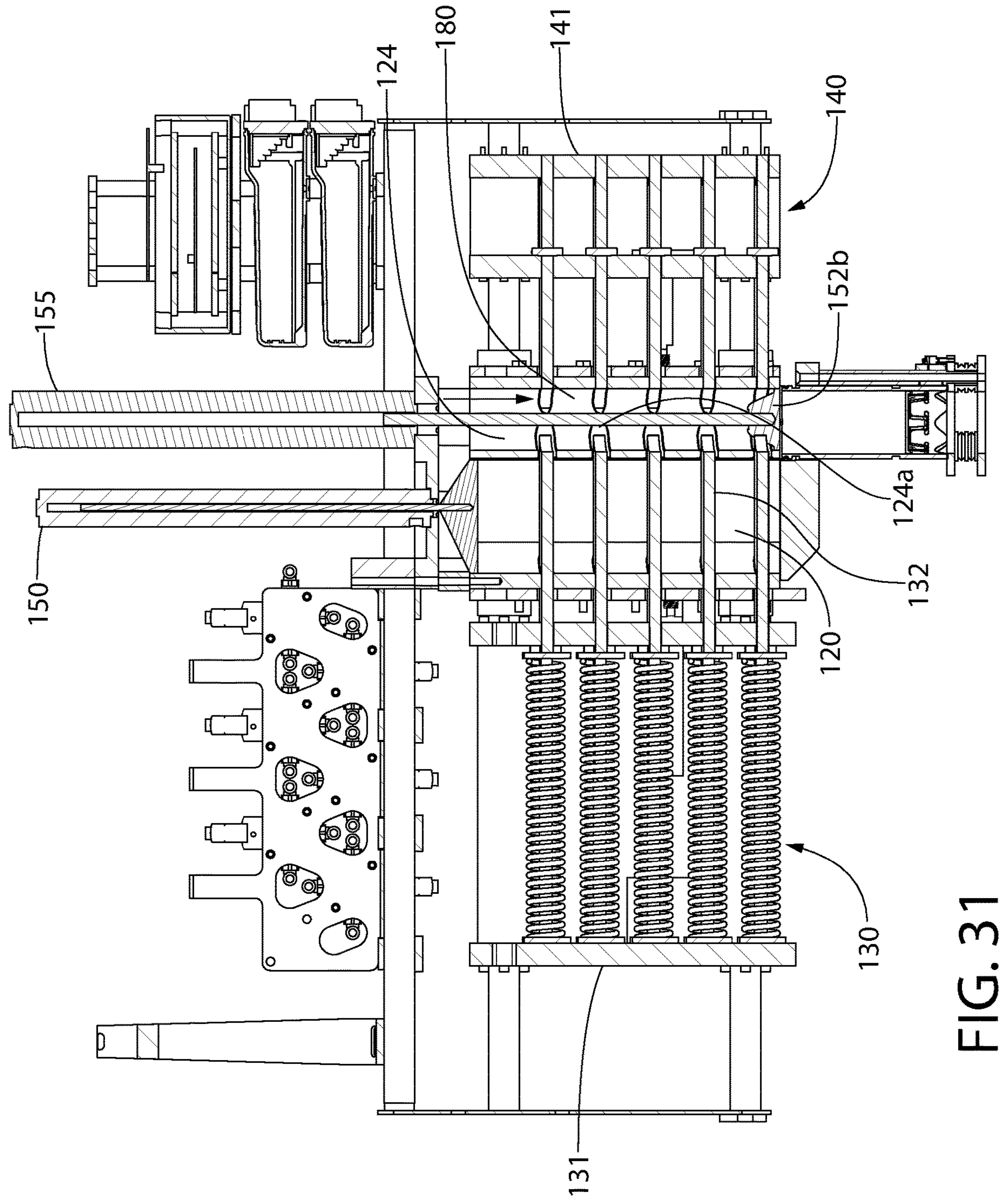
FIG. 31 is a front cross-sectional view thereof showing the sample transfer piston-plunger in its downward extended/projected position.

Sample transfer piston-plunger 155 may then be actuated to ensure all of the soil sample material in collection chamber 180 is positively pushed downwards into the sample tube (see, e.g., FIG. 31). Preferably, this step is conducted while sample blades 132 remain in the die block 124 within die slots 124*a* to ensure that the soil in chamber 180 is not pushed laterally backwards into the die slots 124*a* of die block 124 by the piston-plunger. Piston-plunger 155 may be extended all the into the sample tube 202 to tightly pack the soil in the tube. Notably, the piston-plunger compacts the soil in sample tube 202 while forcing and displacing the push cap 204*b* back downwards incrementally by a distance. This advantageously ensures that soil sample in the tube is a tightly packed sample.

Piston-plunger 155 may then be withdrawn from the sample tube 202 and chamber 180, and returns vertically upwards back to its initial retracted position.

Figure 32:
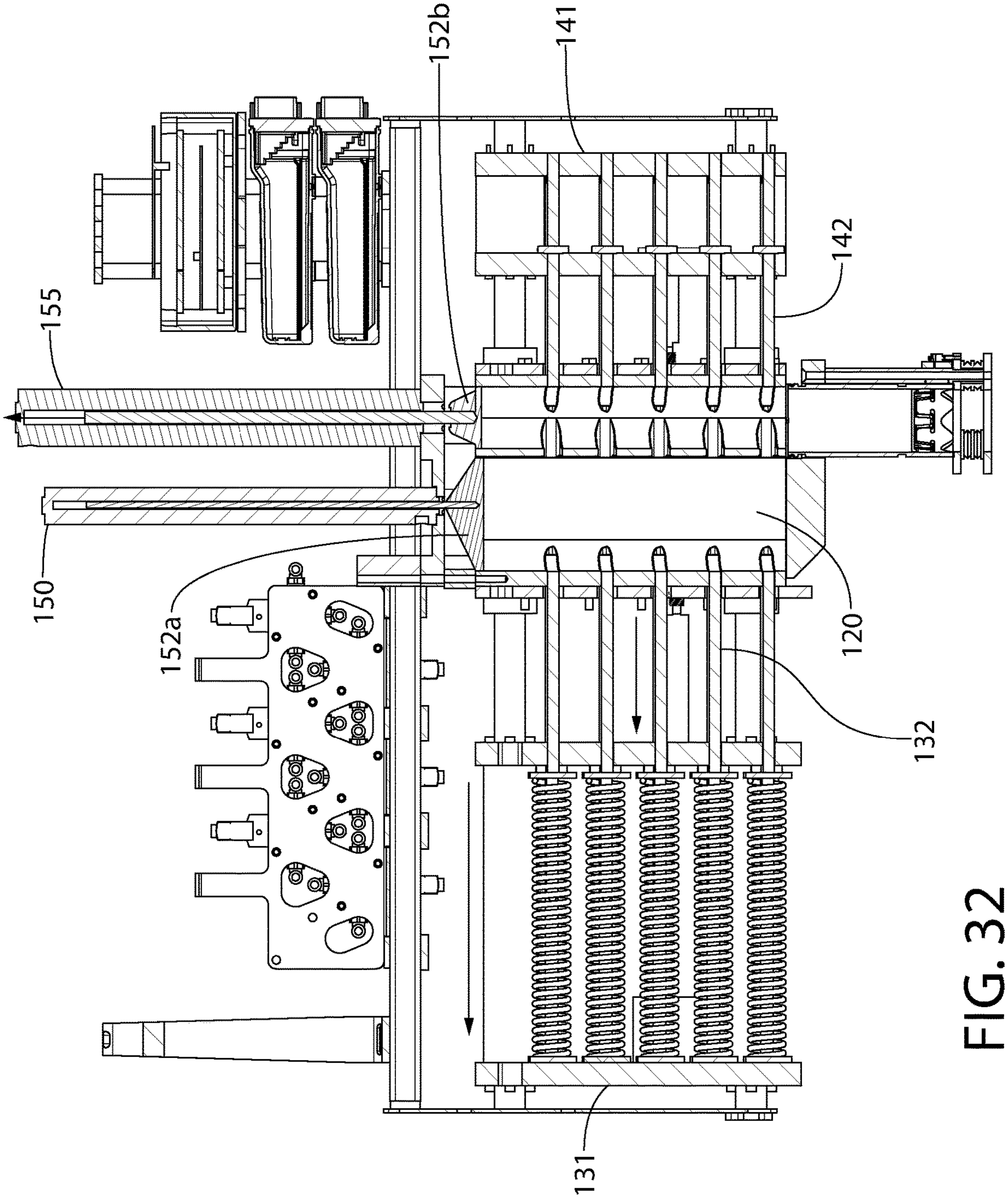
FIG. 32 is a front cross-sectional view thereof showing the sample transfer piston-plunger returned to its upward retracted position.
Figure 33:
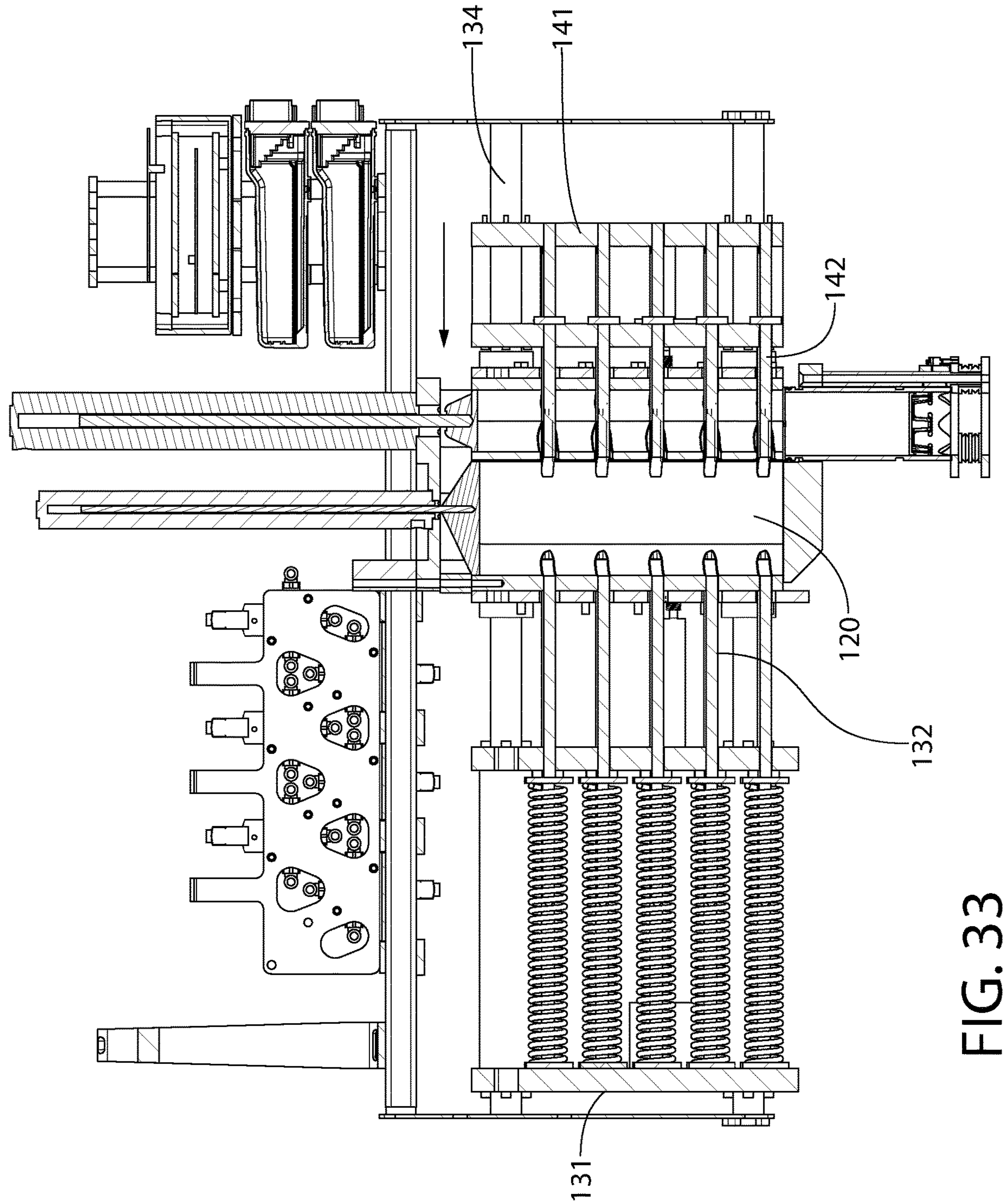
FIG. 33 is front cross-sectional view thereof showing the cleaning blades in their projected position inserted through the sample collection chamber and die block.

The method continues with withdrawing the sample blades 132 from the die block 124 and bulk material chamber 120 by returning the chassis 131 of the sample blade mechanism 130 to the retracted position (e.g., towards the left in FIG. 32).

The method continues with actuating the cleaning blade mechanism 140. Actuator 145 moves the cleaning blade chassis 141 and cleaning blades 142 from the initial retracted position to the projected position previously described herein (e.g., towards the left in FIG. 33). Cleaning blades 142 are inserted through sample collection chamber 180 and die slots 124*a* in the die block. The cleaning blades 142 each push any residual soil residue or particularly hard non-soil debris (e.g. stones, etc.) which may have been trapped in the die slots 124*a* backwards and into the bulk material sample chamber 120.

Figure 34:
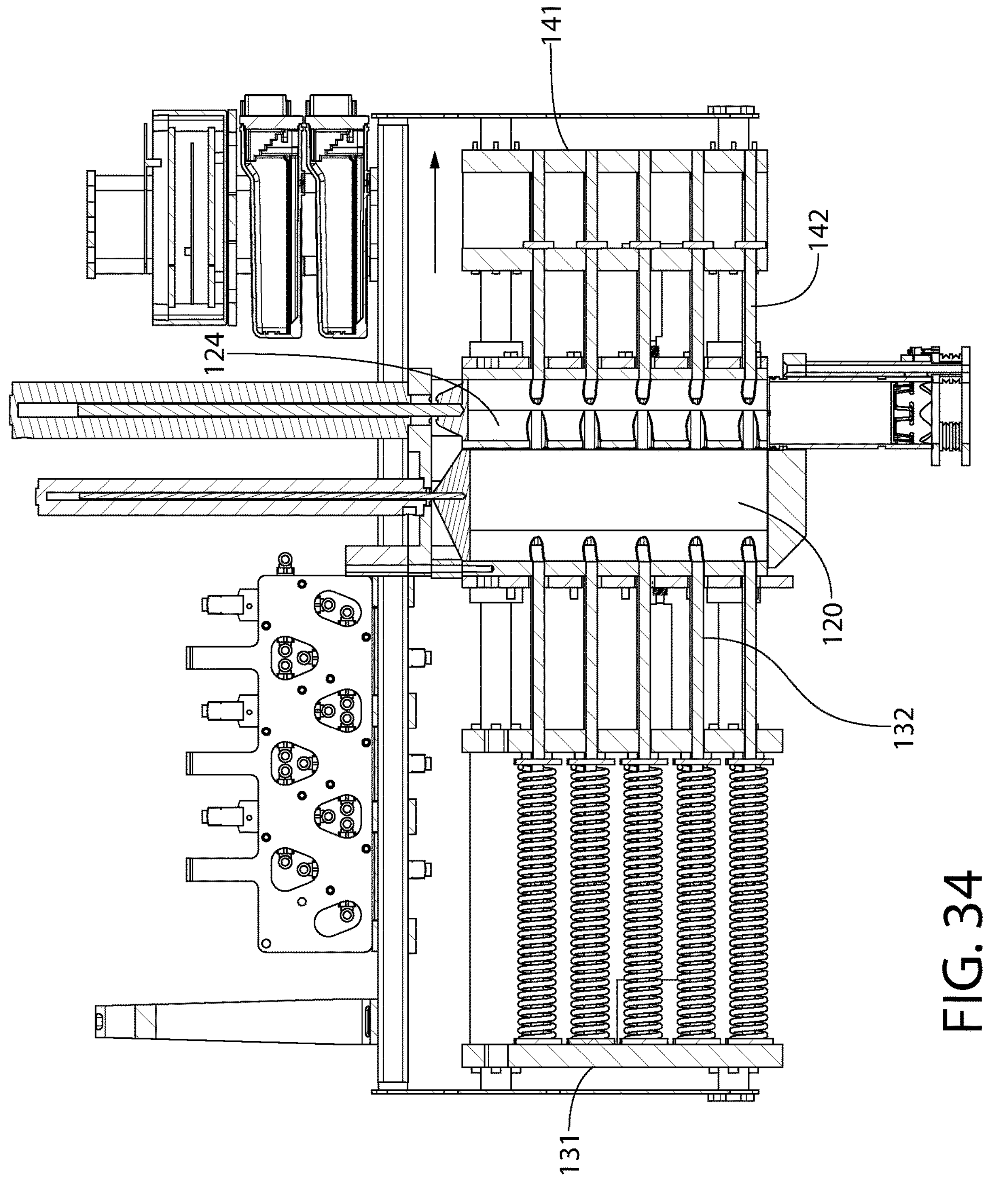
FIG. 34 is a front cross-sectional view thereof showing the cleaning blades returned to their retracted positions.

The cleaning blades 142 are then retracted from the die block 124 and soil collection chamber 180 by reversing the above operation (see, e.g., FIG. 34).

Figure 35:
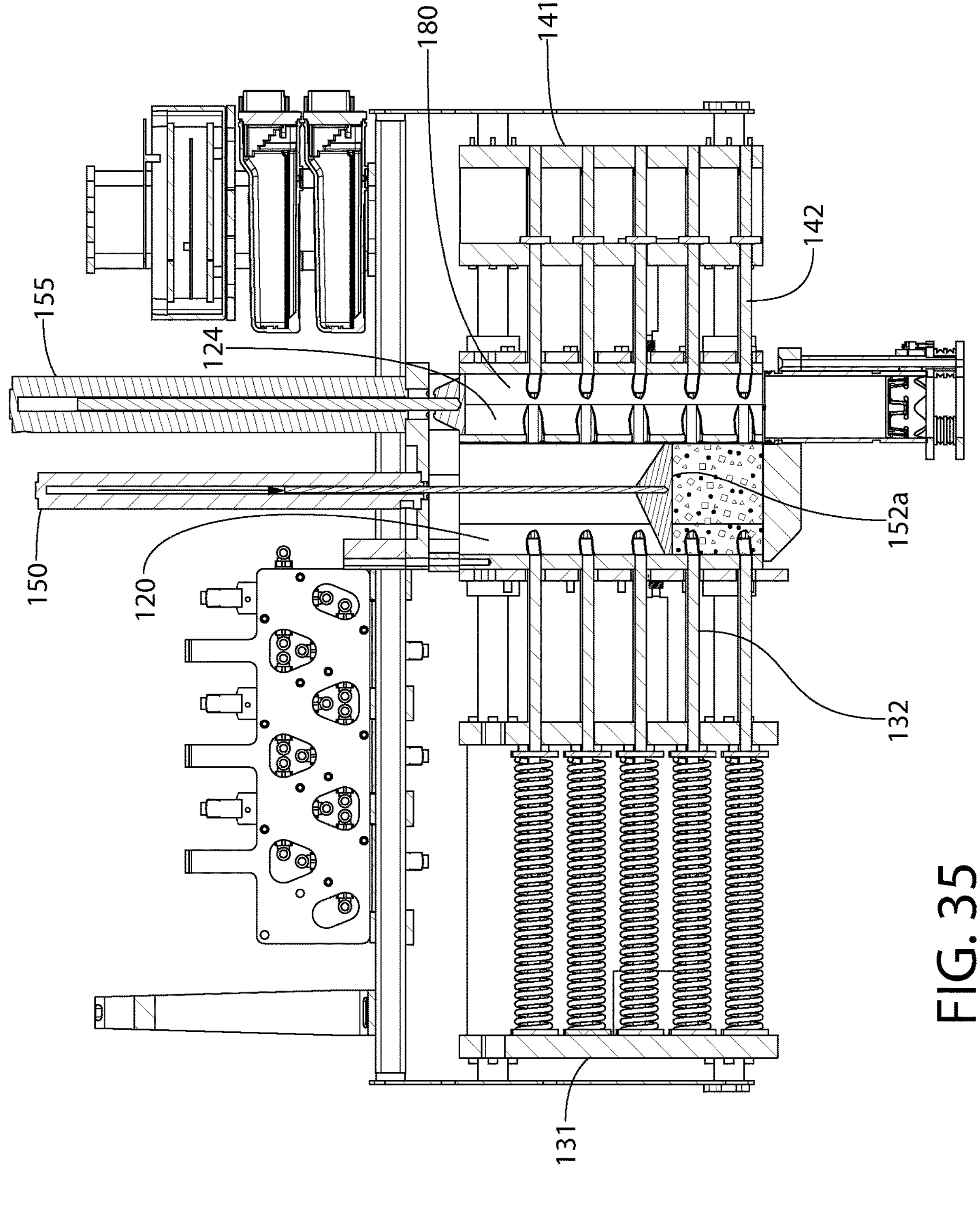
FIG. 35 is a front cross-sectional view thereof showing the compaction transfer piston-plunger in its downward extended/projected position.

Next, compaction piston-plunger 150 is actuated to re-pack the soil in bulk material chamber 120 (see, e.g., FIG. 35). The piston-plunger 150 moves vertically downwards in chamber 120 to compact the remaining soil in the chamber. This is particularly beneficial if moist sticky and dense soil such as clay is being processed. It is possible that the sample blades 132 may leave voids in the self-supporting soil material remaining in chamber 120 when the blades are initially withdrawn from the soil in the chamber when the sample material plugs were first extruded. If so, the next extraction cycle may fail to displace and collect any appreciable amount of soil for the sample due to the presences of the voids. To remedy this possibility and maintain a quick pace of extracting a full soil sample, the piston-plunger 150 advantageously will collapse the soil and remove any such voids.

Figure 36:
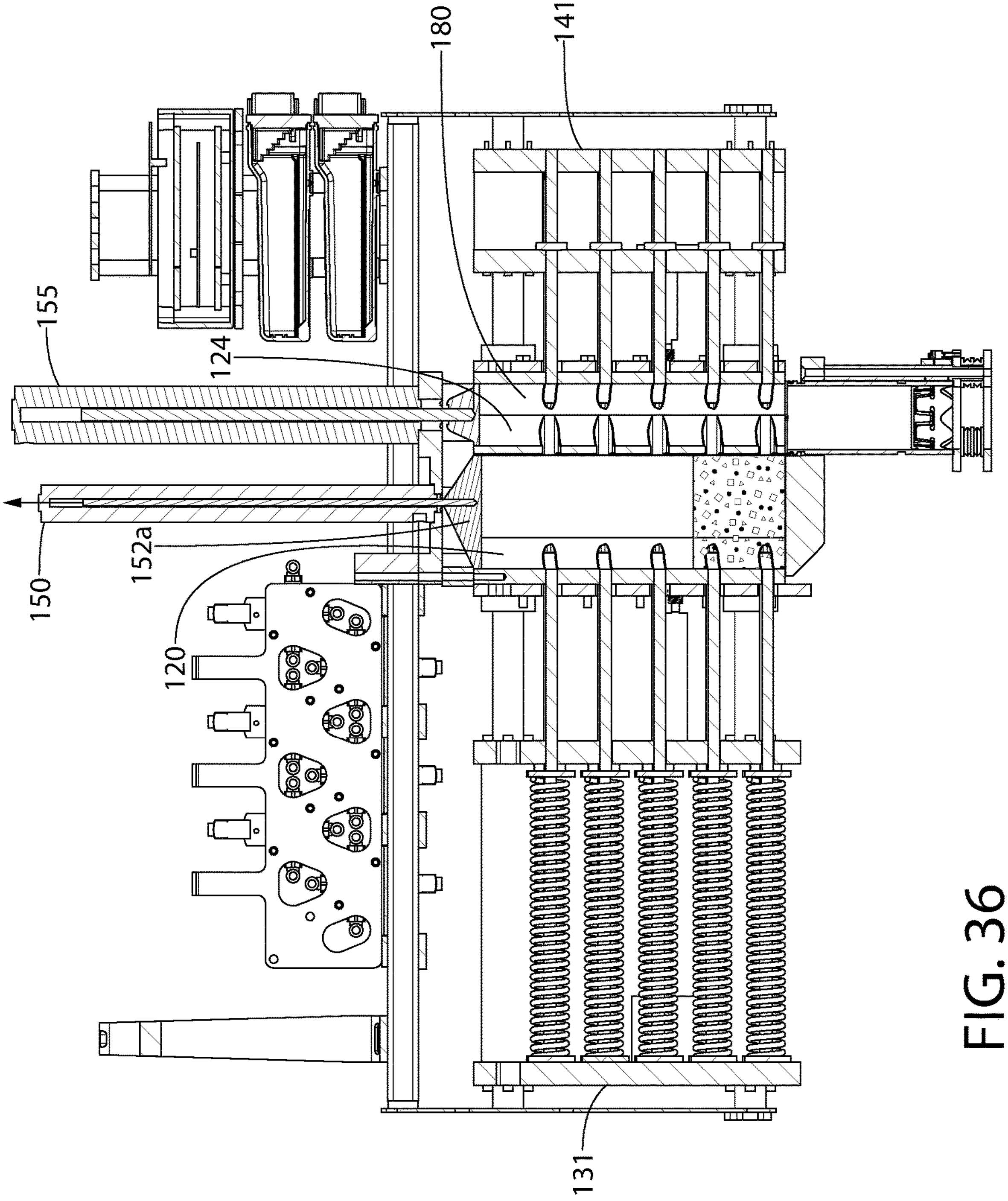
FIG. 36 is a front cross-sectional view thereof showing the compaction piston-plunger returned to its upward retracted position.

Next, the compaction piston-plunger 150 is retracted from bulk material chamber 120 (see, e.g., FIG. 36).

It bears noting that a single soil sample plug or blank extraction cycle as described above may not be sufficient to sufficiently fill the sample tube 202 with enough soil for further processing and eventual chemical analysis. Accordingly, the entire cycle may be repeated multiple times to extract a sufficient amount of the soil sample material for chemical testing in a related process.

It should also be noted that in sample packaging apparatus 110 embodiments including the cap actuator 160, the push cap 204*b* gradually advances farther downwards inside sample tube 202 as the tube is gradually filled and packed down by piston-plunger 155 as previously described herein. The retention protrusions 205 of cap 204*b* eventually re-engage and snap back into the retention slots 202*c* of the sample tube. This represents the lowermost position of the cap 204*b* in the tube and maximum volumetric capacity of the tube.

Figure 38:
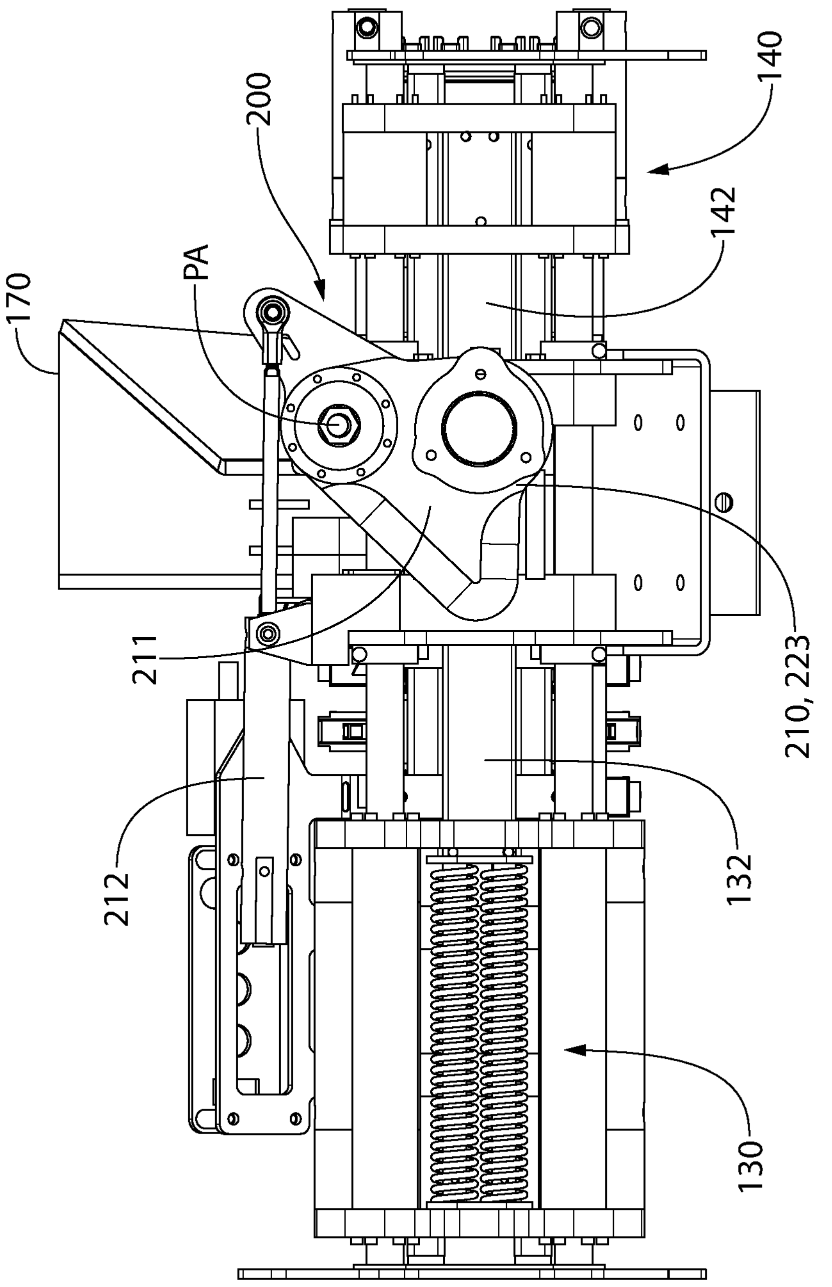
FIG. 38 is a bottom view of the apparatus showing the carousel and sample container rotated to the inward closed position ready for filling with the agricultural sample material.
Figure 39:
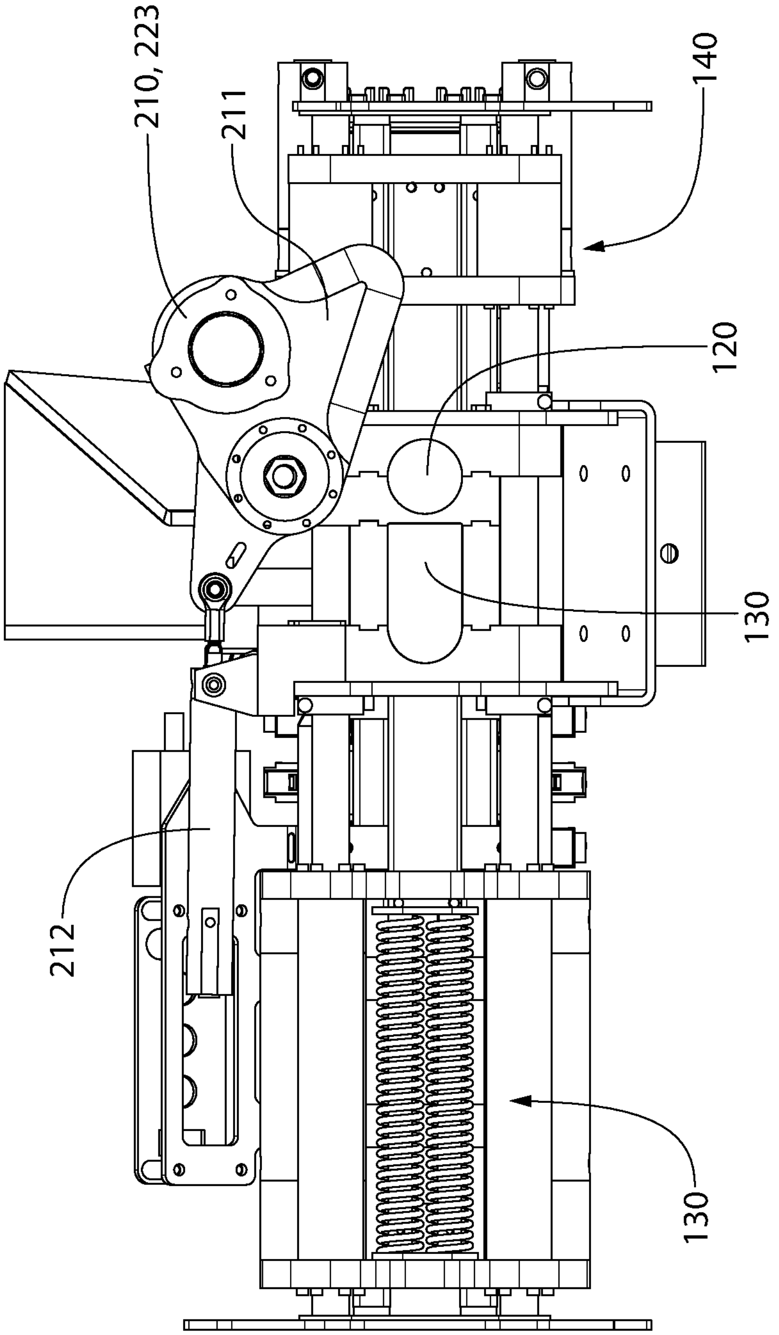
FIG. 39 is bottom view of thereof showing the carousel in the outward open position to enable removal of a filled sample container from the apparatus.

Once the sample tube 202 is full, the carousel 200 is rotated back to the outwards open position (see, e.g., FIGS. 38-29). The carousel is configured such that it screeds the top of the tube to remove any soil mounded above the top rim of the tube so that the top end cap 204*a* can be installed without having to manually level off any upwardly protruding mound of soil. Any mound of soil will be screeded or scraped off by the bottom surface of the chamber block 123 portion adjacent to sample collection chamber 180 as the baseplate 211 of the carousel 200 rotates to its open outward position. The stationary end cap 204*a* may then be manually removed from RFID reader 2850 with RFID tag 2850*a* and coupled to the open top end 203*a* of the tube to seal the sample. If the tag 2850*a* is not located on the stationary top end cap 204*a*, that cap need not be placed on an RFID reader and may be recovered from wherever stored. In either case, the packed and sealed sample tube 202 may then be removed from packaging apparatus 110 for further processing and eventual chemical analysis.

Figure 40:
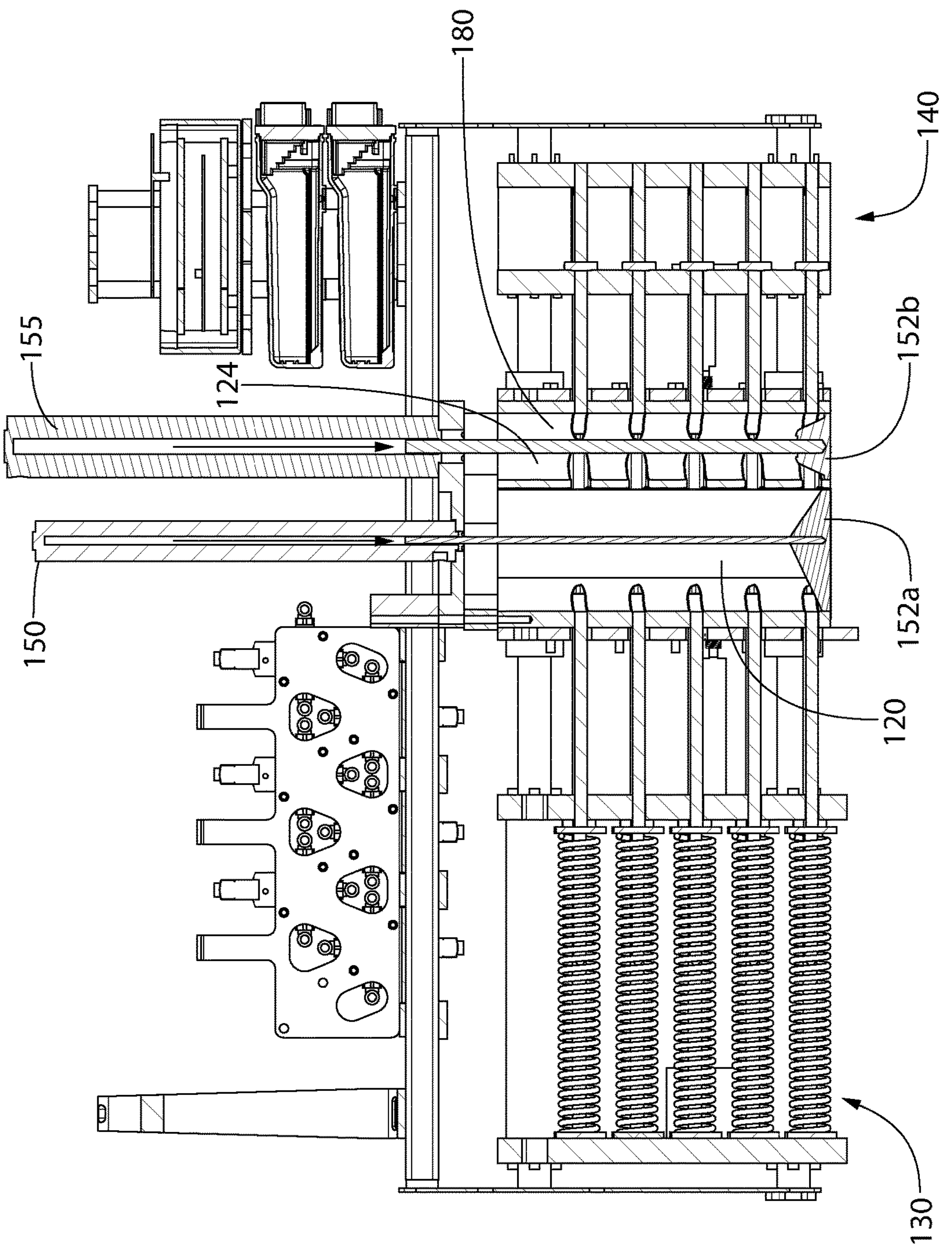
FIG. 40 is a front cross-sectional view of the apparatus showing the sample transfer piston-plunger and compaction plunger in their downward projected positions.
Figure 41:
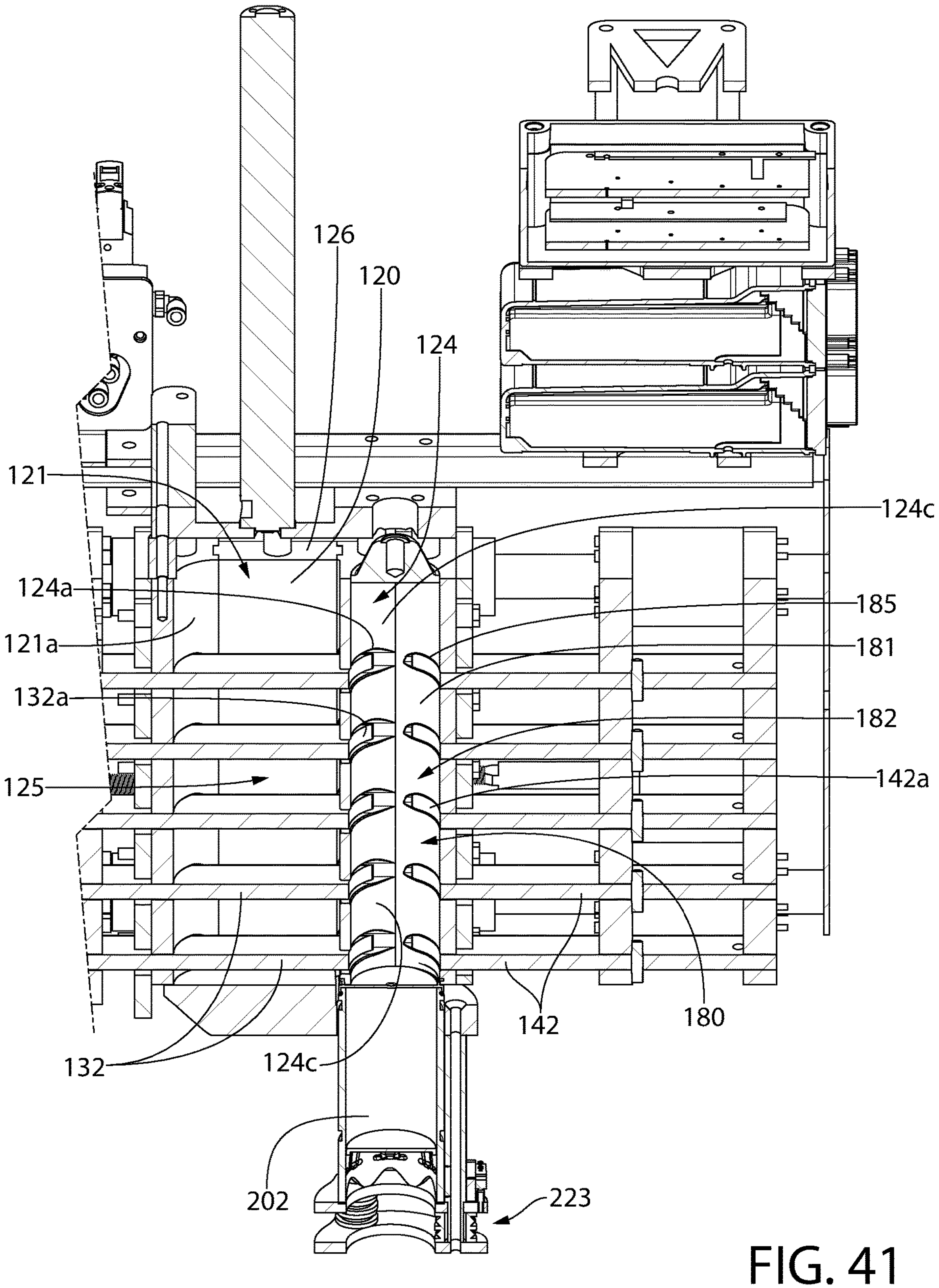
FIG. 41 is an enlarged partial front cross-sectional view of the chambers and die block of the apparatus.

With the carousel still in the outward open position, sample transfer piston-plunger 155 and compaction piston-plunger 150 may be run back through their respective soil collection and bulk material chambers 180, 120 to remove any residual soil in preparation for the next round of extracting the soil samples (see, e.g., FIG. 40).

The sample transfer piston-plunger 155 and compaction piston-plunger 150 may remain in this downward position with disk 152*a*, 152*b* exposed at the bottom ends of the bulk material chamber 120 and sample collection chamber 180. After the sample tube 202 has been loaded into the carousel 200 for the next set of soil sample extractions, rotating the carousel to inward closed position will wipe the exposed faces of the piston-plungers 150, 155 clean as the closure arm 211*c* passes beneath both piston-plungers. The piston-plungers can each be returned to their upward position before soil is added to the bulk material chamber 120 for the sample plug/blank extractions.

It bears noting that compaction piston-plunger 150 doubles as a scraper to clean the ends of the sample blades 132 when in their retracted position each time the plunger moves downwards and upwards in the bulk material chamber 120. In a similar manner, the sample transfer piston-plunger doubles 155 which travels upwards/downwards in sample collection chamber 180 acts as a scraper to clean the ends of the sample blades 132 when in the projected position extending through the die block 124 and the ends of the cleaning blades 142 with each downward/upward movement of the plunger. This is possible because, as previously described herein, the terminal ends of the sample blades 132 form part of the exposed inner walls of the chamber 120 when retracted and part of the inner walls of chamber 180 when projected. In a similar vane, the terminal ends of cleaning blades 142 form part of the inner walls of chamber 180.

Figure 37:
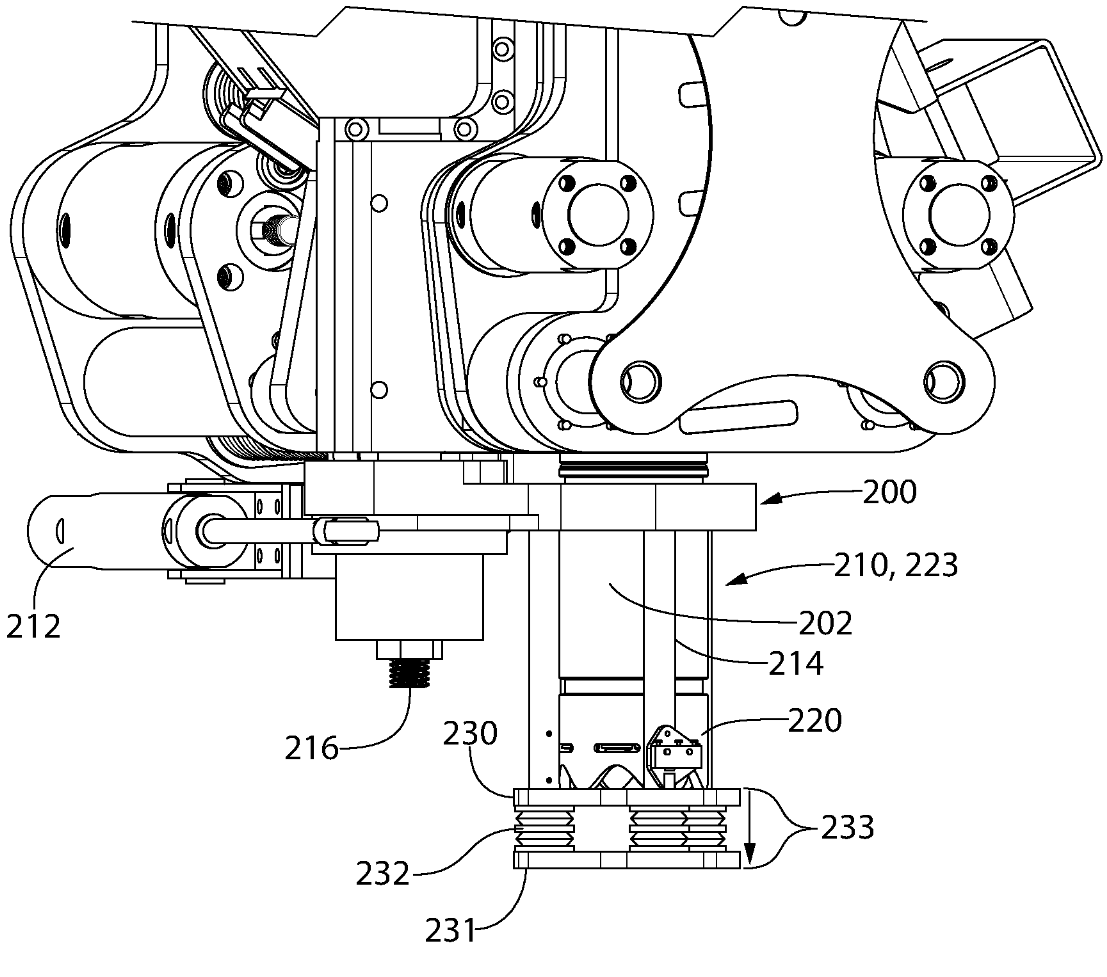
FIG. 37 is partial front perspective view of the carousel showing a collapsible embodiment of the container holder with container sensor.

FIGS. 22 and 37 depict an alternative embodiment of a sample container holder assembly which omits the end cap actuator 160. In this embodiment, the present container holder 223 comprises a collapsible dual support plate assembly 233 which is supported and suspended by spacer rods 214 beneath the base member 211 of carousel 200. The dual plate assembly comprises a lower fixed plate 231 rigidly coupled to the bottom ends of spacers rods 214 and upper floating plate 230 vertically slideable up and down on the spacer rods relative to fixed plate 231. Fixed plate 231 thus remains stationary relative to the base member 211 of carousel 200 and spacer rods 214. The fixed and floating plates 231, 230 are spaced apart by plurality of springs 232 coupled between the plates. The sample tube 202 is seated on the upper floating plate when the tube is positioned on the packaging apparatus 110. The support plate assembly 233 is movable between an expanded condition in which the floating and fixed plates 230, 231 are spaced apart by springs 232 by a maximum extent and distal to each other, and a collapsed condition in which the plates 230, 231 are proximate to each other or closest when the springs are compressed by piston-plunger 155 as further described herein.

In operation, the general steps in foregoing description of the method for packaging an agricultural sample remain the same and will not be repeated for sake of brevity. The differences in the method when using the present container holder 223 is as follows. First, the push cap 204*b* is not unlocked and moved upward in sample tube 202 before adding soil to the tube since the cap actuator 160 is omitted in the present embodiment. Accordingly, cap 204*b* remains in its lowermost position proximate to bottom end 203*b* of tube and locked to the retention slots 202*c* of the tube. In some embodiments, the cap 204*b* could be replaced by a fixed immovable cap coupled to the bottom end of the tube similar to cap 204*a* coupled to the top tube end 203*a*.

A second difference in the method for packaging the agricultural sample is that the movable dual plate assembly 233 is activated and collapsed when the sample tube 202 is completely filled to capacity. The dual plate assembly 233 begins in the expanded condition when the sample tube is loaded onto the present container holder 223. After several tube fill cycles previously described herein, the tube will become full as the sample transfer piston-plunger 150 tamps and packs the soil into the tube. Once the maximum volume has been reached, the last tamping action will push the soil in the tube 202 and tube itself downwards together. This in turn moves the upper floating plate 230 downwards compressing the springs 232 counter to their upward biasing action. Support plate assembly 233 is now in the collapsed condition.

A full sample tube sensor 220 fixedly mounted adjacent to the bottom end of one of the spacer rods 214 is activated by the floating plate moving downward and configured detect movement of the floating plate, which is indicative of the tube being filled to capacity and ready for removal from the packaging apparatus 110. Sensor 220 sends a signal to the local machine controller 2811 onboard apparatus 110 and/or main system controller 2820 indicating the same. It bears noting that floating plate 230 will only be displaced when the tube 202 is filled to capacity as described above.

Any suitable type commercially available presence or contact sensing sensor including micro limit switches of suitable type, Hall effect sensors, etc. may be used to detect the presence or movement of floating plate 230. In one embodiment, a plunger type micro limit switch may be used as shown which comprises a depressible spring-biased plunger 221 that contacts upper floating plate 230 which the dual plate assembly dual support plate 233 is in the expanded condition (see, e.g., FIG. 46). If a micro limit switch is used, electrical contacts in the switch may be either opened (in a normally closed circuit) or closed (in a normally open circuit). In other embodiments, suitable load or force sensing sensors may be used. In yet other embodiments, non-contact type proximity sensors including inductive proximity, capacitive proximity, and photoelectric sensors may be used. Accordingly, there are a number of sensor options and the invention is not limited by the type of sensor employed so long as an appropriate “full tube” signal is transmitted to the local machine and/or main system controllers 2811, 2820.

It should be noted that the sample transfer piston-plunger 155 which tamps the sample into sample tube 202 does not directly apply force directly to the tube. Piston-plunger 155 applies its force directly to the sample in tube, and then the sample transmits its received force to the tube. This indirect force transfer allows the sample to be compressed consistently by the piston-plunger within the tube before triggering a full tube condition via sensor 220.

In other embodiments, full sample tube sensor 220 may be a commercially-available “load” or “force” sensor operably coupled to packaging machine controller 2811. This may be accomplished using controls and feedback via packaging machine controller 2811 with a commercially available actuator or load/force cells in place of the springs 232 of in container holder 223. The load/force cell sensor would be disposed between the lower fixed plate 231 and upper floating plate 230 of the dual support plate assembly 233 which are in abutting contact with each other. Commercially-available thin film type sensors can be used for this application sandwiched between plates 231 and 230. When the actual load/force sensed during the sample tube 202 filling operation reaches a predetermined load/force setpoint preprogrammed into controller 2811, the controller determines the tube is filled to capacity by comparing the setpoint to the actual sensed load/force. The load/force sensing arrangement is clear to those skilled in the art based on the foregoing description without further undue elaboration or need for drawings.

It bears noting that after the piston-plunger 155 returns to its upward position, the dual support plate assembly 233 returns to the expanded condition as floating plate 230 returns upwards via the upwards biasing action of springs 232 acting on the floating plate as the springs expand.

Control System

In one embodiment, the foregoing method or process for operating agricultural sample packaging system 100 may be controlled by a microprocessor controlled processing system including programmable local machine controller 2811 and/or main system controller 2820. Controller 2811 and/or controller 2820 is operably and communicably coupled and linked to all of the actuators, sensors, and other devices disclosed herein and programmable to execute suitable control logic/program instructions (e.g., software) to automatically control operation of the entire sample packaging system 100. In some embodiments, operation of the sample packing apparatus 110 may be initiated by one or more local actuators 2811*a*, 2811*b* (FIG. 22) which activates the controller 2811 and/or controller 2820 to start the sample packaging operations. These actuator switches are operably coupled to controller 2811 (which in turn is operably coupled to controller 2820 as further described below) and may be located anywhere on sample packaging apparatus 110.

Figure 2:
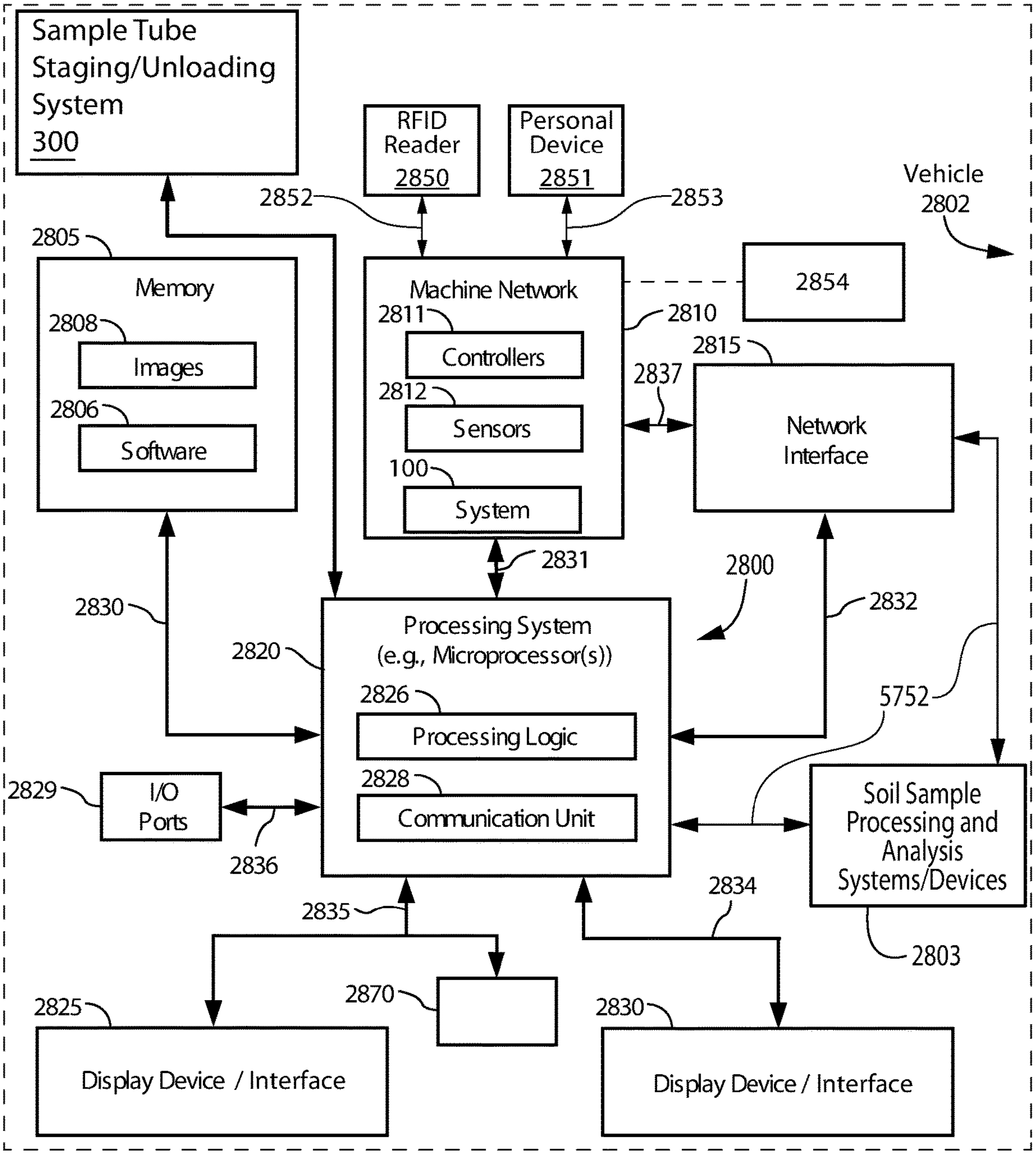
FIG. 2 is a schematic system diagram of a programmable processor-based central processing unit (CPU) or system controller for controlling the systems and apparatuses disclosed herein associated with the agricultural sample packaging system.
Figure 3:
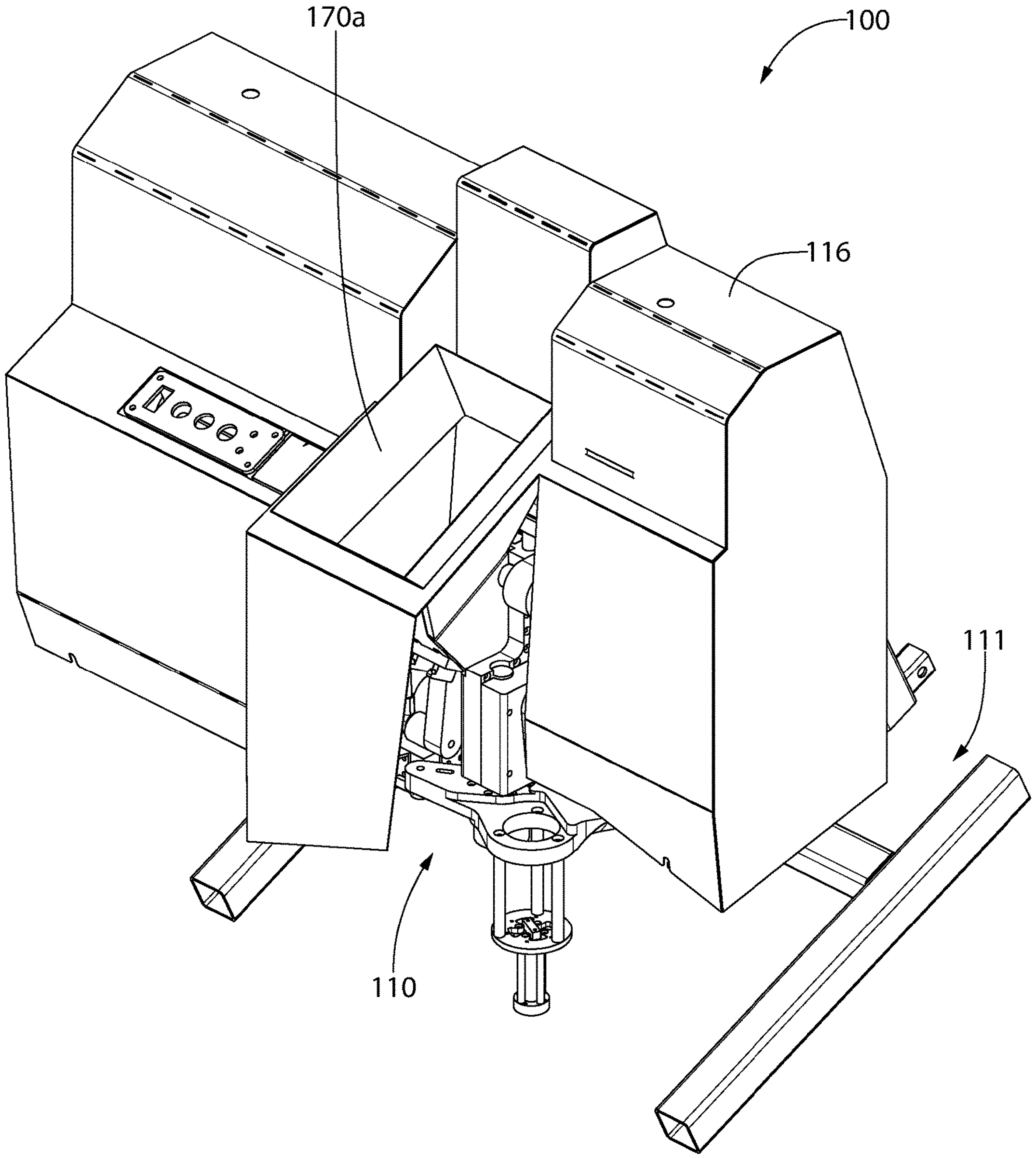
FIG. 3 is right top front perspective view of the sample packaging apparatus of the system.
Figure 4:
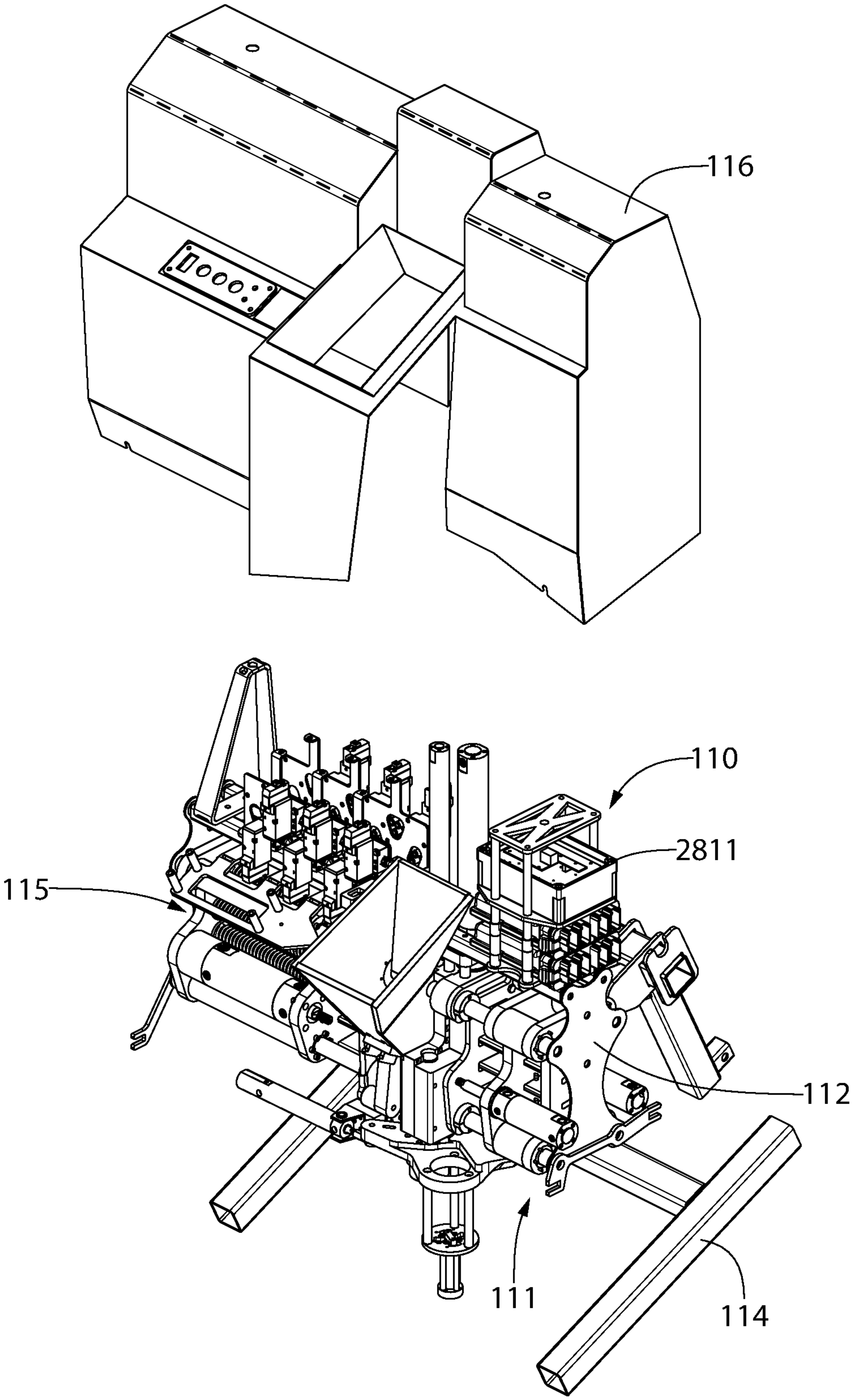
FIG. 4 is an exploded perspective view thereof showing the outer protective housing removed.
Figure 5:
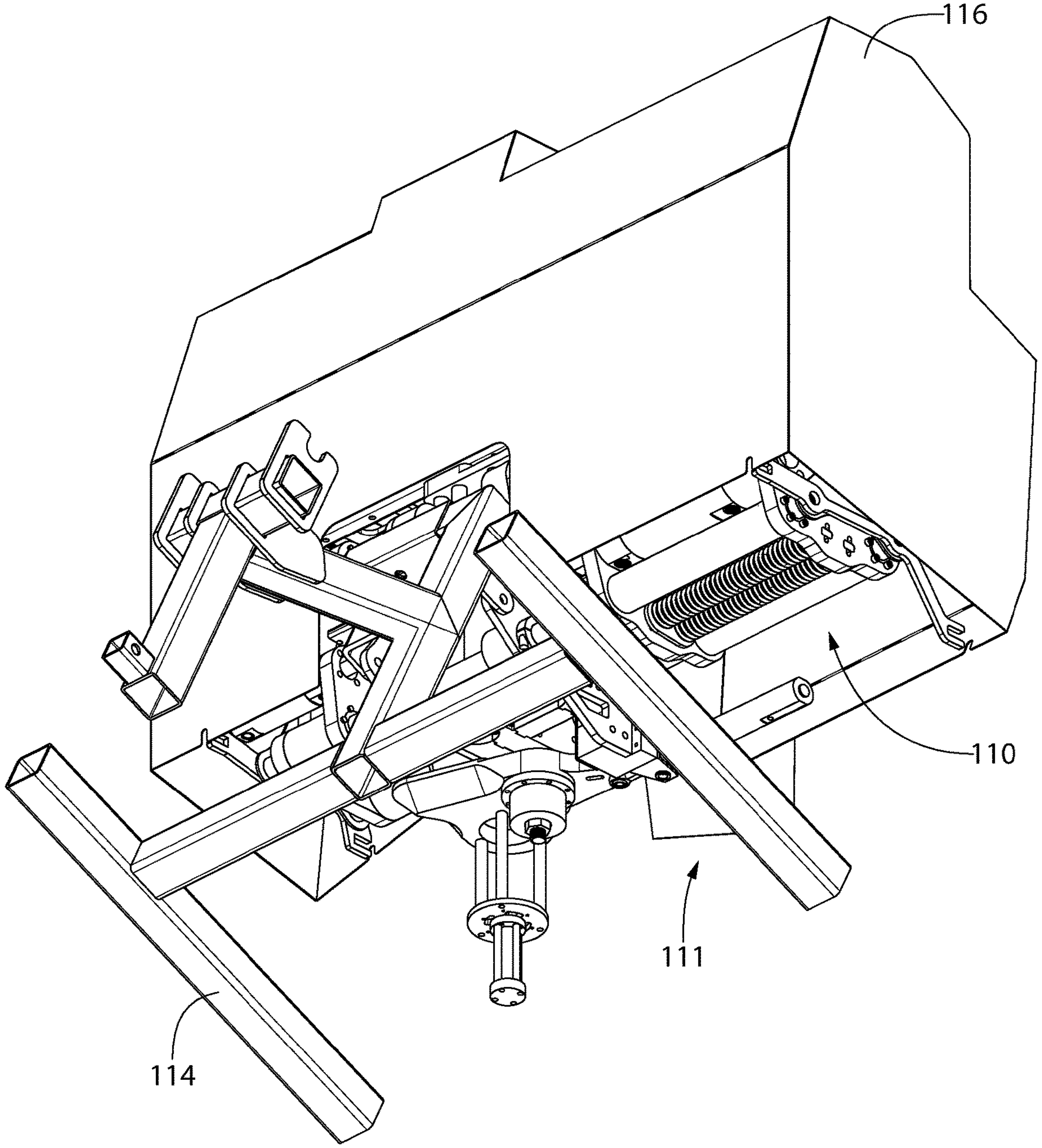
FIG. 5 is a bottom left rear perspective of the packaging apparatus.
Figure 6:
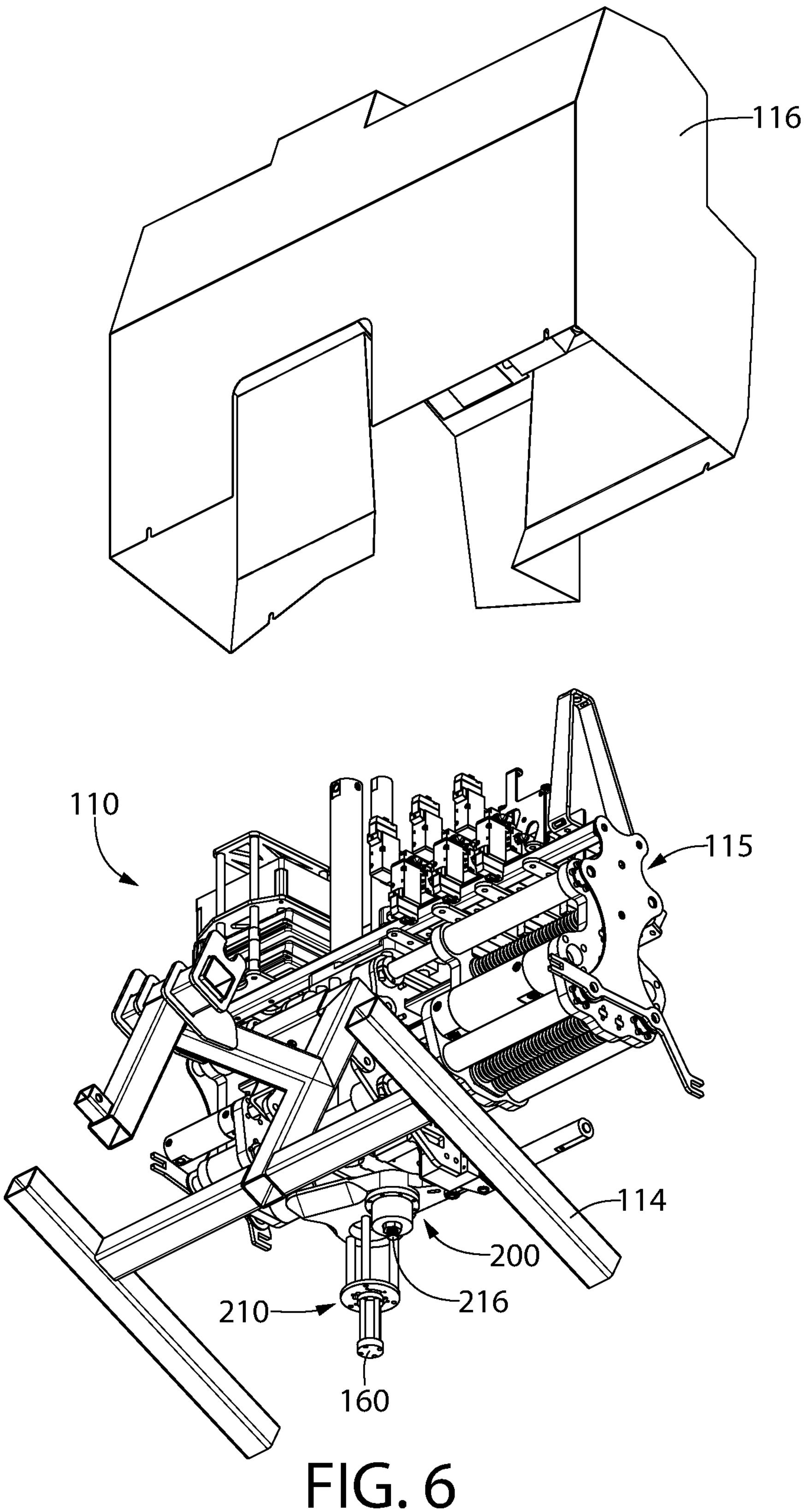
FIG. 6 is an exploded perspective view thereof.
Figure 7:
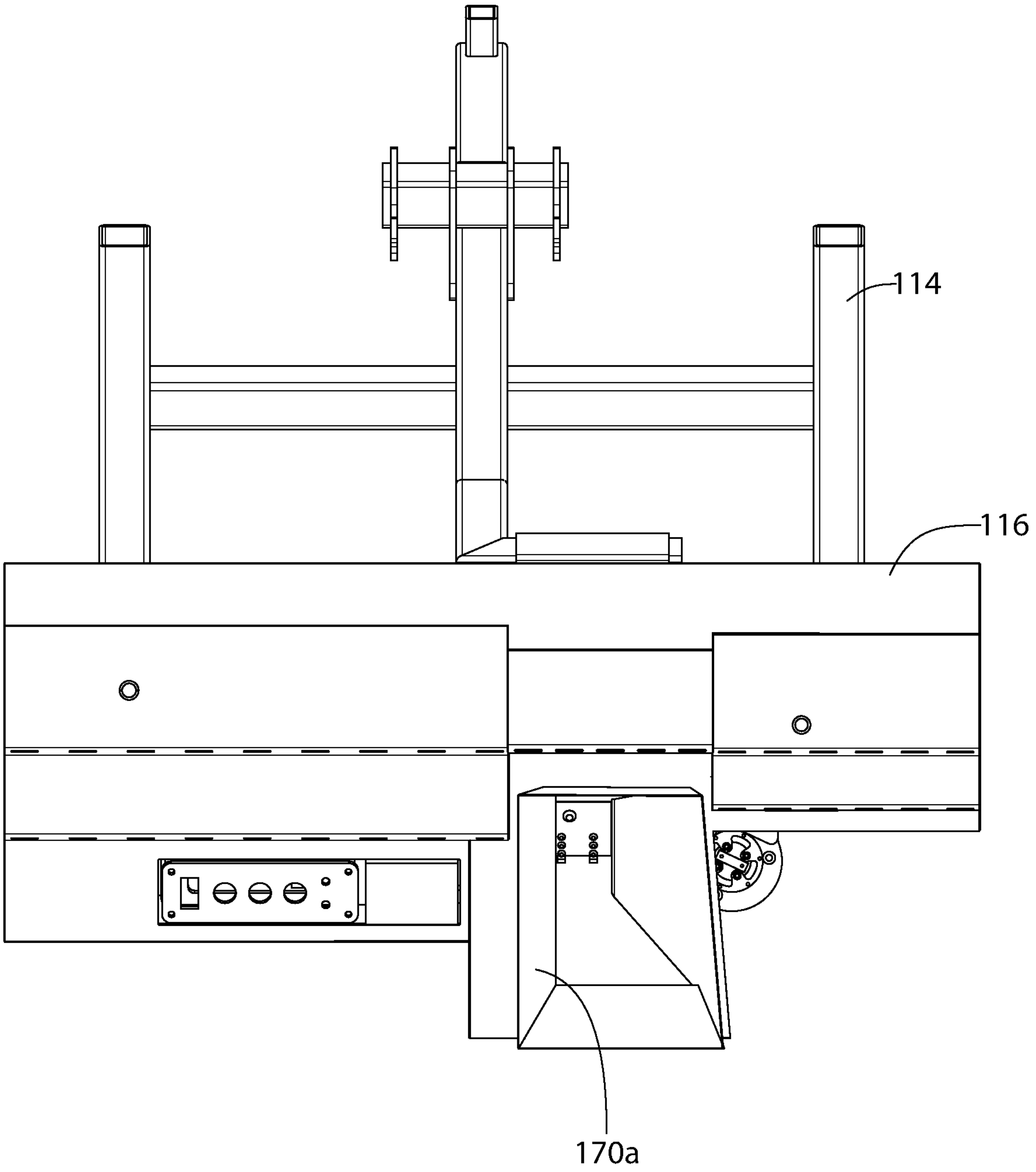
FIG. 7 is a top view of the packaging apparatus.
Figure 8:
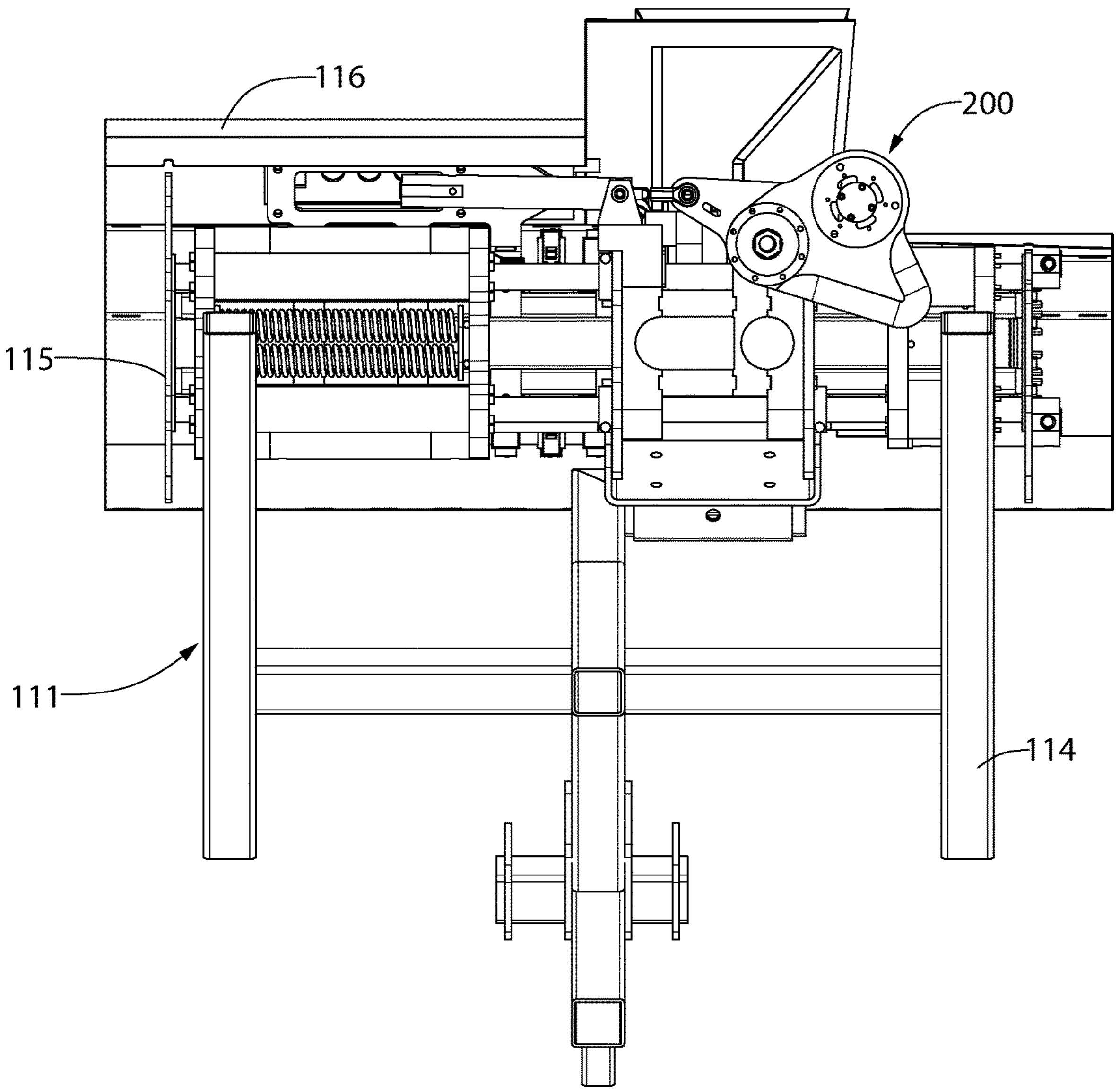
FIG. 8 is a bottom view thereof.
Figure 9:
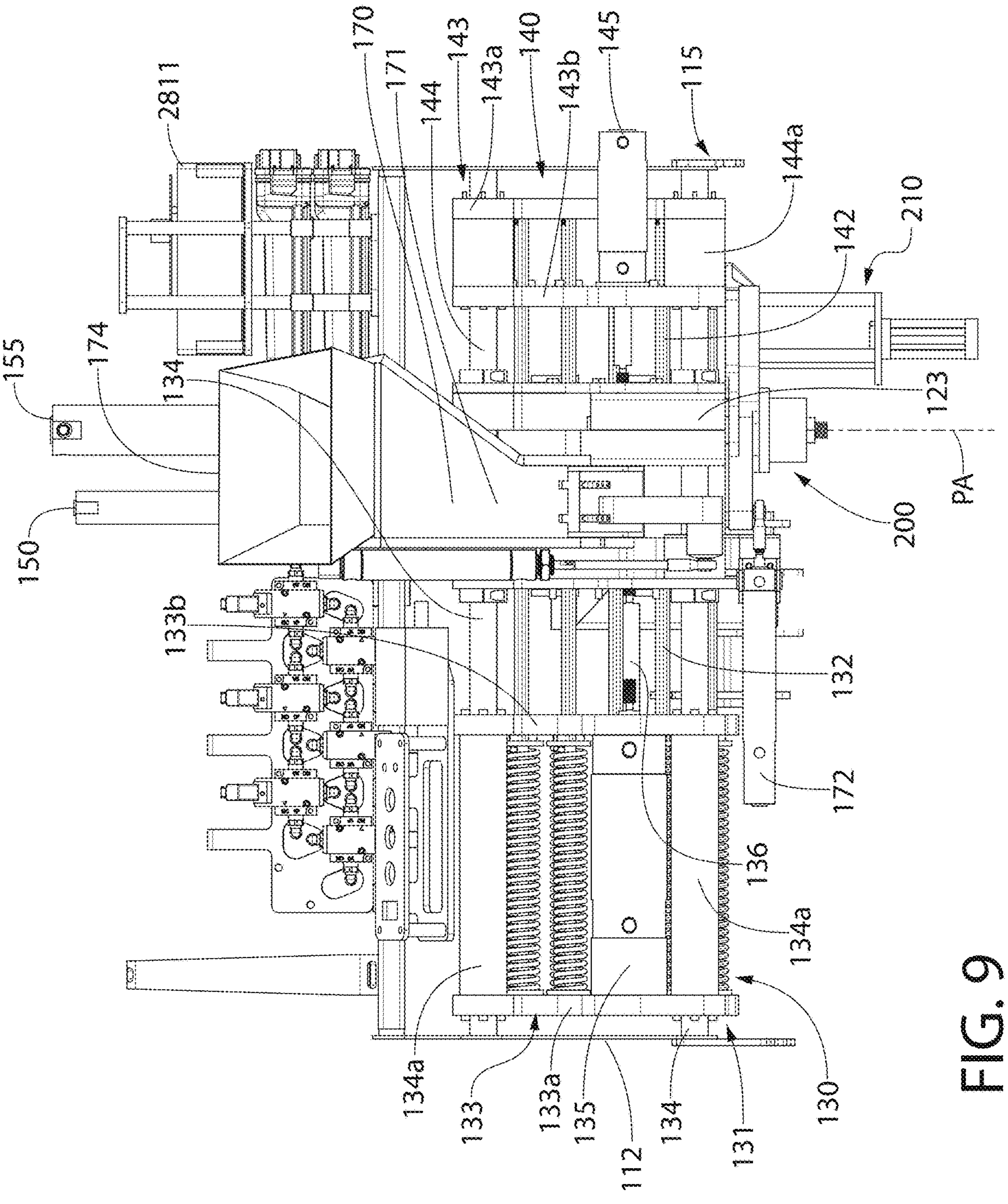
FIG. 9 is a front view thereof without the housing.
Figure 10:
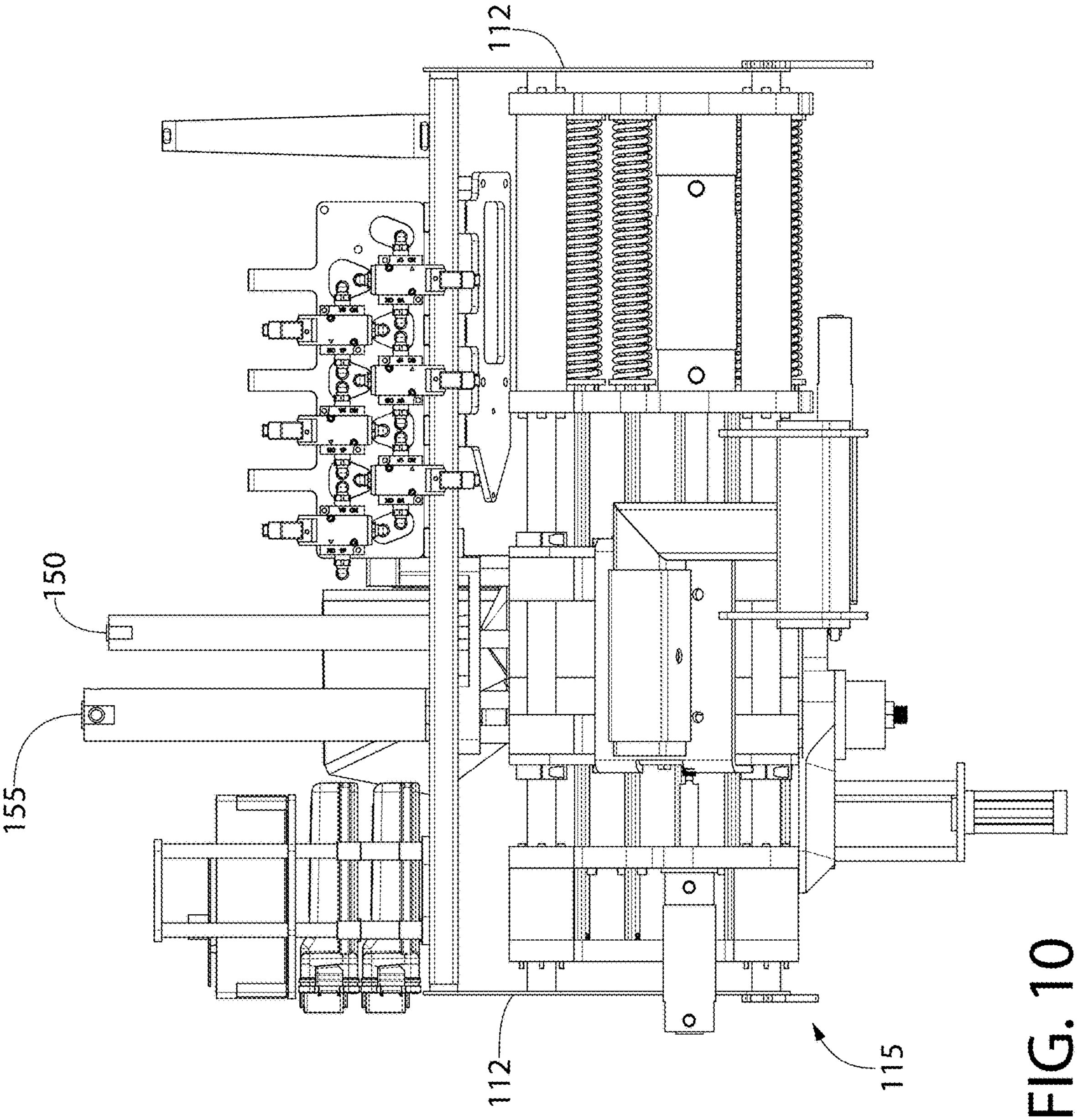
FIG. 10 is a rear view thereof.
Figure 11:
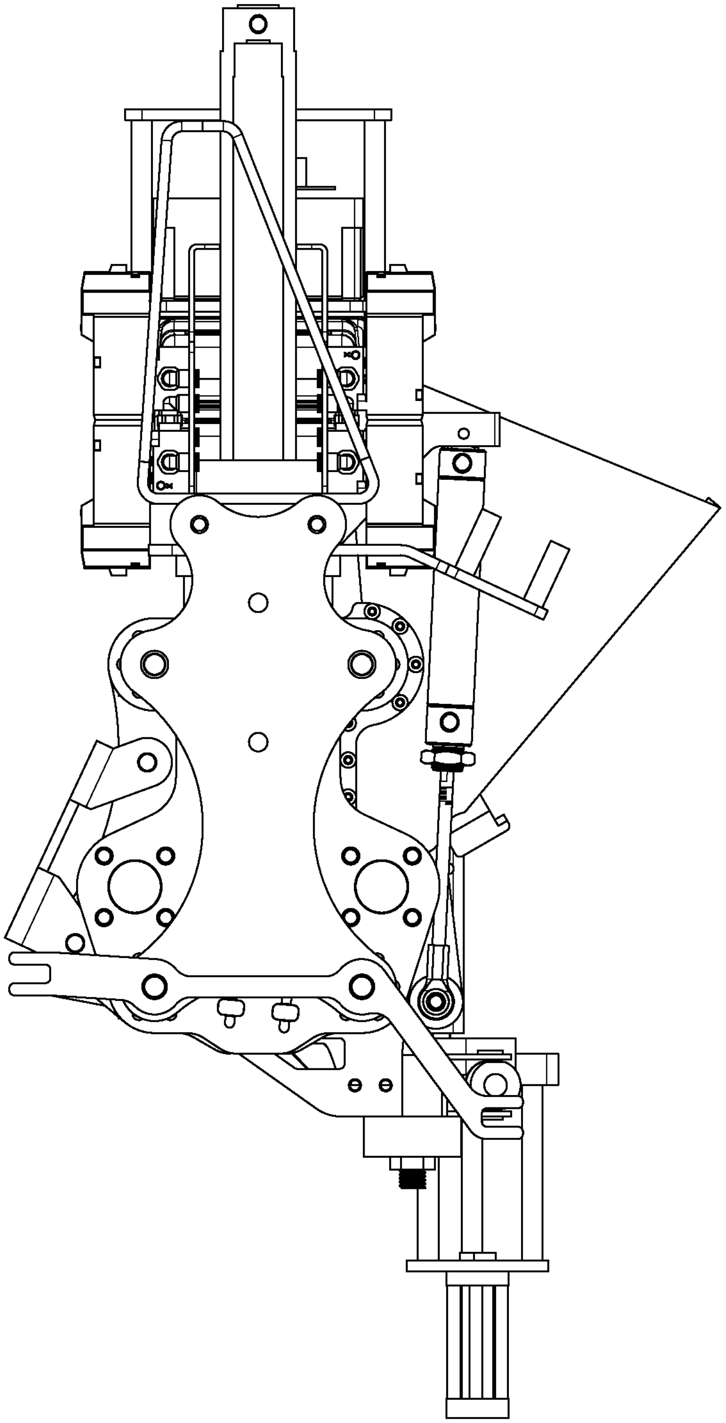
FIG. 11 is a right side view thereof.
Figure 12:
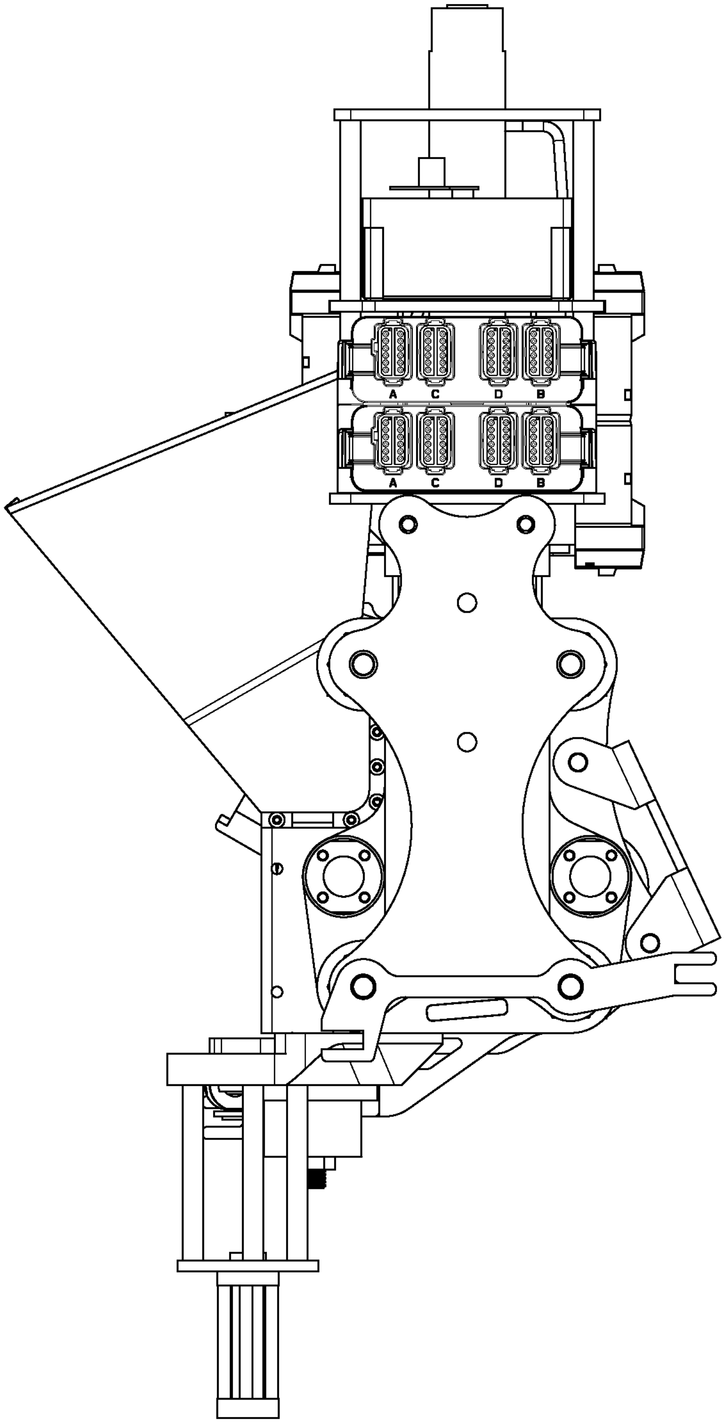
FIG. 12 is a left side view thereof.
Figure 13:
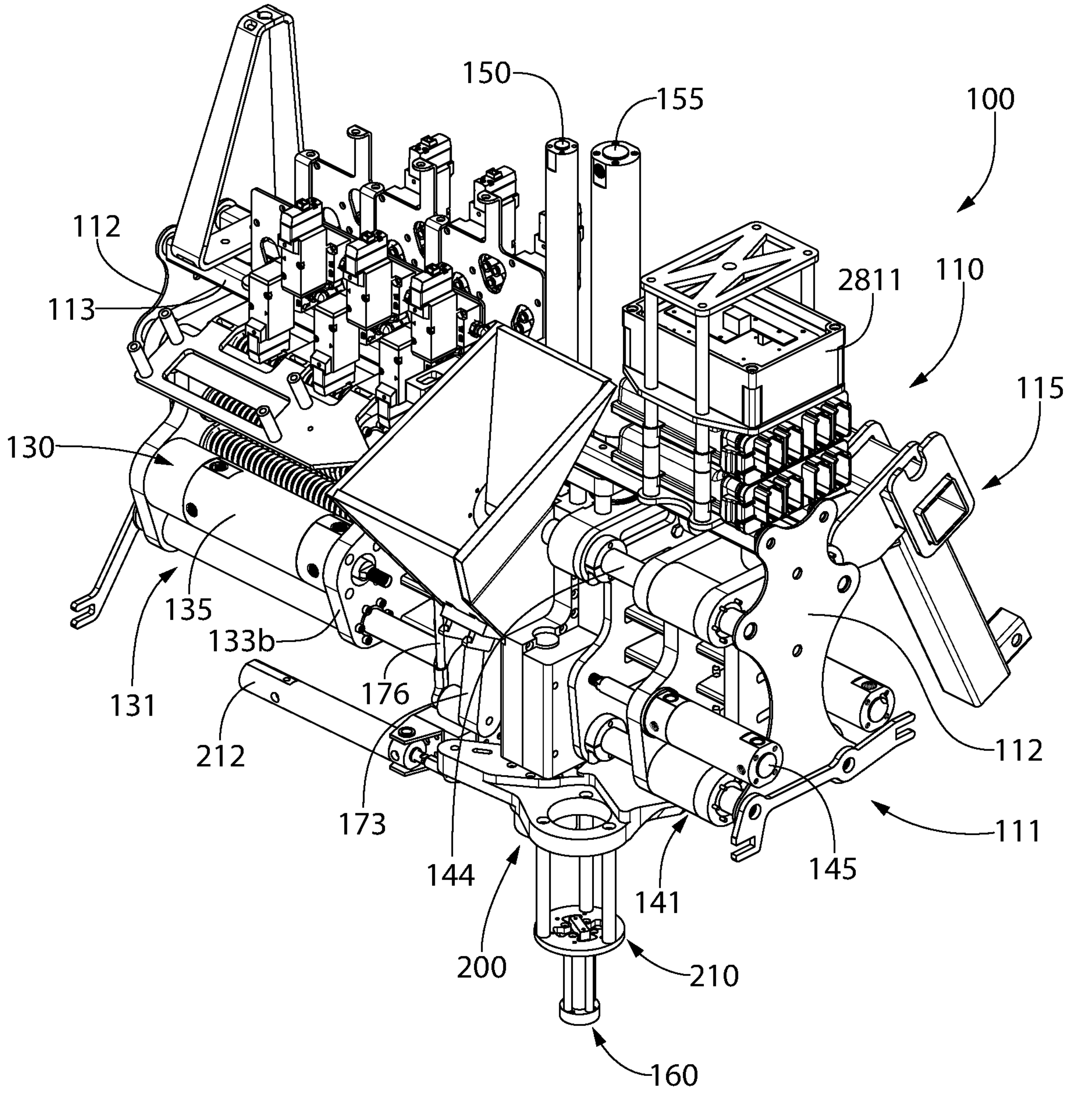
FIG. 13 is a top right front perspective view thereof.
Figure 14:
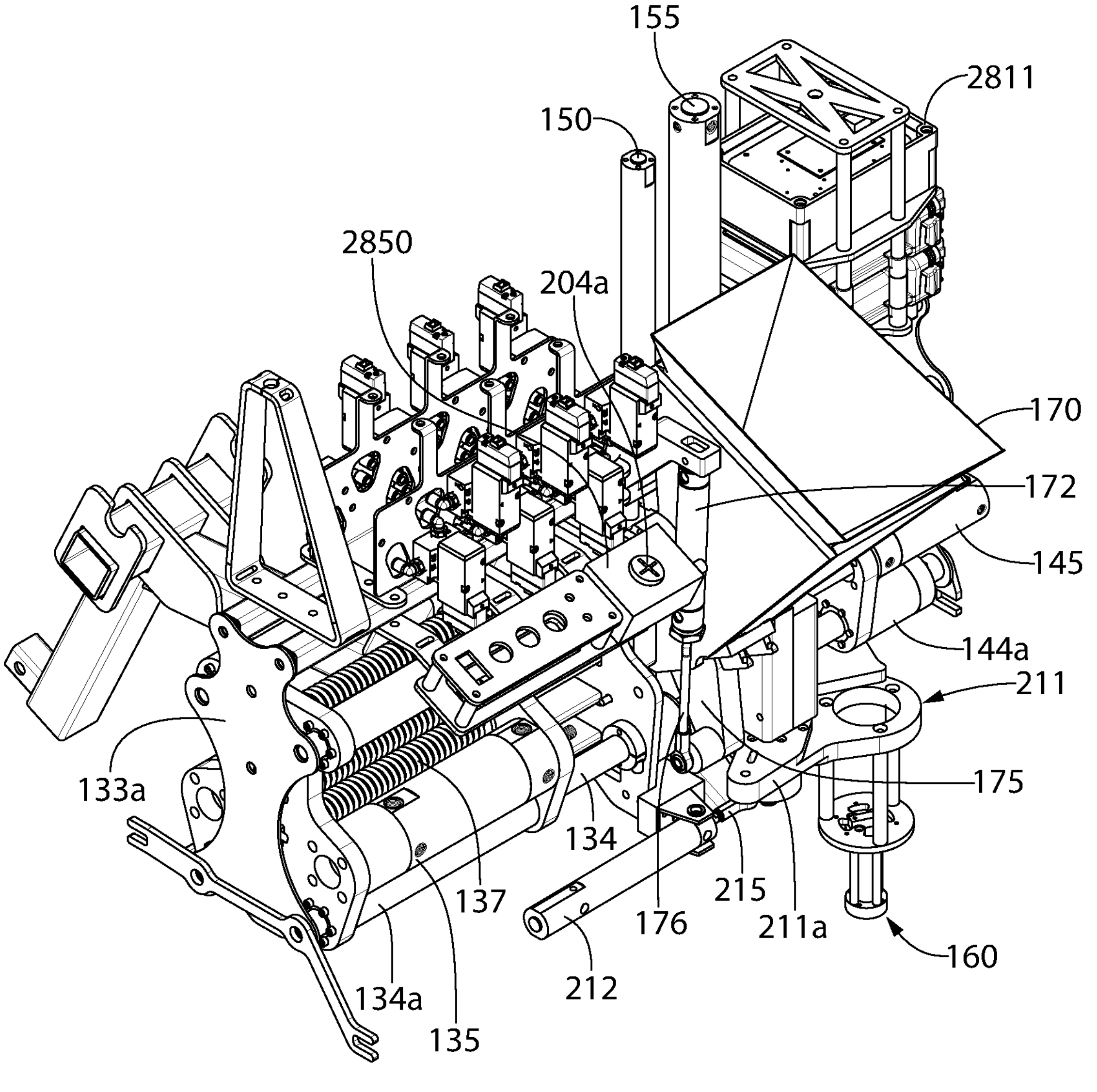
FIG. 14 is a top left rear perspective view thereof.
Figure 15:
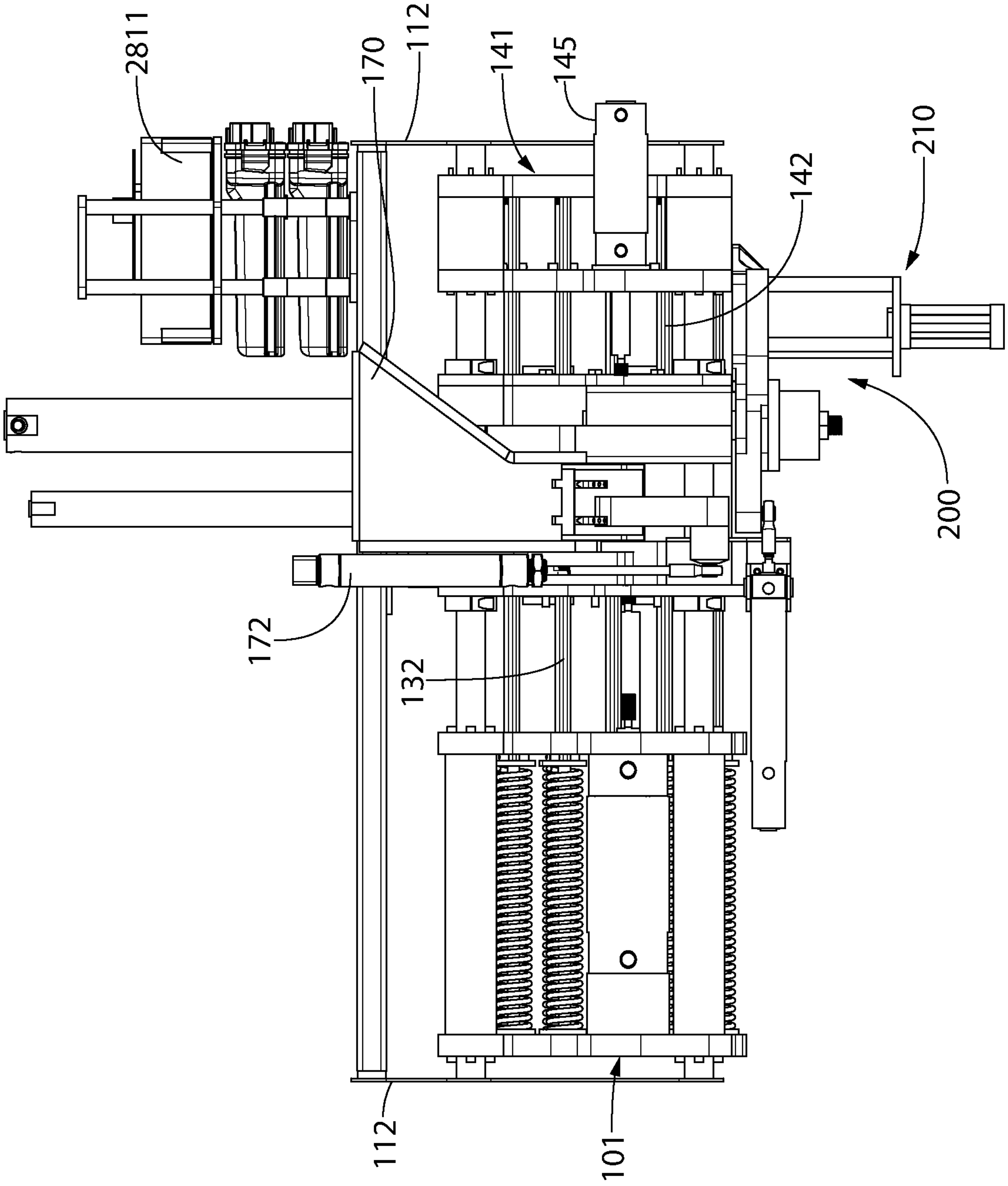
FIG. 15 is a front view thereof with some equipment removed to better show the sample blade mechanism components.
Figure 16:
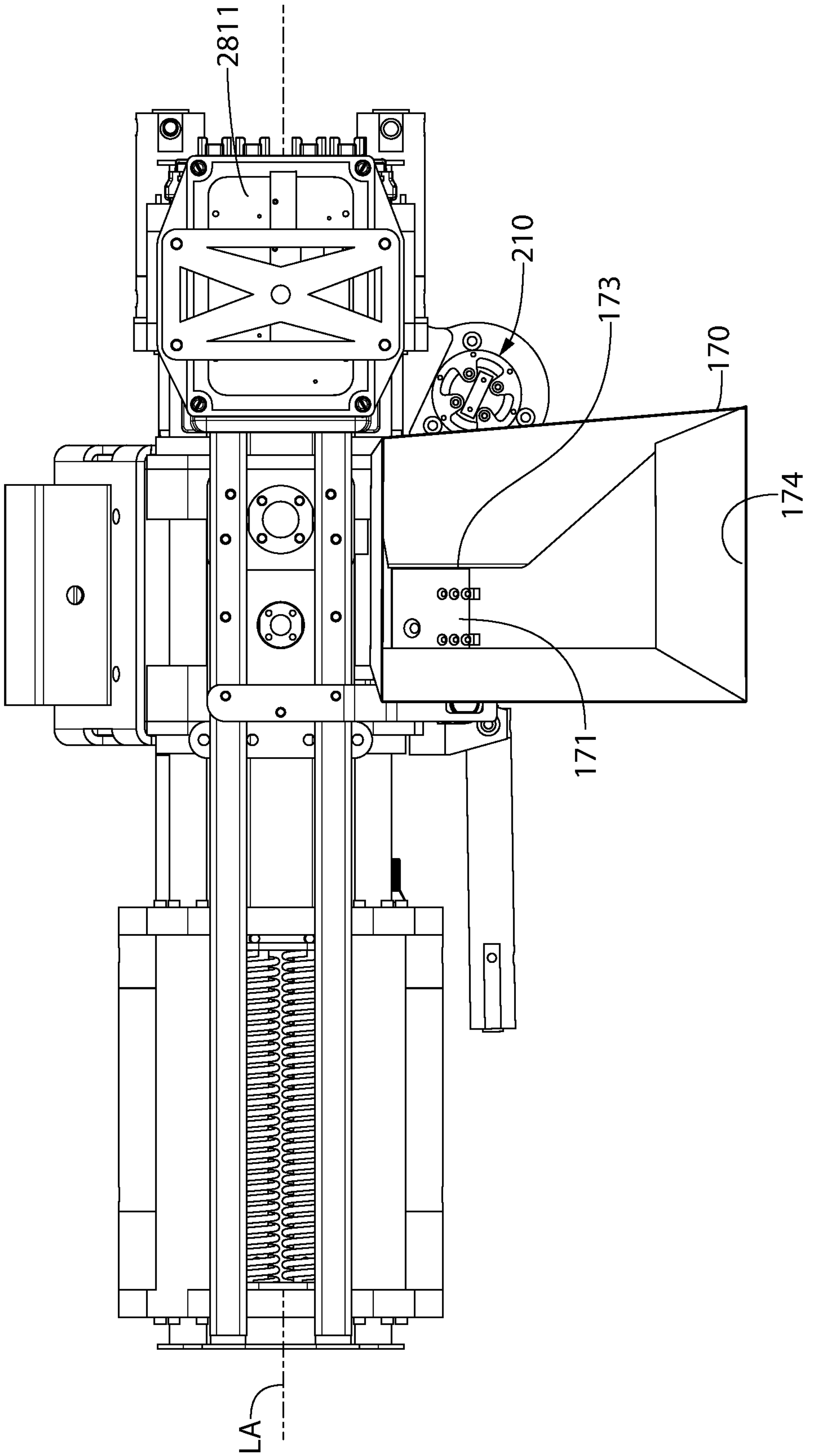
FIG. 16 is a top view thereof.
Figure 17:
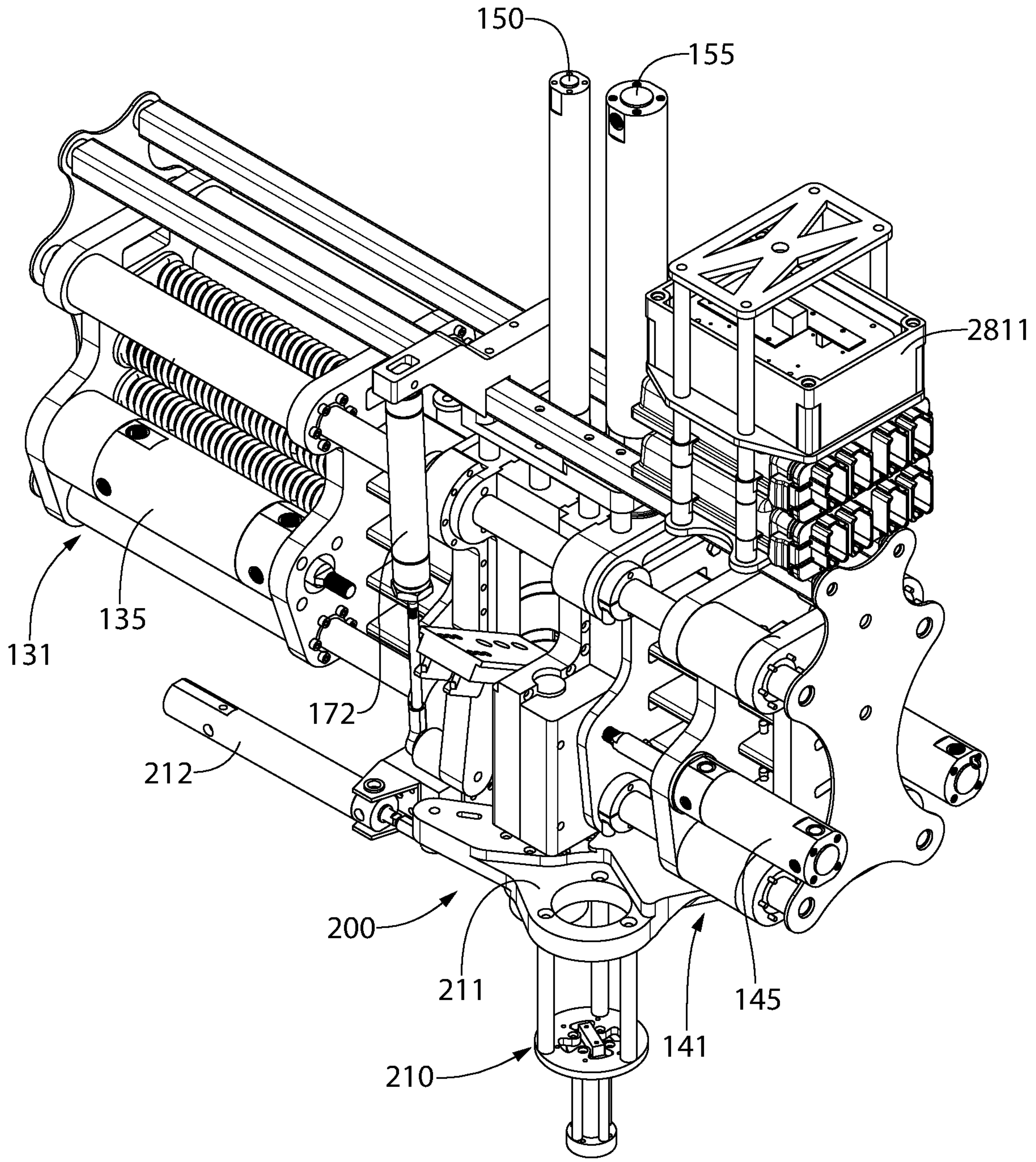
FIG. 17 is a right top front perspective view thereof.
Figure 18:
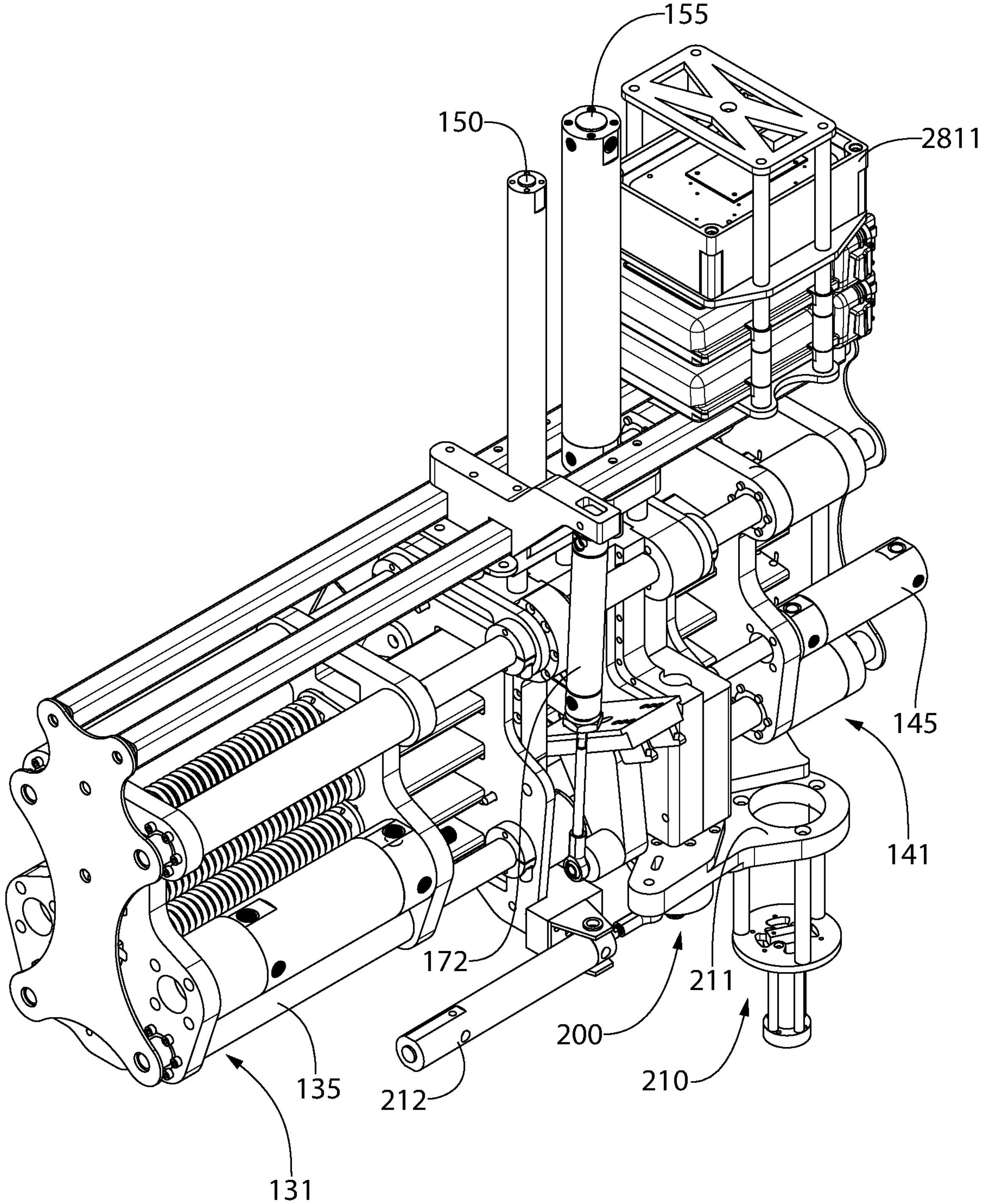
FIG. 18 is a left top front perspective view thereof.
Figure 19:
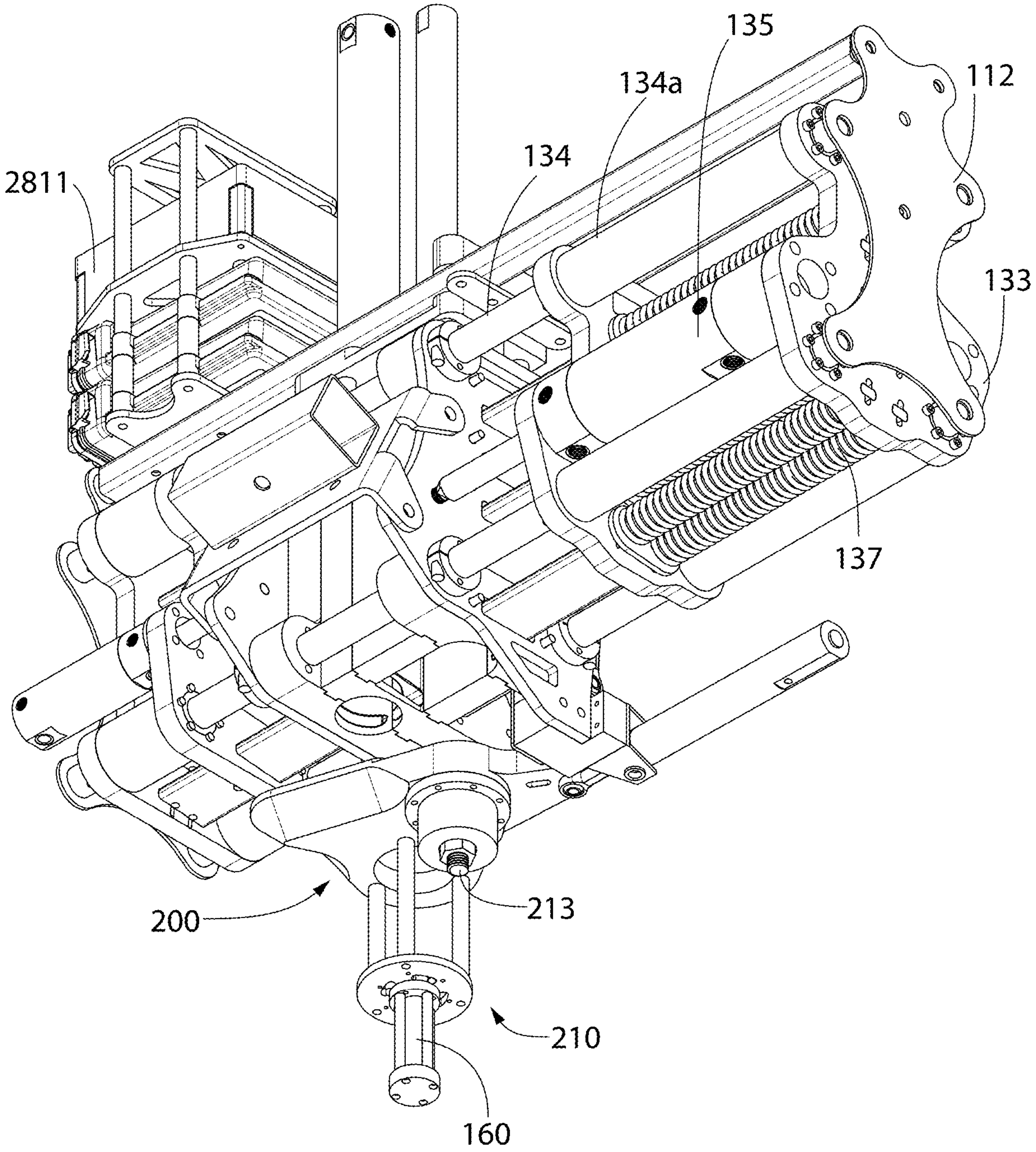
FIG. 19 is a left bottom rear perspective view with the lower portion of the apparatus support frame removed.

FIG. 2 is a high-level system block diagram showing the control system 2800 including programmable processor-based machine controller 2811 and main system controller 2820 referenced herein. System controller 2820 may include one or more processors, non-transitory tangible computer readable medium, programmable input/output peripherals, and all other necessary electronic appurtenances normally associated with a fully functional processor-based controller. Control system 2800, including controller 2820, is operably and communicably linked to the different soil sample processing and analysis systems and devices described elsewhere herein via suitable wired or wireless communication links to control operation of those systems and devices in a fully integrated and sequenced manner.

Referring to FIG. 2, the control system 2800 including programmable main system controller 2820 and/or local machine controller 2811 may be mounted on a translatable self-propelled or pulled vehicle 2802 (e.g., tractor, trailer, combine harvester, truck, ATV, etc.) including those disclosed in U.S. Application Nos. 3/260772 filed on 31 Aug. 2021; 63/260,776 filed on 31 Aug. 2021; and 63/260,777 filed on 31 Aug. 2021. The vehicle may be the same vehicle which collects the agricultural samples such as soil samples. In other embodiments, the controller may be part of a stationary workstation or facility. The sampling vehicle 2802 and its boundaries are designated by dashed box in FIG. 2 (those items within the box being mounted onboard the sampling vehicle in the illustrated embodiment). The packaging apparatus 110 may be mounted on the same vehicle 2802 or a stationary workstation as the main system controller 2820, or be separate therefrom. Local machine controller 2811 is mounted on packaging apparatus 110.

Main control system 2800 generally includes programmable controller 2820, non-transitory tangible computer or machine accessible and readable medium such as memory 2805, and a network interface 2815. Computer or machine accessible and readable medium may include any suitable volatile memory and non-volatile memory or devices operably and communicably coupled to the processor(s). Any suitable combination and types of volatile or non-volatile memory may be used including as examples, without limitation, random access memory (RAM) and various types thereof, read-only memory (ROM) and various types thereof, hard disks, solid-state drives, flash memory, or other memory and devices which may be written to and/or read by the processor operably connected to the medium.

Both the volatile memory and the non-volatile memory may be used for storing the program instructions or software. In one embodiment, the computer or machine accessible and readable non-transitory medium (e.g., memory 2805) contains executable computer program instructions which when executed by the system controller 2820 cause the system to perform operations or methods of the present disclosure including measuring properties and testing of soil and vegetative samples. While the machine accessible and readable non-transitory medium (e.g., memory 2805) is shown in an exemplary embodiment to be a single medium, the term should be taken to include a single medium or multiple media (e.g., a centralized or distributed database, and/or associated caches and servers) that store the one or more sets of control logic or instructions. The term "machine accessible and readable non-transitory medium" shall also be taken to include any medium that is capable of storing, encoding or carrying a set of instructions for execution by the machine and that cause the machine to perform any one or more of the methodologies of the present disclosure. The term "machine accessible and readable non-transitory medium" shall accordingly also be taken to include, but not be limited to, solid-state memories, optical and magnetic media, and carrier wave signals.

Network interface 2815 may be configured to communicate with the soil or other bulk agricultural material collection system on the vehicle which is retrieving samples (e.g., soil, etc.) from the agricultural field, and sample post-packaging/containerizing systems such as a sample slurry preparation, processing, and chemical analysis systems and devices (collectively represented by box 2803 in FIG. 2).

The agricultural sample packaging system 100 machine network 2810 can include at least one local microprocessor-based machine controller 2811 and a plurality of different type sensors 2812. Sensors 2812 may be operably and communicably linked to local machine controller 2811 and optionally system controller 2820 through controller 2811; each controller being configured to receive and send data/signals from/to the sensors. In some embodiments, packaging apparatus 110 with local machine controller 2811 mounted thereto may be one vehicle which traverses the agricultural field along with the bulk sample collection system and main system controller 2820 may be located on a remote separate vehicle or in a stationary location.

The sensors 2812 may include full sample tube sensor 220 previously described herein, and other linear positional or status sensors 2812*a* integrated with cap actuator 160, compaction and sample transfer piston-plungers 150 and 155 respectively, sample blade mechanism actuator 135, and cleaning blade mechanism 140 actuator 145 to apprise the system controller 2820 of the position or status of the those devices (e.g., piston-plungers up or down, sample and cleaning blades mechanism inserted or withdrawn from die block 124, etc.). The status sensors may also include accelerometers to provide feedback to the system controller 2820 that a device of the packaging system physically moved in response to an action/motion initiated by a control signal from the controller (e.g. sample and cleaning blades mechanism inserted/withdrawn, piston-plungers up/down, etc.). Geolocation tracking sensors such as GPS (global positioning system) may also be included if the sample packaging system is mounted on a vehicle which travels across the agricultural field. Accordingly, the control system knows the operational status, position, and condition of each of at least the major components of the agricultural sample packaging system 100 under its control at any given moment. This information is used by the machine network controller 2811 and/or system controller 2820 to automatically control the entire agricultural sample packing operations of the packaging apparatus 110 via machine network 2810, and detect if an operational malfunction of packaging apparatus has occurred. This is particularly useful if the apparatus 110 is being controlled from a remote location via a communicably linked laptop, tablet, cell phone, etc. In addition, the GPS sensor 2854 communicably linked to the packaging machine network 2810 as seen in FIG. 2 permits the machine and/or system controllers 2811, 2820 to pinpoint where in the agricultural field the soil sample was collected if the sample collection system equipment is used alongside the packaging apparatus 110 when the sample is collected and then packaged. The RFID tag associated with each packaged sample permits the associated GPS geolocation information to be tracked for each sample.

The local machine controller 2811 which may be mounted onboard packaging apparatus 110 controls operation of the agricultural sample packaging system 100 in cooperation with system controller 2820 in one embodiment. In other embodiments, machine controller 2811 may control operation of the packaging apparatus 110 alone via preprogrammed control logic/instructions if the controller is not linked to a main system controller 2820, or still be communicably coupled to the main system controller for data/information exchange and programming, but not for purposes of direct control of the sample packaging system components.

Local machine controller 2811 includes all of the usual appurtenances and auxiliary electronic devices similar to main system controller 2820 (e.g., memory, power supply, etc.) for forming a normal fully functional microprocessor-based control system configured to control operation of packaging apparatus 110.

With continuing reference to FIG. 2, the RFID scanner or reader 2850 previously described herein which is mounted on or may be nearby packaging apparatus 110 is operably and communicably coupled to packing system machine network 2810 via communication link 2852. Communication link 2852 may be wired or wireless. The unique RFID tag 2850*a* associated with each collected and packaged agricultural sample in sample tube 202 may be automatically scanned and read in one embodiment when end cap 204*a* which contains the tag is placed on the reader at the start of the sample tube filling operation. The tag may be read in some embodiments when the Fill Tube actuator 2811*a* is manually activated (e.g., pushed or thrown) by the packaging apparatus operator. This ensures that the correct geolocation is associated with the sample as the operator and vehicle should still be in the same physical location where the soil sample was collected from the agricultural field at that time. As previously described herein, the RFID tag may alternatively be located on the cylindrical body of the sample tube 202 or slideable plunger cap 204*b* inside the tube and read by controller 2811 of the machine network 2810. The unique sample ID information is transmitted to packaging system machine controller 2811, which may in turn may share that information with the main system controller 2820. The unique RFID tag associated with each sample tube 202 and its sample contents allows the sample to be tracked from initial packaging, other staging and processing of the sample pending chemical system, and finally chemical analysis. With use of the GPS information collected for with each sample that identifies the exact location in the agricultural field where the sample was collected, the chemical analysis results of the analytes of interest may be readily correlated back to a particular location or region in the field to determine the soil amendments necessary there.

The packaging system 100 may be locally controlled by machine controller 2811, which in turn is controlled and programmed by an personal electronic device (PED) 2851 with onboard microprocessor, memory, power supply, and all other usual auxiliary device and components associated with such devices. Such personal electronic devices 2851 may include for example without limitation a tablet, laptop, notebook, cell phone, and other similar devices located onboard vehicle 2802. Device 2851 acts as a user interface and input device which initiates automated operation of the agricultural sample packaging system 100 and packaging apparatus 110 via machine controller 2811. Personal electronic device 2851 may have a graphic user interface such as a touchscreen for such a purpose. Personal electronic device 2851 is operably and communicably coupled to packing system machine network 2810 via communication link 2853, which may be wired or wireless.

It bears noting that in embodiments where the entire agricultural sampling collection, packaging, and chemical analysis systems are mounted on a single field vehicle 2802 for in-situ analysis of the samples, the agricultural sample packaging system 100 may be controlled by the main system controller 2820 in lieu of a separate machine controller 2811. In such a case, the array of packaging system sensors 2812 may communicate directly with system controller 2820.

The network interface 2815 can be configured for wired and/or wireless bidirectional communications which may include at least one of a GPS transceiver, a WLAN transceiver (e.g., WiFi), an infrared transceiver, a Bluetooth transceiver, Ethernet, Near Field Communications, or other suitable communication interfaces and protocols for communications with the other devices and systems including the agricultural sample packaging system 100. The network interface 2815 may be integrated with the control system 2800 as illustrated in FIG. 2, the machine network 2810, or elsewhere. The I/O (input/output) ports 2829 of control system 2800 (e.g., diagnostic/on board diagnostic (OBD) port) enable communication with another data processing system or device (e.g., display devices, sensors, etc.).

The programmable controller 2820 may include one or more microprocessors, processors, a system on a chip (integrated circuit), one or more microcontrollers, or combinations thereof. The processing system includes processing logic 2826 for executing software instructions of one or more programs and a communication module or unit 2828 (e.g., transmitter, transceiver) for transmitting to and receiving communications from the machine network 2810 of sampling machine or vehicle 2802 via direct communication link 2831 or network interface 2815. The communication unit 2828 may be integrated with the control system 2800 (e.g. controller 2820) or be separate from the controller. In one embodiment, the communication unit 2828 may be in operable data communication with the machine/vehicle network 2810 via a diagnostic/OBD port of the I/O ports 2829.

Programmable processing logic or instructions 2826 of the control system 2800 which directs the operation of system controller 2820 including one or more processors may process the communications (i.e. data/information) received via the communication unit 2828 or network interface 2815 from the agricultural sample packaging system 100 including without limitation sensor associated with the status and operation of the packaging apparatus 110 and components thereof under the control of programmable system controller 2820. The memory 2805 of control system 2800 is configured for preprogrammed variable or setpoint/baseline values, storing collected data, and computer instructions or programs for execution (e.g. software 2806) used to control operation of the controller 2820, which in turn controls operation of packaging apparatus 110 and sample processing/analysis devices 2803. The memory 2805 can store, for example, software components such as testing software for analysis of soil and vegetation samples for performing operations of the present disclosure, or any other software application or module, images 2808 (e.g., captured images of crops), alerts, maps, etc. The system 2800 can also include an audio input/output subsystem (not shown) which may include a microphone and a speaker for, for example, receiving and sending voice commands or for user authentication or authorization (e.g., biometrics).

In some embodiments of agriculture sample packaging system 100 can further preferably include a sensing system 2812 comprising a plurality or array of different type sensors useful and associated with packaging and tracking the soil sample. The sensing system and its sensors are in data and control communication with packaging system machine controller 2811 and/or main system controller 2820. Other sensors which communicate with system controller 2820 may be associated with operation of the sample collection apparatus 8002 and components thereof including various equipment positional or orientation sensors, proximity sensors, etc. The agricultural material sample packaging system in combination with sensing system can provide complete automated control of the sample collection apparatus 8002 via the packaging system machine controller 2811 and/or main system controller 2820.

The main system controller 2820 communicates bi-directionally with memory 2805 via communication link 2830, machine or sample collection system network 2810 directly via communication link 2831 and/or alternatively via communication link 2837 associated with network interface 2815, the network interface 2815 via communication link 2832, display device 2830 and optionally a second display device 2825 via communication links 2834, 2835, and I/O ports 2829 via communication links 2836. System controller 2820 further communicates with the soil sample processing and analysis systems and devices 2803 via the wired/wireless communication links 5752 previously described herein via the network interface 2815 and/or directly as shown.

Display devices 2825 and 2830 can provide visual user interfaces for a user or human operator. The operator may be located onboard the mobile vehicle in one embodiment which traverses the agricultural field or at a remote operating position or station distal from the packaging apparatus 110. The display devices may include display controllers with onboard programmable microprocessors. In some embodiments, the computerized display device 2825 may therefore be a portable tablet device, cell phone, laptop, notebook, or other processor-based computing device with a touchscreen and/or keyboard (software based or physical hardware) that acts as an input/output device and which displays data (e.g., equipment status and position, and other relevant operational and maintenance information) and communicates with controller 2820. The computerized display device 2825 therefore receives input from the user or operator for controlling packaging apparatus 110.

The agricultural sample packaging, staging, and unloading systems disclosed herein are usable with and may form part of an overall agricultural sampling and analysis systems, such as but not limited to those described in U.S. Patent Application Publication No. 2018/0124992A1 and PCT Publication No. WO2020/012369, and other systems are described in U.S. Application Nos. 62/983,237, filed on 28 Feb. 2020; 63/017,789, filed on 30 Apr. 2020; 63/017,840, filed on 30 Apr. 2020; 63/018,120, filed on 30 Apr. 2020; 63/018,153, filed on 30 Apr. 2020; 63/191,147, filed on 20 May 2021; 63/191,159, filed on 20 May 2021; 63/191,166, filed on 20 May 2021; 63/191,172, filed on 20 May 2021; Ser. No. 17/326,050, filed on 20 May 2021; 63/191,186, filed on 20 May 2021; 63/191,189, filed on 20 May 2021; 63/191,195, filed on 20 May 2021; 63/191,199, filed on 20 May 2021; 63/191,204, filed on 20 May 2021; Ser. No. 17/343,434, filed on 9 Jun. 2021; 63/208,865, filed on 9 Jun. 2021; Ser. No. 17/343,536, filed on 9 Jun. 2021; 63/213,319, filed on 22 Jun. 2021; 63/260,772, filed on 31 Aug. 2021; 63/260,776, filed on 31 Aug. 2021; 63/260,777, filed on 31 Aug. 2021; 63/245,278, filed on 17 Sep. 2021; 63/264,059, filed on 15 Nov. 2021; 63/264,062, filed on 15 Nov. 2021; 63/264,065, filed on 15 Nov. 2021; 63/268,418, filed on 23 Feb. 2022; 63/268,419, filed on 23 Feb. 2022; 63/268,990, filed on 8 Mar. 2022; 63/269,060, filed 9 Mar. 2022; 63/269,064, filed 9 Mar. 2022; 63/365,243, filed 24 May 2022; 63/365,244, filed 24 May 2022; 63/366,673, filed 20 Jun. 2022; 63/366,674, filed 20 Jun. 2022; 63/369,722, filed 28 Jul. 2022; 63/369,724, 28 Jul. 2022; 63/369,765, filed 28 Jul. 2022; 63/369,988, filed 1 Aug. 2022; 63/370,072, filed 1 Aug. 2022; 63/370,077, filed 1 Aug. 2022; 63/370,081, filed 1 Aug. 2022; and PCT/IB2021/051076, filed on 10 Feb. 2021; PCT Application Nos. PCT/IB2021/051077, filed on 10 Feb. 2021; PCT/IB2021/052872, filed on 7 Apr. 2021; PCT/IB2021/052874, filed on 7 Apr. 2021; PCT/IB2021/052875, filed on 7 Apr. 2021; PCT/IB2021/052876, filed on 7 Apr. 2021. Other sampling systems are described in U.S. Application Nos. 62/983,237, filed on 28 Feb. 2020; 63/017,789, filed on 30 Apr. 2020; 63/017,840, filed on 30 Apr. 2020; 63/018,120, filed on 30 Apr. 2020; 63/018,153, filed on 30 Apr. 2020; PCT/IB2021/051076, filed on 10 Feb. 2021; and PCT Application Nos. PCT/IB2021/051077, filed on 10 Feb. 2021; PCT/IB2021/052872, filed on 7 Apr. 2021; PCT/IB2021/052874, filed on 7 Apr. 2021; PCT/IB2021/052875, filed on 7 Apr. 2021; PCT/IB2021/052876, filed on 7 Apr. 2021.

Examples—Sample Packaging Apparatus

The following are non-limiting examples of the sample packaging apparatus.

Example 1—an agricultural sample packaging apparatus comprising: a bulk material chamber configured for receiving a sample; a sample collection chamber; a die block disposed between the bulk material and sample collection chambers, the die block including a plurality of through die slots in communication with the bulk material and sample collection chambers; a sample blade mechanism comprising a plurality of elongated sample blades movably insertable through the bulk material chamber and die slots from a first side of the die block, wherein the sample blades are operable to extrude the sample from the bulk material chamber through the die slots and into the sample collection chamber.

Example 2—the apparatus according to Example 1, wherein the apparatus comprises a rotatable carousel including a container holder configured to removably hold a sample container.

Example 3—the apparatus according to Example 2, wherein the carousel is rotatable between an inward closed position in which the sample container is positioned beneath the sample collection chamber and an outward open position in which the sample container is not beneath the sample collection chamber.

Example 4—the apparatus according to any one of Examples 2 to 3, wherein the apparatus comprises a cleaning blade mechanism comprising a plurality of elongated cleaning blades movably insertable through the sample collection chamber and die slots from a second side of the die block.

Example 5—the apparatus according to any one of Examples 2 to 4, further comprising a compaction piston-plunger configured to compress the sample in the bulk material chamber.

Example 6—the apparatus according to Example 5, further comprising a sample transfer piston-plunger configuration to force the sample downwards and outwards from the sample collection chamber.

Example 7—the apparatus according to any one of Examples 2 to 6, further comprising a programmable controller configured to control operation of the sample packaging apparatus.

Example 8—the apparatus according to any one of Examples 2 to 7, wherein the sample is soil.

Example 9—the apparatus according to any one of Examples 2 to 8, wherein the apparatus comprises a support frame configured for mounting to a mobile vehicle.

Example 10—the apparatus according to Example 1, wherein each of the sample blades comprises a compression spring.

Example 11—the apparatus according to Example 10, wherein each sample blade comprises a bifurcated end comprising a pair of the springs which act on a pair of spaced apart spring plates coupled to each sample blade.

Example 12—a method for packaging an agricultural sample comprising: adding a sample to a bulk material chamber; inserting a plurality of sample blades through the bulk material chamber; forcing the sample through a die block with the sample blades forming sample material plugs; and collecting the sample material plugs in a sample collection chamber.

Example 13—the method according to Example 12, further comprising before the insertion step, a step of rotating a carousel holding a sample container and positioning the sample container beneath the sample collection chamber.

Example 14—the method according to Example 13, further comprising depositing the sample material plugs in the sample container.

Sample Unloading System

Figure 45:
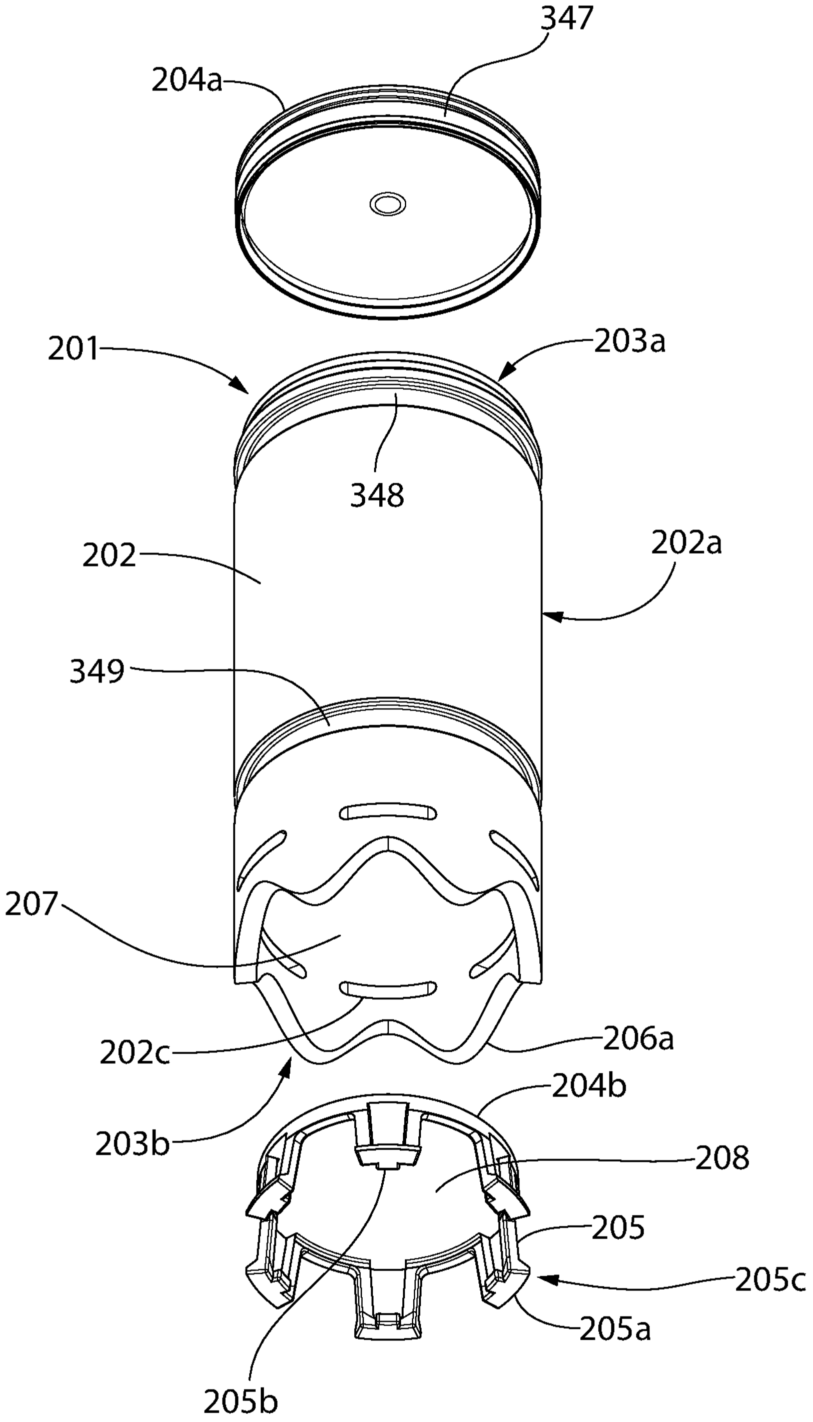
FIG. 45 is a bottom exploded perspective view of the sample container.
Figure 47:
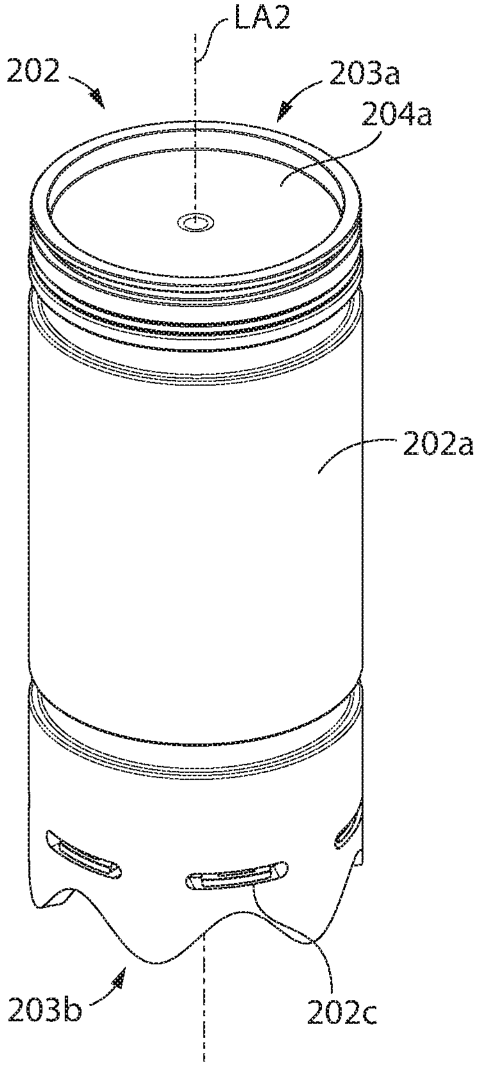
FIG. 47 is a top perspective view of the sample container.
Figure 48:
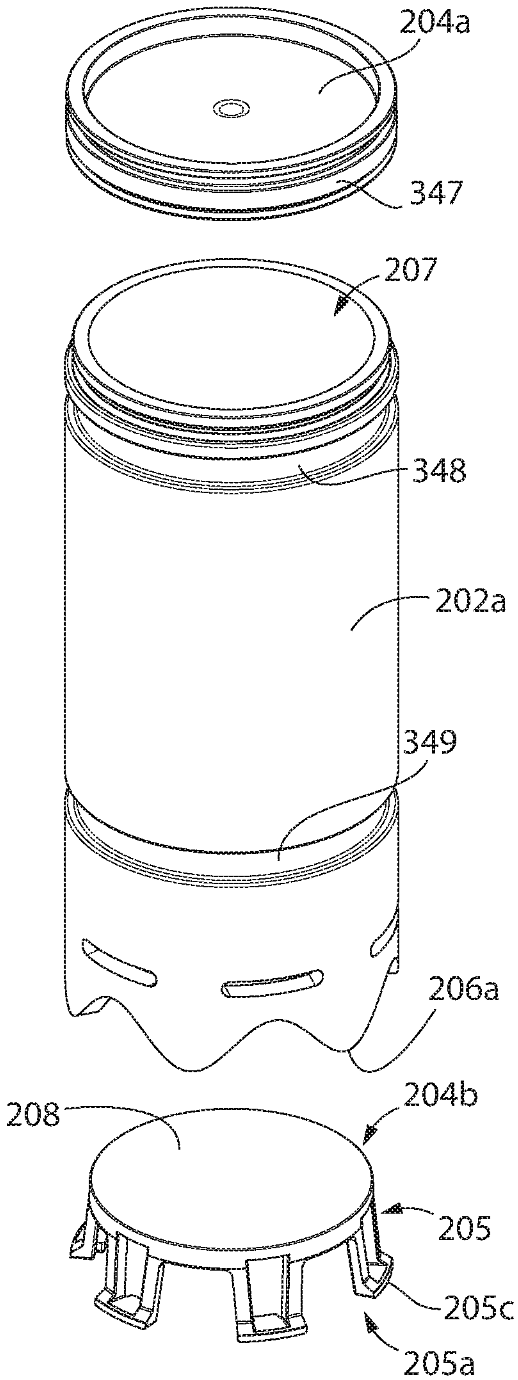
FIG. 48 is an exploded perspective view thereof.
Figure 49:
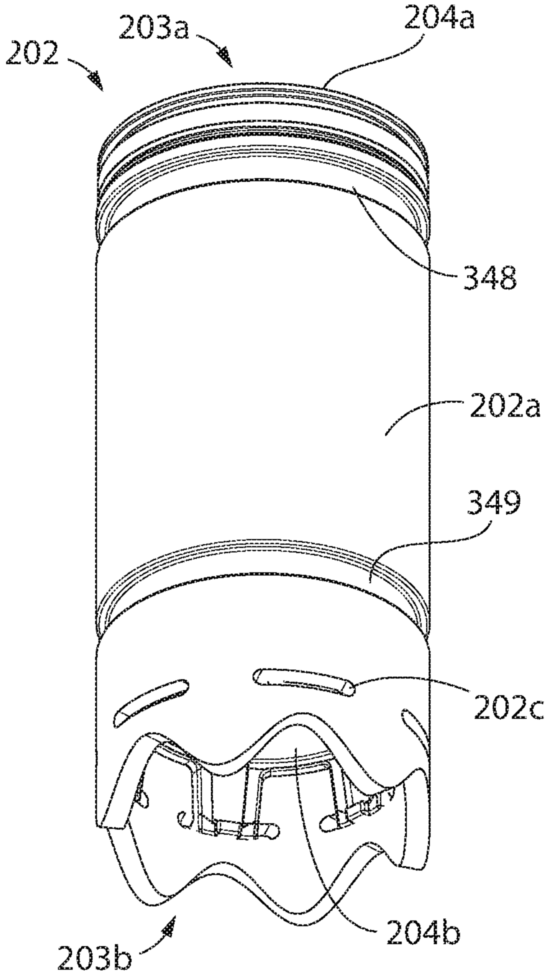
FIG. 49 is a bottom exploded perspective view thereof.
Figure 110:
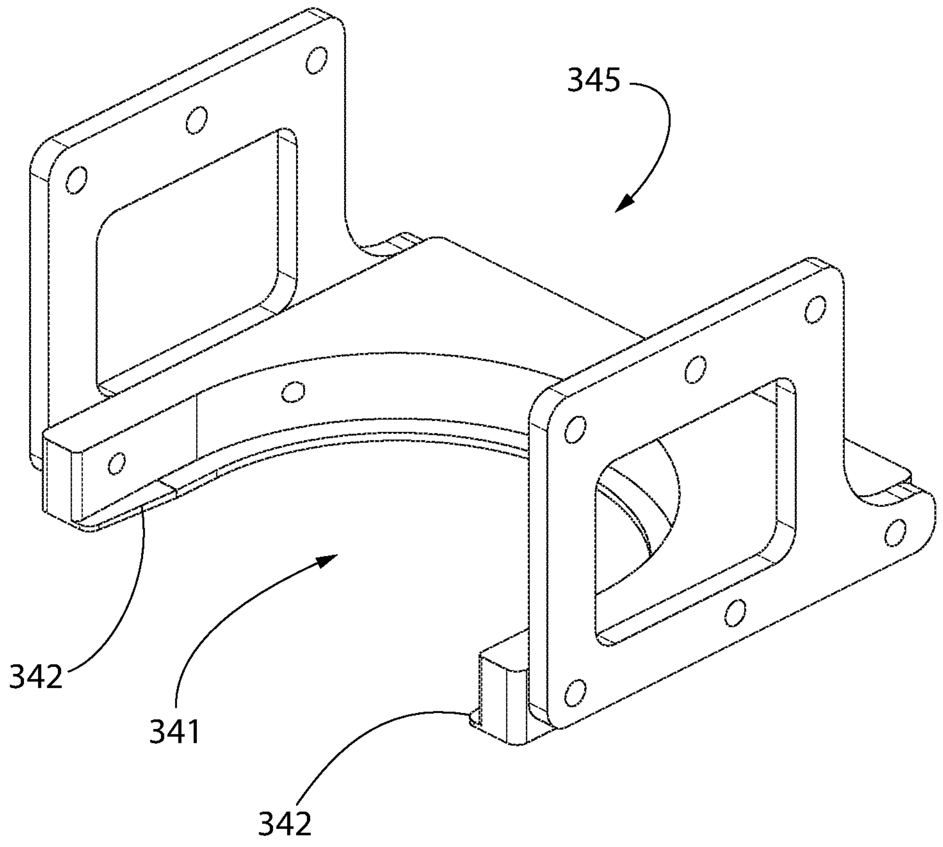
FIG. 110 is a perspective view of the decapper of the unloading apparatus.

FIGS. 45 and 47-110 depict one non-limiting embodiment of an agricultural sample handling system and various parts thereof comprising an unloading system 300 according to the present disclosure. General reference is intended to these FIGURES below. Specific FIGURES may be called out where appropriate which illustrate specific aspects or features of the unloading system being discussed.

The unloading system 300 is configured and operable to both stage the sample containers 201 in a sequenced manner such as sample tubes 202 packed with the collected agricultural samples (e.g. soil, plant, etc.) by sample packaging system 100 as described above, and then unload the samples from the tubes for further processing and eventual chemical analysis.

System 300 generally includes a sample staging rack 302 and unloading apparatus 304 operably coupled to the rack. Sample transfer mechanism 306 is configured and operable to transfer the sample container 201 such as sample tube 202 from the staging rack to the unloading apparatus. The transfer mechanism may load a single tube at a time into the unloading apparatus 304 in a serial manner for unloading in one non-limiting embodiment. Staging rack 302 and unloading apparatus 304 are physically closely coupled and adjacent each other in a preferred but non-limiting embodiment. In some embodiments, the rack may be physically coupled to the unloading apparatus, but in other embodiments may be simply located adjacent thereto. Each of these features and aspects of system 300 and operation to stage and remove the samples from the sample tubes 202 will now be described in further detail below.

Figure 57:
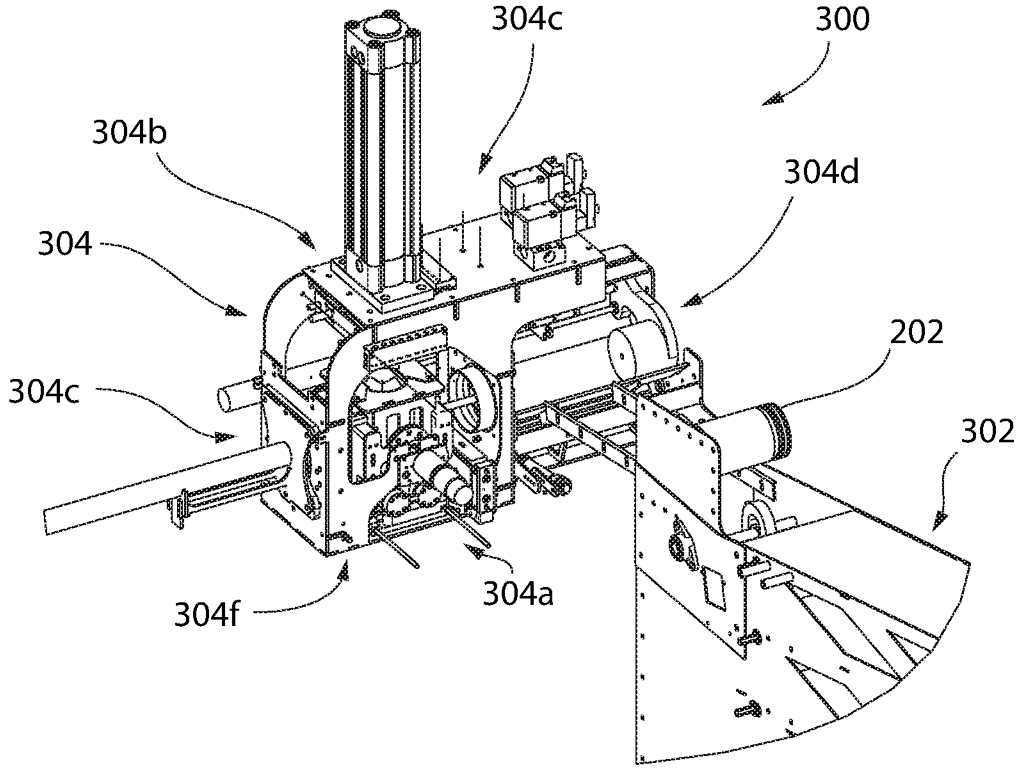
FIG. 57 is an enlarged detail taken from FIG. 56.
Figure 59:
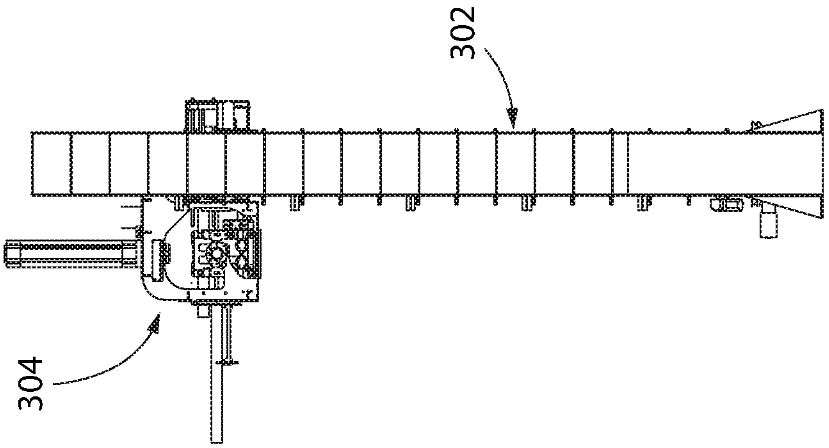
FIG. 59 is a distal end view thereof.
Figure 58:
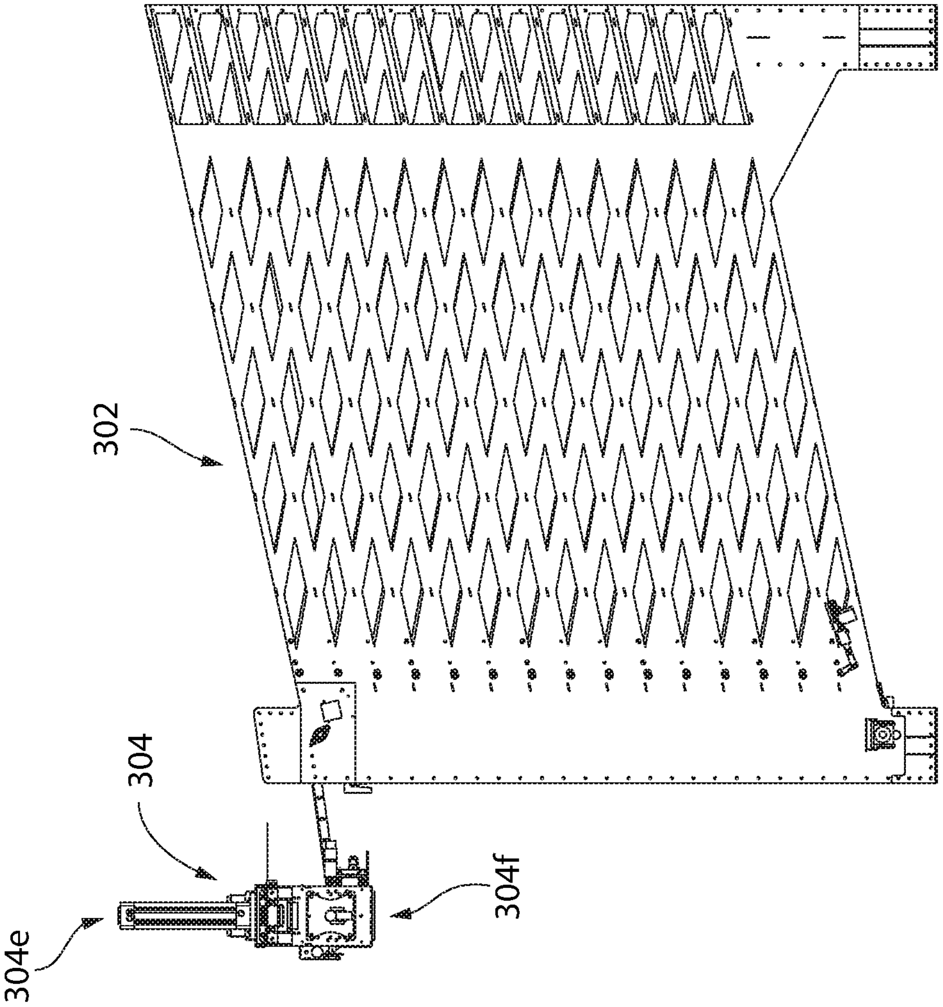
FIG. 58 is a side view of the sample unloading system.
Figure 60:
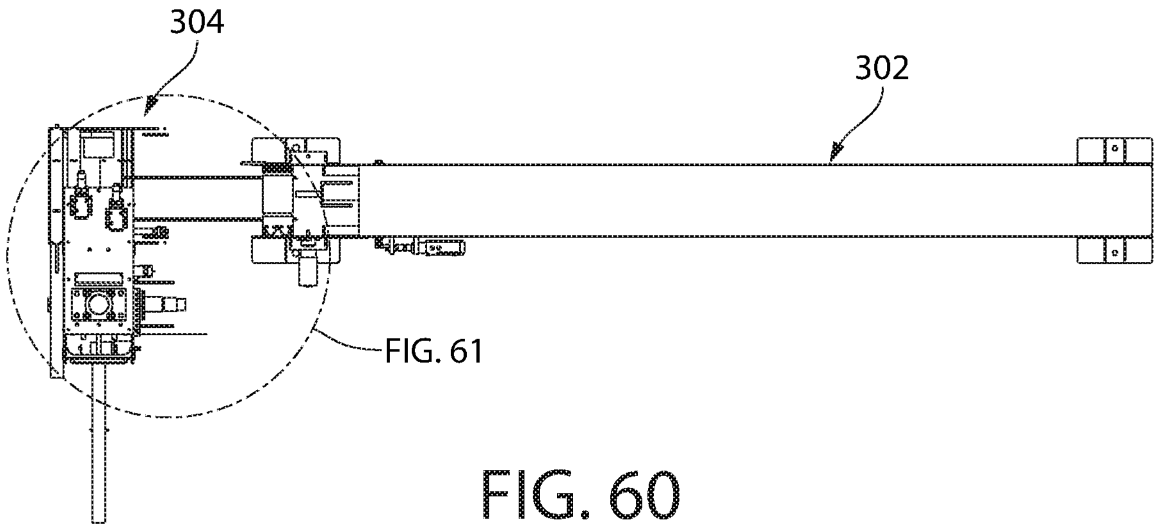
FIG. 60 is a top view thereof.
Figure 61:
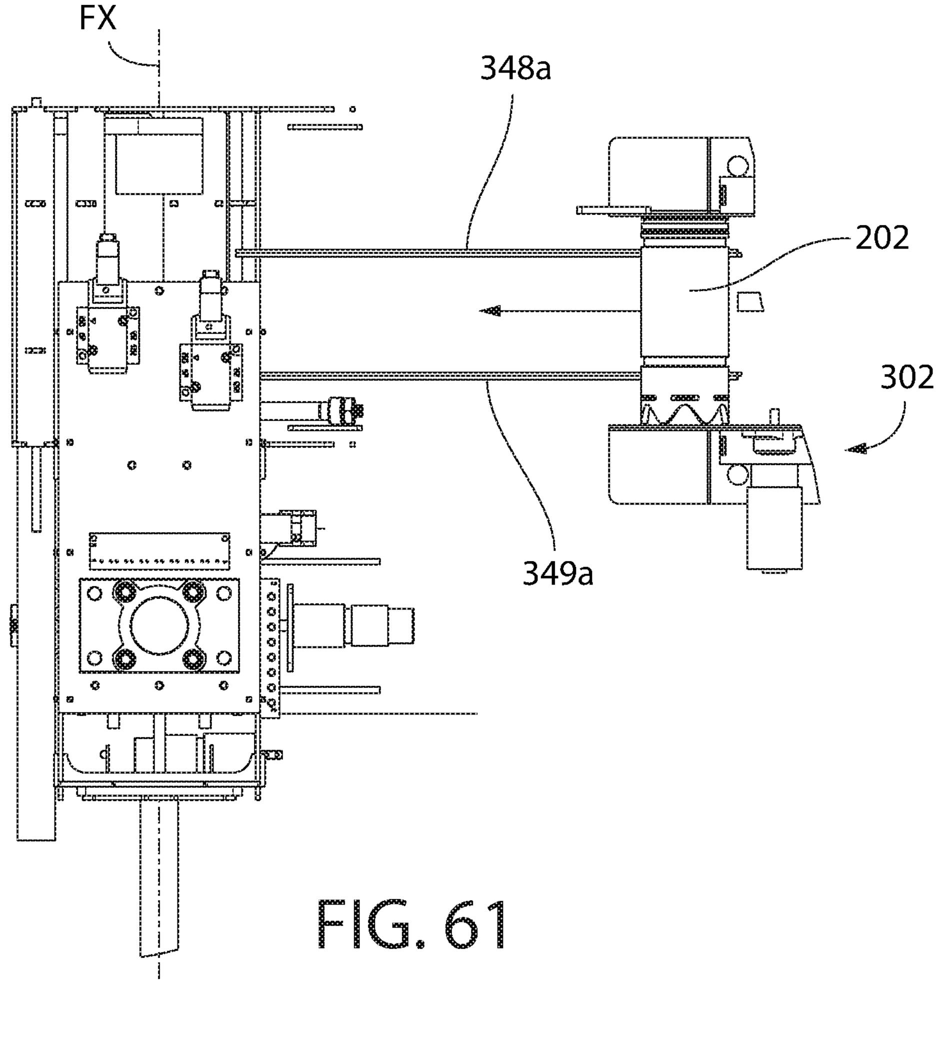
FIG. 61 is an enlarged detail taken from FIG. 60.
Figure 63:
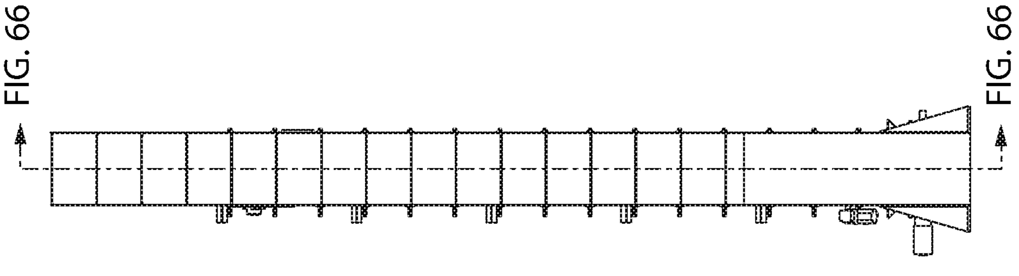
FIG. 63 is a distal end view thereof.
Figure 62:
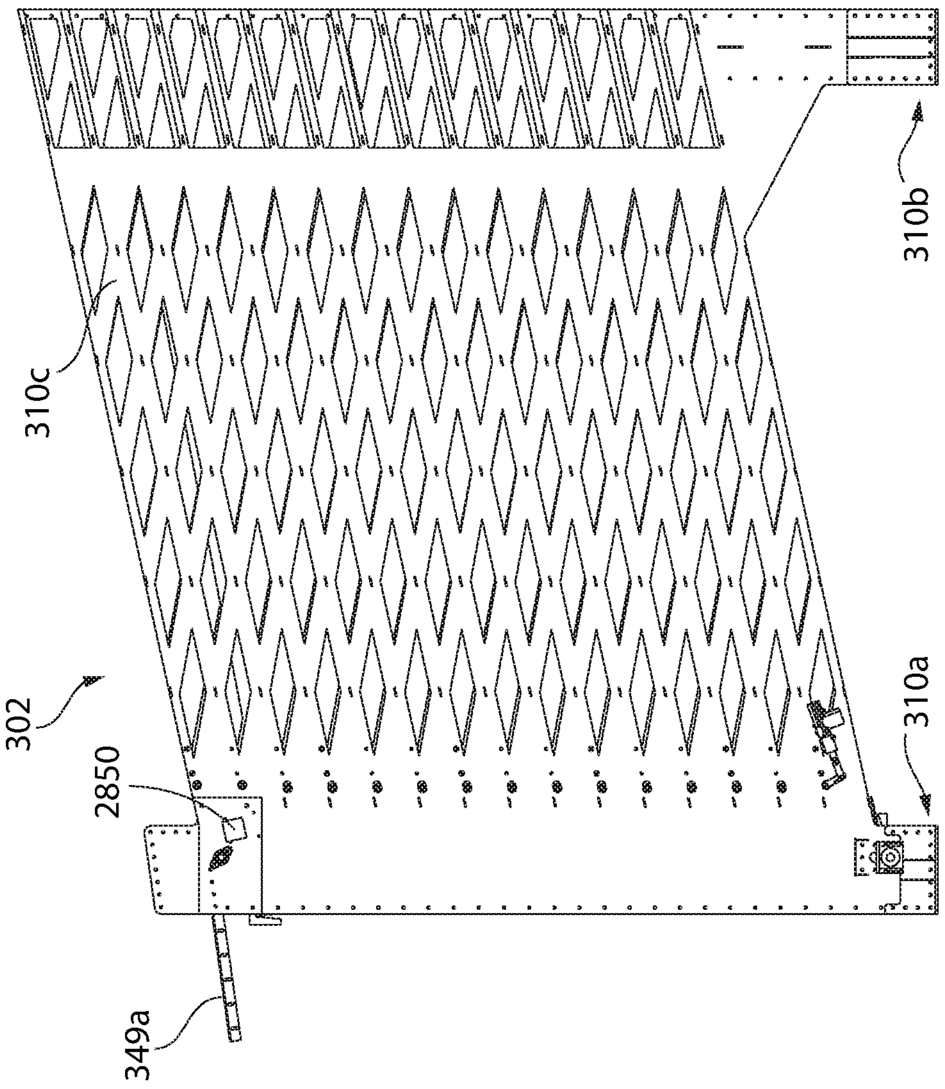
FIG. 62 is a first side view of the container staging rack alone.
Figure 65:
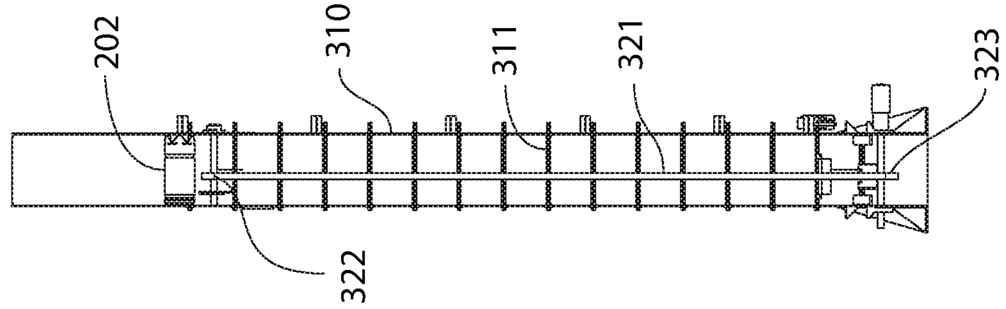
FIG. 65 is a proximal end view of the staging rack.
Figure 64:
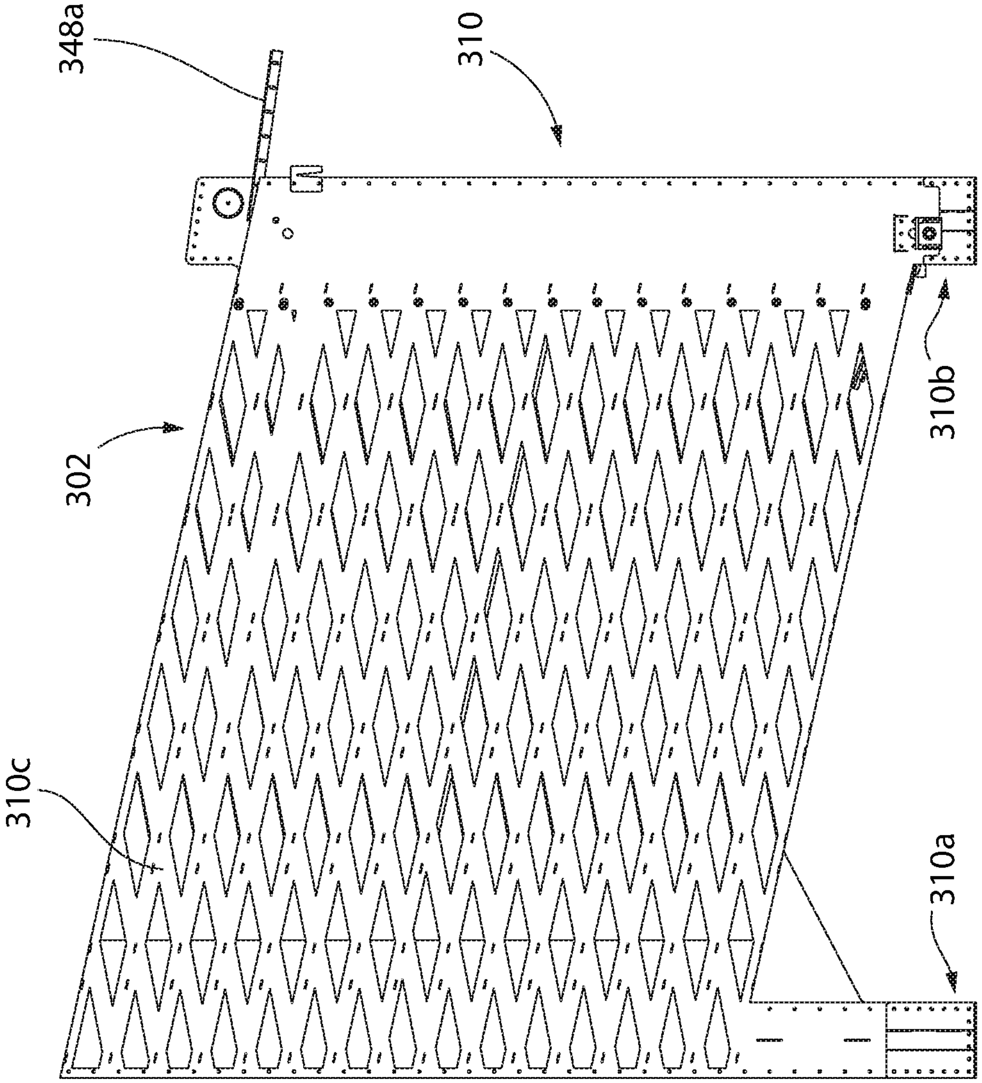
FIG. 64 is a second side view thereof showing the side opposite the side in FIG. 62.
Figure 67:
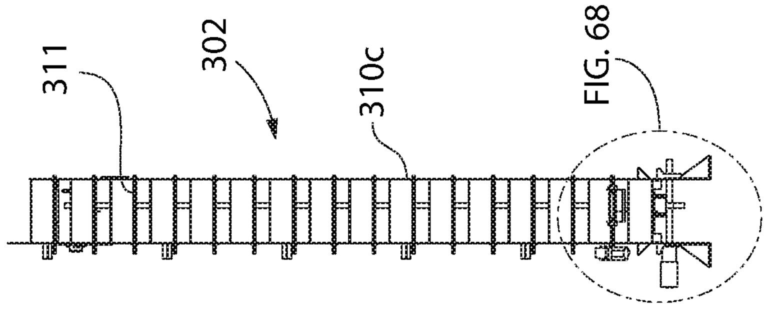
FIG. 67 is a transverse view thereof taken from FIG. 66.
Figure 66:
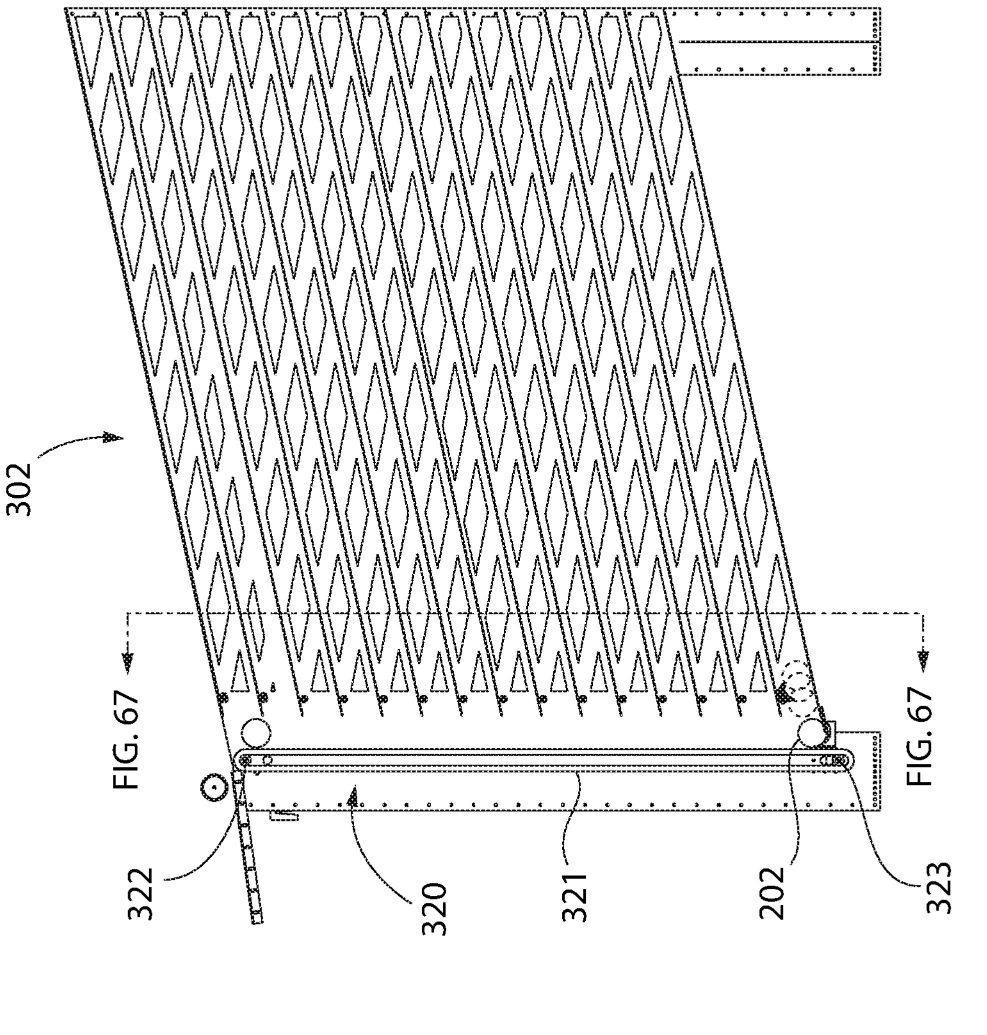
FIG. 66 is a longitudinal cross sectional view of the staging rack taken from FIG. 63.
Figure 68:
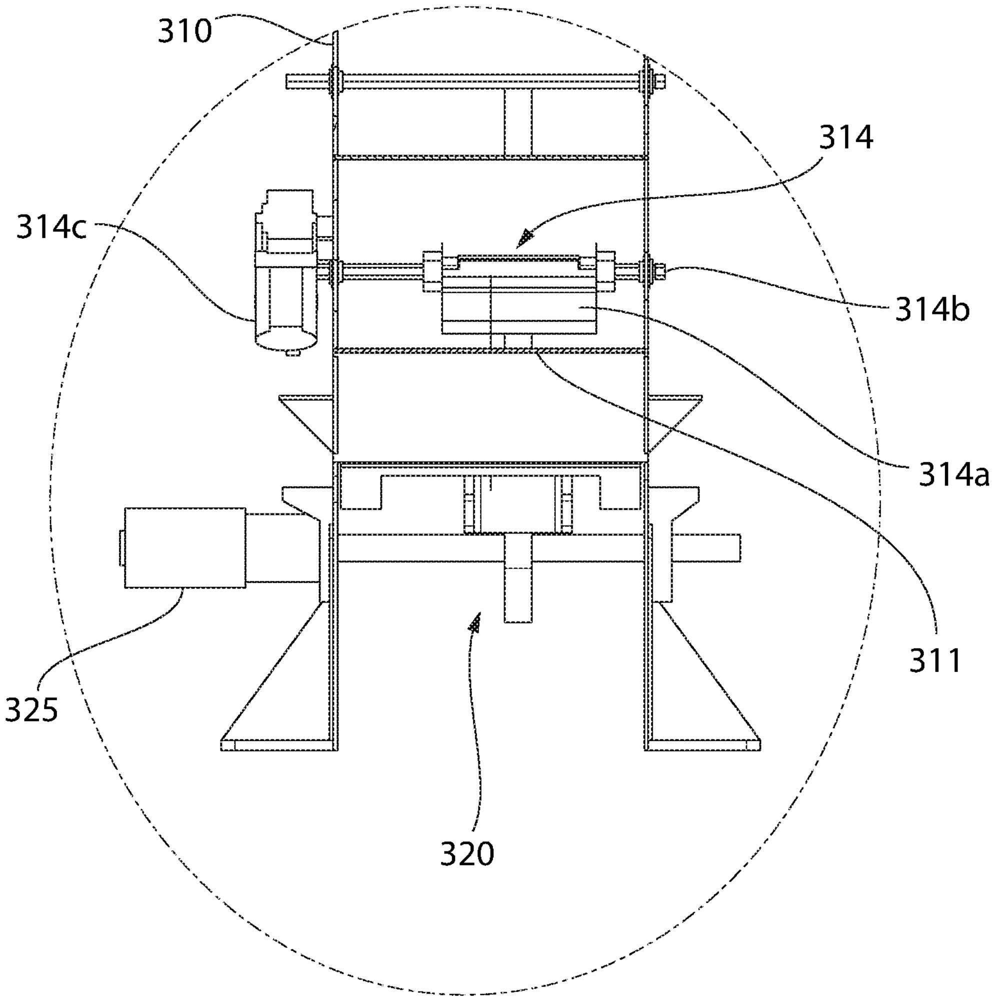
FIG. 68 is an enlarged detail taken from FIG. 67.
Figure 69:
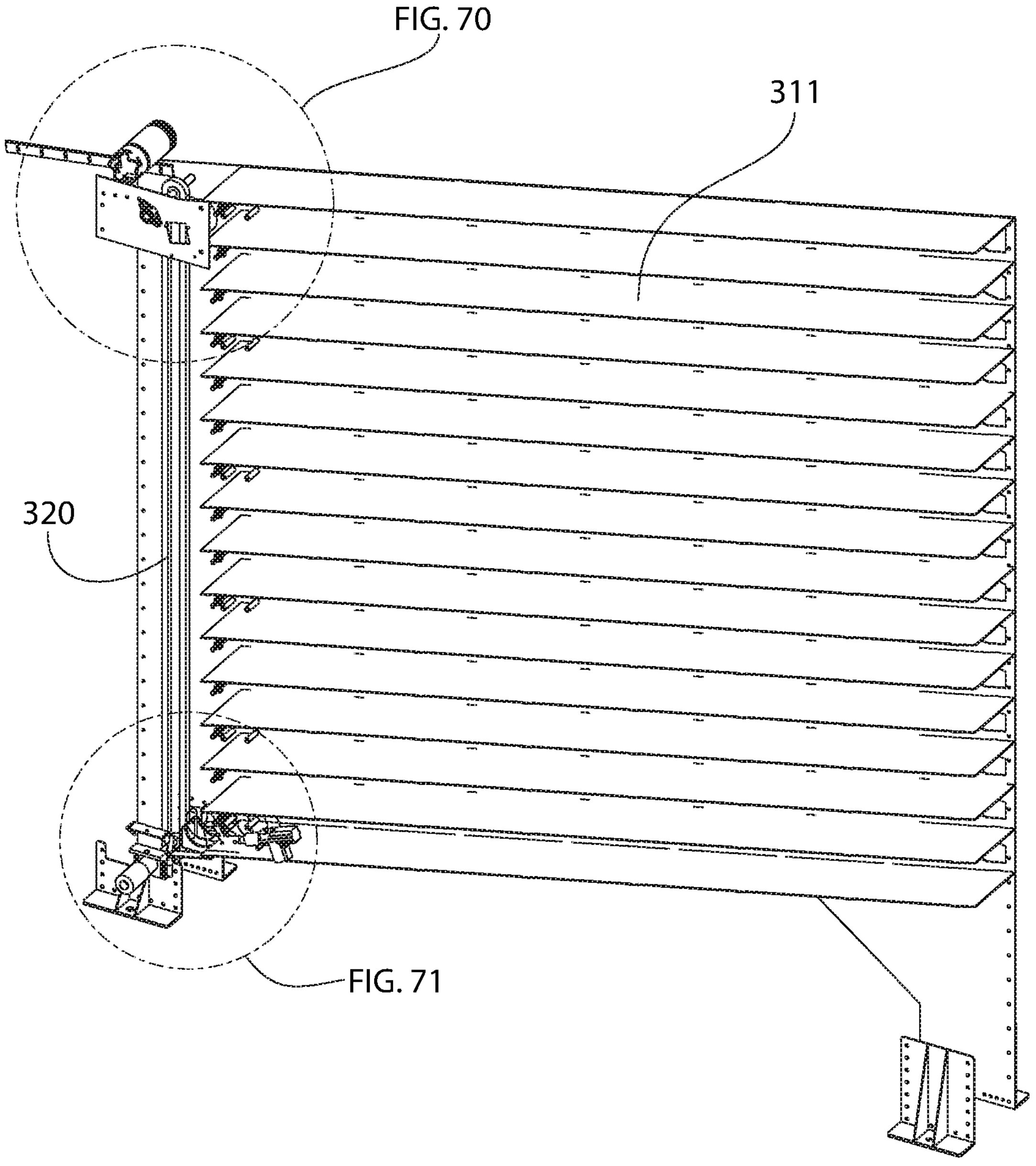
FIG. 69 is a first side perspective view of the staging rack with the side panel plate removed to reveal the inclined feed ramps of the rack.
Figure 78:
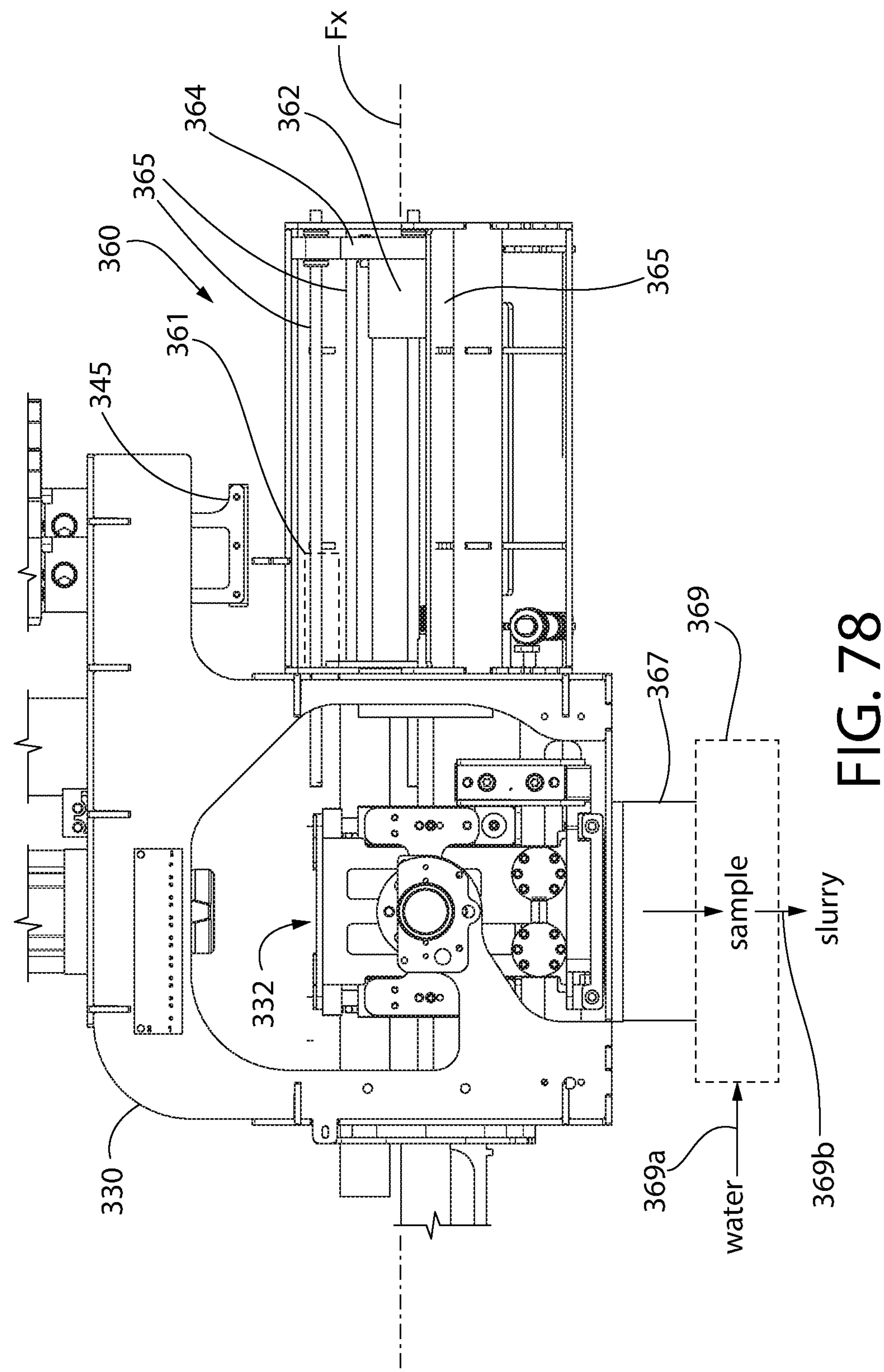
FIG. 78 is an enlarged detail taken from FIG. 77.
Figure 79:
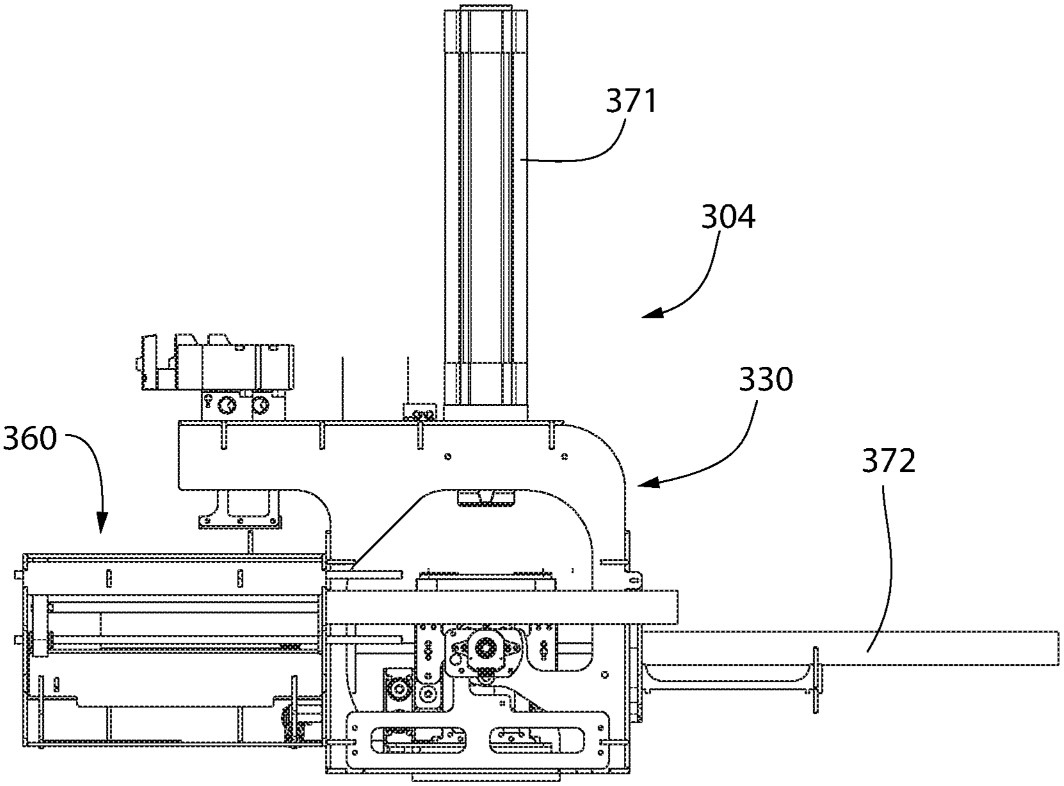
FIG. 79 is a rear view of the unloading apparatus.
Figure 84:
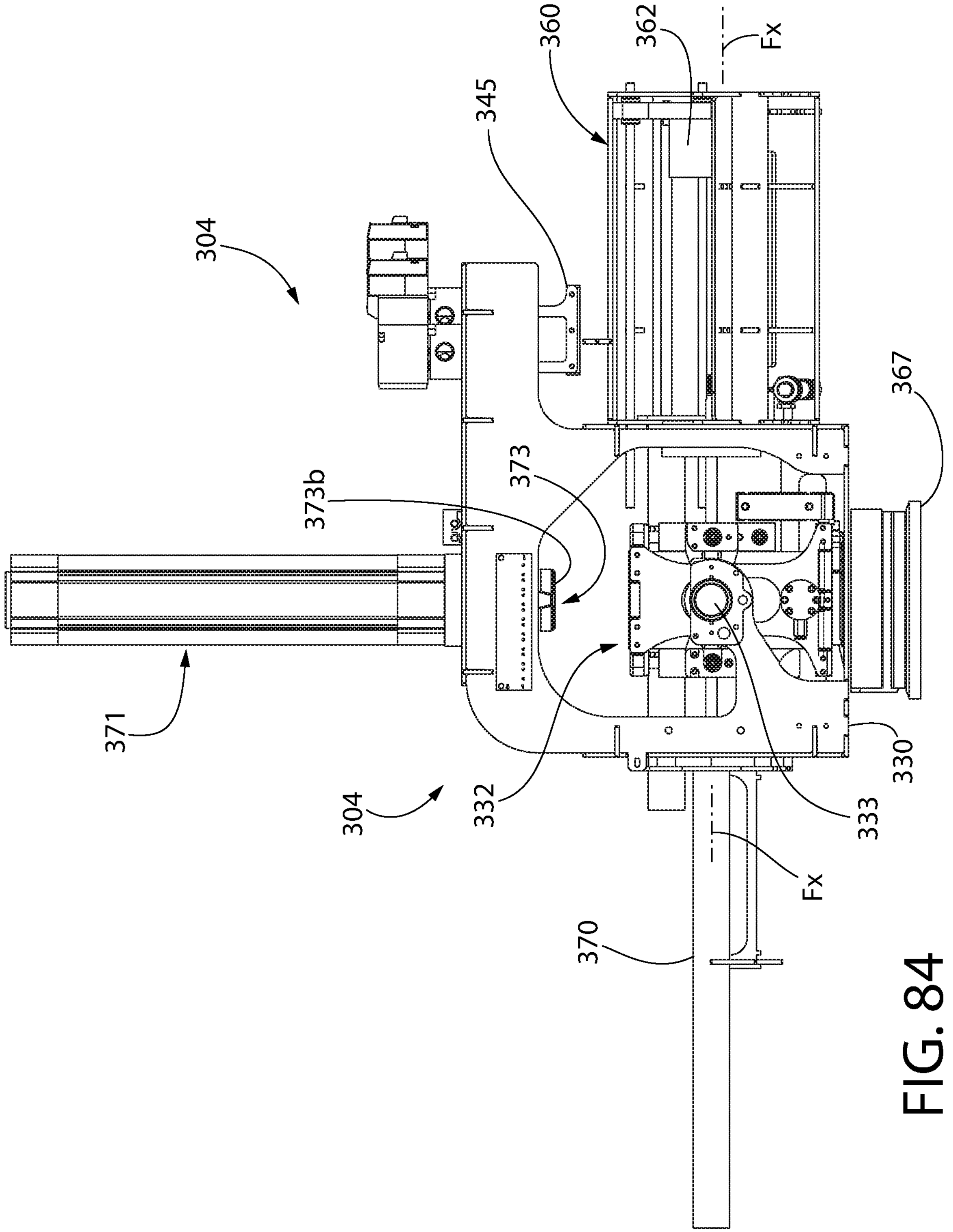
FIG. 84 is a front view of the container unloading apparatus showing the container carriage and container rotated into a horizontal position/orientation.

For convenience of description and directional reference only, unloading apparatus 304 may be considered to define a front 304*a*, rear 304*b*, left lateral side 304*c*, and right lateral side 304*d* in top plan view (see, e.g., FIG. 57). Apparatus 304 may also be considered to define a top 304*e* and bottom 304*f*. A longitudinally-extending sample container feed axis FX is defined extending through lateral sides 304*c*, 304*d* (see, e.g., FIGS. 78 and 84). Transverse directions and orientations are defined herein as being disposed at a perpendicular 90 degree or acute angles to axis FX.

Sample staging rack 302 comprises a support frame 310 configured to rest on a generally horizontal support surface which may be a stationary floor, flat bed of a wheeled vehicle such as a truck, trailer, agricultural implement, or any other suitable type surface to which the rack may be rigidly mounted in a stable manner. The frame in some embodiments may therefore include a pair of distal and proximal feet 310*a*, 310*b* configured for seating on the support surface. The terms "distal" is defined herein as being farthest from unloading apparatus 304 and "proximal" is defined as closest thereto. The frame 310 includes a side panel plate 310*c* on each side which at least partially encloses the feed ramps 311 to prevent the sample tubes 202 from sliding out of the staging rack 302. Plates 310*c* may include plural openings to allow the user to view the sample tubes 202 on the staging rack feed ramps. Frame 310 in various embodiments may be formed of an assemblage of various types and shapes of suitable metal structural members connected together by any means to form a self-supporting support frame. Any suitable shape and construction of the frame may be used. Staging rack 302 is horizontally elongated and may be oriented perpendicularly to sample unloading apparatus 304 and container feed axis FX.

Frame 310 supports at least one inclined feed ramp 311 configured and having an elongated horizontal length for receiving and staging one or more sample tubes 202. In a preferred but non-limiting embodiment, a plurality of feed ramps are provided in vertically stacked and parallel relationship. The ramps 311 each hold a plurality of the elongated tubes 202, which may be cylindrical, in a horizontally abutting and crosswise manner oriented transversely to the length of the ramps. The cylindrical walls of tubes are therefore in abutting contact in sidewall to sidewall relationship. The ramps are vertically spaced apart by a distance which can accommodate the diameter of the sample tubes 202 while allowing them to roll freely.

Feed ramps 311 of staging rack 302 slope downwards at a suitable angle towards unloading apparatus 304 so that the sample tubes 202 may automatically and freely roll towards the unloading apparatus via gravity. The sample tubes therefore roll from a distal ends 312 of the rack and feed ramps towards a proximal end 313 of the rack adjacent to unloading apparatus 304.

In one embodiment, the staging rack 302 is coupled to the unloading apparatus 304 by a pair of spaced apart track rails 348*a*, 349*a* spanning between the rack and tube loading mechanism 306 of the apparatus. The rails rollingly engage a pair of circumferential grooves 348, 349 formed on the exterior surface of the cylindrical wall 202*a* of sample tube 202 proximate to each end to guide the tube onto the tube feed chute 363 of the tube loading mechanism 360 of the unloading apparatus.

Referring to FIGS. 68 and 71-73, sample transfer mechanism 306 in one aspect includes a rotary paddle feed gate 314 positioned at the proximal end of each feed ramp 311. The feed gates stop the leading sample tubes 202 from rolling off staging rack 302 into a vertically-extending passageway 315 at the proximal end 313 of rack 302 between the rack and unloading apparatus 304. Gates 314 are configured and operable to provide sequenced feeding of the sample tubes into unloading apparatus 304 according to a preprogrammed tube feed sequence in system controller 2820, as further described herein.

Paddles feed gates 314 are each horizontally elongated in the side-to-side rear direction of the unloading apparatus 304 and positioned to engage the leading sample tube 202 on each feed ramp 311 of the staging rack 302 (i.e. tube closest on ramp to unloading apparatus 304). A feed gate 314 is positioned above the proximal ends of each feed ramp 311 just beneath the next feed ramp above in the staging rack such that the sample tube 202 passes beneath the gate when fed and admitted to the transfer mechanism.

Figure 73:
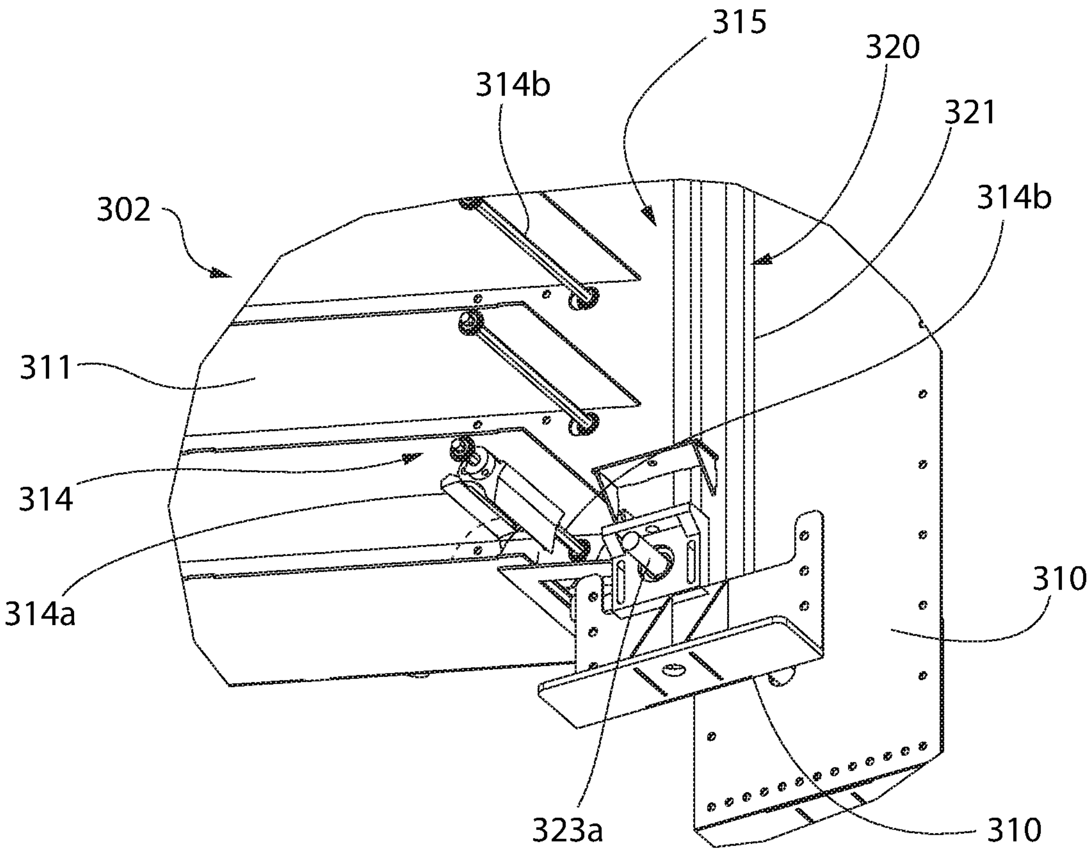
FIG. 73 is an enlarged detail taken from FIG. 72.

In one embodiment, the feed gates 314 each include a plurality of radial blades 314*a* rotatable about the transverse pivot axis of the gate defined by a transverse pivot pin 314*b* mounted to frame 310 of staging rack 302 at each side of the feed ramp (see, e.g., FIG. 73). In one embodiment, each feed gate 314 comprises a pair of radial blades disposed at an acute angle to each other and spaced angularly apart to engage and receive the sidewalls of a sample tube 202 (note FIG. 73 shows only a single feed gate on one feed ramp 311 to avoid clutter in the FIGURE—other pivot pins 314*b* however visible on ramps above). The feed gates 314 are each pivoted back and forth in a toggle action to pass the leading sample tube 202 to the transfer mechanism 306 by a separate dedicated actuator 314*c* (best shown in FIG. 71), while blocking the second leading sample tube on the feed ramp. One actuator 314*c* may be coupled to the pivot pin 314*b* of each gate, such as in one non-limiting embodiment by an L-shaped angled link arm 314*d* (best shown in FIG. 71) configured to produce the desired toggle action of the gate. Link arm 314*d* has a proximal pinned pivot joint between each leg of the arm to allow the arm legs to rotate relative to each other for turning the pivot pin 314*b* of the feed gate 314. Actuator 314*c* may be any suitable commercially-available linear electric actuator, pneumatic actuator, or hydraulic actuator configured and operable to actuate link arm 314*d* and pivot the feed gate. The feed gate operates to engage, pivot, and push a lead sample tube forward to the proximal end of the feed ramp 311 to a position where it can be engaged and loaded into the unloading apparatus 304 by the transfer mechanism 306, as further described herein.

The sample transfer mechanism 306 in another aspect further comprises a tube elevator 320 configured and operable to engage and extract a sample tube 202 dispensed from the active feed gate 314 of staging rack 302. In one non-limiting embodiment, the tube elevator 320 may comprise a chain drive including a circulating continuous-loop chain 321, toothed upper sprocket 322, toothed lower sprocket 323, and forked lifting member 324 fixedly coupled to and movable vertically with the chain. The chain may be of a type generally similar to a bicycle chain for comparison; however, other types of chains may be used. Lifting member 324 may be somewhat L-shaped in one embodiment and configured to engage, lift, and remove the sample tube 202 from the rotary paddle feed gate 314, and load the sample tube into the unloading apparatus 304 from the staging rack 302. The lifting member in one non-limiting embodiment may have a pair of outwardly projecting prongs 324*a* configured to engage and extract the tubes 202 from the rack. Prongs 324*a* may be arcuately curved in one embodiment with a radiused engagement surfaces 324*a* coinciding to the radius of the sample tube 202 to snugly engage the wall 202*a* of the tube.

Figure 70:
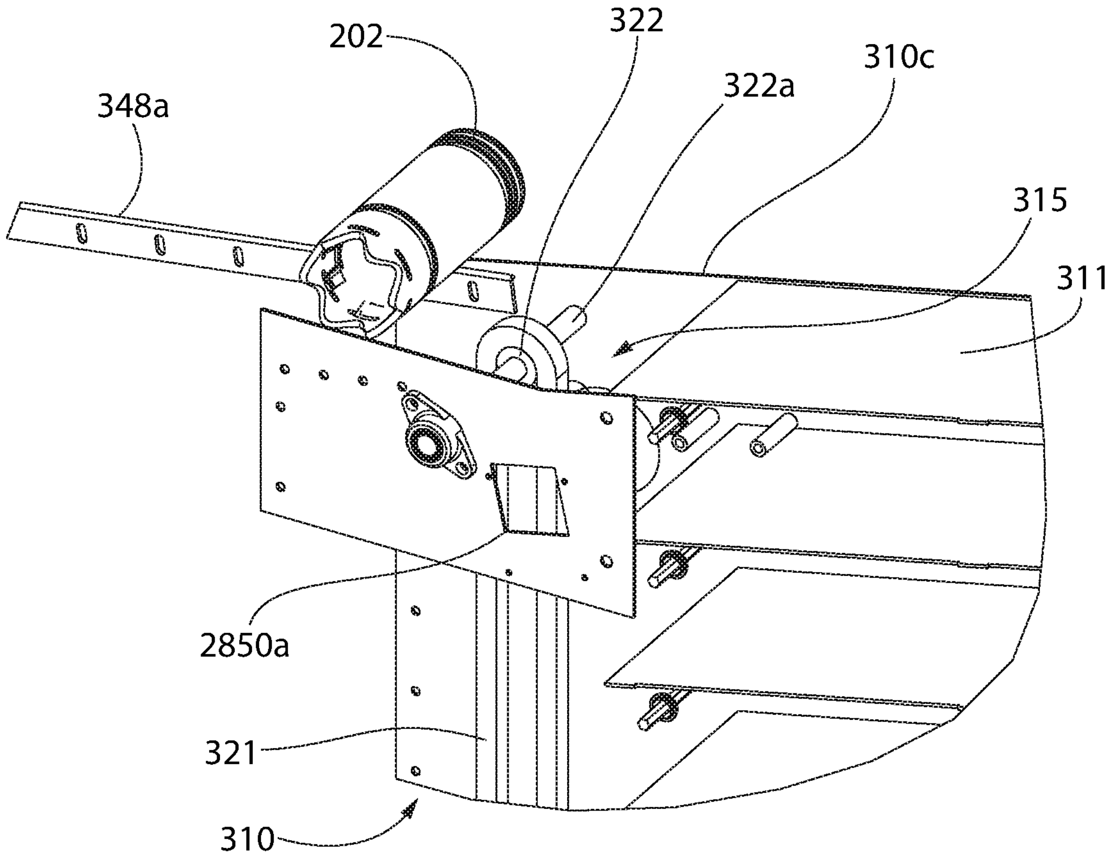
FIG. 70 is a first enlarged detail taken from FIG. 69.
Figure 71:
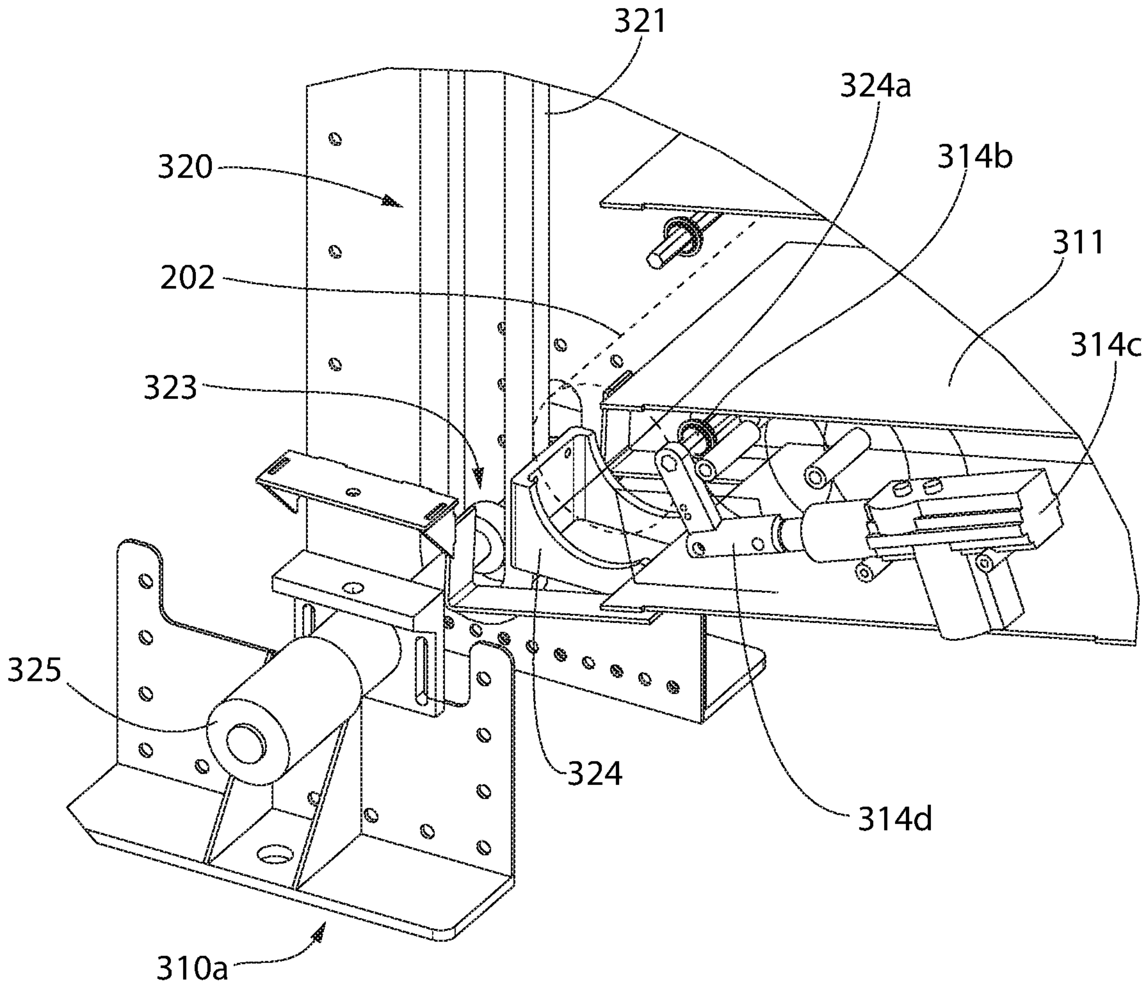
FIG. 71 is a second enlarged detail taken from FIG. 69.
Figure 72:
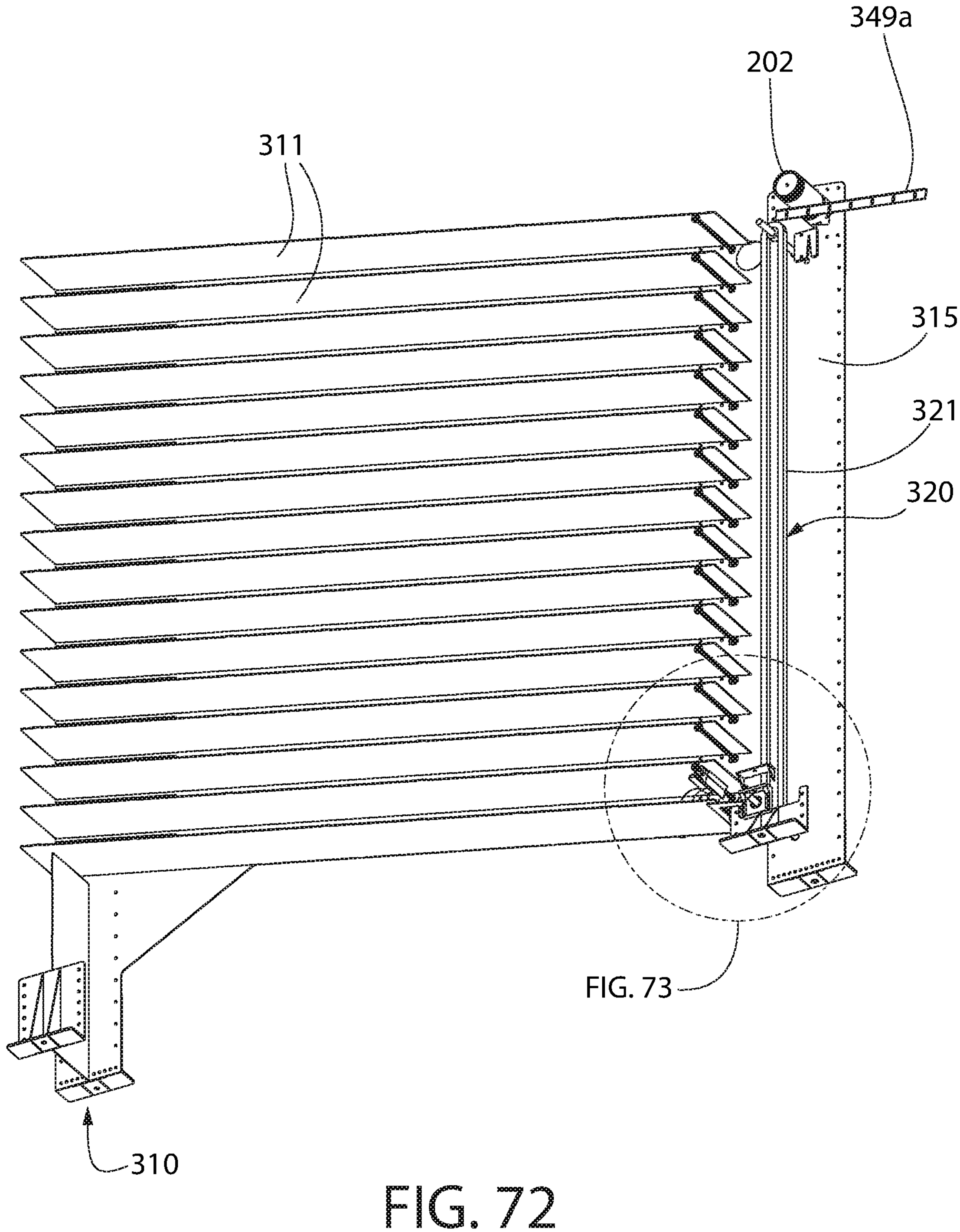
FIG. 72 is a second side perspective view of the staging rack opposite the first side perspective view of FIG. 69 with the side panel plate removed to reveal the inclined feed ramps of the rack.

The tube elevator 320 is located in vertically-extending passageway 315 between staging rack 302 and unloading apparatus 304. An electric motorized chain drive 325 coupled to either one of the shafts 322*a* or 323*a* of the upper sprocket 322 or lower sprocket 323 respectively rotates the chain between the sprockets such that lifting member 324 moves vertically in the passageway past the proximal ends of each feed ramp 311. Lifting member 324 receives and grasps a sample tube 202 from the feed ramp when presented for loading into apparatus 304 by operation of one of the rotary paddle feed gates 314. Chain 321 is vertically oriented and elongated as shown. Each sprocket shaft 322*a*, 323*a* is rotatably supported at its ends between opposing the sides of the frame 310, such for example as between side panel plates 310*c* (see, e.g., FIG. 70).

In operation, the segment or side of the chain loop closest to the ends of the feed ramps 311 moves upwards past the feed gates 314, and the segment or side of the loop closest to unloading apparatus 304 concomitantly moves downwards as the chain rotates. Lifting member 324 rising with the upward moving segment or side of the chain plucks a sample tube 202 passed on by one of the rotary paddle feed gates 314 presented for loading and carries the tube up with the chain to the top. As previously described herein, the feed gate 314 has a pivotable toggle action such that the gate pivots back and forth to pass the leading sample tube through the gate for engagement by the lifting member 324, while at the same time engages the next tube in line on the feed ramp 311 to hold it on the ramp. Other arrangements are possible.

When the lifting member 324 rotates over the upper sprocket 322 at top of the tube elevator towards the unloading apparatus 304, the sample tube is tossed onto guide rails 348*a*, 349*a* previously described herein by the lifting member when it reverses direction with the downward moving side of the chain loop. The sample tube 202 is guided into unloading apparatus 304 by the rails 348*a*, 349*a* which engage circumferential grooves 348, 349 in the tube, respectively. The intermeshing rail and groove arrangement keeps the tube in line as it rolls into the unloading apparatus. The lifting member 324 on the chain loop will pass beneath the lower sprocket 323 and then reverse direction vertically to begin travel back upwards with the chain 321 to extract the next sample tube presented to the tube elevator 320. It bears noting that the chain 321 travels in the same direction during the tube loading/feeding process in a loop. In some embodiments, the tube transfer unloading operation into unloading apparatus 304 and sample tube feed may be timed by preprogrammed steps executed by system controller 2820 so that the tube elevator circulates continuously or intermittently, thereby advantageously allowing tubes to be staged for feed into the unloading apparatus while a tube is being unloaded in the unloading apparatus without any appreciable gap in time. This efficiently processes the sample tubes for unloading in the most optimum time expedient manner possible.

Although a chain elevator has been described and shown for tube elevator 320, the elevator may be embodied in other types of devices that perform the same function. For example, some embodiments of tube elevator 320 may comprise a belt type system comprising a circulator belt to which lifting member 324 is coupled and pulleys in place of the upper and lower sprockets. Other means of feeding sample tubes into unloading apparatus 304 for unloading which do not involve rotating belts or chains may be used. Accordingly, the invention is not limited to chain or belt drives alone.

Staging rack 302 further includes a sample tube tracking system comprising a plurality of tracking tag readers, such as RFID reader 2850 in one non-limiting embodiment. One RFID reader may be located at the proximal end of each feed ramp 311 and mounted to frame 310. A window 2850*a* may be provided in the frame at the end of each feed ramp so that the reader is exposed to the sample tube 202 on the ramp to read the tag. In other embodiments, the tracking tag may be a bar code readable by a visual barcode scanner in lieu of an RFID reader. Other forms of readable tracking tags and corresponding tag reading systems be they electronic or visual in nature may be used.

Sample unloading apparatus 304 will now be described in further detail. With continuing general reference to FIGS. 45 and 47-110, apparatus 304 comprises a support housing 330 configured to mount the apparatus to any suitable structure which may be a floor, vehicle such as a truck, trailer, agricultural implement, or any other suitable structure to provide a rigid and stable mounting. Any suitable shape and construction of apparatus housing may be used.

Figure 80:
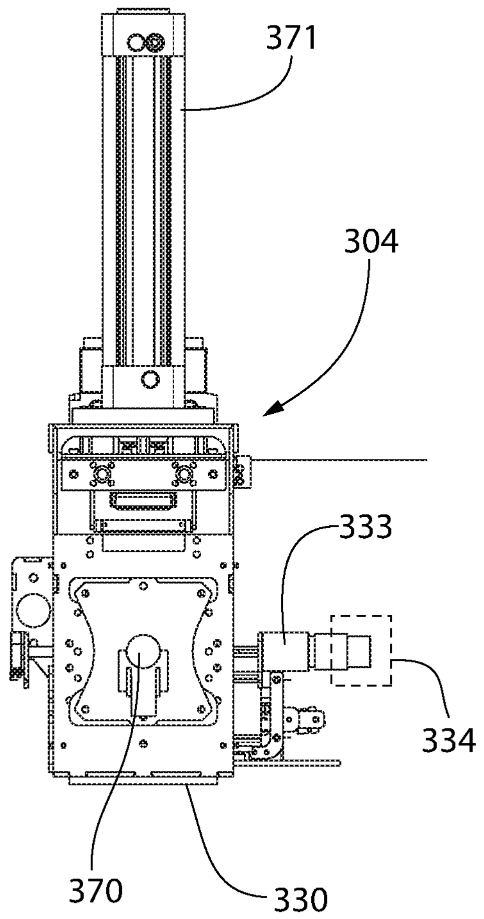
FIG. 80 is a left end view thereof.
Figure 81:
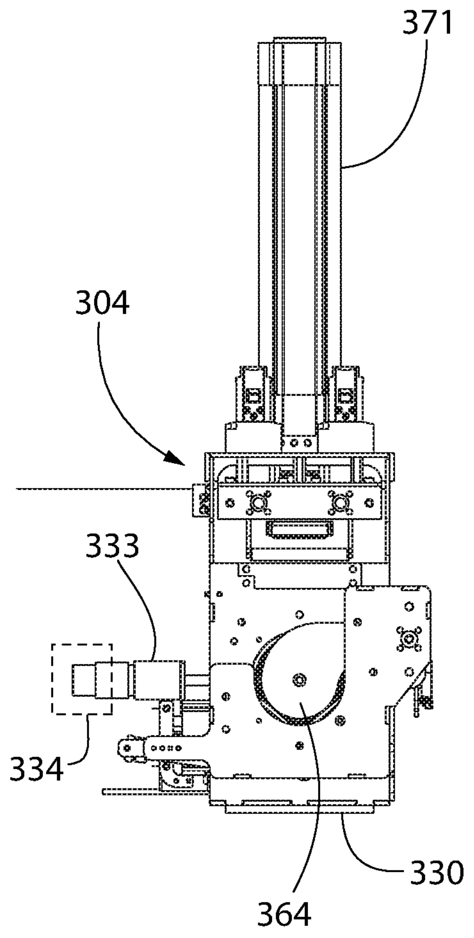
FIG. 81 is a right end view thereof.
Figure 82:
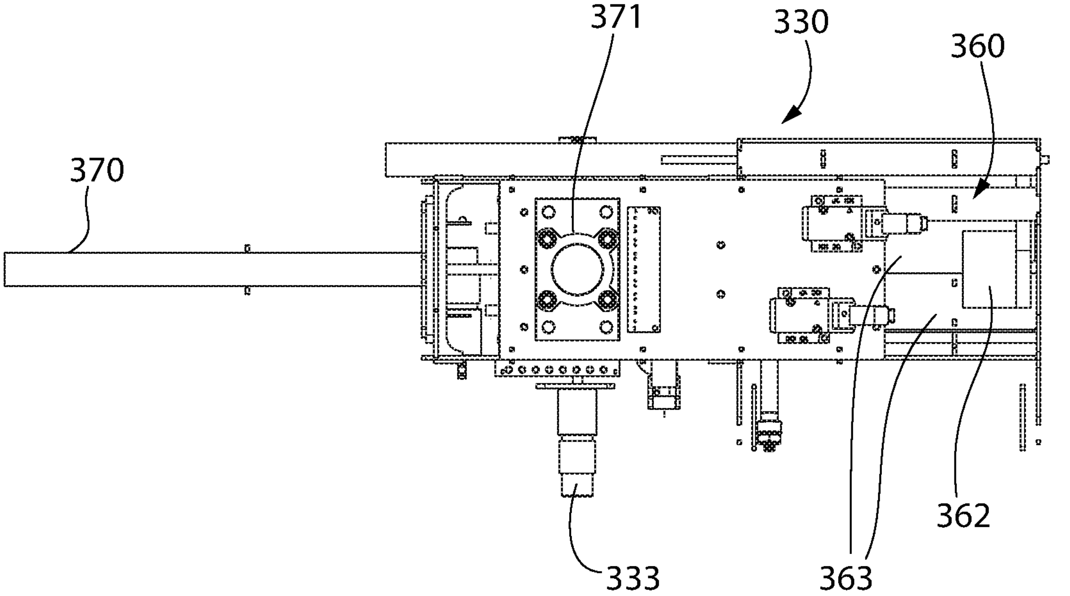
FIG. 82 is top view thereof.
Figure 83:
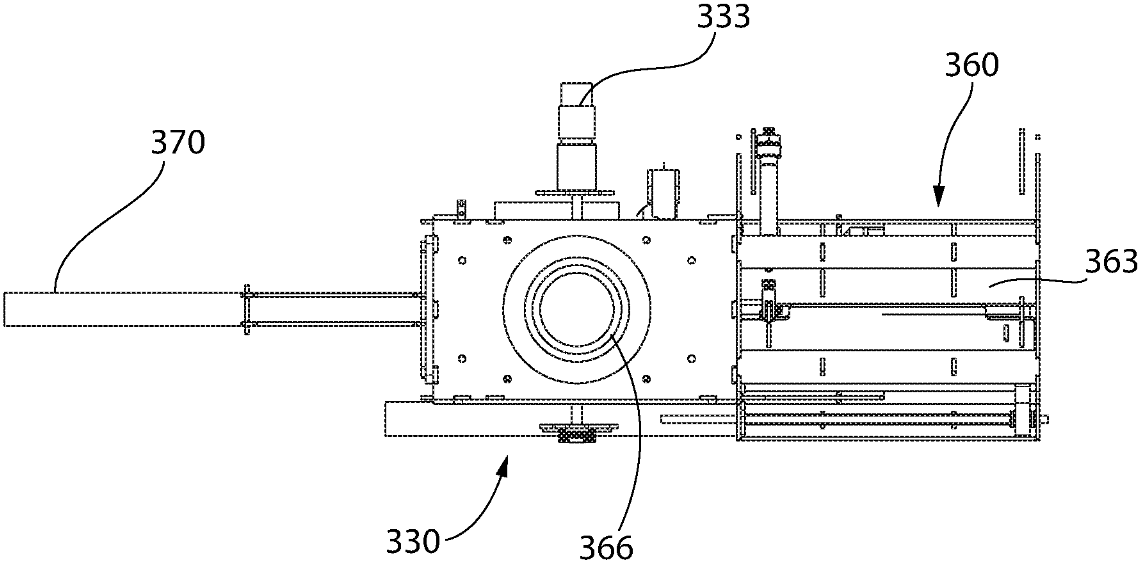
FIG. 83 is a bottom view thereof.

Unloading apparatus 304 further comprises a trunnion mechanism 329 rotatably supported by housing 330. In one non-limiting embodiment, the trunnion mechanism may include a rotatable and slideable container/tube carriage 332 configured to hold the sample tube 202. Carriage 332 is fixedly coupled to crosswise trunnion drive shaft 333 rotatably supported by the housing. Shaft 333 is oriented and elongated in the front to rear direction of the unloading apparatus perpendicularly to the container/tube feed axis FX. Carriage 332 is rotatable with shaft 333 in opposing rotational directions. In one implementation, the tube carriage can be rotated 360 degrees in either direction by trunnion drive motor 334 (shown schematically in dashed lines FIGS. 80-81) coupled to drive shaft 333.

The rotatable carriage 332 further comprises a container receptacle 336 defining an elongated interior space configured for receiving, maneuvering, and supporting the sample tube 202 in a secure manner during the sample unloading process. Carriage 332 is operable to rotate the sample tube between an upright vertical position and an inverted vertical position via drive motor 334. Receptacle 336 includes an annular castellated support ring 337 at the bottom 338 and an open top 339 through which the sample tube can be inserted. Support ring 337 has an open center to allow the tube ejector piston-plunger 372 to enter the receptacle to access and engage the sample tube for ejecting the tube from the carriage 332. Support ring 337 defines an undulating surface which is complementary configured to mesh with the undulating castellated bottom end 203*b* of sample tube 202. Anti-rotation protrusions 206*a* on the tube lockingly engage the mating anti-rotation protrusions 337*a* formed by the castellated support surface 337 in the receptacle to rotationally lock the tube relative to carriage 332 (see, e.g., FIG. 95). This ensures that free terminal ends 205*a* of the retention protrusions 205 on slideable push cap 204*b* remain rotationally clocked or timed to engage their corresponding elongated retention slots 202*c* in the cylindrical walls of sample tube 202 (previously described herein) when the cap slides inside tube 202 and then re-engages the slots, as further described herein. The peaks and valleys of castellated support surface 337 and bottom end 203*b* of sample tube 202 may be arcuately curved or rounded. This advantageously guides the mating castellated surfaces together if the peaks and valleys of each are not rotationally aligned when first meshed together.

Figure 90:
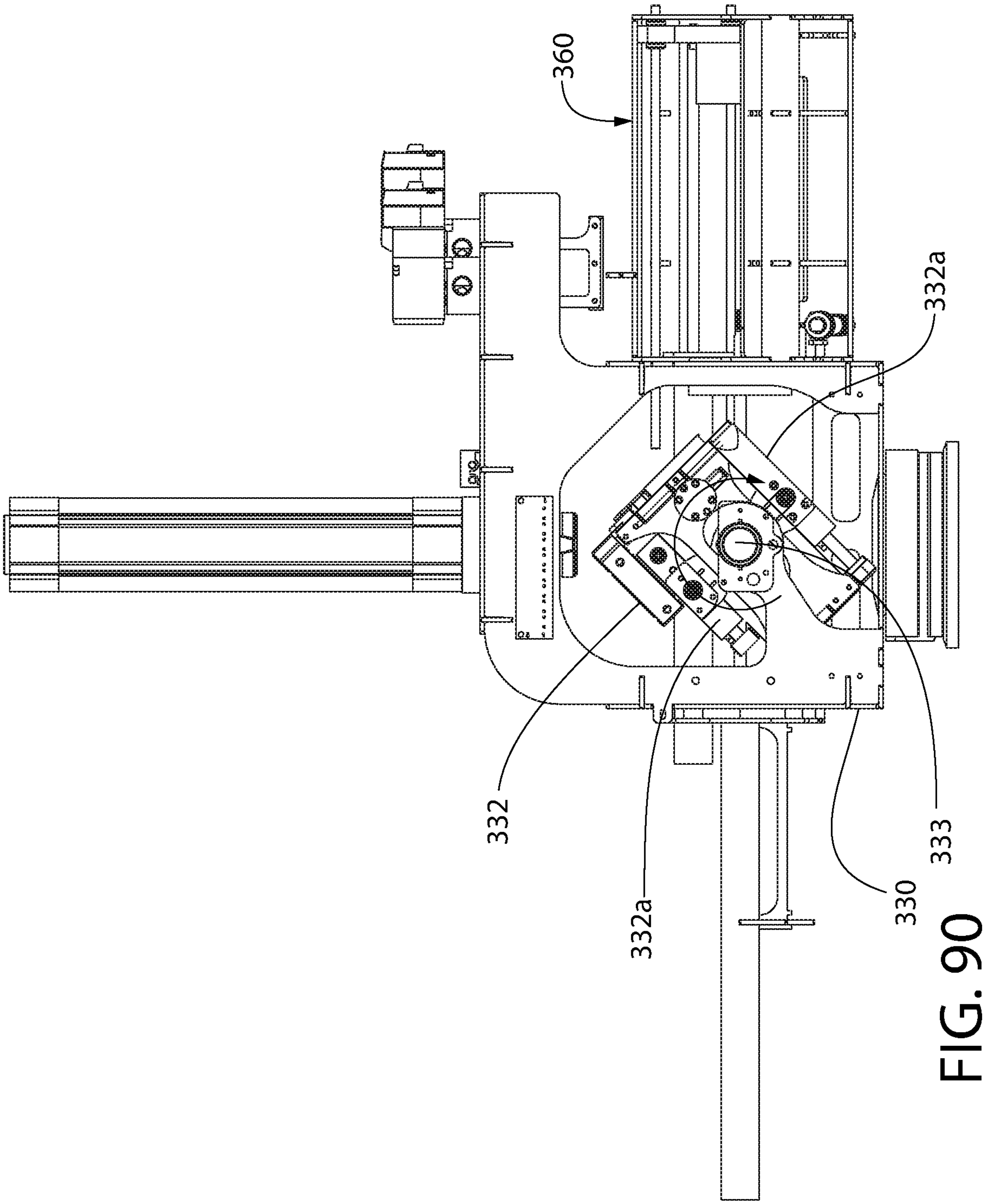
FIG. 90 is a front view of the unloading apparatus showing the carriage and container partially rotated from the upright position/orientation.
Figure 91:
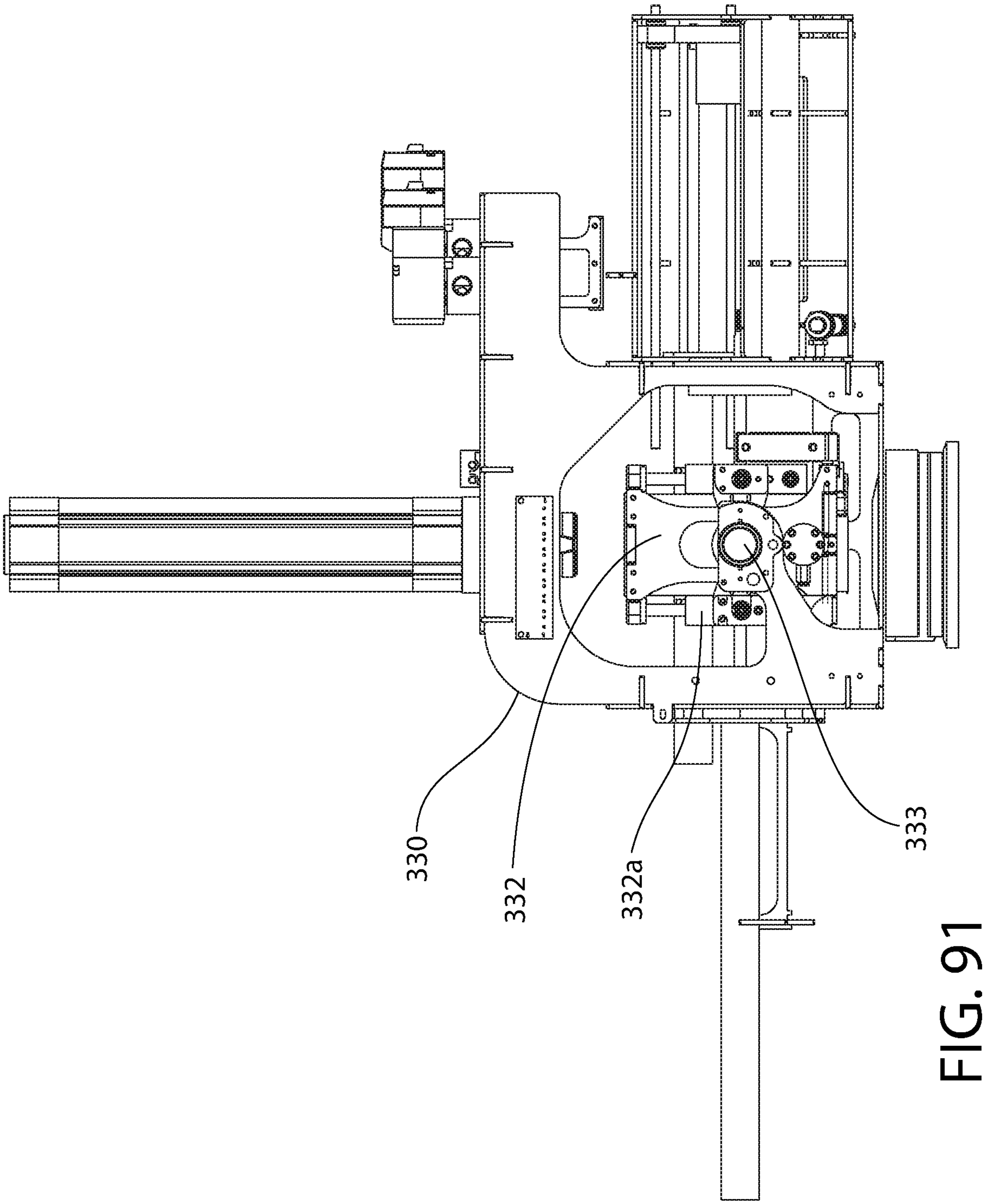
FIG. 91 is a front view of the unloading apparatus showing the carriage and container rotated into a vertical inverted position/orientation.
Figure 92:
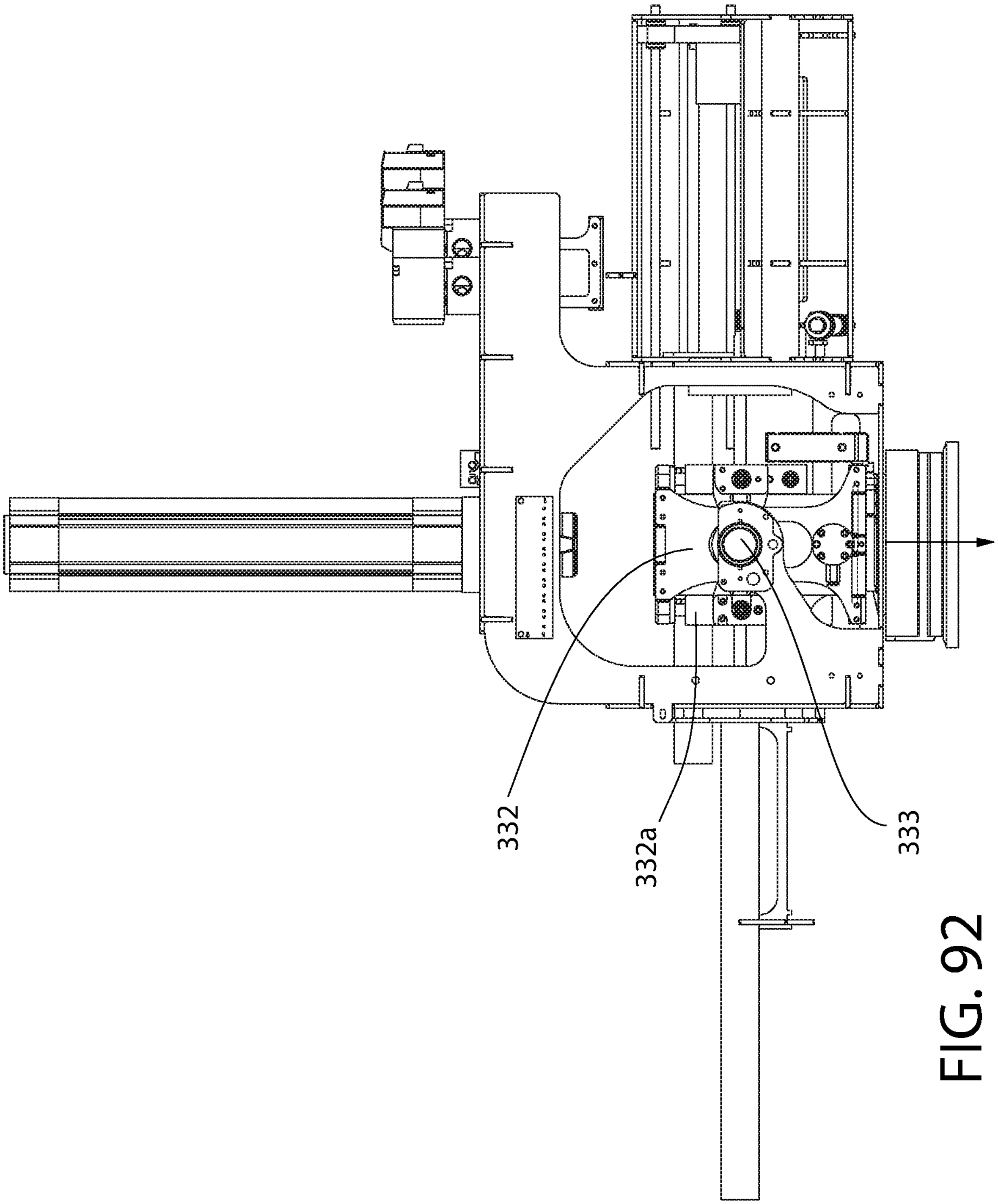
FIG. 92 is a front view of the unloading apparatus showing the carriage shifted downward towards an unloading port of the apparatus.

Carriage 332 further includes a pair of linear actuators 332*a* configured to slideably move the carriage linearly in two opposing directions within housing 330 between inward and outward positions (see, e.g., FIGS. 90-92). Actuator 337 may be any suitable commercially-available linear electric actuators, pneumatic actuators, or hydraulic actuators. In one embodiment, the actuators 332*a* may comprise a pair of pneumatic cylinder actuators; one actuator being coupled to each of two opposite sides of the carriage. It bears noting that the cylinder actuators are therefore rotatable with the carriage 332 during the sample unloading process. The cylinder actuators are used to uncap the sample tube 202 during the sample unloading process, as further described herein.

Unloading apparatus 304 further includes a movable closure plate 350 configured and operable to temporarily cover and close the open top end of sample tube 202 when in the upright vertical position and end cap 204*a* is removed in the carriage 332 for unloading the sample. Plate 350 has a generally flattened and broader body, which may be any suitable shape such as circular, rectilinear (square or rectangular), etc. Movement and operation of the closure plate 350 is controlled by actuator 351 coupled to the plate. Actuator 351 may be any suitable commercially-available electric actuator, pneumatic actuator, or hydraulic actuator. In one embodiment as shown, closure plate 350 may be circular and is pivotably movable via actuator 351 of a rotary type between an inward closed position cover the top end of sample tube 202, and an outward open position uncovering the tube. In other embodiments, closure plate 350 may be slideably movable in a linear manner between the open and closed positions by the actuator 351 of a linear type.

Figure 74A:
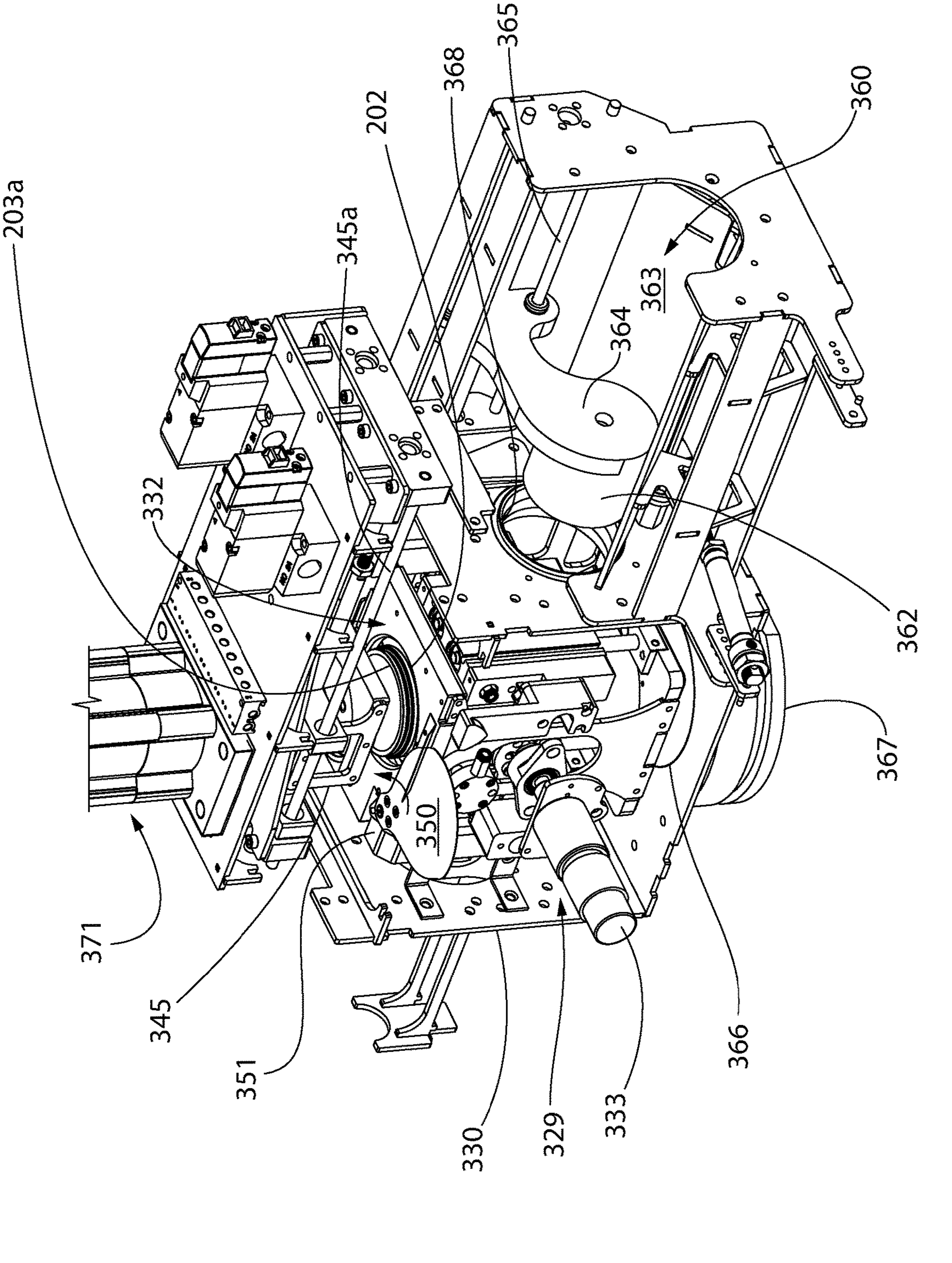
FIG. 74A is a partial perspective view of the unloading apparatus showing the container closure plate rotated outwards from the container positioned in the rotatable carriage of the apparatus.
Figure 74B:
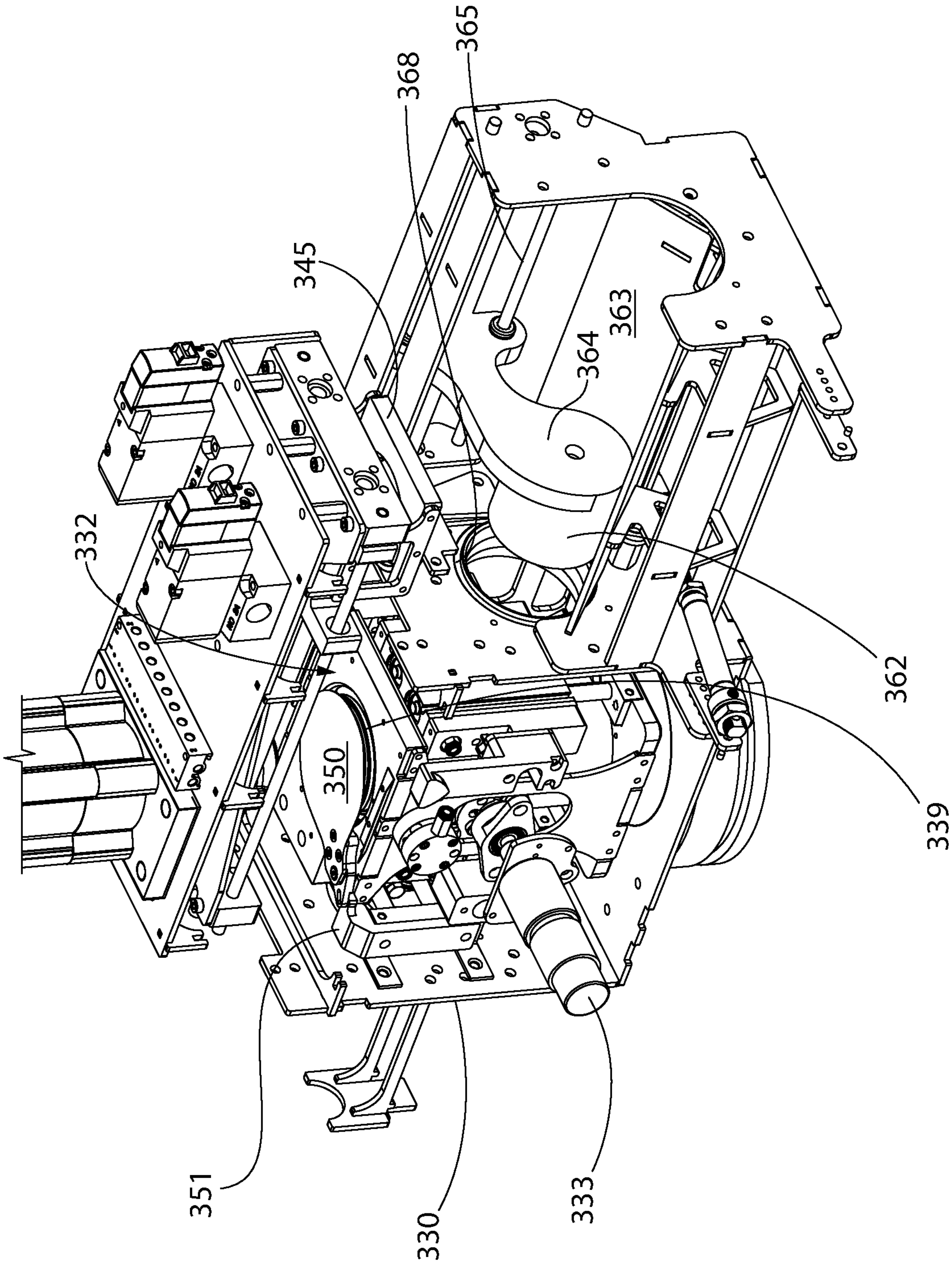
FIG. 74B is a partial perspective view thereof but showing the closure plate rotated inwards to cover the open top end of the container.
Figure 74C:
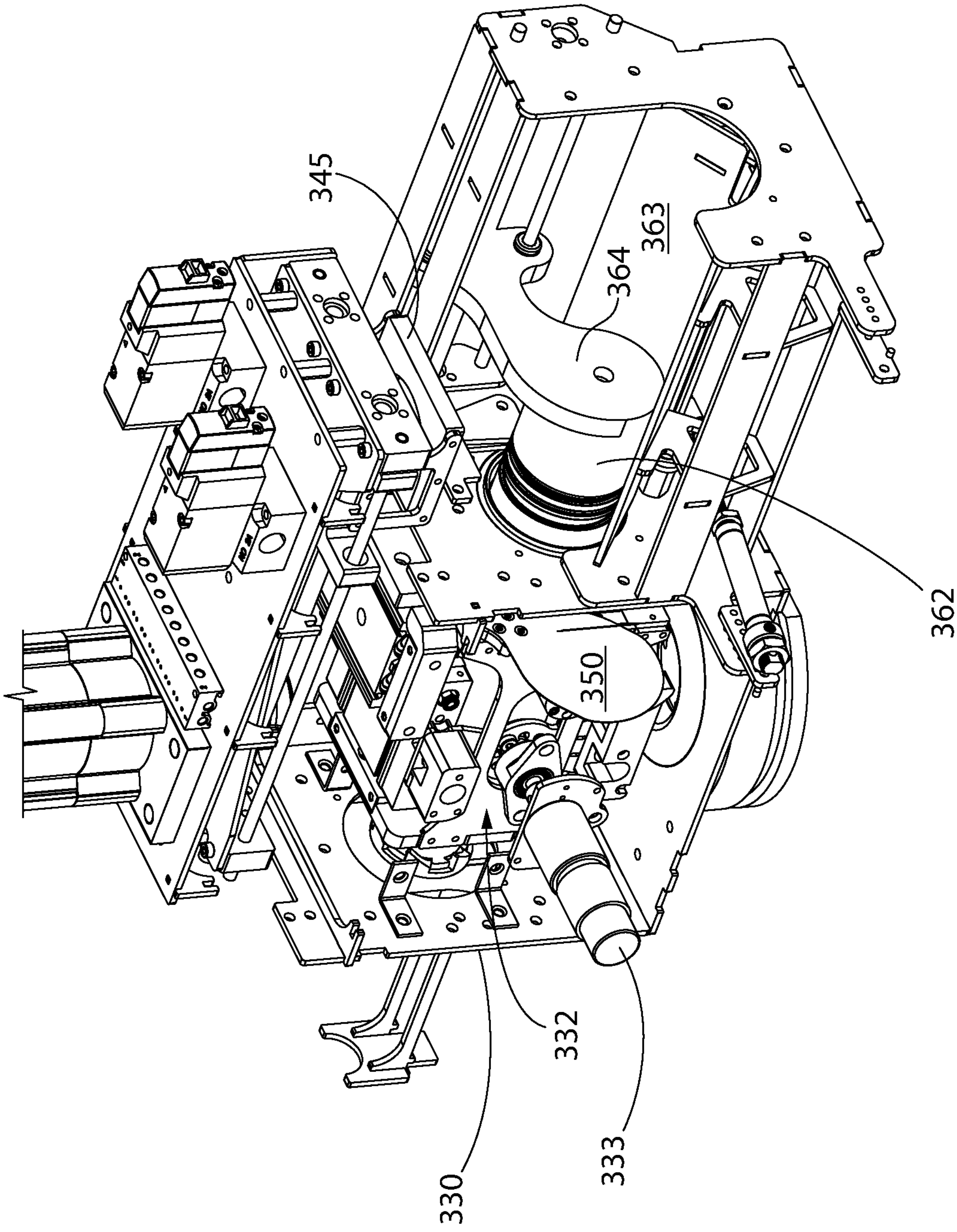
FIG. 74C is a partial perspective view thereof showing the carriage rotated 90 degrees from FIGS. 74A-B and the closure plate rotated outwards.
Figure 75:
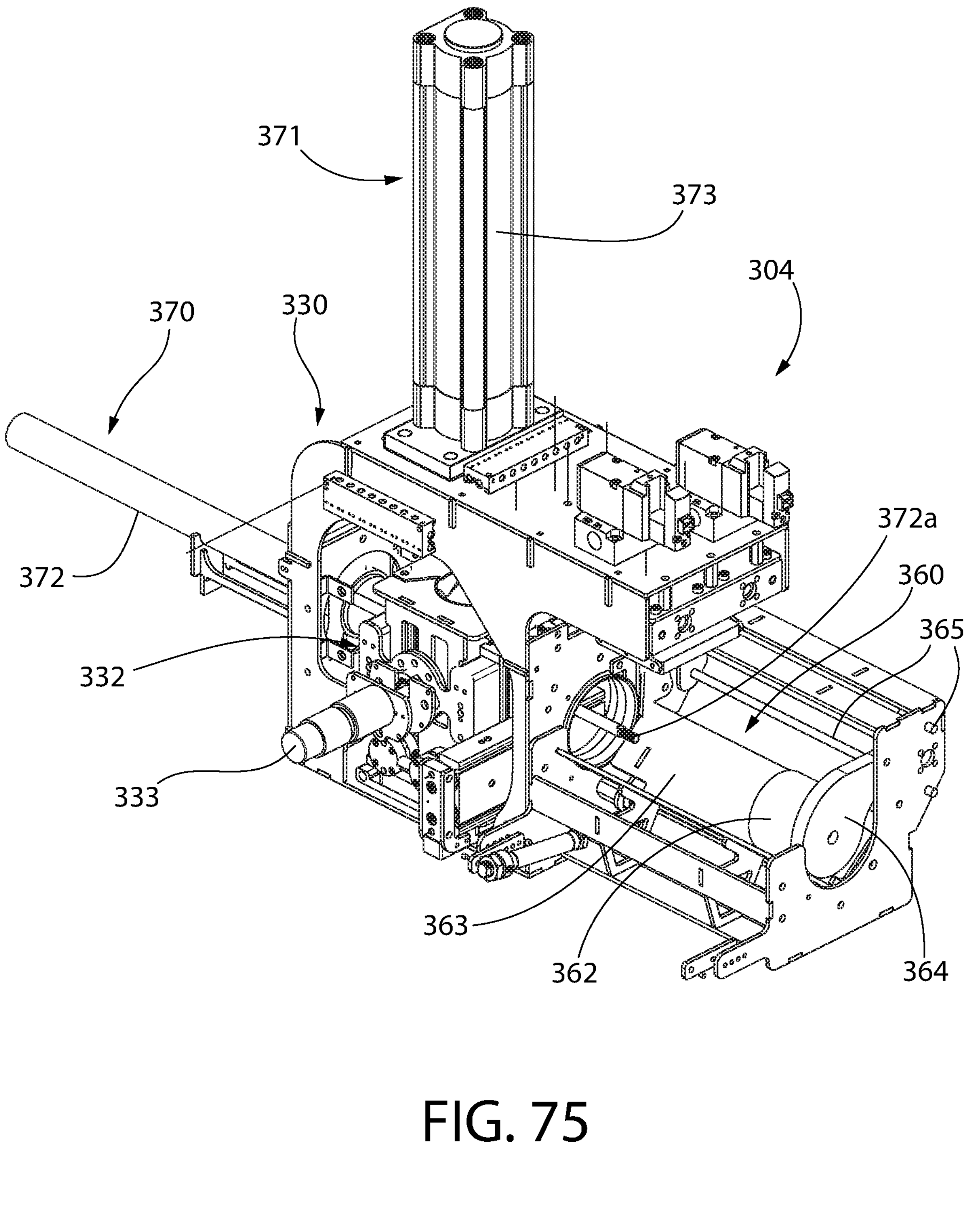
FIG. 75 is a top perspective view of the entire unloading apparatus.
Figure 76:
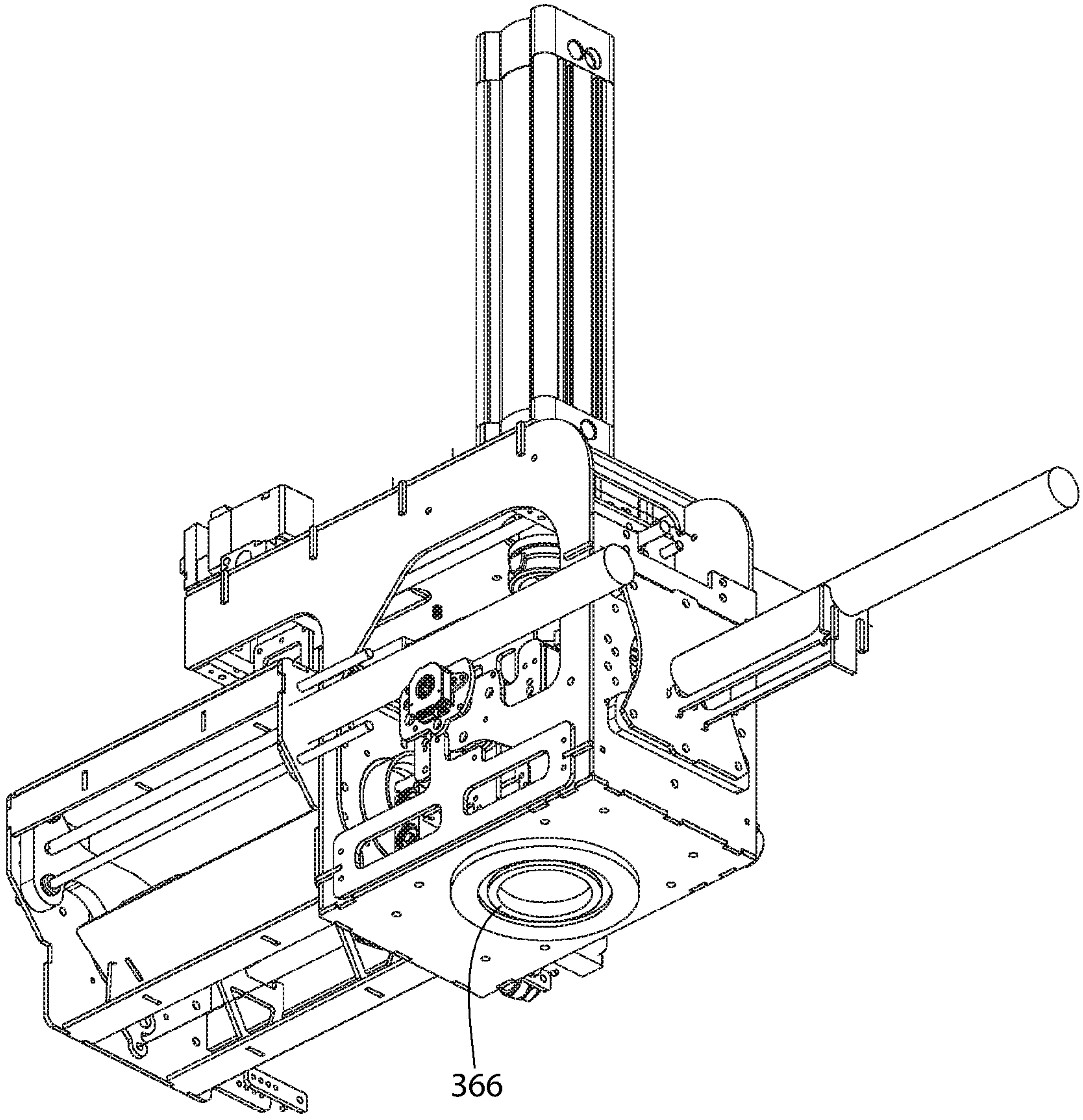
FIG. 76 is a bottom perspective view thereof.
Figure 77:
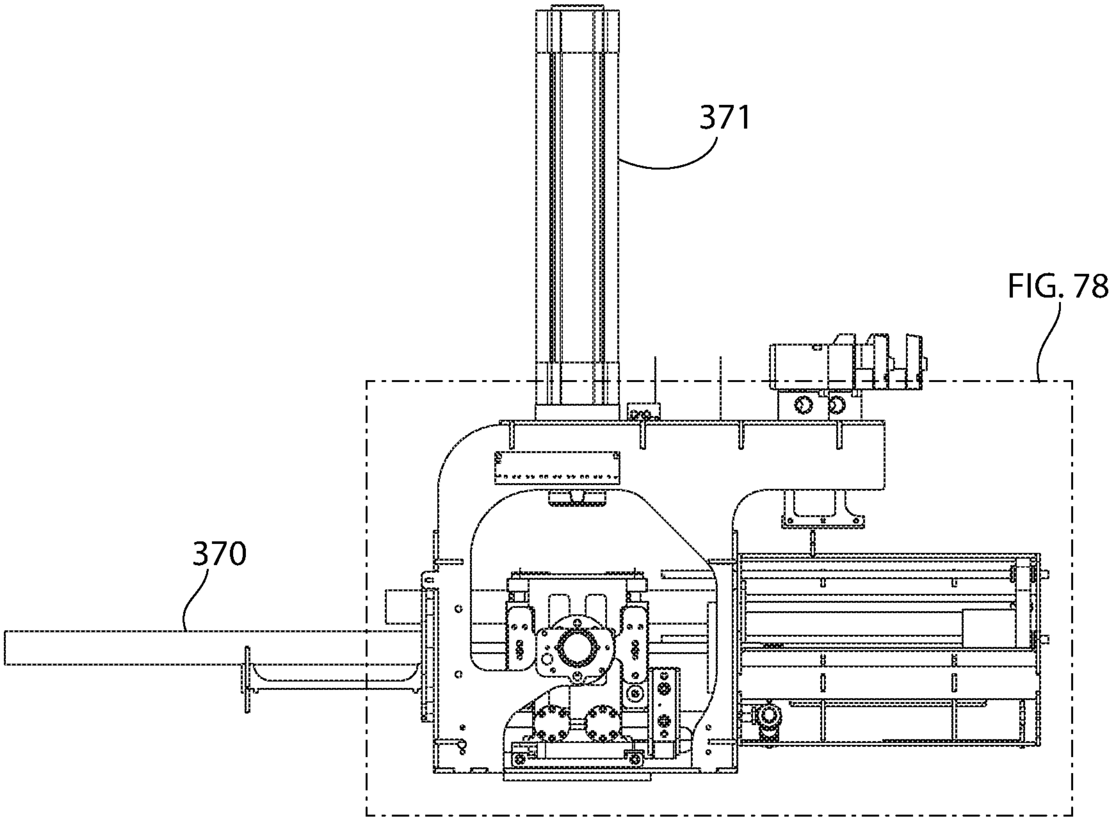
FIG. 77 is a front view thereof.
Figure 96:
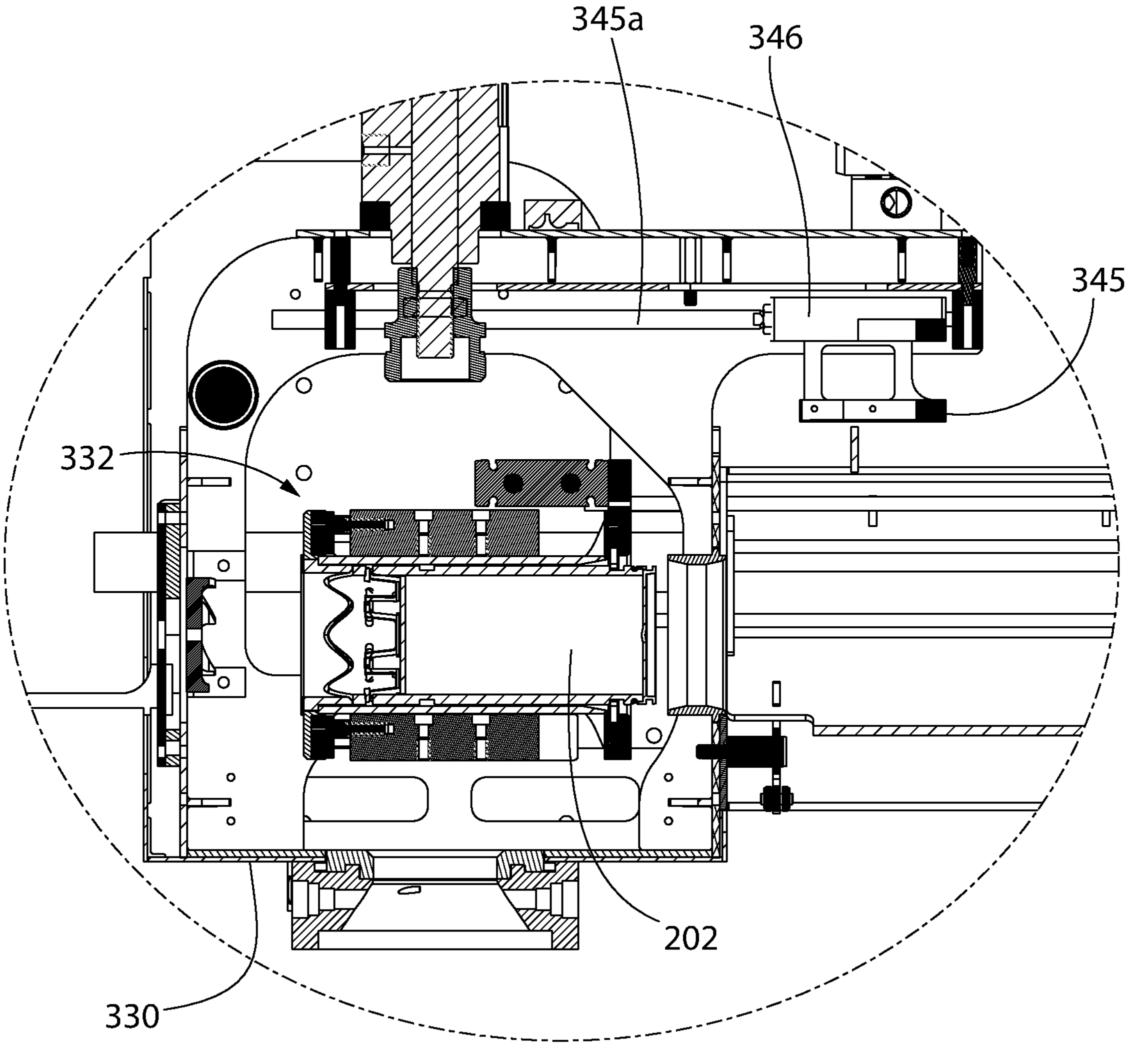
FIG. 96 is a second cross sectional view thereof.

Referring primarily to FIGS. 74A, 96, and 110, carriage 332 further includes a movable decapper 345 which is an apparatus operable to remove detachable end cap 204*a* from the top end 203*a* of sample tube 202. In one embodiment, the decapper may be slideably movable in linear manner along feed axis FX on a pair of overhead guide rods 345*a*; however, pivotable movement may be provided in other embodiments. In addition, decapper 345 may be moveable in linear directions other than along feed axis FX so long as the decapper may engage and remove the end cap 204*a*. The decapper 345 is suspended from the guide rods above and projects downwards. The decapper may include a flattened plate-like body defining a C-shaped concave recess 341 facing towards carriage 332 and configured to slideably receive and engage the top end cap 204*a* of sample tube 202. A pair of opposed inwardly projecting rails 342 are formed within in the recess (e.g., one rail on each side) which engage a complementary configured circumferential groove 347 in the sample tube top end cap 204*a* (best shown in FIG. 110).

Figure 55:
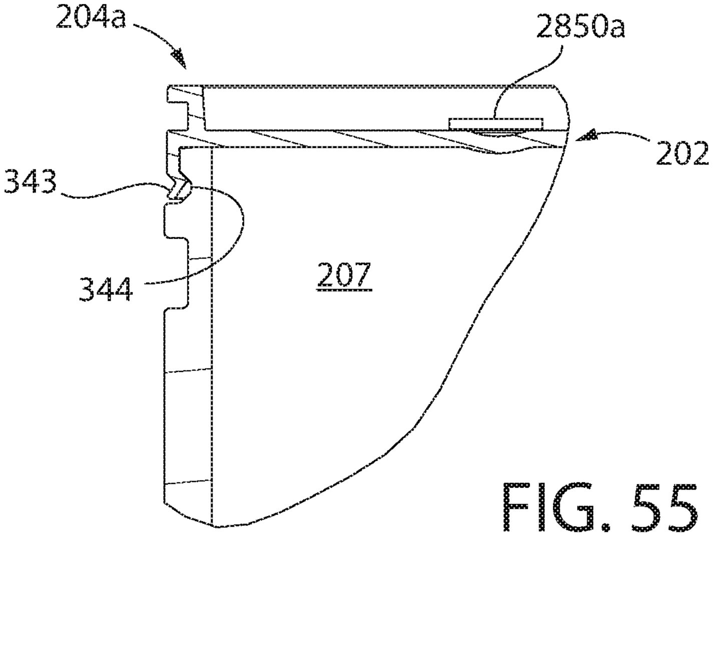
FIG. 55 is an enlarged detail taken from FIG. 52 showing the snap-fit top cap and corresponding snap-fit features of the sample container and cap.
Figure 56:
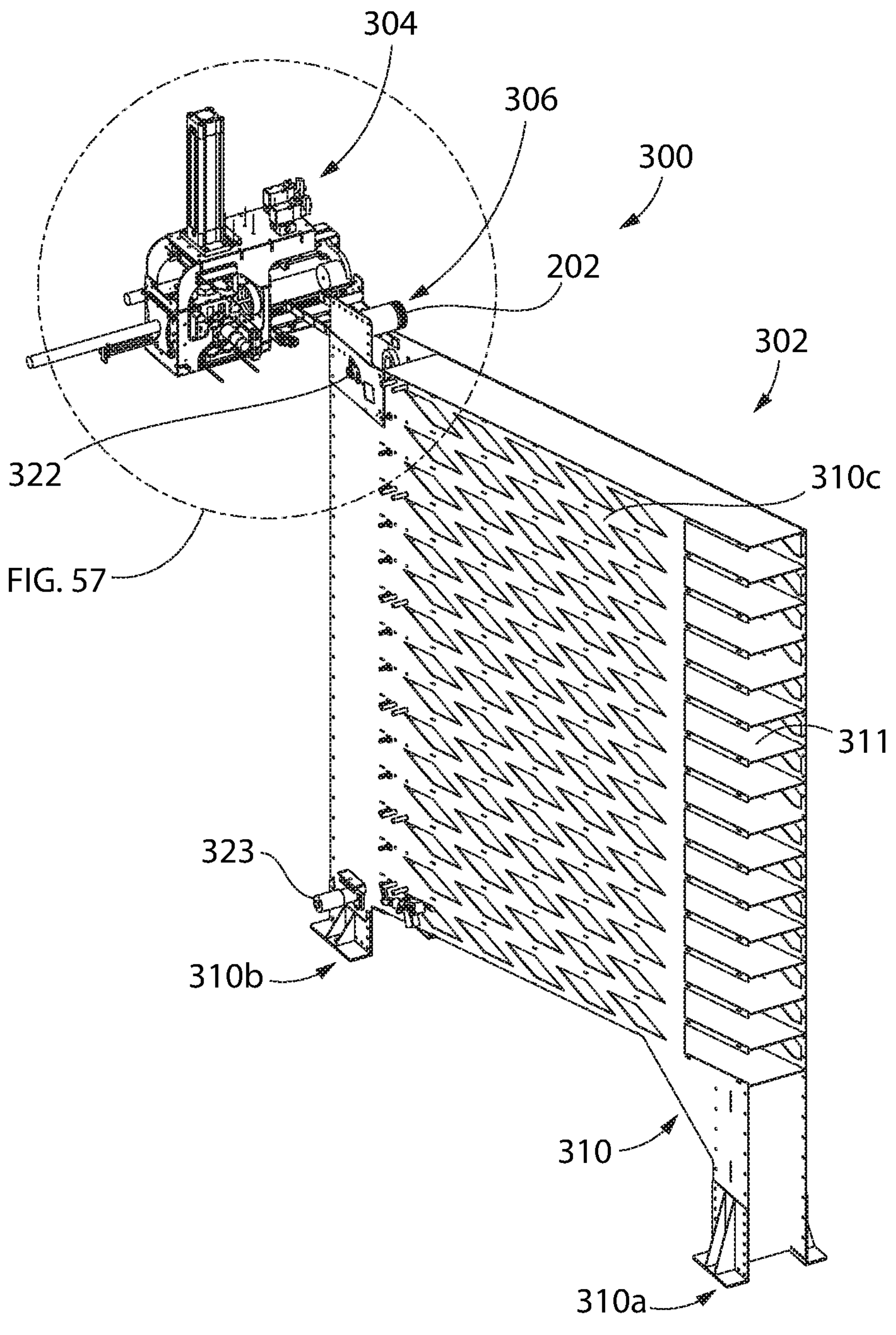
FIG. 56 is a first perspective view of an agricultural sample unloading system according to the present disclosure, including a sample container staging rack, unloading apparatus, and container transfer mechanism.

The decapper 345 is movable between an inward position towards receptacle 336 of carriage 332 to engage cap 204*a* of a newly loaded sample tube 202, and an outward position away therefrom via operation of an actuator 346 (see, e.g., FIG. 96). Actuator 346 may be any suitable commercially-available electric actuator, pneumatic actuator, or hydraulic actuator. In operation, the decapper initially in the outward position moves and engages end cap 204*a*. Specifically, rails 342 of the decapper 345 engage groove 347 on opposite circular sides of the cap. With the cap thus engaged, the carriage 332 moves from the outward to inward position which uncouples and removes the cap from the sample tube 202. In one embodiment, the end cap 204*a* may be retained on and sealed to sample tube 202 via a snap fit, which in one embodiment may be formed by circumferentially-extending and inward projecting snap protrusion 343 formed on the sides of lid 204*a* which resiliently engages corresponding snap groove 344 formed on the tube 202 adjacent to top end 203*a* (see, e.g., FIG. 55). End cap 204*a* is formed of a plastic material in one embodiment which has the required elastic deformation properties necessary to form the snap fit to the sample tube body.

To load sample tubes 202 into and from the carriage 332, unloading apparatus 304 includes a tube loading mechanism 360. The mechanism in one embodiment comprises loading actuator 361 including a linearly and horizontally movable ramrod 362 and a tube chute 363. Ramrod 362 may be coupled to actuator 361 via mounting plate 364 slideably movable on a pair of guide rods 365. The actuator 361 (shown schematically in dashed lines FIG. 78) may be coupled to and operable to move mounting plate 364 with ramrod 362 in a linear bi-directional manner towards and away from the carriage 332. Actuator 361 may be any suitable commercially-available linear electric actuator, pneumatic actuator, or hydraulic actuator operable to move plate 364 and ramrod 362 coupled thereto inwards and outwards relative to carriage 332. Tube chute 363 is configured to slideably engage the cylindrical walls 202*a* of the sample tube. The tube chute receives the loaded sample tube 202 from staging rack 302 via transfer mechanism 306 previously described herein. In one embodiment, chute 363 may be V-shaped in cross section being comprised of two flat plates disposed at an acute angle to each other. In one embodiment, tube chute 363 is pivotably mounted at one end to unloading apparatus 304 and movable for discharging/discarding the empty sample tube after the sample has been unloaded, as further described herein. Tubes are loaded into carriage 332 by ramrod 362 through a loading port 368 formed in housing 330 of the unloading apparatus.

Unloading apparatus 304 further includes a sample tube ejector 370 and sample ejector 371. Tube ejector 370 is configured and operable to push the empty sample tube back out of the carriage tube receptacle 336 after the sample is unloaded. In one embodiment, the tube ejector comprises a horizontally movable piston-plunger 372 which may each be any suitable type commercially available electric linear rod actuator, pneumatic cylinder, or hydraulic cylinder with retractable/extendible operating rod 372*a* terminated with a diametrically enlarged cylindrical plug disk 372*b* (see, e.g., FIG. 108). In one embodiment, piston-plunger 372 is coaxially aligned with tube feed axis FX and arranged directly opposite ramrod 362 on the lateral side of carriage 332 opposite the lateral side where the ramrod is located. Ramrod 362 is also coaxially aligned with feed axis FX. Accordingly, in this embodiment, the sample tube 202 is both loaded into and unloaded from receptacle 336 of the tube carriage 332 along the same linear path coaxially with feed axis FX which passes through the geometric center of the receptacle interior space when in its horizontal position in the carriage. In operation, cylindrical plug disk 372*b* of piston-plunger 372 is configured to fit inside sample tube 202 to abuttingly engage push cap 204*b* and force the sample tube back out through loading port 368 in housing 330 of the unloading apparatus.

Sample ejector 371 is configured and operable to eject the sample from the sample tube 202 when in its inverted vertical position when the detachable end cap 204*a* is removed from the top end of the tube. Sample ejector 371 in one embodiment comprises a vertically movable piston-plunger 373 which may each be any suitable type commercially available electric linear rod actuator, pneumatic cylinder, or hydraulic cylinder with retractable/extendible operating rod 373*a* terminated with a diametrically enlarged cylindrical plug disk 373*b*. Plug disk 373*b* is configured for insertion into and through the sample tube 202 from end to end to eject and unload the agricultural sample therefrom.

Figure 50:
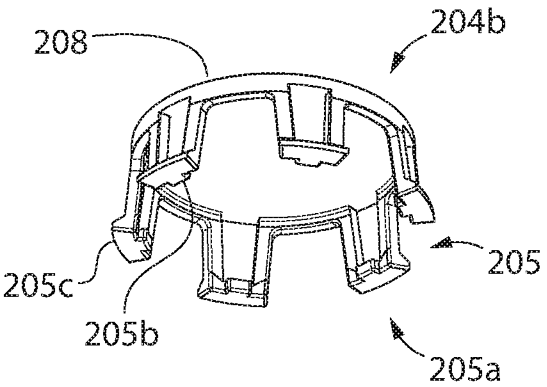
FIG. 50 is a bottom perspective view of the slideable spring-action push cap of the sample container.
Figure 51:
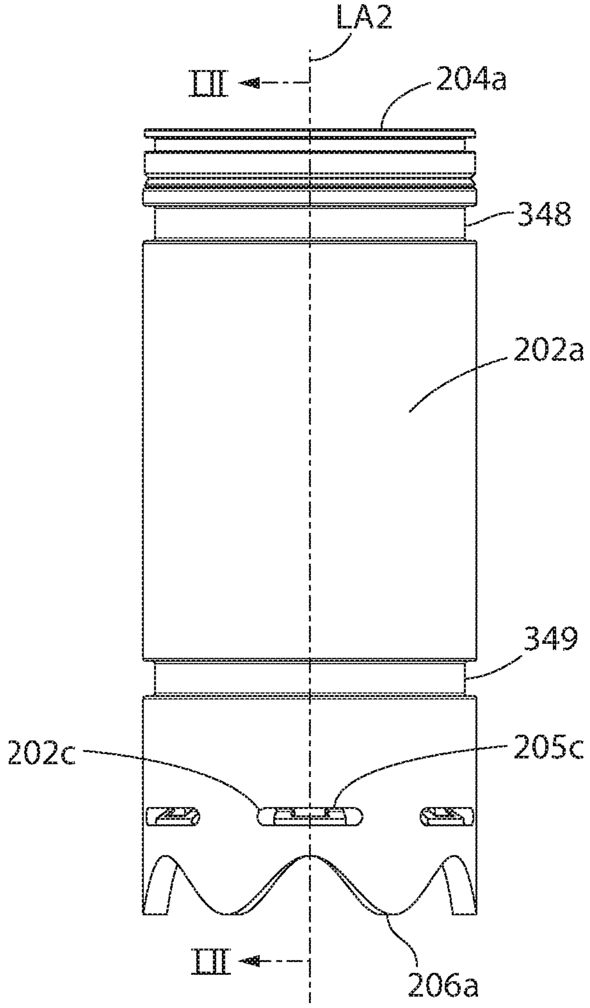
FIG. 51 is a side view of the sample container.
Figure 52:
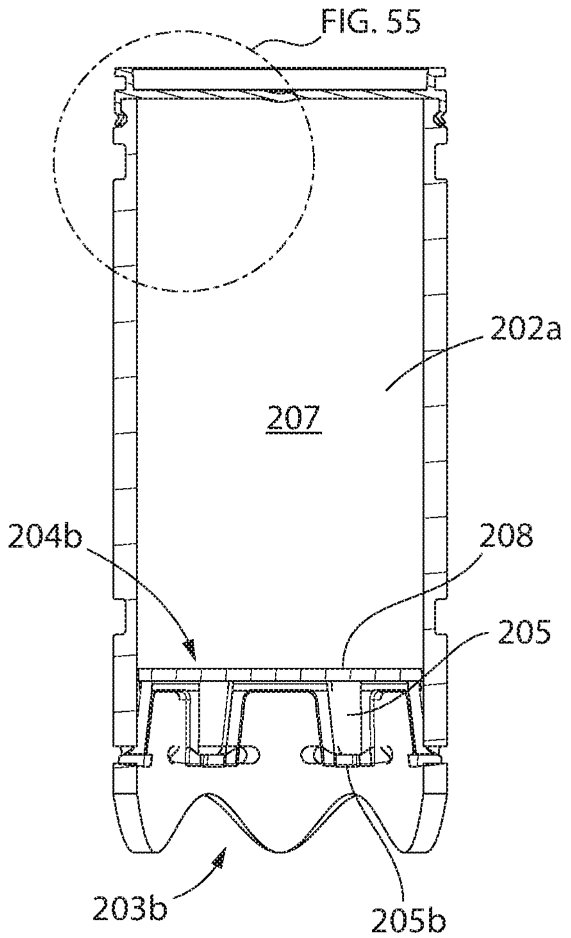
FIG. 52 is a side cross sectional view thereof.
Figure 53:
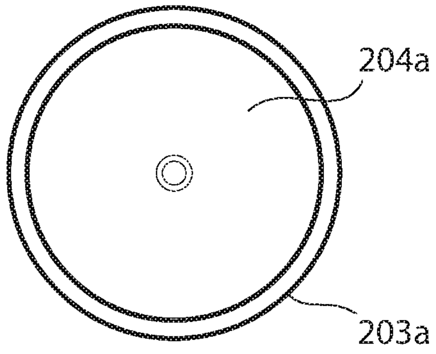
FIG. 53 is a top view thereof.
Figure 54:
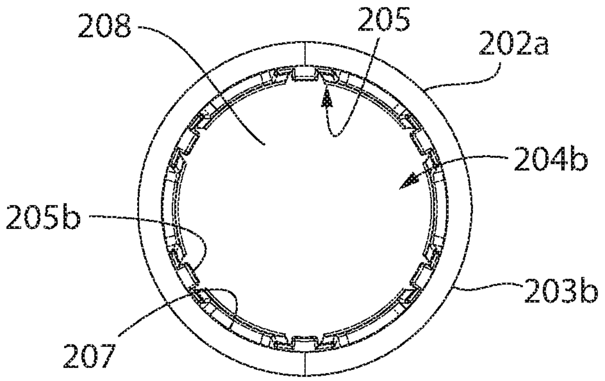
FIG. 54 is a bottom view thereof.
Figure 106:
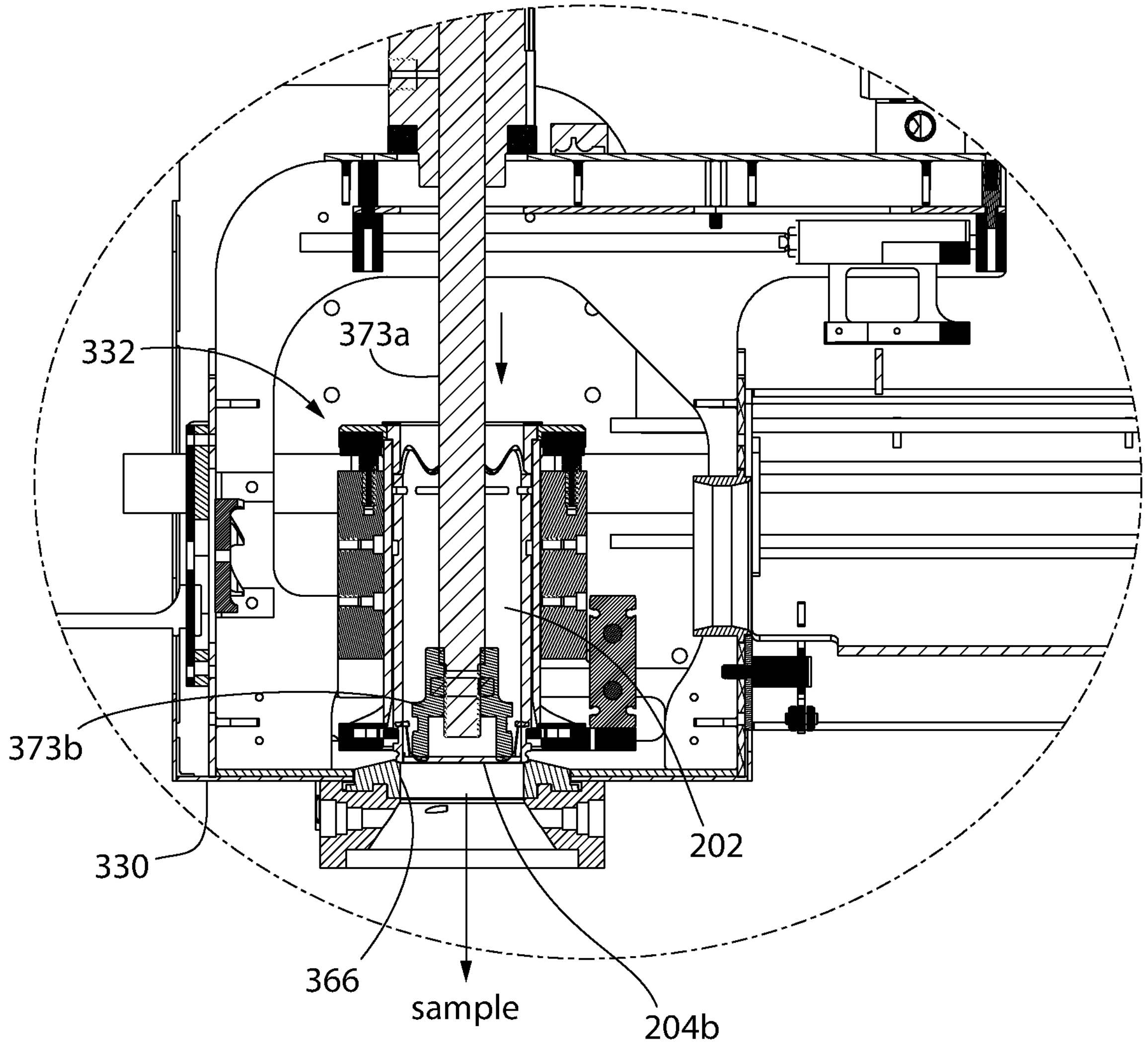
FIG. 106 is a twelfth cross sectional view thereof.
Figure 107:
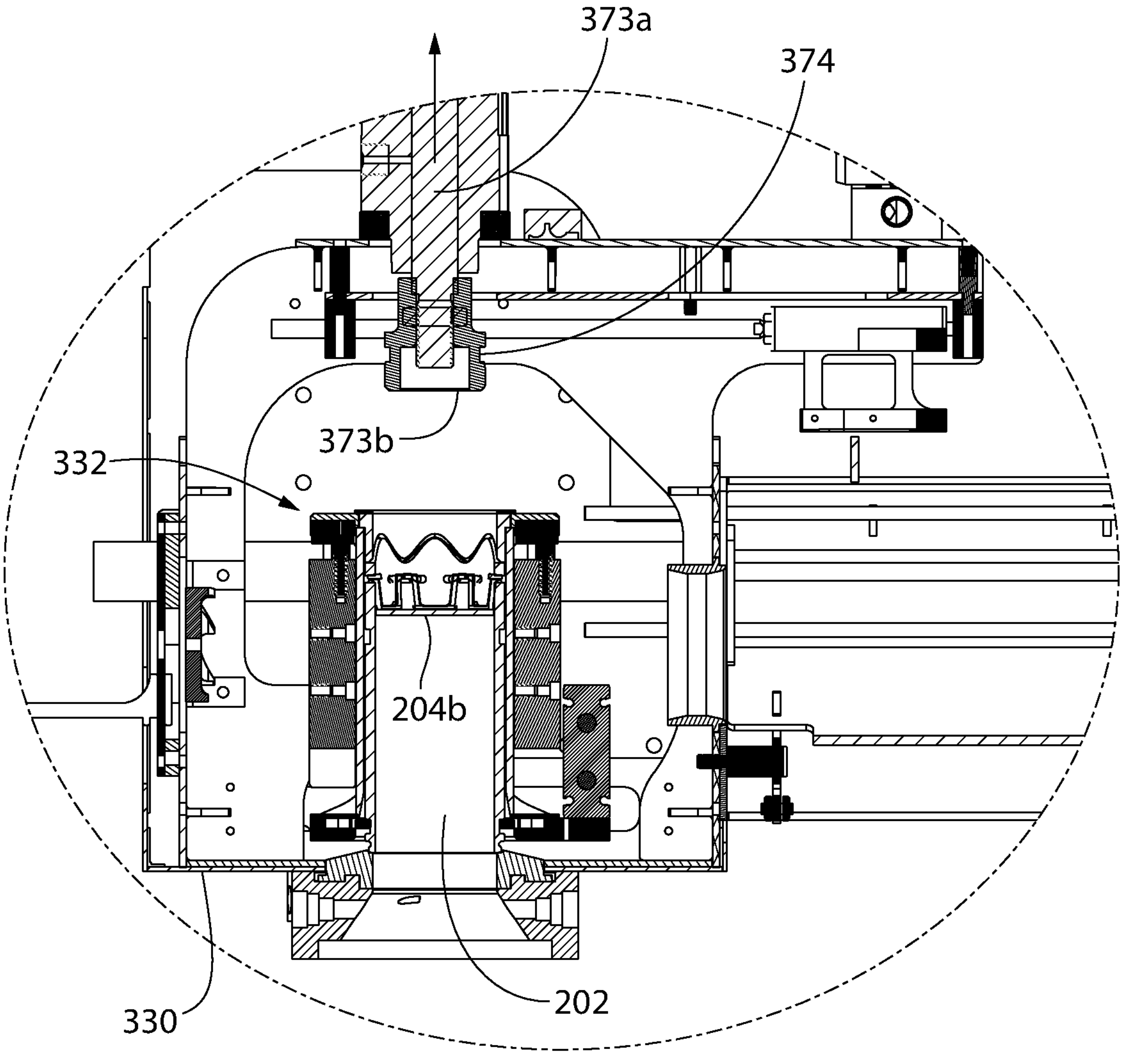
FIG. 107 is a thirteenth cross sectional view thereof.

In one embodiment, plug disk 373*b* is configured to selectively and lockingly engage the slideable push cap 204*b* of sample tube 202. The plug disk includes a circumferential groove 374 on its exterior surface (see, e.g., FIG. 107) which is engageable with an inward projecting tab 205*b* on the spring-action retention protrusions 205 of cap 204*b* (see, e.g., FIG. 50). In one embodiment, tabs 205*b* are formed on the free terminal ends 205*a* of the retention protrusions opposite the outward projecting tabs 205*c* which engage the retention slots 202*c* in the sample tube wall 202*a* (see also FIG. 45). In operation, the sample ejector piston-plunger 373 is operable in a linear downward stroke to both push and slide tube cap 204*b* downwards inside the sample tube 202 when inverted in carriage 332 toward its top end 203*a* (see, e.g., FIG. 106), and then in a linear n upwards stroke pull and return the cap back upwards to re-lock the cap to the retention slots 202*c* in the tube (see, e.g., FIG. 107), as further described herein. Engagement between groove 374 of plug disk 373*b* and tab 205*b* of push cap 204*b* enables return of the cap back upwards with the plug disk. It bears noting that the retention protrusions 205 of push cap 204*b* are pressed and deflected radially inwards when the outward protruding locking tabs 205*c* are disengaged from retention slots 202*c* in sample tube 202 as the sample ejector plug disk 373*b* pushes downwards on the push cap. The inwardly deflected retention protrusions 205 can resiliently spring back outward since the outward protruding locking tabs 205*c* are maintained inwards by the inside wall surfaces of the sample tube. This in turn maintains between circumferential groove 374 of plug disk 373*b* and tab 205*b* of the push cap retention protrusions 205 as the cap slides downwards and upwards inside the sample tube 202 until the retention protrusions reach the tube retention slots 202*c* and are then resiliently biased back outwards.

A method or process for unloading an agricultural sample container will now be described using unloading system 300 and various components thereof previously described disclosed herein. FIG. 109 is a high level flow chart showing the general steps in the method or process. Reference will also be made below to FIGS. 84-108, which show more detail of some of the sequential steps in processing and unloading the sample container. FIGS. 95-108 specifically are enlarged cross-sectional views of unloading apparatus 304 specifically showing the sample container (e.g., sample tube 202 in this embodiment) in receptacle 336 of the tube carriage 332 and its various rotational orientations and axial positions during the sample unloading process. References to rotational movement and directions are from the perspective of the equipment as viewed in these foregoing FIGURES, for convenience of description.

Prior to the specific steps of the sample unloading process described below which are performed by unloading apparatus 304, the staging rack 302 and transfer mechanism 306 first perform their functions previously described herein to stage and then load a sample tube 202 onto feed chute 363 of the unloading apparatus 304. These tube staging and feed steps may include first (1) system controller 2820 executes the preprogrammed control logic/program instructions (software) to select the feed ramp 311 from which one of the sample tubes 202 is to be released for loading into sample unloading apparatus 304. (2) The feed gate actuator 314*c* actuates the rotatable feed gate 314 of the selected "feed ramp" to release the selected sample container to the sample tube elevator 320. (3) Elevator 320 carries the selected sample tube 202 to either the elevator tube lifting member 324, or in some embodiments a vertical position or location along the staging rack 302 where the sample ID on the sample tube can be scanned by the RFID, visual, or other type electronic reader (as described elsewhere herein). If the sample ID is recognized, the authenticated sample tube is loaded into unloading apparatus and the process continues to the first step of sample unloading process in the flow chart in FIG. 109 and as further described below starting with FIG. 95. If sample ID is not recognized for some reason, the sample tube is rejected and ejected from feed chute 363 of the tube feed mechanism 360 after being loaded into the unloading apparatus.

Figure 85:
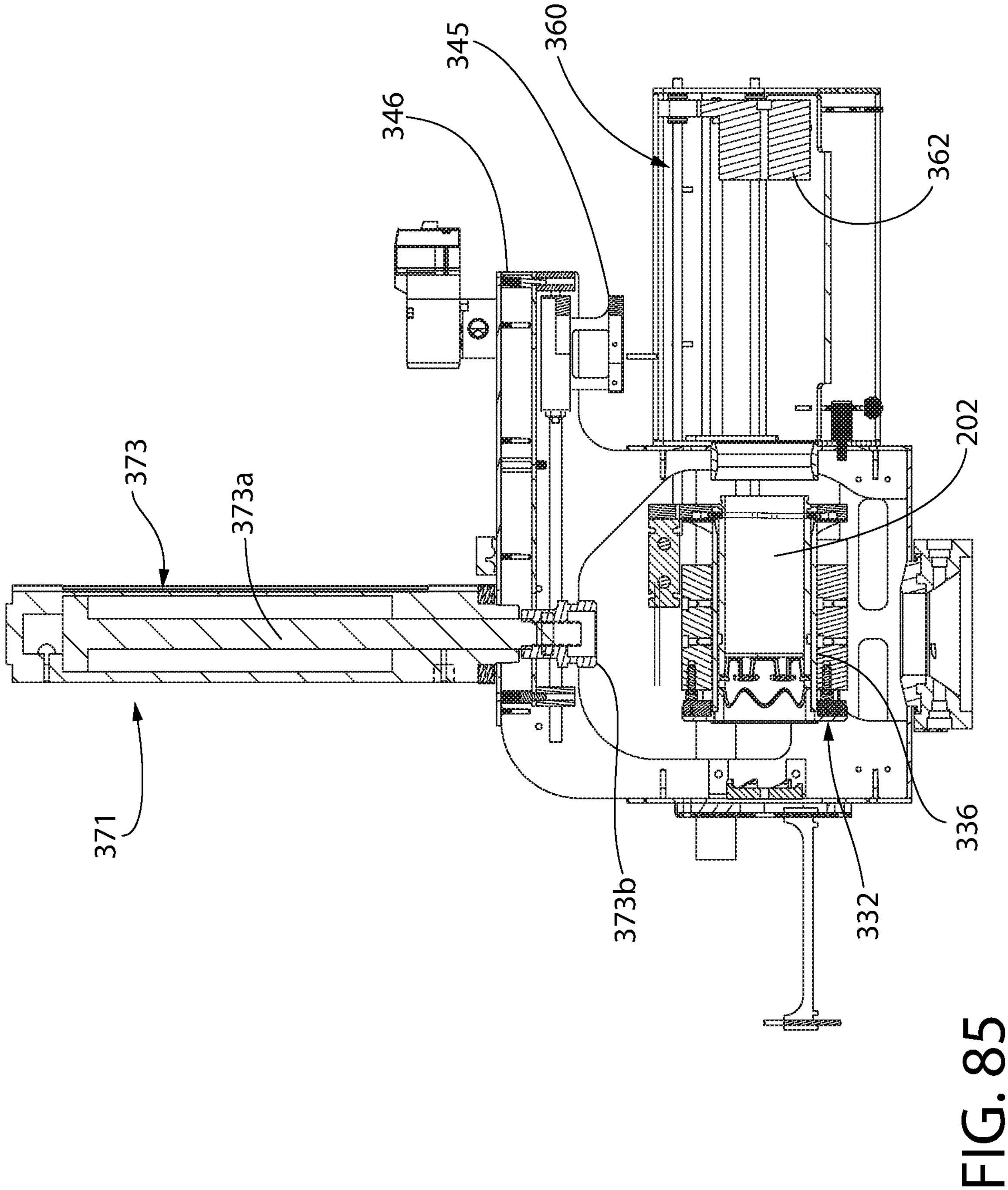
FIG. 85 is a cross-sectional view of FIG. 84.
Figure 95:
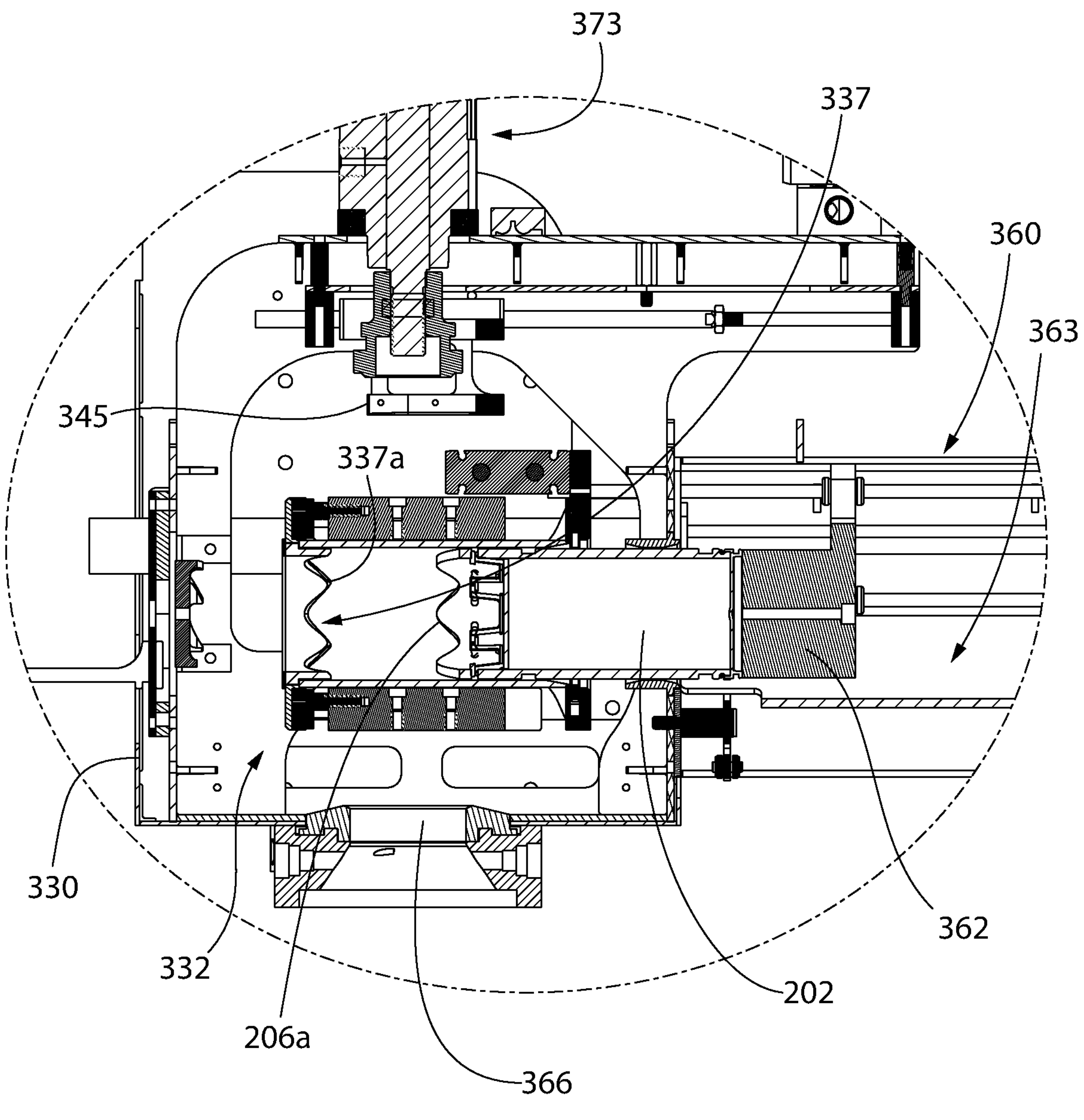
FIG. 95 is a first cross sectional view of the unloading apparatus in a series of sequential views illustrating a sample container unloading process according to the present disclosure.

FIG. 95 now shows the accepted capped sample container 200 in the form of the authenticated sample tube 202 which has been loaded onto feed chute 363 of tube loading mechanism 360 from the staging rack 302 by transfer mechanism 306; each previously described herein. The sample tube contains the agricultural sample (e.g., soil or other) and oriented on the slide so that bottom end 203*b* is facing left towards carriage 332 of the apparatus. Carriage 332 and concomitantly receptacle 336 is rotated 90 degrees clockwise to the right in a horizontal position so that the open top 339 of the receptacle faces towards the feed chute and is readied for receiving the sample tube (see also FIG. 84). The sample tube is being pushed and loaded into receptacle 336 bottom end first by ramrod 362 of the tube loading mechanism 306. FIGS. 85 and 96 show the sample tube fully inserted in the carriage. Castellated support surface 337 in tube receptacle 336 engages complementary configured castellated bottom end 203*b* of the tube 202.

Figure 97:
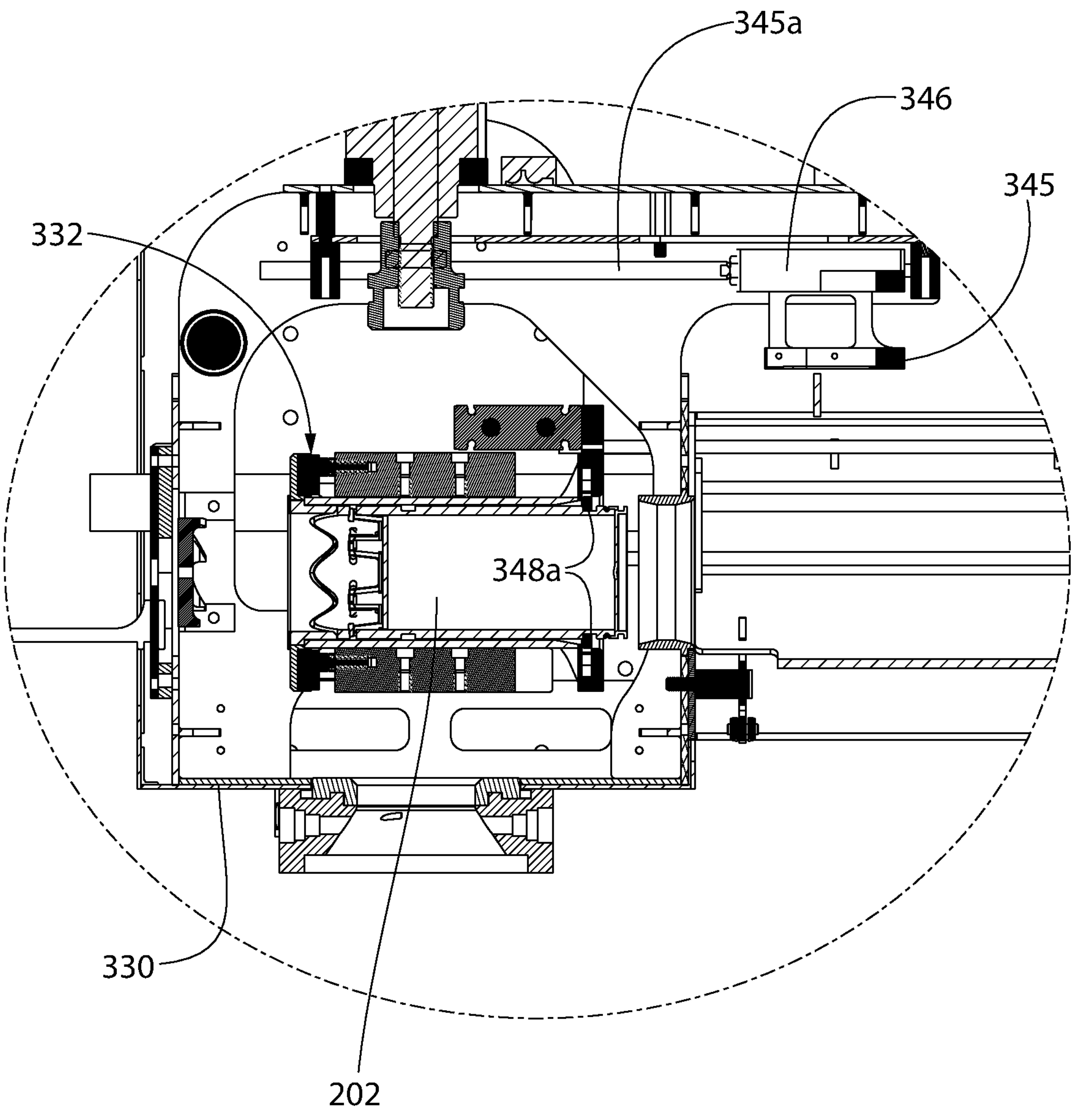
FIG. 97 is a third cross sectional view thereof.
Figure 111:
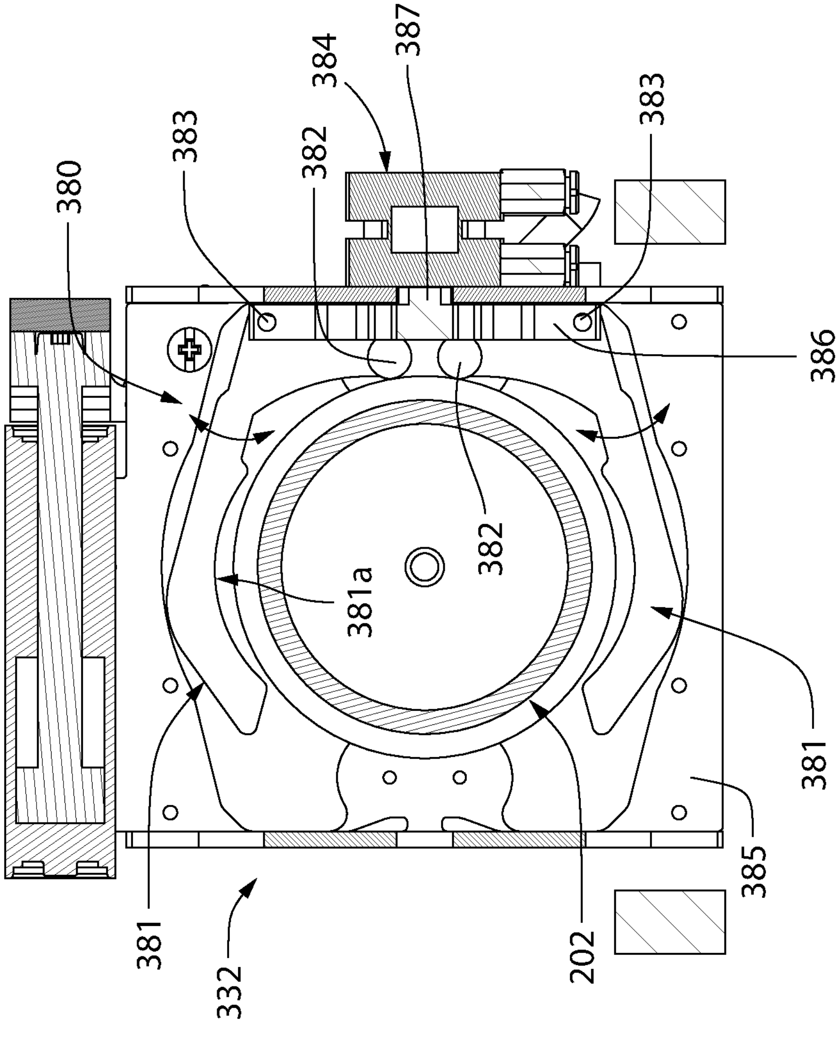
FIG. 111 is a perspective view of a sample container gripping mechanism according to the present disclosure.
Figure 112:
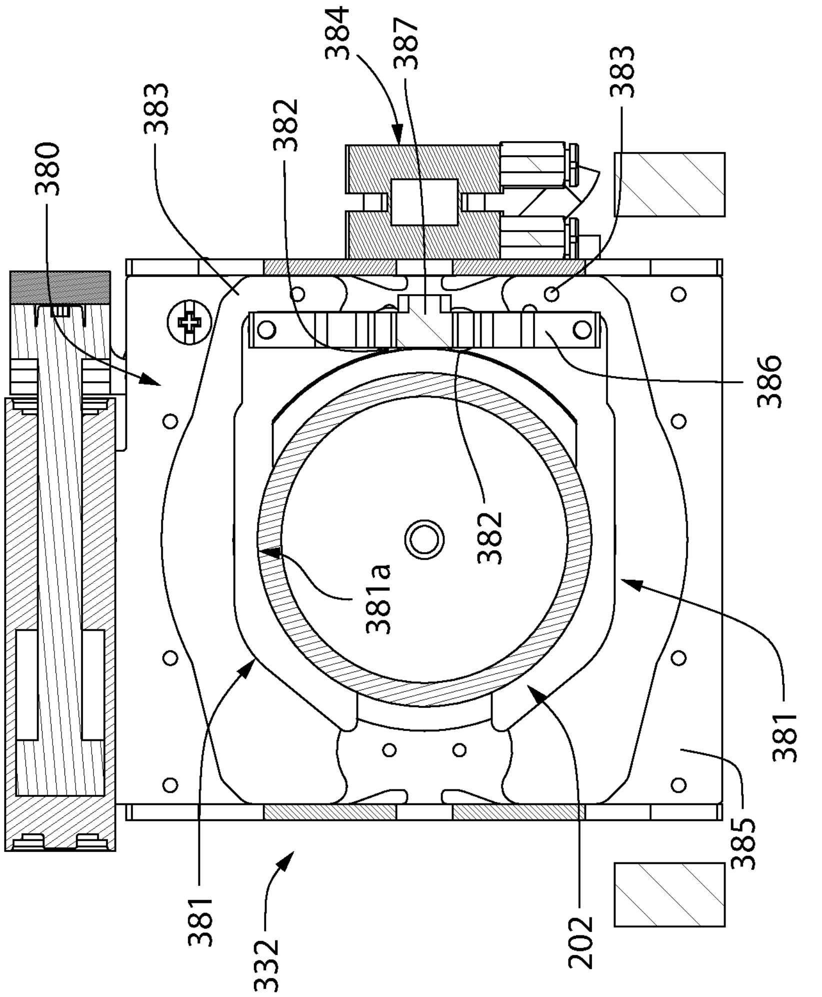
FIG. 112 is a plan view thereof showing the gripping mechanism in an outward open position disengaged from the sample container.
Figure 113:
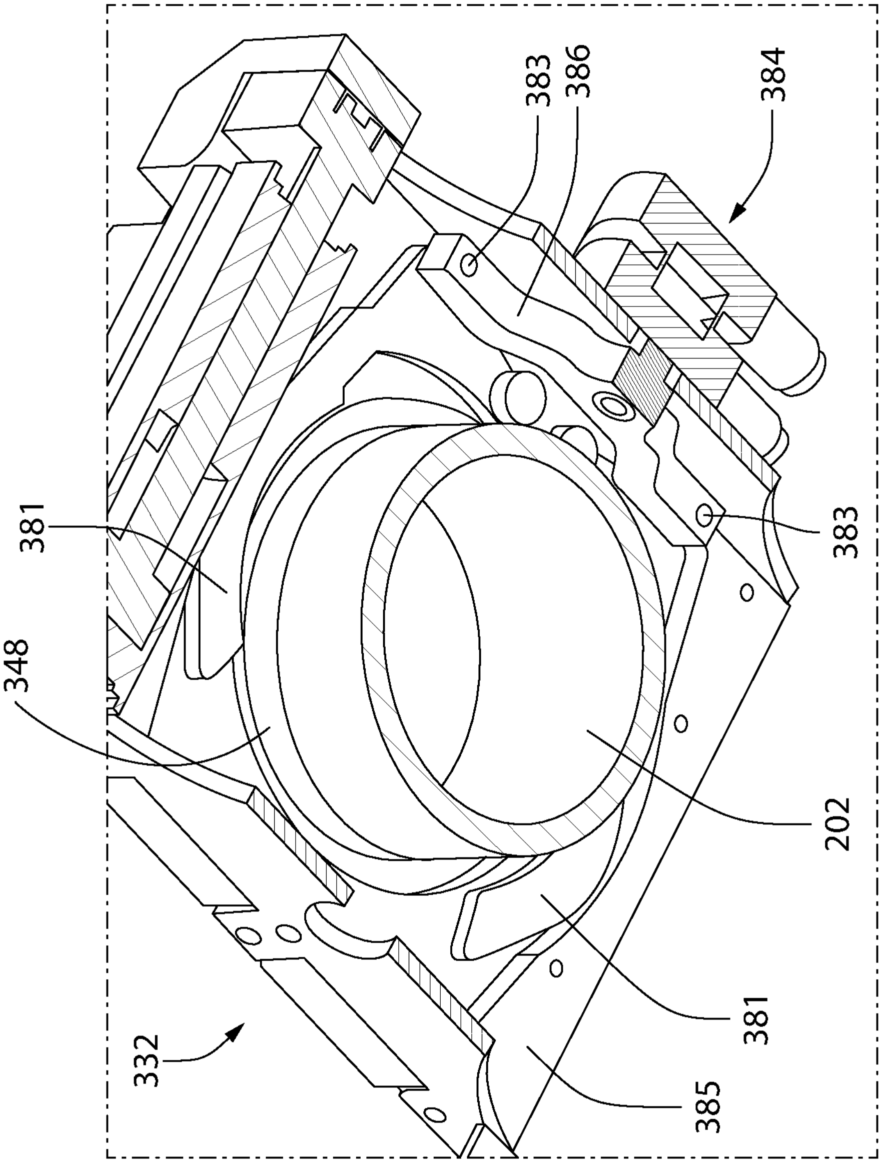
FIG. 113 is a plan view thereof showing the gripping mechanism in an inward closed position lockingly engaged with the sample container.
Figure 114:
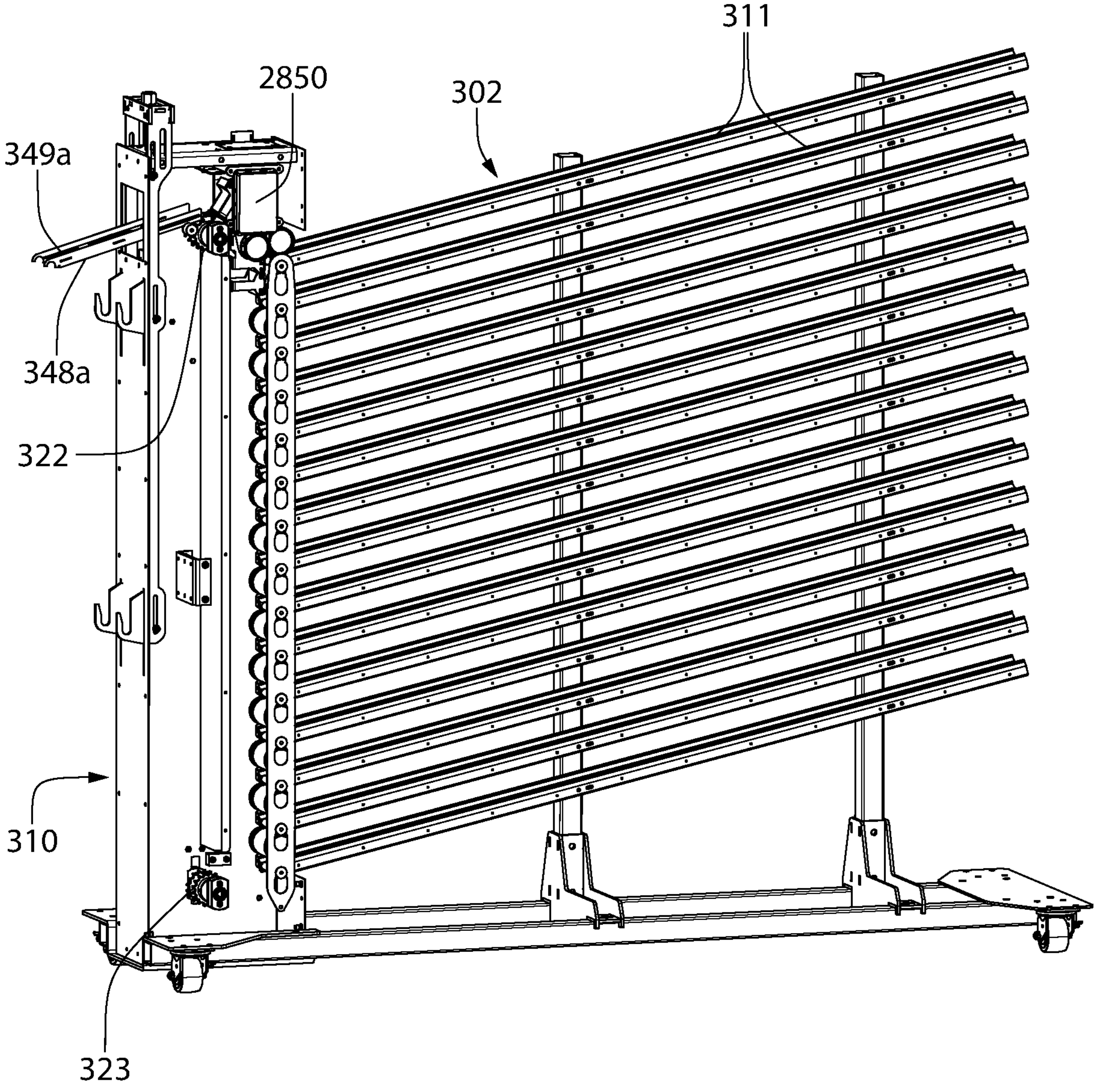
FIG. 114 is a first perspective view of an alternative embodiment of the container staging rack.
Figure 115:
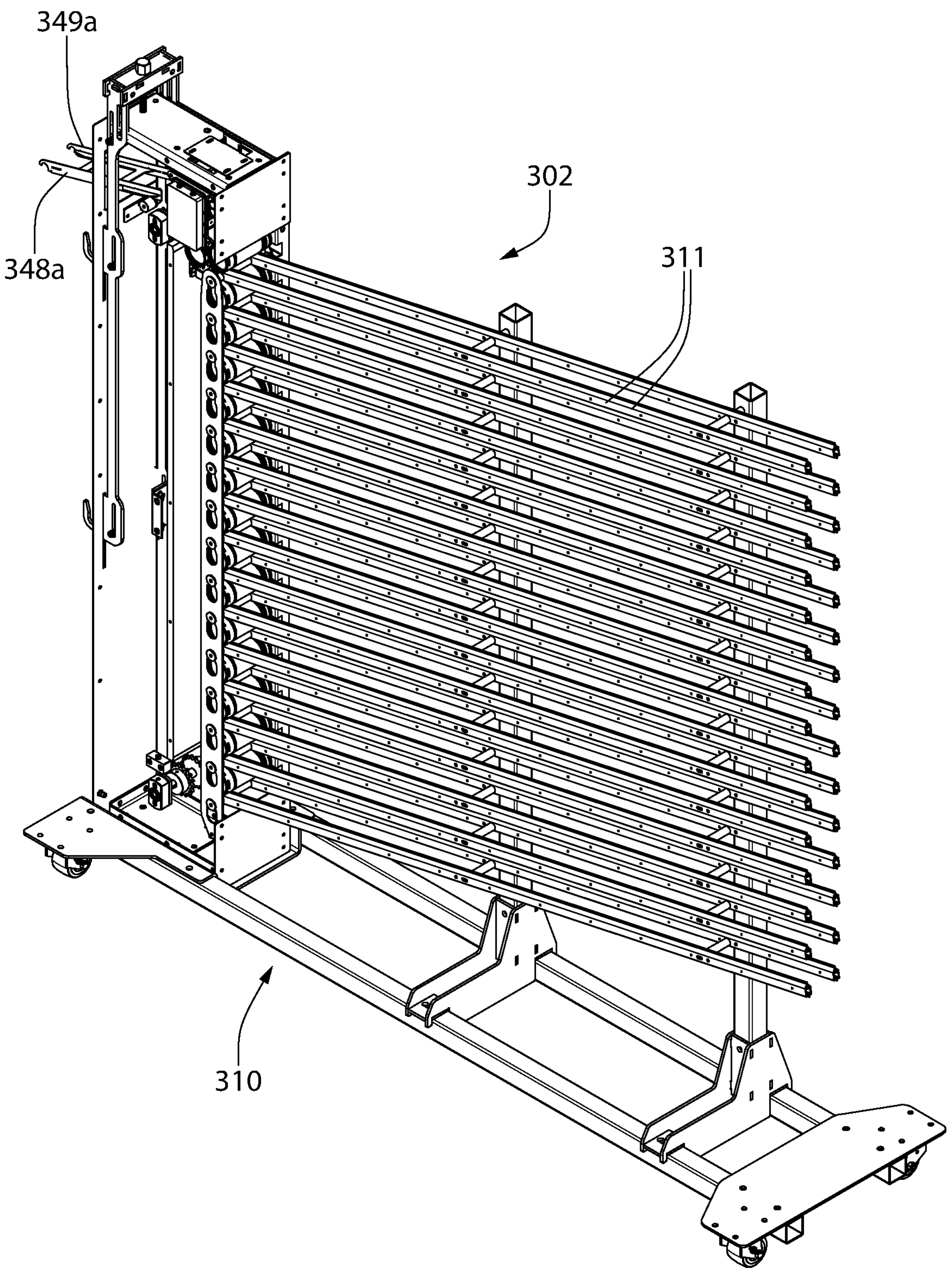
FIG. 115 is a second perspective view thereof.
Figure 117:
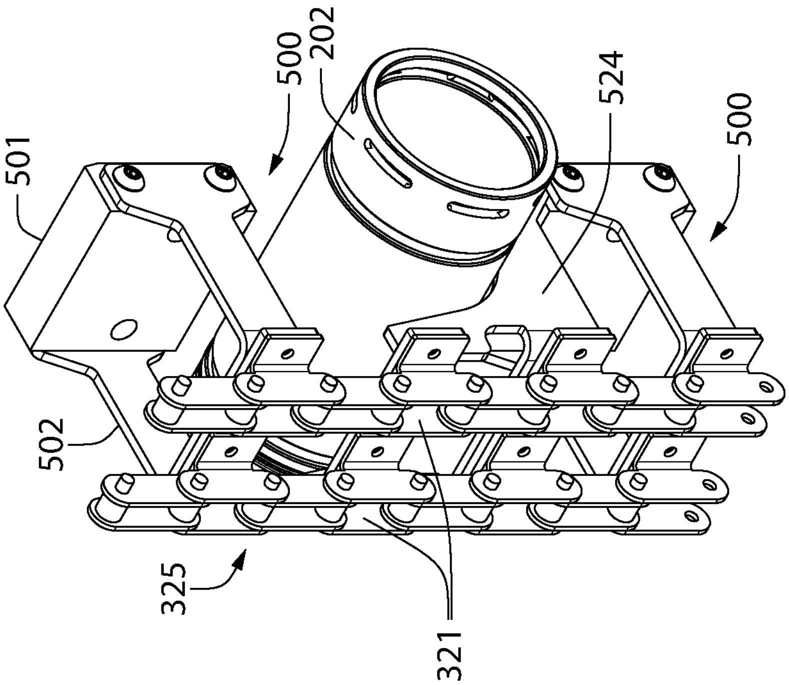

Next, with the sample tube 202 now docked in receptacle carriage 332, FIG. 97 shows movable gripping arms 381 of a sample container or tube gripper 380 of carriage 332 moving inwardly to engage circumferential retention groove 348 formed on the exterior surface of sample tube 202 via a pivotable clamping action of the arms. This retains and locks the tube in receptacle 336 of the carriage when inverted for unloading the sample. With additional reference to FIGS. 111-113 showing the gripper in more detail, each gripping arm 381 of tube gripper 380 is an elongated structure rotatably mounted to the flat top plate 385 of carriage 332 by a pivot bolt 382 (e.g., should bolt). Each gripping arm 381 of the gripping mechanism is further pivotably coupled to a separate pivot pin 383 carried by an elongated bar-shaped actuation member 386. Actuation member 386 is linearly movable inwards and outwards towards or away from sample tube 202 when positioned in tube receptacle 336 of the carriage 332 via operation of a linear actuator 384. Actuator 384 may be any suitable commercially-available electric linear rod actuator, pneumatic actuator, or hydraulic actuator with retractable/extendible operating rod 387 coupled to actuation member 386. Pivot pins 383 are located outboard of the pivot bolts 382 as shown such that moving actuation member 386 inwards and outwards concomitantly produces an openable/closeable claw-like action of the gripping arms 381. The gripper 380 is moveable via actuator 384 between (1) an inwards closed position in which the gripping arms simultaneously move inwards to engage retention groove 348 on the sample tube 202, and (2) an outward open position in which the gripping arms move outwards to disengage the sample tube. Each gripping arm 381 may include an inward facing and arcuately curved grip surface 381*a* engageable with groove 348 in the sample tube body to lock the tube in receptacle 336 of carriage 332.

Figure 86:
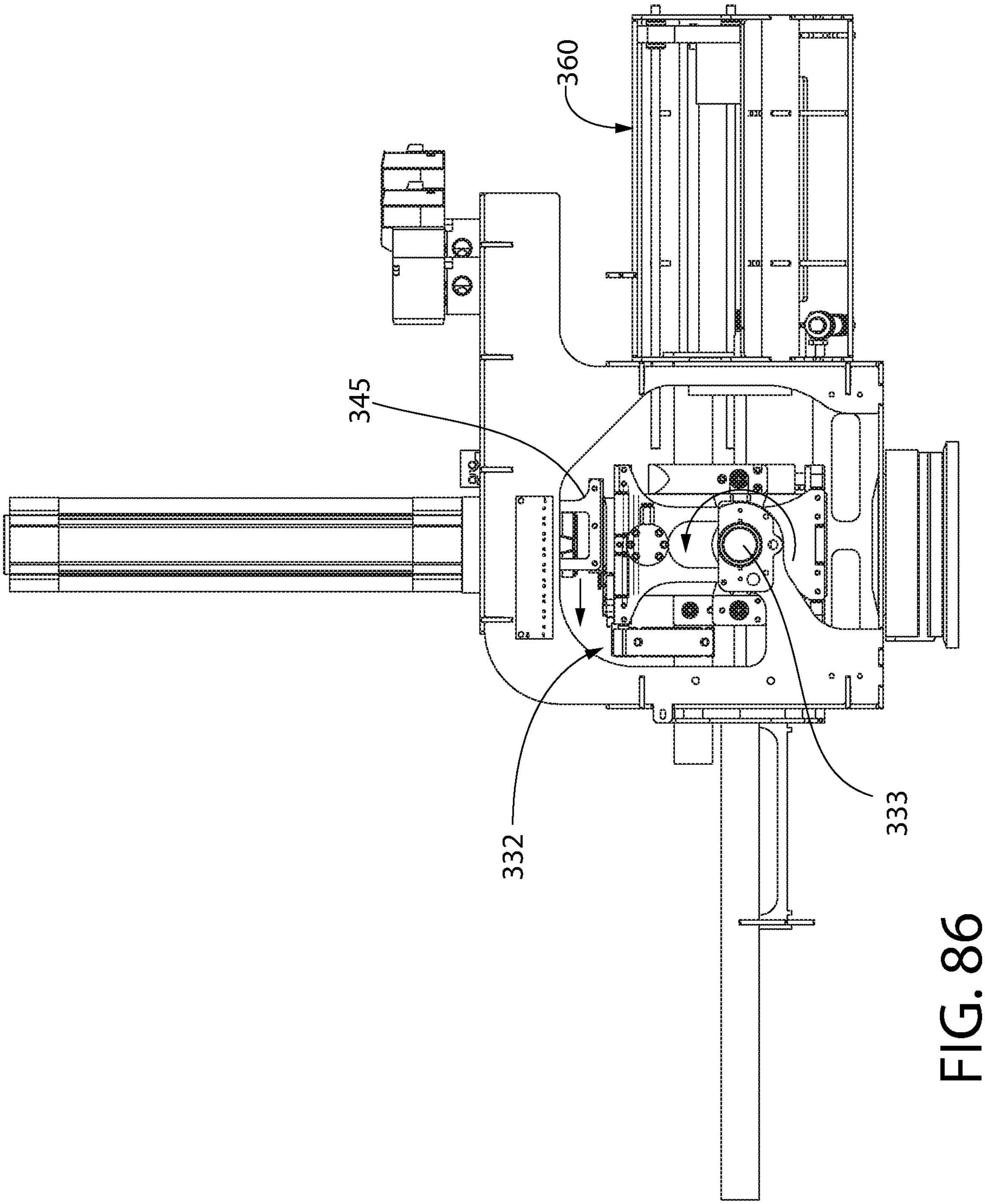
FIG. 86 is a front view of the unloading apparatus showing the carriage and container rotated into a vertical upright position/orientation and decapper engaged with the top cap of the container.
Figure 87:
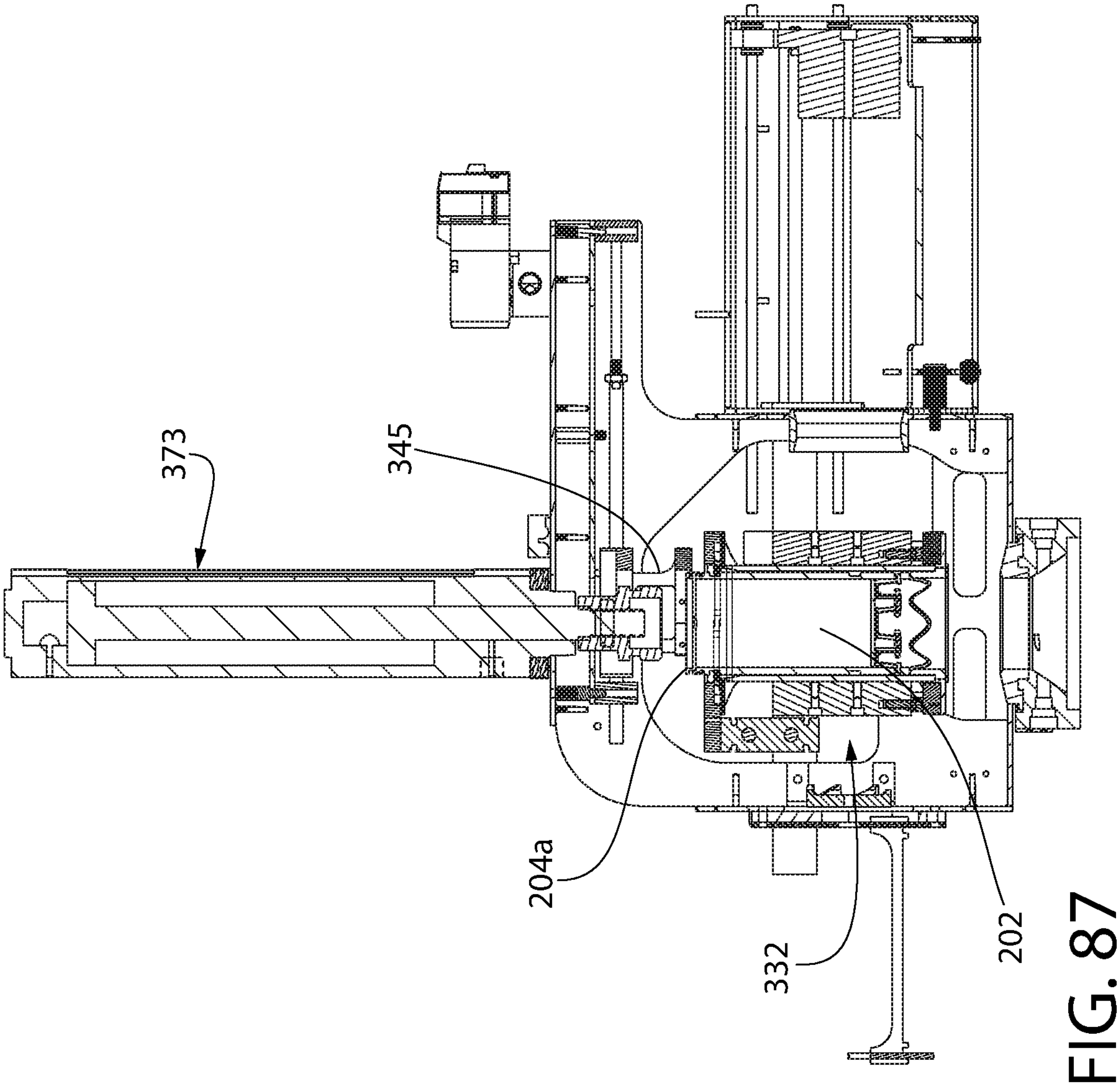
FIG. 87 is a cross-sectional view of FIG. 86.
Figure 88:
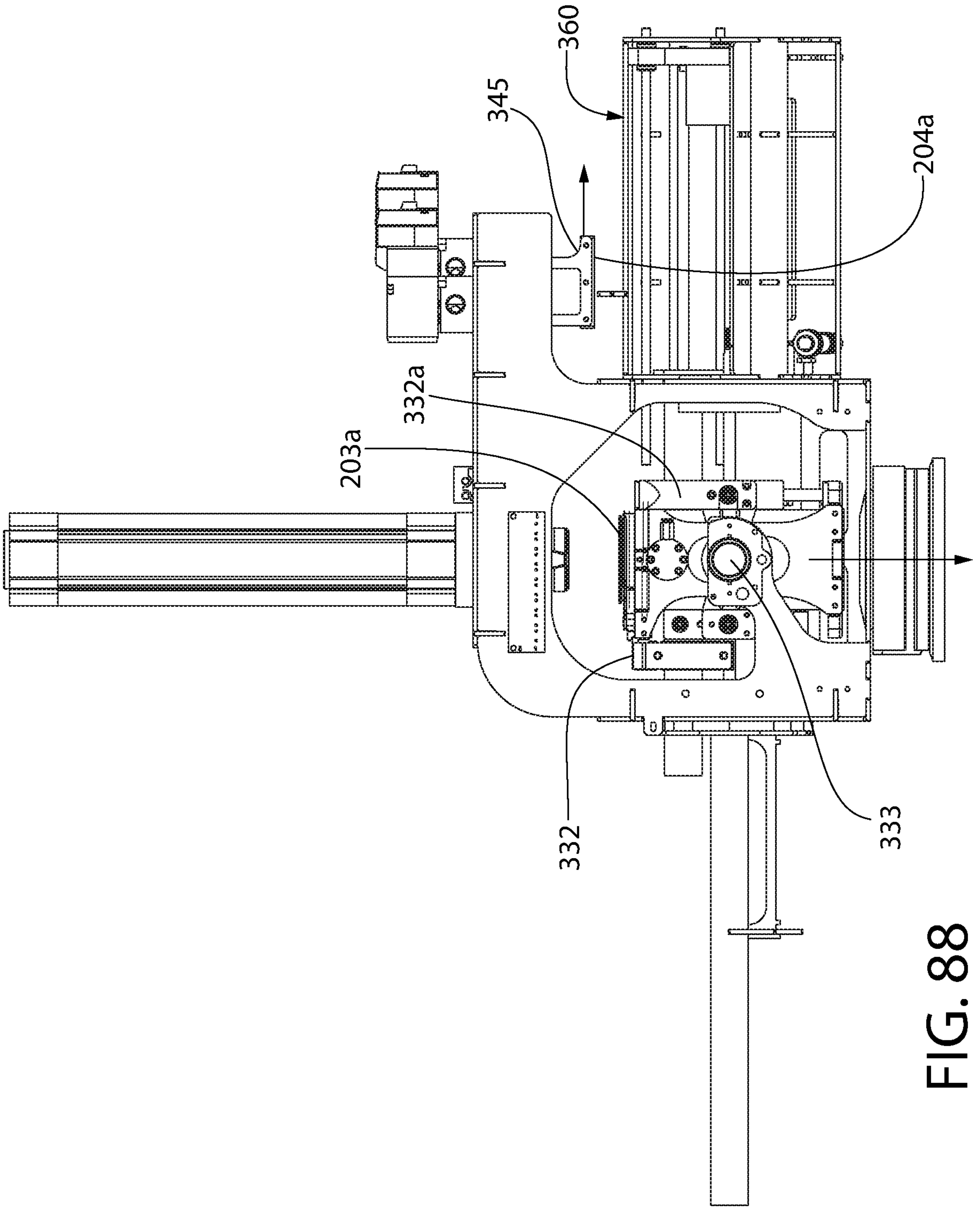
FIG. 88 is a front view of the unloading apparatus showing the carriage shifted downward to remove the top cap of the container and decapper having moved away from the container with the top cap.
Figure 89:
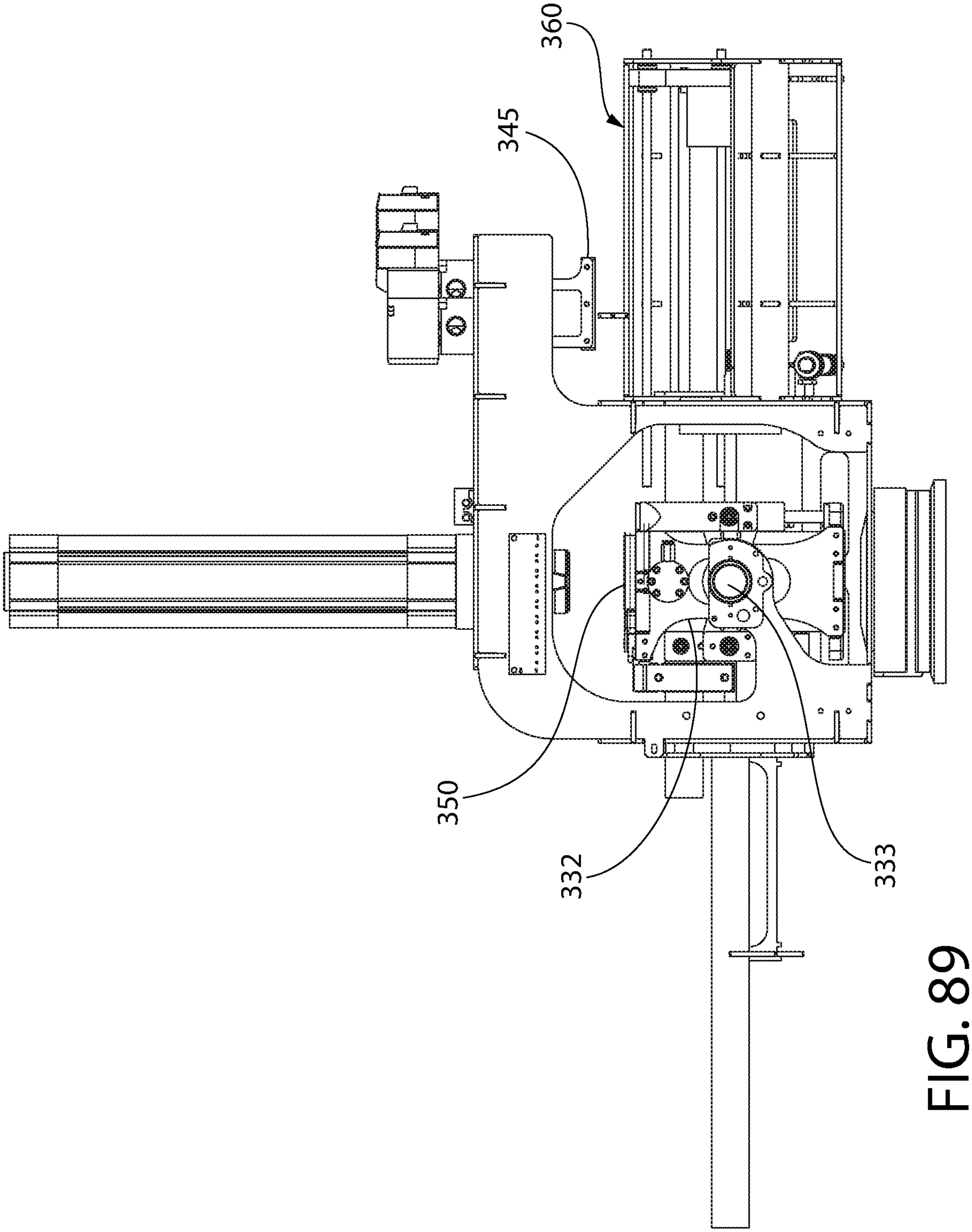
FIG. 89 is a front view thereof showing a closure plate moved onto and closing the top of the open container.
Figure 98:
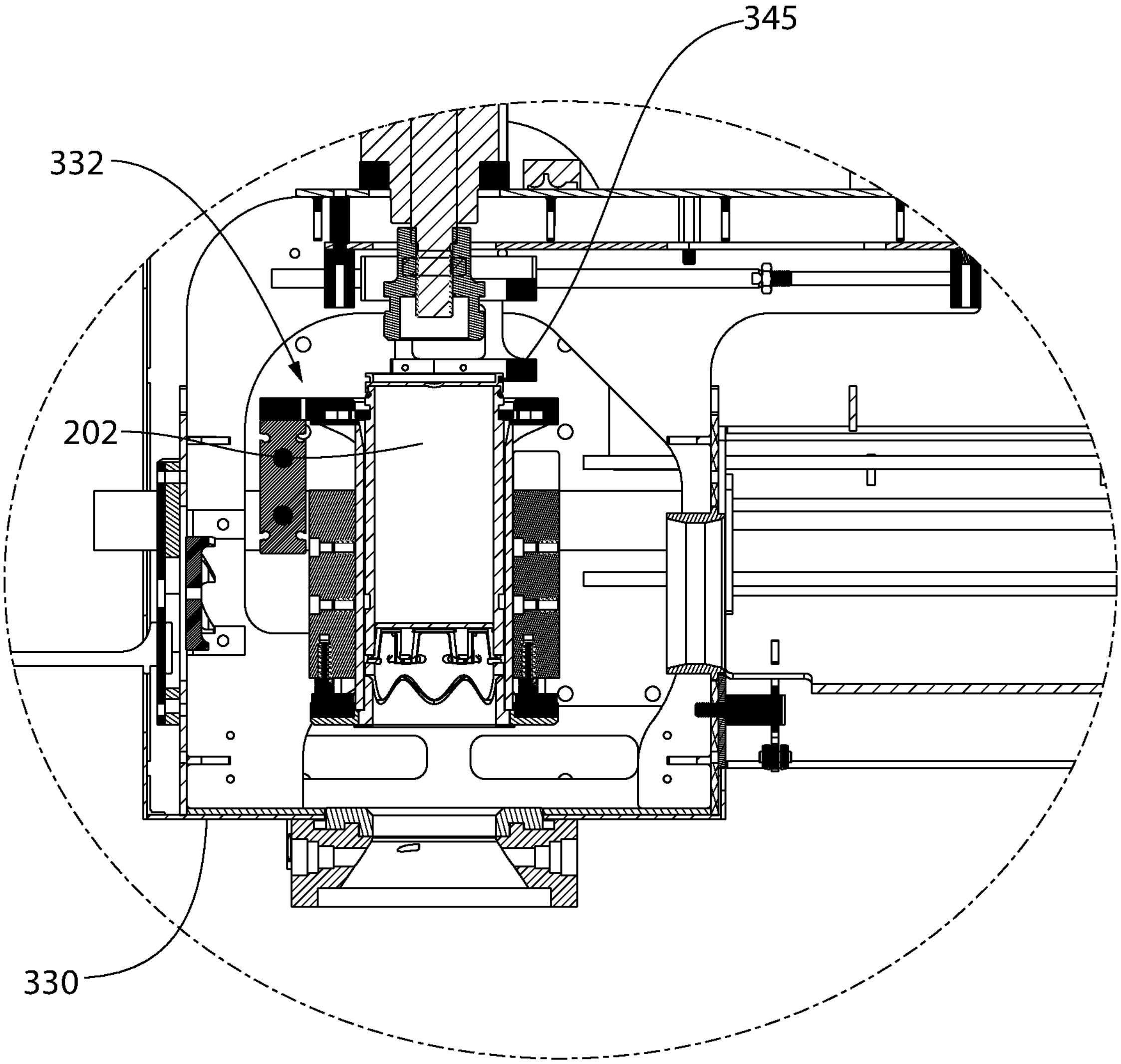
FIG. 98 is a fourth cross sectional view thereof.
Figure 99:
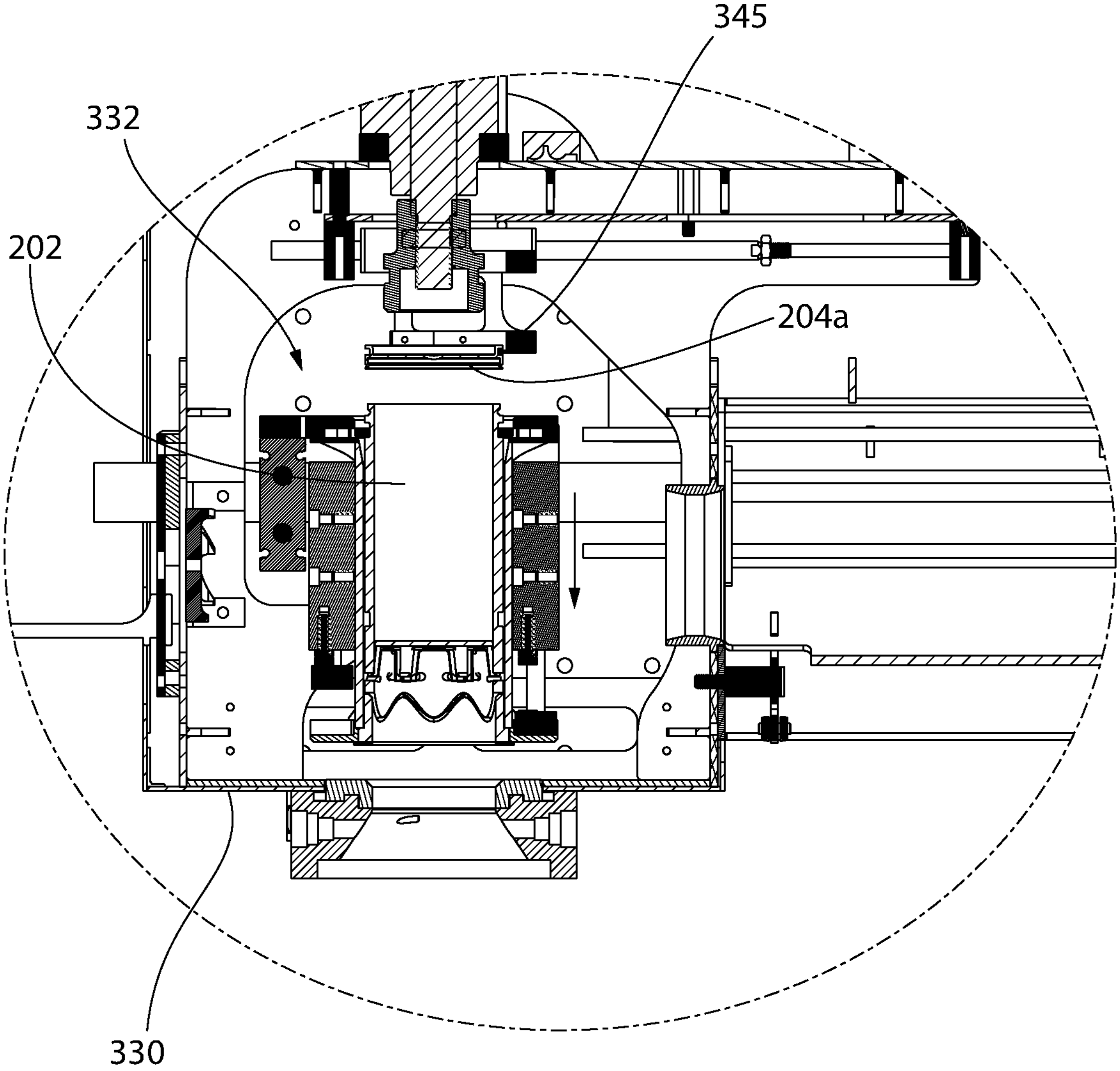
FIG. 99 is a fifth cross-section sectional view thereof.
Figure 100:
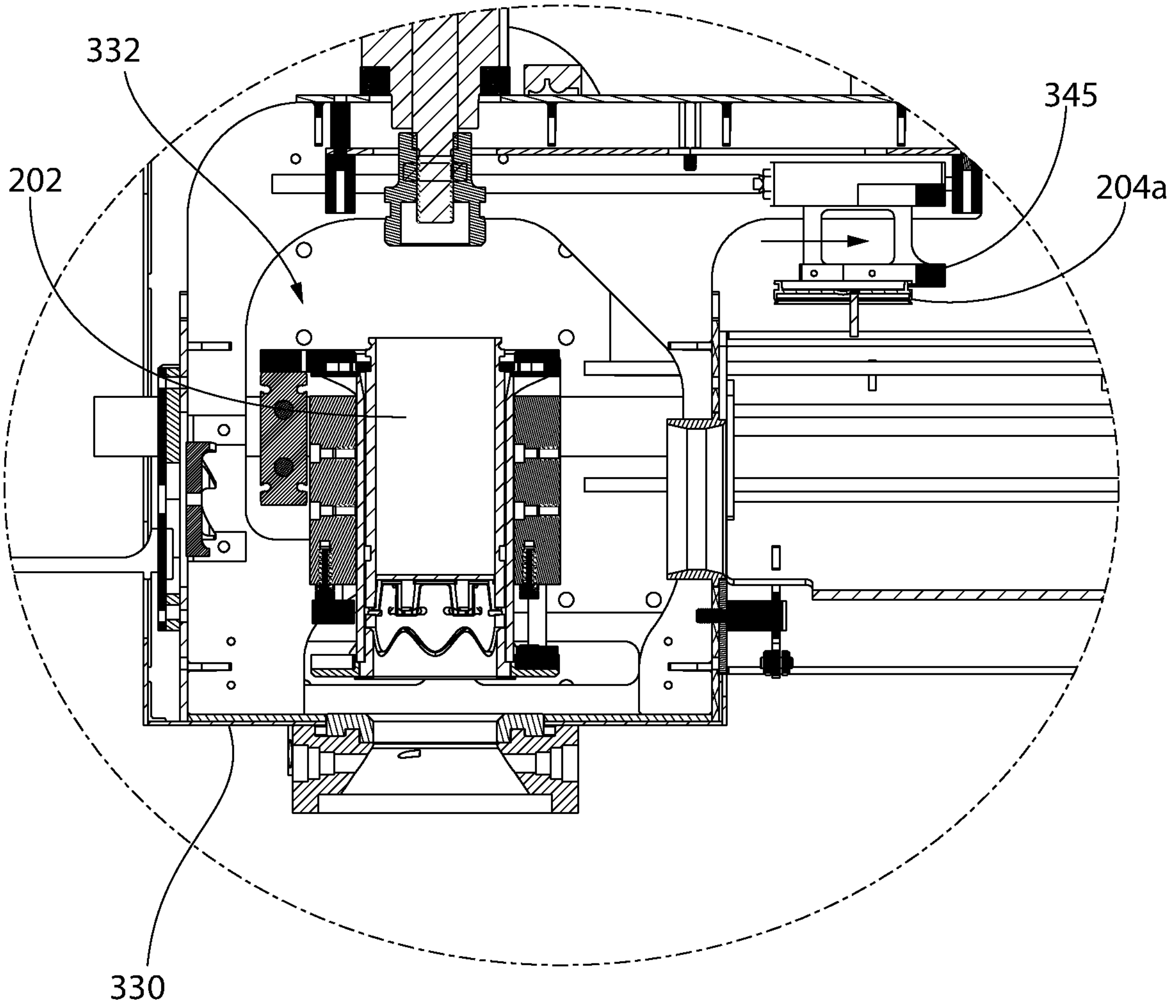
FIG. 100 is a sixth cross sectional view thereof.
Figure 101:
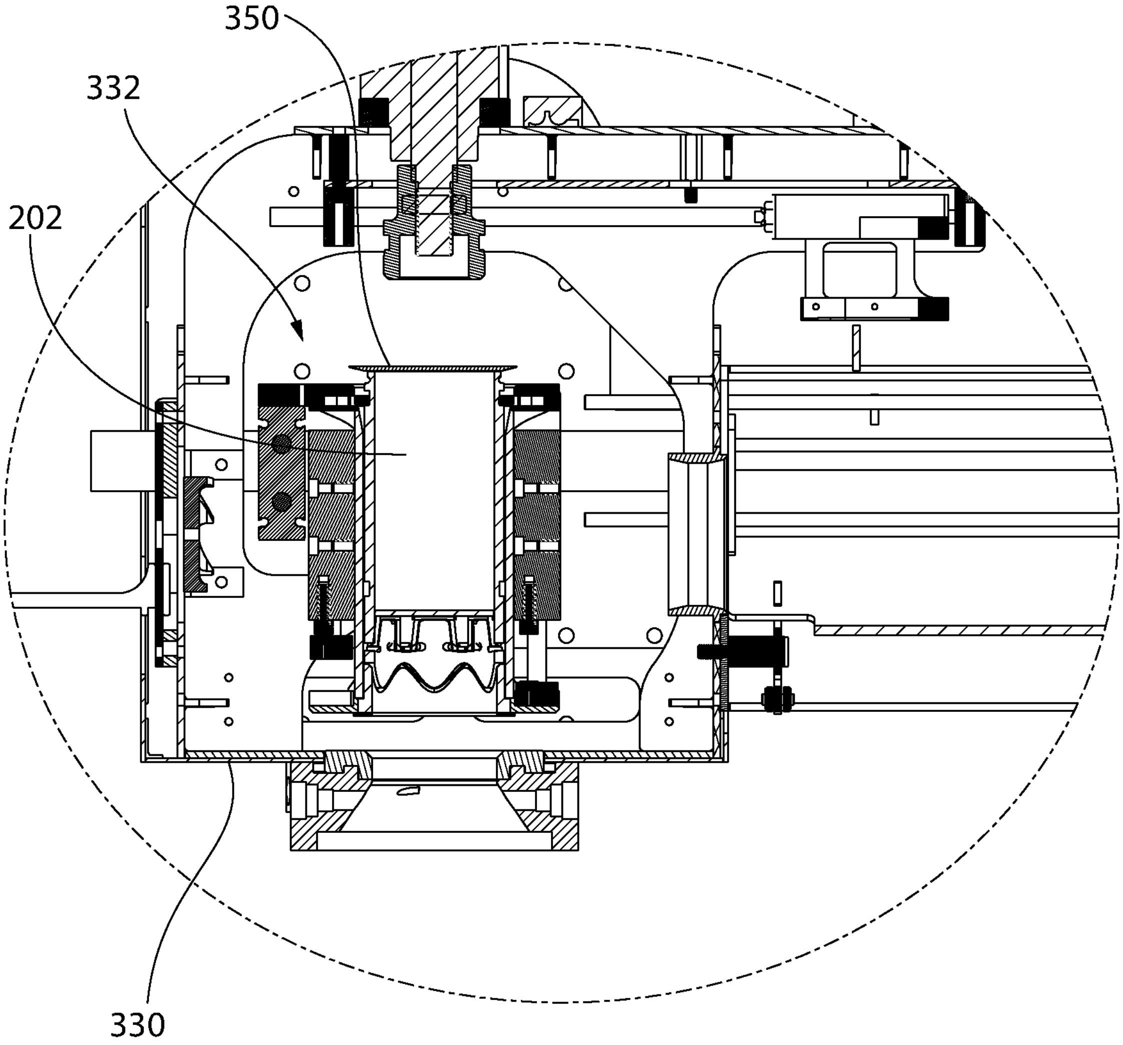
FIG. 101 is a seventh cross sectional view thereof.

FIGS. 86-87 and 98 next shows the carriage which has been rotated 90 degrees counterclockwise to its upright vertical position. Detachable tube end cap 204*a* is now positioned at top of the sample tube 202 in the carriage. The decapper 345 has moved inwards to engage the end cap as shown. Rails 342 of the decapper slideably engage groove 347 in cap 204*a* as previously described herein. With the cap thus engaged, the tube carriage 332 and concomitantly sample tube 202 are moved downwards and inwards relative to carriage housing 330 and its rotating drive shaft 333 (FIGS. 88 and 99) via linear actuators 332*a*; one each coupled to each side of carriage 332 in one embodiment. Actuators 332*a* may be any suitable commercially-available electric actuator, pneumatic actuator, or hydraulic actuator configured and operable to slideably move carriage 332 inwards and outwards relative to carriage housing 330 and carriage drive shaft 333. The downward shift in position of the carriage relative to decapper 345 with cap 204*a* engaged thereto which remain stationary uncouples and "pops" the snap-fit cap 204*a* off the tube. The decapper 345 with cap 204*a* then moves back outwards from the carriage 332 with the cap (see, e.g., FIG. 100). The cap may be dropped into an available bin for reuse later during another sample collection run. Alternatively the reverse process could be conducted after the sample has been unloaded to re-install the cap back on the tube. This advantageously allows the operator to handle only the tube assembly without having to handle the caps separately, primarily but not limited to when tubes are being loaded.

To cover the now open top end 203*a* of sample tube 202 with exposed sample, closure plate 350 moves inwards over the top end 203*a* to temporarily enclose the tube and its contents (see, e.g., FIGS. 74A-B, 89, and 101 showing plate 350 moving from outward to inward position).

Figure 102:
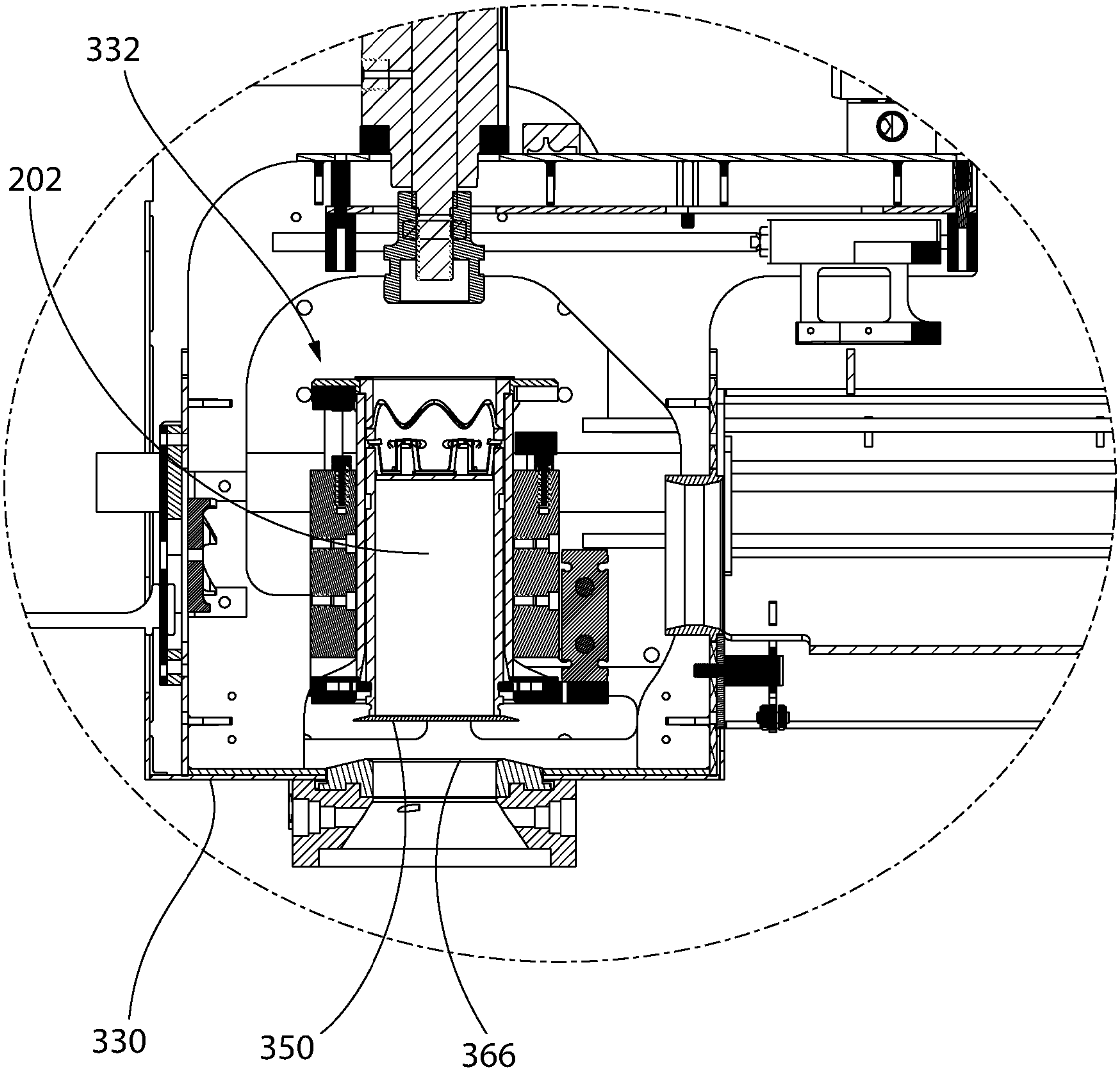
FIG. 102 is an eighth cross sectional view thereof.

Carriage 332 is then rotated 180 clockwise from its upright vertical position to the inverted vertical position while closure plate 350 covers the now inverted sample tube 202 to prevent or minimize leakage of the sample from the receptacle 336. FIG. 90 shows carriage 332 part way through the rotation in an angled position relative to tube feed axis FX. The full inverted position is shown in FIGS. 91 and 102.

Figure 103:
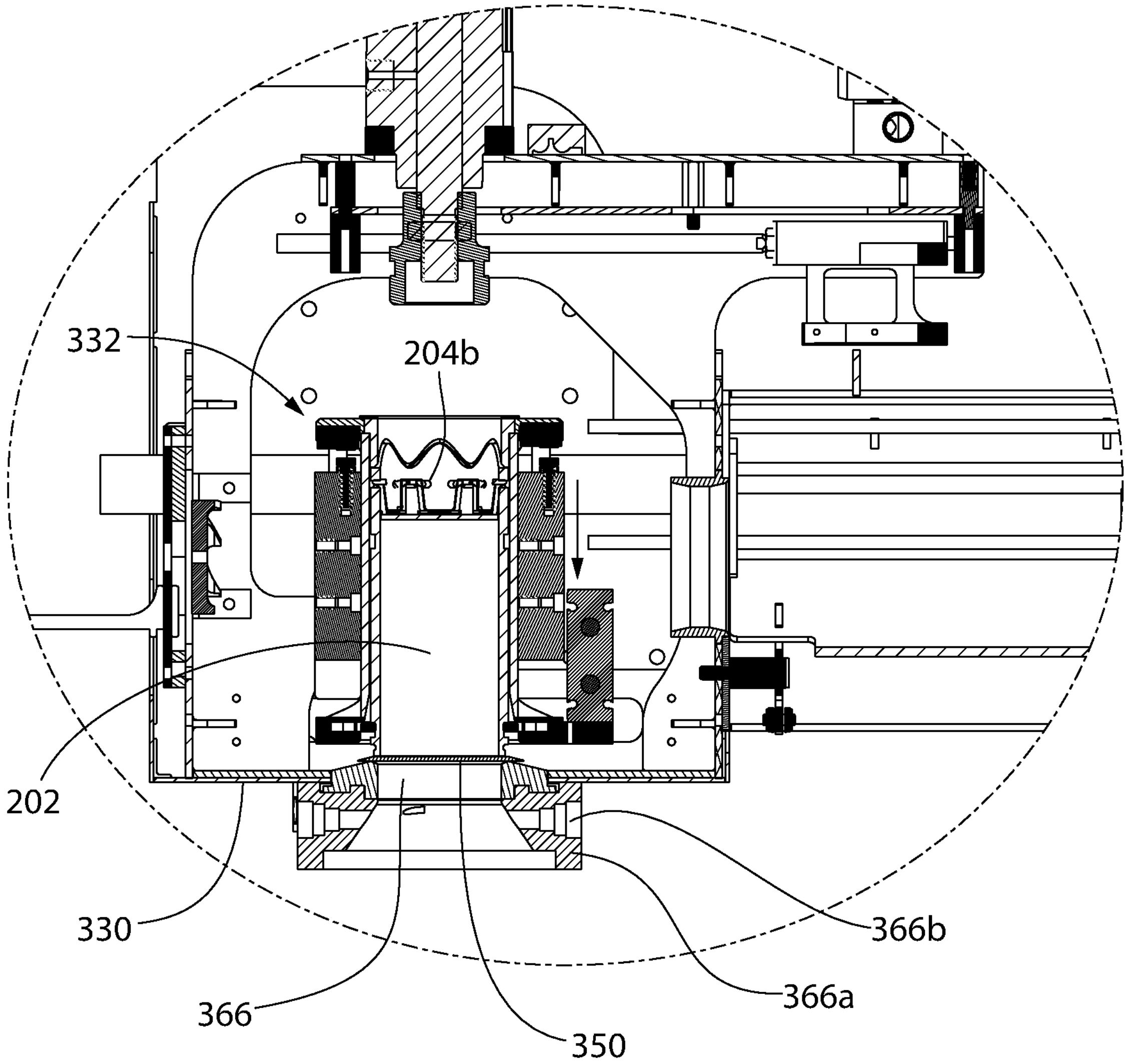
FIG. 103 is a ninth cross sectional view thereof.
Figure 104:
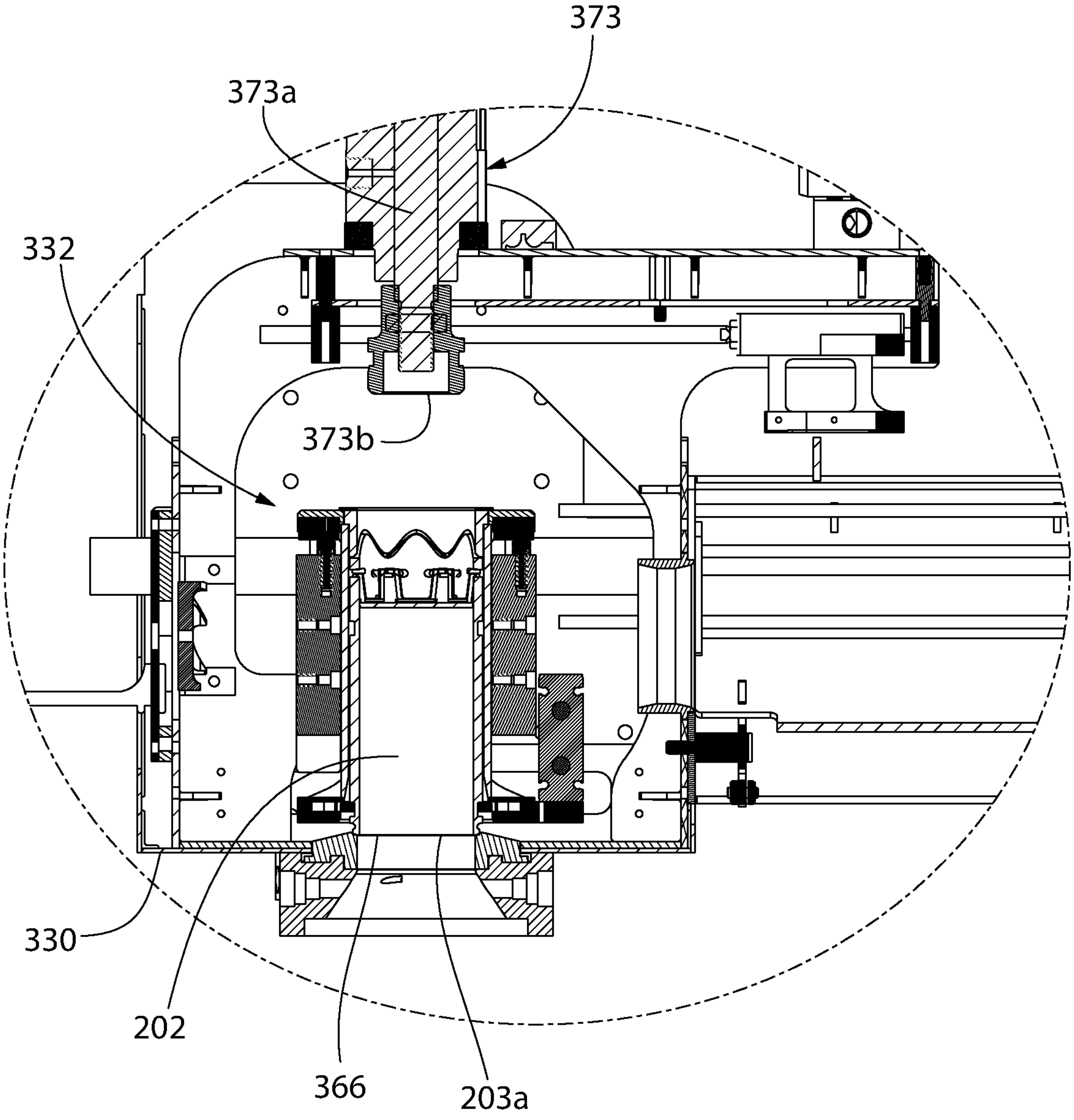
FIG. 104 is a tenth cross sectional view thereof.

Next, the inverted carriage 332 is moved vertically downwards and outward relative to carriage housing 330 and drive shaft to position the concomitantly inverted top end 203*a* of sample tube 202 closer to and adjacent sample unloading port 366 at the bottom of the carriage housing 330 (see, e.g., FIGS. 92 and 103). Unloading port 366 is open upwards and downwards as shown. The unloading port 366 may be defined by a block structure 366*a* attached to the bottom of carriage housing 330 and may include one or more nozzles 366*b* configured for coupling to a water source to clean out soil from the port and associated passageway through the block structure between each sample unloading cycle. The closure plate 350 is next moved outwards to uncover the open end of the sample tube 202 which is now exposed to the unloading port 366 (see, e.g., FIG. 104).

Figure 93:
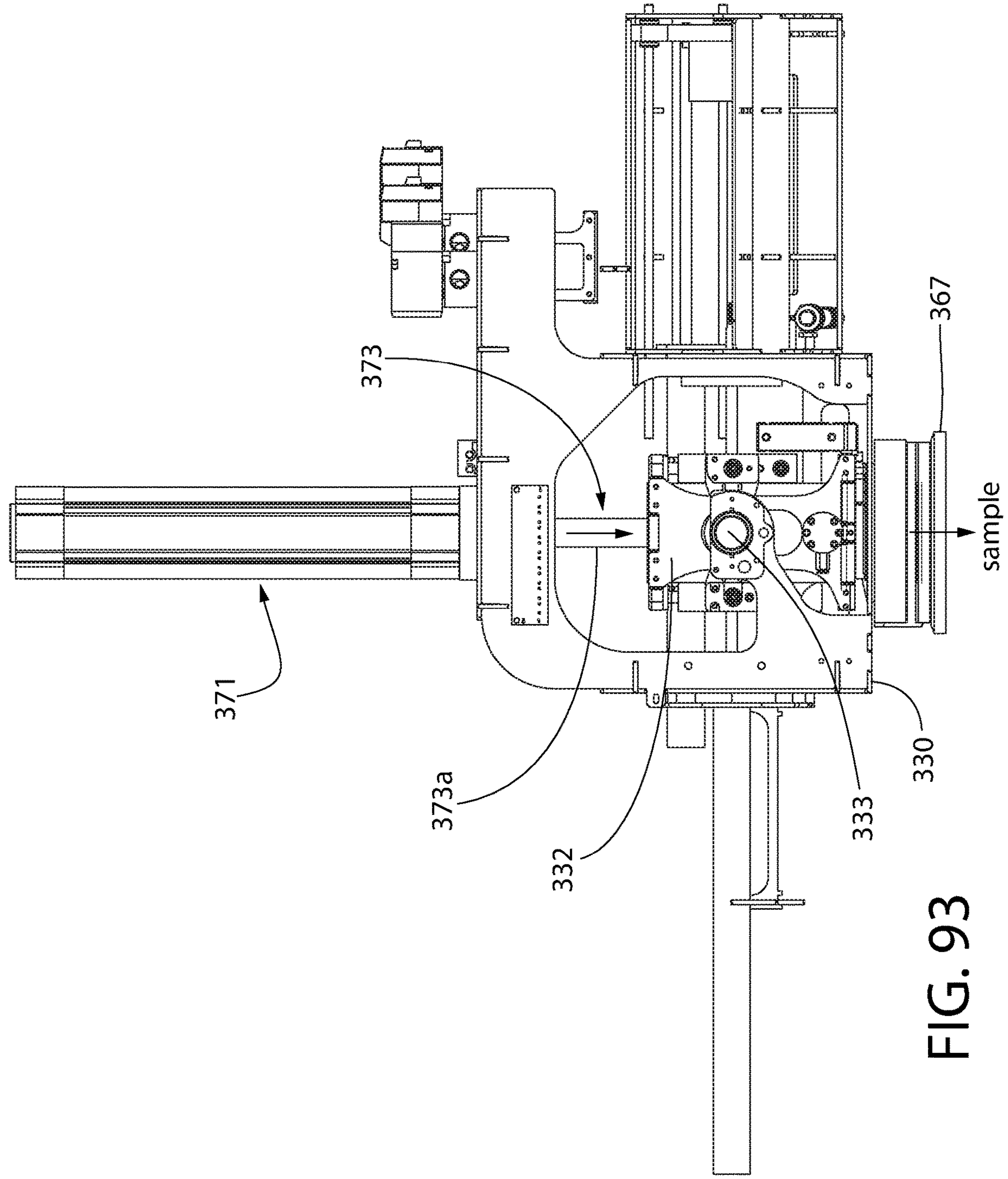
FIG. 93 is a front view thereof showing the sample ejector piston-plunger moved downwards to eject the sample for the container.
Figure 94:
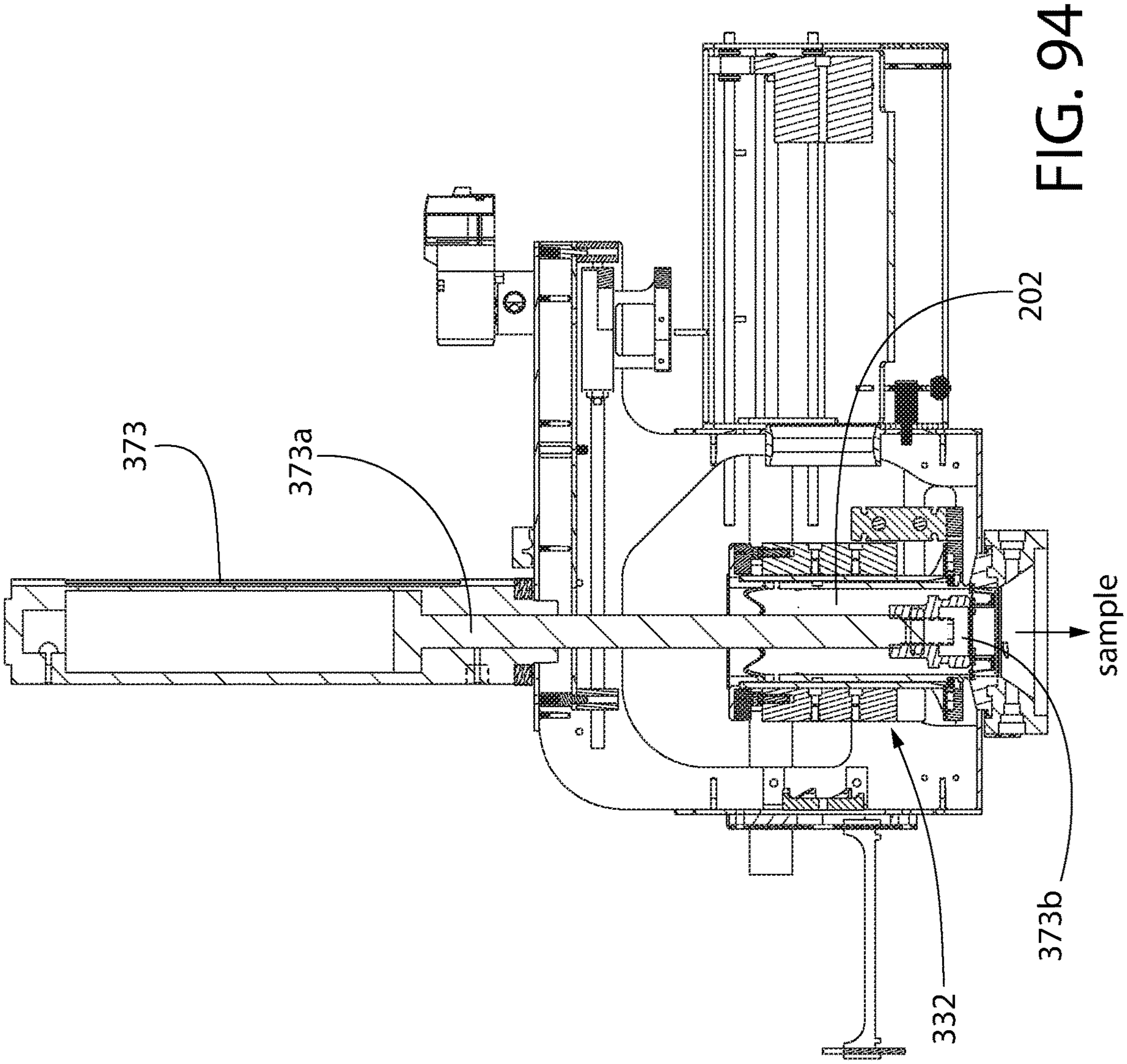
FIG. 94 is a cross sectional view of FIG. 93.
Figure 105:
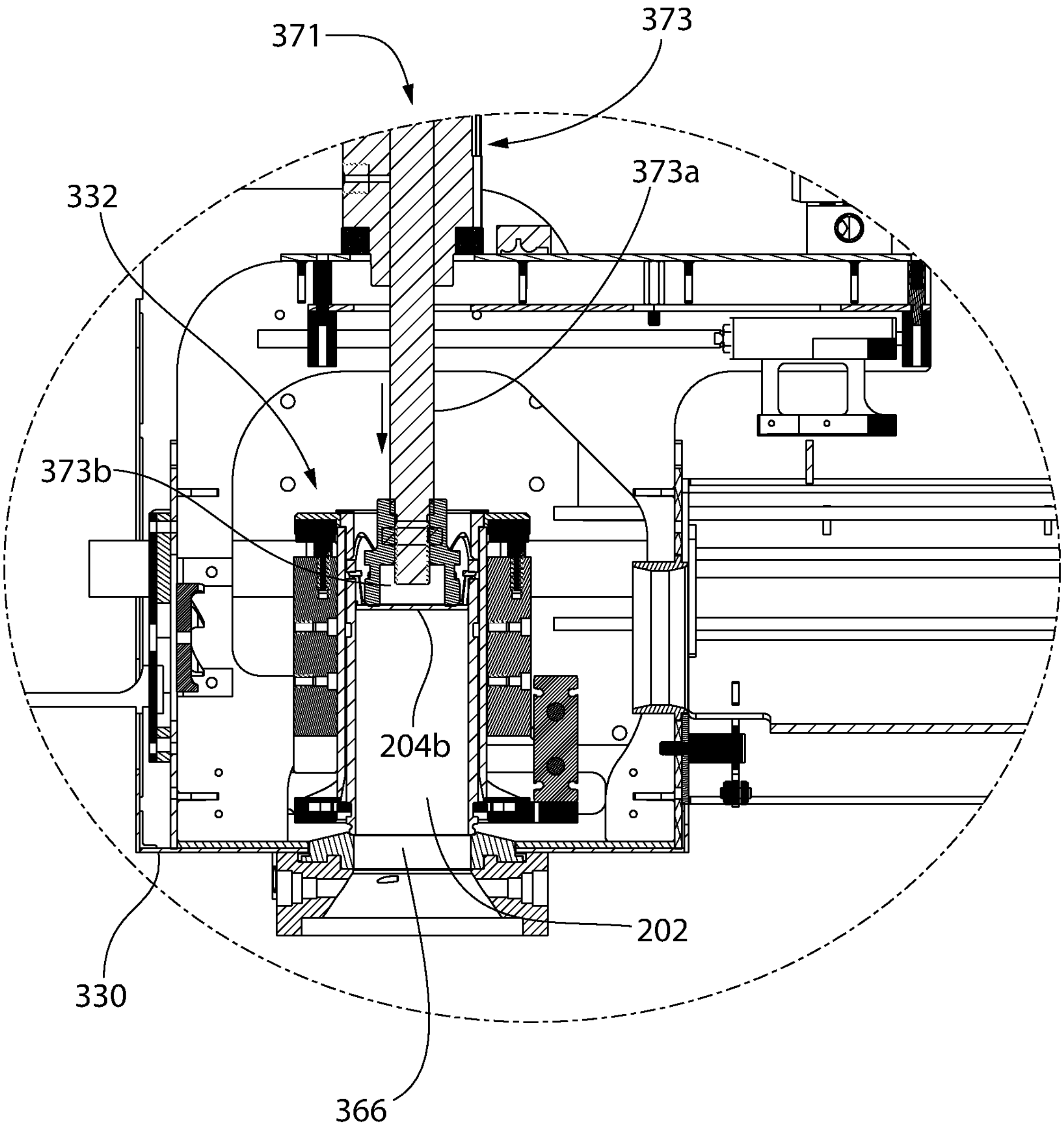
FIG. 105 is an eleventh cross sectional view thereof.

Next, the sample ejector 370 is activated to eject the sample from the sample tube (see, e.g., FIGS. 93 and 105). The sample ejector piston-plunger 373 moves vertically downwards and enters the bottom end 203*b* of the tube to lockingly engage slideably push cap 204*b*. Specifically, circumferential groove 374 in plug disk 373*b* of the piston-plunger lockingly engages the inward projecting tabs 205*b* on the spring-action retention protrusions 205 of cap 204*b* (FIG. 105). Engagement between the retention protrusions 205 and inside surfaces of the sample tube 202 forces the protrusions inwards which maintains locking engagement between groove 374 in the plug disk and tabs 205*b*. Piston-plunger 373 unseats the cap 204*b* from retention slots 202*c* in the sample tube walls 202*a* as it continues to move downward fully in the tube with the cap 204*b* to eject the entire sample from the tube (see, e.g., FIGS. 94 and 106). The piston-plunger may be cycled upwards and downwards within sample tube 202 two or more times to ensure the entire contents of the tube are emptied. After the last downward stroke, the piston-plunger draws the cap 204*b* back upwards and reseats/relocks the cap in the retention slots 202*c* of sample tube 202. The piston-plunger is completely withdrawn from the tube carriage 332 to allow the carriage to be rotated (see, e.g., FIG. 107).

The sample material ejected by the ejector piston-plunger 373 falls via gravity into the unloading funnel 367 positioned beneath unloading port 366. The funnel directs the sample to the sample preparation system (shown schematically by dashed lines FIG. 78), which may include a sample slurry preparation chamber 369 for preparing a slurry by combining the sample material with water via one or more water inlets 369*a* for further processing and eventual chemical analysis. Chamber 369 includes a slurry outlet 369*b*. If slurry preparation occurs below the funnel immediately after ejecting the sample, the closure plate 350 may be moved back inwards to re-cover the open-ended sample tube 202 and prevent water from splashing and entering the carriage. If the slurry preparation equipment has its own closure device or the slurry is prepared at a later time or remote from the funnel 367, the closure plate 350 may remain in the outward position.

Figure 108:
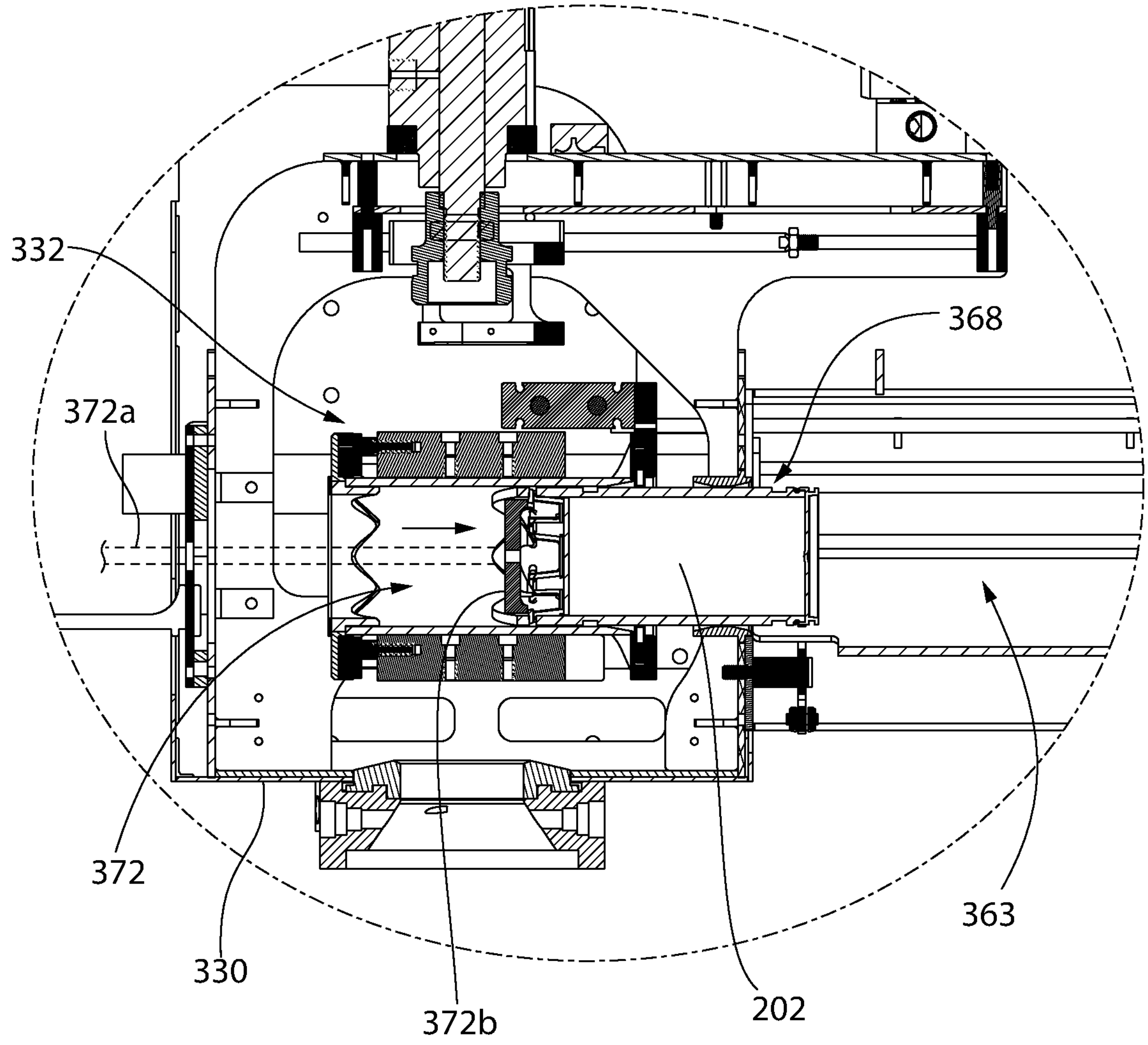
FIG. 108 is a fourteenth cross sectional view thereof.
Figure 109:
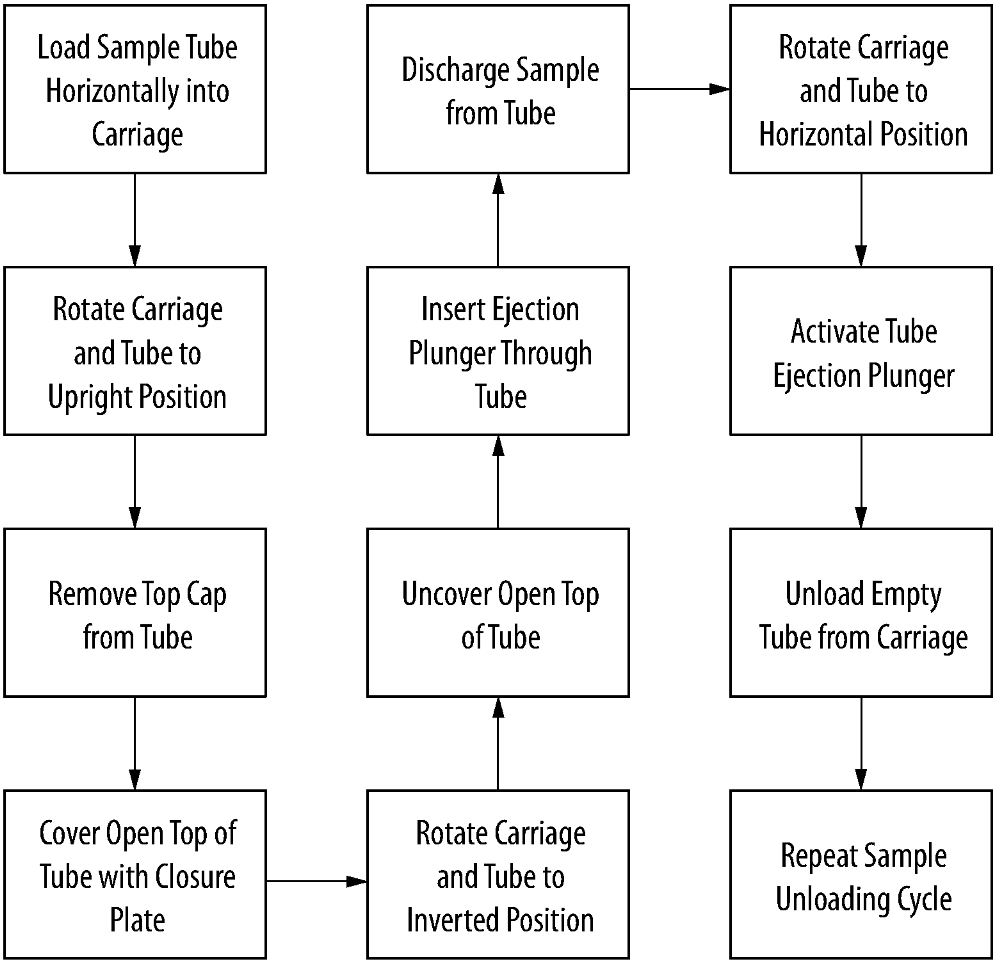
FIG. 109 is a high level flow chart showing the general steps of the sample container unloading process.

In either of the above slurry preparation scenarios, the carriage 332 is then rotated 90 degrees counter-clockwise to horizontally align receptacle 336 and sample tube 202 with the tube feed axis FX (see, e.g., FIG. 108). If closure plate 350 is still inward and covering the open top end of the tube and receptacle, the closure plate is moved outwards to open them. Sample tube ejector 370 is then actuated to eject the empty tube. Piston-plunger 372 moves to the right along feed axis FX into carriage 332 through support ring 337 in receptacle 332 and pushes the empty tube outwards to the right and back onto tube feed chute 363 of the loading mechanism which is in a horizontal position. Feed chute 363 is then pivotably rotated to an angular position to dump the empty tube into an available bin or container for re-use. The feed chute is then rotated back to the normal horizontal tube feed position and ready for receiving and unloading the next filled sample tube by repeating the foregoing method/process.

Performance of the foregoing sample tube unloading method/process and operation associated equipment described of the sample unloading system 300 may be automatically controlled by the programmable system controller 2820 shown in FIG. 2 and already described in detail above. System 300 is operably coupled to controller 2820 via suitable wired and/or wireless communication links as shown. For example, once filled sample tubes 202 are manually loaded onto staging rack 302, the simple activation of the control system via a hard or "soft" (software) start button automatically feeds the tubes via transfer mechanism 306 previously described herein into the unloading apparatus 304 from the staging rack. Tubes are loaded into the unloading apparatus in a serial manner one at a time to unload the sample material according to a sequenced tube feed plan preprogrammed into the controller. The tube feed plan establishes the order in which the sample tubes from various feed ramps 311 are staged to be removed from staging rack 302 and fed into the unloading apparatus 304 to unload the samples. The controller thus directs the transfer mechanism 306 to conduct the tube feed and loading into the unloading apparatus according to the preprogrammed feed plan. In various tube feed scenarios of the plan, certain feed ramps 311 may be emptied completely for unloading the sample tubes before proceeding to the next feed ramp, or certain feed ramps may be partially emptied before moving to certain other feed ramps. This allows the user to preprogram the controller 2820 to prioritize processing and unloading of certain sample tubes first. It will therefore be appreciated that numerous different sample tube feeding scenarios and order of processing the tubes may be implemented for various reasons.

System controller 2820 then controls operation of the unloading apparatus 304 to process and unload the contents of each sample tube 202 in the manner described above and shown in FIGS. 84-109 via executing preprogrammed control logic/program instructions (e.g., software). It is well within the ambit of those skilled in the art to code the program instructions and steps disclosed herein to operate the unloading apparatus 304 in the manner described to unload the agricultural sample from the sample tube 202. All unloading apparatus associated equipment described herein may therefore be automatically controlled by the controller so no manual intervention is required other than the user or operator activating the hard or soft start button. In other possible embodiments, a combination of manual and automatically controlled operation and steps may be used.

EXAMPLES

The following are non-limiting examples.

Example A1—A sample unloading system comprising: a sample staging rack 302 comprising at least one inclined feed ramp 311 configured for receiving an elongated sample tube 202 configured for holding the sample, the sample tube including a first end cap **204*a* and a second end cap 204*b*; an unloading apparatus 304 coupled to the staging rack, the unloading apparatus configured to receive the sample tube from the staging rack; and a transfer mechanism 306** operable to transfer the sample tube from the staging rack to the unloading apparatus.

Example A2—the system according to any one of Example A1, wherein the unloading apparatus 304 comprises a rotatable carriage 332 configured to hold and rotate the sample tube 202 in opposing directions.

Example A3—the system according to Example A2, wherein the unloading apparatus 304 comprises a loading mechanism 360 operable to load the sample tube 202 into the carriage 332.

Example A4—the system according to any one of Examples A2 or A3, wherein the carriage 332 is operable to rotate the sample tube 202 between an upright vertical position and an inverted vertical position.

Example A5—the system according to Example A4, wherein the carriage 332 is operable to rotate the sample tube 202: 90 degrees in a first direction to the upright vertical position; and 180 degrees therefrom in an opposite second direction to the inverted vertical position.

Example A6—the system according to Example A4, wherein the first end cap **204*a* is detachably coupled to a first end of the sample tube 202, and the second end cap 204*b*** is slideably movable inside the sample tube towards and away from the first end cap.

Example A7—the system according to Example A6, wherein the unloading apparatus 304 further comprises a decapper 345 operable to remove the first end cap **204*a* from the sample tube 202** when in its upright vertical position.

Example A8—the system according to Example A7, wherein the unloading apparatus 304 comprises a sample ejector 371 configured to eject the sample from the sample tube 202 when in its inverted vertical position when the first end cap is removed.

Example A9—the system according to Example A8, wherein the sample ejector 371 comprises a vertically movable plunger 373 which engages and slides the second end cap **204*b* inside the sample tube 202** to eject the sample.

Example A10—the system according to any one of Examples A4-A9, wherein the unloading apparatus 304 comprises a movable closure plate 350 movable between an inward position operable to retain the sample in the sample tube 202 when in its inverted vertical position when the first end cap **204*a*** is removed, and an outward position operable to release the sample from the sample tube when in its inverted vertical position.

Example A11—the system according to Example A10, wherein the closure plate 350 engages an open end of the sample tube 202 created when the first end cap is removed.

Example A12—the system according to Example A11, wherein the closure plate 350 is further operable to engage the open end of the sample tube 202 when in its upright vertical position.

Example A13—the system according to any one of Examples A1-A12, wherein the staging rack 302 comprises a plurality of inclined feed ramps 311 arranged in parallel relationship to each other.

Example A14—the system according to Example A13, wherein the transfer mechanism 306 comprises a rotary feed gate 314 configured to grasp the sample tube 202 on the staging rack and pass the sample tube towards the unloading apparatus.

Example A15—the system according to Example A14, wherein the rotary feed gate 314 is positioned at a proximal end of the inclined feed ramp 311 adjacent to the unloading apparatus.

Example A16—the system according to Examples A15, wherein the transfer mechanism 306 comprises a tube elevator 320 comprising a movable chain 321 with lifting member 324 configured to engage and load the sample tube 202 into the unloading apparatus 304 from the staging rack 302.

Example A17—the system according to Example A3, wherein the loading mechanism 360 comprises a ramrod 362 operable to push the sample tube 202 into a receptacle 336 of the carriage 332.

Example A18—the system according to Example A17, wherein the unloading mechanism 360 comprises an unloading plunger 372 operable to push the sample tube 202 out of the receptacle 336 of the carriage 332.

Example A19—the system according to Examples A17 or A18, wherein the unloading mechanism 304 comprises a feed chute 363 pivotably coupled to the unloading apparatus.

Example A20—the system according to any one of Examples A1-A19, further comprising a programmable controller 2820 operably coupled to and configured to control operation of the unloading apparatus 304 and transfer mechanism 306.

Example A21—the system according to any one of Examples A1-A20, wherein the sample is a soil sample.

Example A22—A method for unloading a sample container 200 comprising: inserting a capped sample tube 202 containing a sample into an unloading apparatus 304; rotating the sample tube 202 a first time to an upright vertical position; uncapping the sample tube which creates an open top end 203*a*; rotating the sample tube a second time to an inverted vertical position; and ejecting the sample from the sample tube.

Example A23—the method according to Example A22, wherein the unloading apparatus 304 comprises a movable carriage 332 including an elongated receptacle 336 into which the sample tube 202 is inserted.

Example A24—the method according to Examples A22 or A23, further comprising after the uncapping step, a step of covering the uncapped sample tube 202 with a closure plate 350 before rotating the sample tube the second time.

Example A25—the method according to Example A24, further comprising before the ejecting step, a step of uncovering the uncapped sample tube 202 by removing the closure plate 350.

Example A26—the method according to Example A22, wherein the ejecting step comprises inserting a sample ejector piston-plunger 373 through the sample tube 202 in a downward stroke.

Example A27—the method according to Example A26, wherein the sample ejector piston-plunger 373 lockingly engages a push cap 204*b* slideably disposed inside the sample tube 202 and moves the push cap downwards towards the open top end 203*a* of the sample tube to eject the sample.

Example A28—the method according to Example A27, further comprising after the ejecting step, a step of moving the sample ejector piston-plunger 273 in an upward stroke which draws the push cap 204*b* back upwards in the sample tube 202.

Example A29—the method according to Example A23, wherein the uncapping step includes engaging a decapper 345 with a snap-fit cap 204*a* on the top end 203*a* of the sample tube 202, and moving the carriage 332 to lower the tube with the decapper engaged with the snap-fit cap to remove the cap.

Example A30—the method according to Example A23, wherein inserting step comprises engaging a castellated bottom end 203*b* of the sample tube 202 with a mating castellated surface 337 inside the receptacle 336.

Example A31—the method according to Examples A23 or A30, wherein the inserting step includes pushing the sample tube 202 into the receptacle 336 with a ramrod 362 slideably movable on the unloading apparatus 304.

Example A32—the method according to Example A31, wherein the ramrod 362 engages the sample tube 202 on a V-shaped feed chute 363 aligned with a loading port 368 of the unloading apparatus 304 to guide the sample tube into the receptacle 336.

Example A33—the method according to Example A23, further comprising after the ejecting steps of rotating the sample tube 202 a third time to a horizontal position, and pushing the sample tube out of the unloading apparatus 304 with a movable carriage 322.

Example A34—the method according to Example A33, wherein the sample tube 202 is both inserted into the unloading apparatus 304 and pushed out of the unloading apparatus in opposing linear directions along a common feed axis FX.

Example A35—the method according to any one of Examples A22-A34, further comprising a programmable controller 2820 operably coupled to the unloading apparatus 304 and configured to control operation of the unloading apparatus.

Example A36—A sample container comprising: an elongated tubular body defining a longitudinal axis LA2, a top end 203*a*, a bottom end 203*b*, and an internal cavity 207 extending between the ends configured for holding the sample; a first cap 204*a* detachably coupled to the top end; and a second cap 204*b* slideably disposed in the cavity, the second cap being movable in opposing directions between the first and second ends.

Example A37—the sample container according to Example A36, wherein the second cap 204*b* comprises a base 208 and a plurality of longitudinally-extending retention protrusions 205 extending downwards from the base.

Example A38—the sample container according to Examples A36 or A37, wherein the body further comprises a plurality of circumferentially spaced apart retention slots 202*c* configured to lockingly engage the retention protrusions 205.

Example A39—the sample container according to Example A38, wherein the retention protrusions 205 are outwardly flared and form outward protruding locking tabs 205*c* which engage the retention slots 202*c*.

Example A40—the sample container according to Examples A38 or A39, wherein retention slots 202*c* are located proximate to the bottom end 203*b* of the tubular body.

Example A41—the sample container according to Example A39, wherein the retention protrusions 205 each further comprise an inward projecting tab 205*b*.

Example A42—the sample container according to Example A36, wherein the tubular body defines a pair of longitudinally spaced apart circumferential grooves 348, 349 formed in an exterior surface of the tubular body.

Example A43—the sample container according to Example A36, wherein the first cap 204*a* comprises an external circumference groove 347.

Example A44—the sample container according to Example A43, wherein the first cap 204*a* is snap-fit to top end of the tubular body via an inwardly projecting annular snap protrusion 343 engageable with a circumferentially-extending snap groove 344 formed in the tubular body.

Example A45—the sample container according to Example A36, wherein the bottom end 206*b* has an undulated castellated configuration.

Alternative Designs and Embodiments

The following description and FIGS. 114-142 present design variations and alternative embodiments of the agricultural sample unloading system 300 including the sample staging rack 302 and unloading apparatus 304 previously described herein.

Sample Staging Rack

FIGS. 114-122 depict an alternative embodiment of a staging rack 302. In this design, the multiple rotary paddle feed gates 314 positioned at the proximal end of each feed ramp 311 are eliminated and replaced by reconfiguring electric motorized chain drive 325. The reconfigured chain drive operates in the same general and similar manner previously described herein; however, the circulating continuous-loop chain 321 has been altered to includes a plurality of blocking members 500. Blocking members 500 are fixedly attached to and circulate with the chain 321 between the toothed upper sprocket 322 and toothed lower sprocket 323 previously described herein. The forked lifting member 324 which grabs a sample tube 202 from the rack and is fixedly coupled to and movable vertically with the chain is retained.

At positions on the chain 321 above and below the lifting 321, however, a blocking member 500 is present which prevent the sample tubes 202 from rolling off staging rack 302 into a vertically-extending passageway 315 at the proximal end 313 of rack 302 between the rack and unloading apparatus 304. Each leading sample tube 202 on the end of each of the feed ramps 311 closest to the unloading apparatus 304 is alternatingly engaged and retained on the feed ramp by the blocking members 500 until the forked lifting member 324 becomes aligned with one of the tubes on one of the ramps. In that case, the leading tube 202 rolls onto and engages the lifting member 324 which raises the tube and discharges the tube onto the track rails 348*a*, 349*a* spanning between the rack and tube loading mechanism 306 of the apparatus, as previously described herein. The location on the chain corresponding to the position of the lifting member 324 is the only vacant space which can receive one of the sample tubes 202 as shown.

The blocking members 500 each comprise a stop block 501 supported in a cantilevered manner from the chain 321 by a pair of support arms 502. In one embodiment, the chain 321 may comprises a pair of chains as shown. Each of the laterally spaced apart arms 502 are fixedly coupled to one of the chains by any suitable means known in the art. The top block may have a rectangular cuboid shape in one embodiment as shown; however, other shaped blocks may be used. The blocks and support arms may be made of preferably rigid metallic materials, non-metallic materials (e.g., plastic), or combinations thereof and do not limit the invention.

Figure 116:
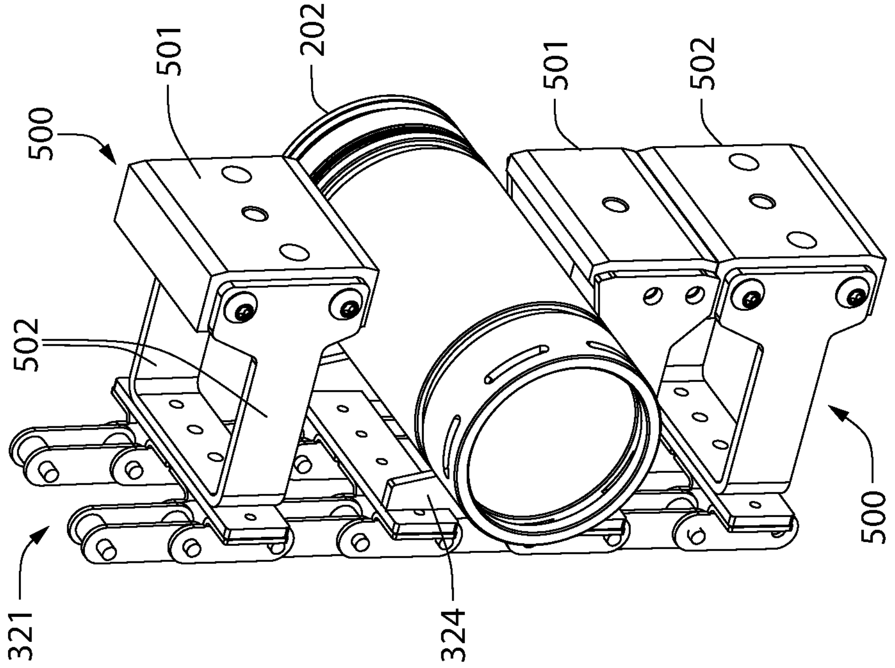
FIG. 116 is a first perspective view of a portion of the chain drive of the staging rack of FIG. 114.
Figure 118:
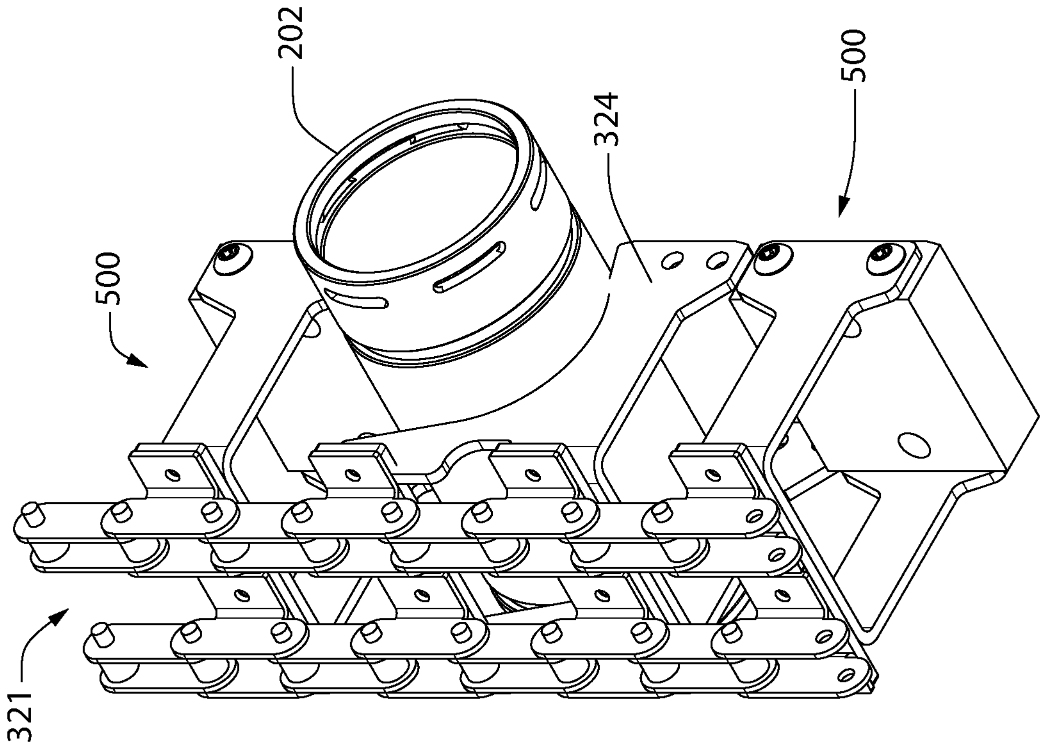
Figure 119:
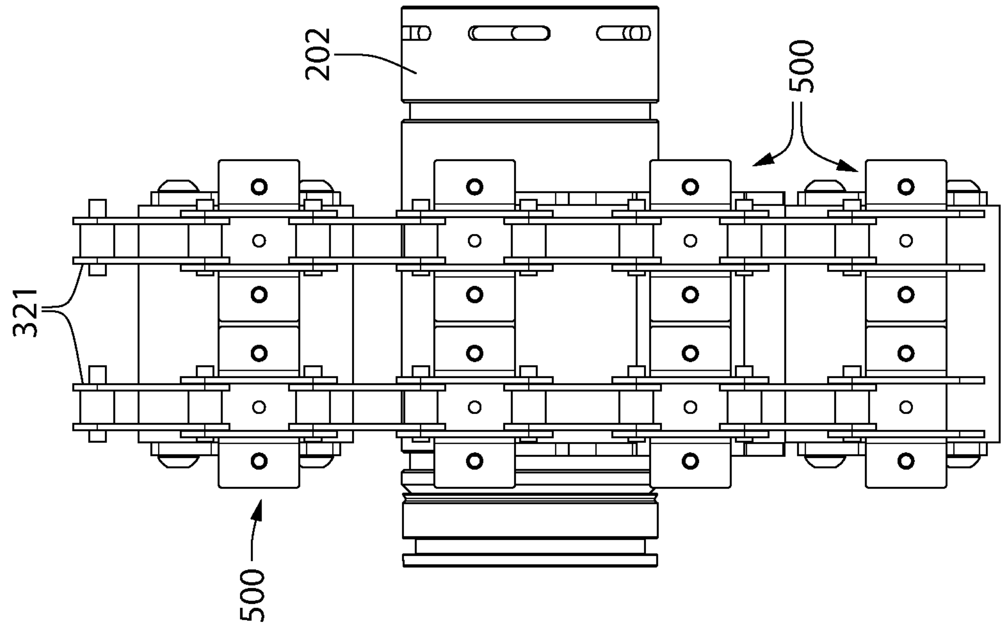
Figure 121:
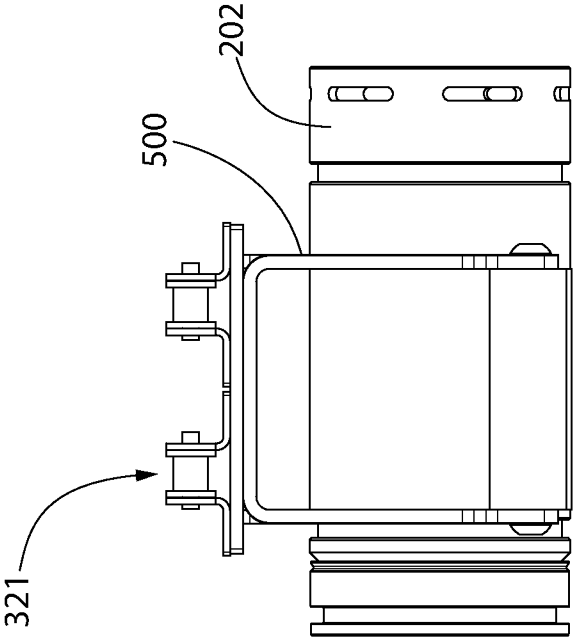
Figure 120:
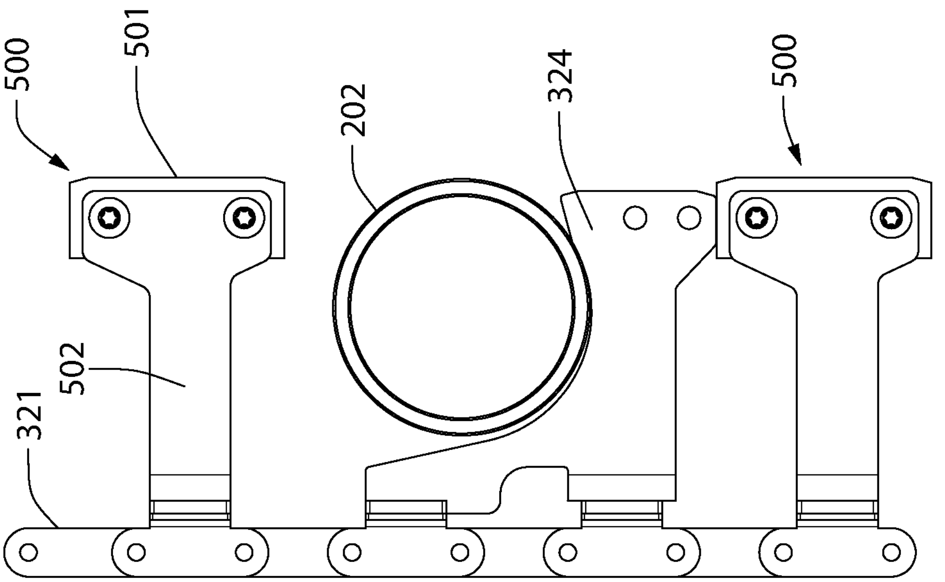
Figure 122:
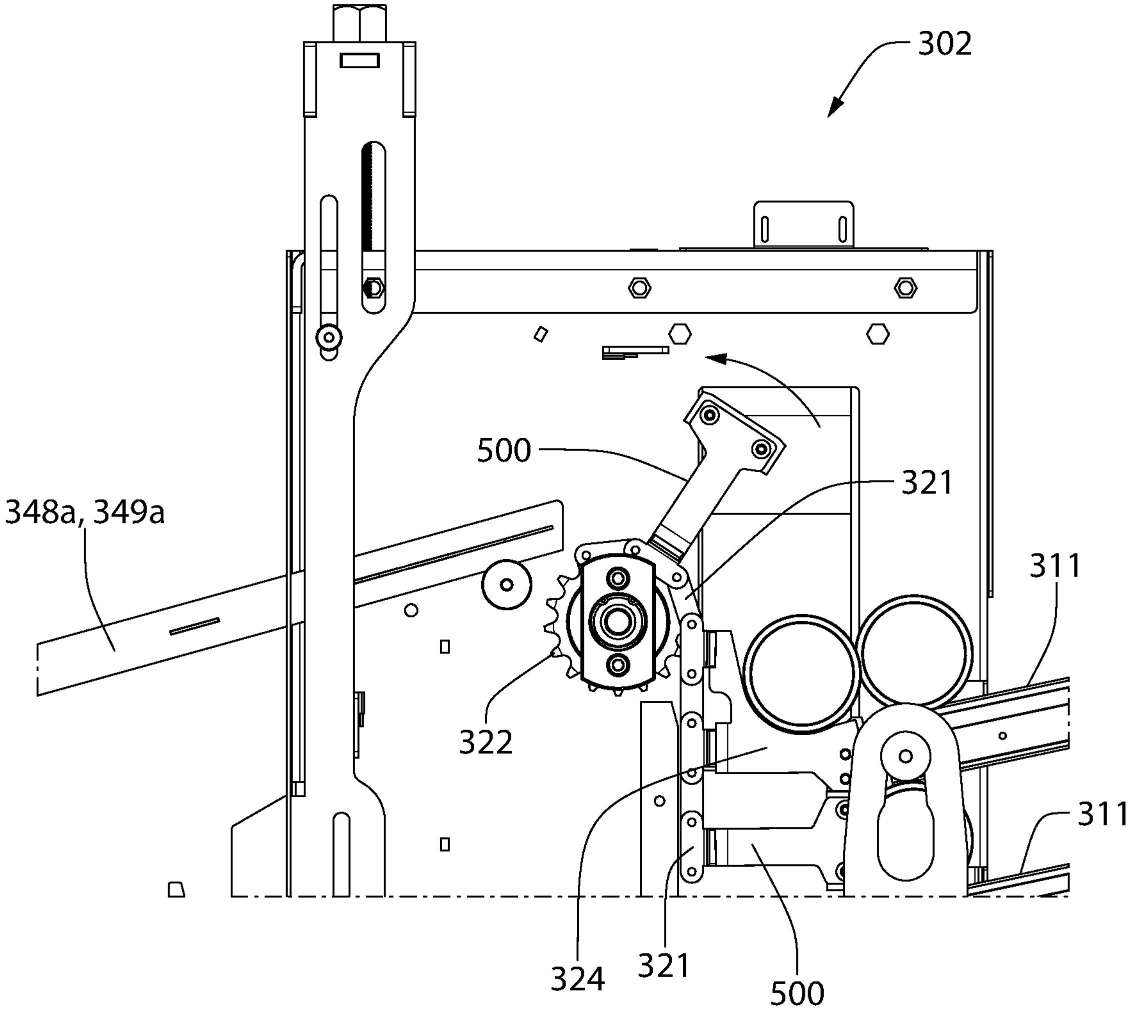

During operation and circulating motion of the chain 321, adjacent blocking members 500 when travelling in the vertical direction along the front or back side of the electric motorized chain drive 325 between the sprockets 322, 323 may abuttingly engage each other to form a continuous traveling wall structure facing the leading sample tubes 202 on the ends of the feed ramps 311 (see, e.g., FIGS. 116 and 122). FIG. 122 shows the topmost blocking member 500 rotating over the upper sprocket 322 of the chain drive and one of the sample tubes 202 being loaded onto the lifting member 324. RFID reader 2850 remains positioned in the same general location as before near the top of the chain drive 325 (see, e.g., FIG. 114) to read the RFID tag 2850*a* of the sample tube 202 which has been loaded onto the forked lifting member 324 on chain 321 before being dispenses to the sample unloading apparatus 304.

It bears noting that although the complete 360 degree continuous-loop chain 321 structure is not shown in FIGS. 114-122 to improve clarity. Accordingly, only select segments of the chain necessary for the foregoing description are illustrated.

The elevator chain 321 can extract sample tubes 202 from the feed ramps 311 of staging rack 302 and load the tubes into the unloading apparatus 304 in at least one of two ways below. Normal operation may entail processing and extracting sample tubes 202 from the top down fore the top half of the feed ramps 311, and then switch directions and process the tubes bottom up until it processes the entire bottom half of the ramps. This ensures that if sample tubes 202 are reloaded when the staging system is still partially full, the tubes on the bottom feed ramps 311 do not remain in the rack for several days without being processed.

Top Down

The chain 321 reverses from a home position to load a sample tube 202 from the top feed ramp 311 that contains one or more tubes, then rotates forward to lift the tube to scan the RFID tag and load it into the machine. Once the top feed ramp 311 containing the sample tubes is empty, the machine progress to load tubes from next feed ramp down that contains tubes.

Bottom Up

The chain 321 can also start by rotating forward (i.e. towards unloading apparatus 304) to load sample tubes 202 into the machine from the lowest feed ramp 311 containing tubes first. Since the single opening on the chain 321 defined by the location of the forked lifting member 324 is now already occupied by a sample tube, that already loaded sample tube can be lifted by the chain past the other feed ramps above in the rack even if they have tubes present since the loaded sample tube prevents additional tubes from leaving their respective feed ramp.

Other variations of the sample tube extraction and loading process and sequence are possible.

Sample Unloading Apparatus

FIGS. 123-142 depict alternative embodiments and optional features of the sample unloading apparatus 304 previously described herein. Several alterations and additions are presented which mechanically simplify the apparatus and provide operational options which can enhance the unloading operation and efficiency of the process.

General reference is made to preceding FIGS. 74A-109 depicting various aspects of sample unloading apparatus 304, and particularly FIGS. 123-142 showing the alterations of and additions to the original design previously described herein. Reference should be made to the prior written description and original drawings for features which appear in FIGS. 123-142, but which might not be numbered therein for brevity.

Referring initially to FIGS. 130 and 133-138, according to a first aspect of the sample unloading apparatus, a wash-down system is provided for cleaning out the unloader between unloading cycles of different sample containers or tubes 202 to prevent cross-contamination of sample materials. As part of this system, the rotatable container/tube carriage 332 which defines container receptacle 336 that removably holds the sample container or tube 202 is located inside a selectively sealable liquid-tight wash-down enclosure 600. Enclosure 600 may be cylindrical in one embodiment and is disposed in and mounted to the support housing 330 of the sample unloading apparatus 304 in a stationary manner. The wash-down enclosure defines an inner chamber 603 which encloses the carriage 332. Enclosure 600 is non-rotatable relative to housing 330, whereas carriage 332 is rotatably relative to both the enclosure and housing via trunnion mechanism 329 rotatably supported by housing 330. Trunnion drive shaft 333 coupled to the carriage as previously described herein may be relocated to the rear of the unloading apparatus 304 in the present embodiment (see, e.g., FIG. 124).

The wash-down enclosure 600 further comprises a resilient and elastically deformable septum 601 mounted at the sample tube entrance opening of the apparatus formed by loading port 368 of the unloading apparatus 304 through which sample tubes are inserted and removed from the carriage. Septum 601 may be formed of an elastomeric sheet comprising a circular insertion aperture or hole 602 slightly smaller than the outside diameter of the sample tube 202. When the sample tube 202 is inserted through the septum and loaded into the rotatable carriage 332, the elastomeric material deforms and stretches over the tubular body of the sample tube 202 at insertion hole 602 of septum 601 to allow the tube to pass through. After the top end cap 204*a* is removed by decapper 545 from the sample tube after it is seated in the carriage 332, the cap is held within hole 602 of the septum which stretches over the sides of the cap to form a liquid-tight seal and block off the sample tube loading port 368. This seals off the inner chamber 603 of the unloader formed inside wash enclosure 600 in a water-tight manner which allows wash down of the sample tube, end caps, and inner chamber after dumping the soil sample material in the manner previously described herein.

A plurality of spray nozzles 610 are fixedly mounted to the rotatable carriage 332 to spray out the inside of the top end cap 204*a* and inside of the wash-down enclosure inner chamber 603 as the carriage is rotated during the wash cycle. Spray nozzles 610 thus are rotatable with the carriage to fully wash all exposed surfaces formed by the circumferentially-extending walls 603*a* inside chamber 603 of enclosure 600 for a full 360 degrees around. Accordingly, all interior surfaces of the wash-down enclosure 600 inside inner chamber 603 and the exposed surface of top end cap 204*a* held in the septum 601 are cleansed.

A suitable wide spray pattern may be provided for each of the spray nozzles 610 for the forgoing washing and flushing purposes. FIGS. 135-137 illustrate an example wide spray pattern in a dotted pattern. The spray pattern of flushing/cleaning water discharged by each nozzle 615 preferably may be greater than 90 degrees as shown in some embodiments.

To supply cleaning water to the spray nozzles 610 on the rotatable carriage 332, a rotating water supply connection is provided. In one embodiment, this connection may include a water inlet pipe 650 which is fluidly coupled to the carriage via a swivel fluid coupling 651. The inlet pipe remains stationary while the carriage rotates thereabout. A flow conduit 652 such as a section of tubing fluidly couples the swivel fluid coupling outlet 653 to spray nozzles 610 which may be mounted to the baseplate 640 of the tube gripper mechanism 630 on carriage 332, further described herein. A fluid inlet 654 on and in baseplate 640 extends internally through the baseplate to each of the spray nozzles 610. Although three spray nozzles are shown, fewer or more may be provided.

To wash down and clean the rotatable carriage 332 itself and those components attached thereto, a fixed or stationary wash nozzle 615 may be mounted to the wash-down enclosure 600 (see, e.g., FIGS. 133 and 138). Wash nozzle 615, fixed in position on the cylindrical wash-down enclosure 600, is configured and operable to discharge washing water inside enclosure inner chamber 603 and spray down all surfaces of the carriage as it is rotated within the enclosure. A suitable wide spray pattern (e.g., greater than 90 degrees) may be provided for spray nozzle 615 for the forgoing washing and flushing purposes to thoroughly cleanse the carriage and its conjoined components.

It bears noting that the rotating sample tube carriage 332 which defines the container receptacle 336 may have a cylindrical configuration similarly to the wash-down enclosure 600. However, the centerline axis of the inner carriage 332 (extending from end to end) is not coaxial with but transverse to the centerline axis of the outer wash-down enclosure 600 (see, e.g., FIG. 133). Further, wash-down enclosure 600 is stationary and not rotatable.

According to another aspect of the sample unloading apparatus 304 design options, the movable decapper 345 previously described herein may be replaced with an alternate design in the form of jaw-like decapper mechanism 545 shown in FIG. 142. The decapper mechanism (or simply decapper for short) may be mounted to the tube loading mechanism 360 and comprises an axially movable decapper actuator 547 operably interacting with a pair of opposing openable/closeable gripping jaws 546. Actuator 547 replaces sample container or tube ramrod 362 previously described herein. Advantageously, decapper 545 is operable to both push the sample tube 202 into and extract the tube from carriage 332 of the unloading apparatus 304, while further functioning to remove the top end cap 204*a* from sample tube 202. Eliminates the need for tow separate mechanism and drives to perform both functions.

Jaws 546 of decapper 545 are each configured to selectively engage circumferential groove 345 formed in top end cap 204*a* (see, e.g., FIG. 45) in order to grip the cap. The jaws may have an arcuately curved shape in one embodiment as shown which conforms to the circular shape of the top end cap. A sensor 548 is located proximate to and between the jaws 546 and configured to sense the presence of sample tube (i.e. top end cap) between the jaws. Any suitable commercially-available proximity or other type sensor may be used for thus purpose.

Decapper actuator 547 may be a commercially-available linear acting actuator configured to alternatingly spread jaws 546 apart outwards to receive or release the top end cap 204*a* of sample tube 202, or collapse the jaws inwards to engage and grip the end cap. When engaged by the decapper, the actuator 547 is operable to slide the sample tube 202 linearly along tube feed rods 660 of the tube loading mechanism 360 through the loading port of the unloading apparatus and into the carriage 332.

In operation when a sample tube 202 to have its sample contents is loaded into the tube loading mechanism 360, the decapper mechanism 545 may engage and grip the top end cap 204*a* of the tube while still attached to the cylindrical tube body. The decapper mechanism may next push and load the tube horizontally into the rotatable carriage 332 through loading port 368 of the unloader. After insertion, with the sample tube still in the horizontal position in the carriage, the decapper mechanism 545 may be partially withdrawn away from the carriage to pop the top end cap 204*a* of the top off of sample tube 202 and engage the end cap with the deformable septum 601 as previously described herein. This seals the inner chamber 603 of the wash-down enclosure 600 in preparation for the eventual wash-down and flushing cleaning operation described above after the sample tube contents are dumped.

According to another aspect of the sample unloading apparatus 304 design options, an alternative tube gripper mechanism 630 is provided which is configured to retain and lock the sample tube 202 in receptacle 336 of the carriage 332 when inverted for unloading the sample material. In this present embodiment, the main actuator that plunges the soil from the sample tube 202 when the tube is in a vertical inverted position (i.e. sample ejector 371 and its vertically movable piston-plunger 373) may be configured and operable for dual use to enhance mechanical simplicity of the unloader 304. In addition to being used to plunge soil from the sample tube as previously described herein, the vertically movable piston-plunger 373 of the sample ejector 373 previously described herein also advantageously serves to actuate the spring-biased tube gripper mechanism 630 when the sample tube is in a horizontal position located inside the carriage 332. This beneficially avoids having to mount and power a separate actuator on the carriage to lock and unlock the canister therefrom.

Reference is made to FIGS. 133-134, 137-139, and 141-142. In one embodiment, present tube gripper mechanism 630 comprises a spring-biased mechanical gripper actuator 631 operably coupled to a pair of collapsible and spreadable gripping arm linkages 632 configured to selectively engage and disengage circumferential retention groove 348 formed on the exterior surface of sample tube 202. Actuator 631 and gripping arms 632 may be mounted to the top of the rotatable carriage 332 as shown.

Gripper actuator 631 comprises a push plate or block 640 movably mounted to a baseplate 641 fixedly mounted to the cylindrical carriage 332, pair of guide rods 642, a cylindrical spring 643 encircling each guide rod, a bushing 644 slideably receiving each guide rod therethrough when the gripper mechanism is actuated. In some embodiments, spray nozzles 610 previously described herein may be mounted to baseplate 641. Push block 640 is configured to be engaged by plug disk 373*b* on the end of vertically movable piston-plunger 373 of the sample ejector 371 (previously described herein) which actuates the tube gripper mechanism 630 (see, e.g., FIG. 134). Each guide rod therefore has an associated spring and bushing as shown. The top ends of guide rods 642 are fixedly coupled to push block 640 such as via a threaded connection or other. Bushings 644 are fixedly coupled to baseplate 641 which may be contoured from front to rear to conform to the arcuate shape of the cylindrical carriage 332.

The baseplate 641 defines a downwardly open operating cavity 645 on its bottom which is configured to receive the bottom ends of guide rods 642 therein when the gripper is actuated. A portion of the cylindrical carriage 332 body beneath the cavity defines a stop limit surface 645*a* which is abuttingly engages by the guide rods when fully actuated to stop the travel of the guide rods and actuator. Push block 640 is linearly movable towards and away from baseplate 641 and carriage 332, and springs 643 bias the push block away therefrom.

With particular reference to FIGS. 137 and 141-142, gripping arm linkages 632 are each pivotably coupled independently to both an end portion of baseplate 641 and an end portion of push block 640. Each arm linkage 632 comprises mounting segment 633 pivotably coupled to baseplate 641 at one end, and a gripping segment 634 pivotably coupled to a second end of the mounting segment. Each mounting segment 633 may comprise a short link generally straight body which is pivotably coupled at one end to push block 640 via a fixed pivot which may be formed by a pivot pin 636. The opposite end of each mounting segment 633 is pivotably coupled to one end of a gripping segment 634 via a pivot which may be formed by pivot pin 637. Mounting segments 633 are pivotably movable about the fixed pivot upon actuation of the tube gripper mechanism 630, which in turn actuates and moves the gripping segments 634 as shown.

Each gripping segment in turn includes a fixed pivot which may be formed by a second pivot pin 636 that pivotably couples the arm linkage (e.g., top end of gripping segment 634) directly to baseplate 641 from the mounting segments. Gripping segments 634 and the arm linkages 632 are pivotably movable about the fixed pivot upon actuation of the tube gripper mechanism 630 to selectively engage or disengage the sample tube 202 in the carriage 332 as further described herein.

The term "fixed pivot" used above refers to the fact that the mounting segments 633 and gripping segments 634 of arm linkages 632 may rotate about the identified fixed pivot points, but are otherwise constrained from moving in a linear manner entirely freely in a non-rotational manner.

Each gripping segment may be generally L-shaped in one non-limiting embodiment and defines an arcuately curved engagement surface 634*a* configured to engage circumferential groove 348 on the exterior of the tubular body of the sample tube 202. The carriage 332 may include elongated slots 635 which allow the gripping segments 634 to pass into the interior of the carriage (receptacle 336) to engage the circumferential groove 348.

Gripping arm linkages 632 are movable between an outward position disengaged from the sample tube 202 (see, e.g., FIG. 142) when the push block 640 is in its downward position, and an inward position engaged with circumferential groove 348 of the sample tube when the push block is in its upward position. Springs 643 bias push block into its upward position and in turn the gripping arm linkages into their inward position to engage the sample tube.

In operation, when an carriage 332 is in a horizontal position, the vertically movable piston-plunger 373 is moved downwards to engage push block 640 and actuate the tube gripper mechanism 630. This compresses springs 643 and splays or spreads the gripping arm linkages 632 to their outward position. Sample tube 202 may then be loaded into the carriage. Piston-plunger 373 is then retracted upwards to disengage push block 640. The springs return the push block to its upward position causing the gripping arm linkages to move to their inward position and engage sample tube 202 (i.e. gripping segments 634) to lock the sample tube inside the carriage.

According to another aspect of the sample unloading apparatus 304 design options, the RFID reader 2850 may instead be mounted on one side of wash-down enclosure 600 (see, e.g., FIG. 132) instead of on the tube staging rack as previously described herein. The RFID reader is positioned to read the RFID tag 2850*a* on the end of sample tube 202.

According to another aspect, the V-shaped tube feed chute 363 of the tube loading mechanism 360 is replaced by a pair of spaced apart tube feed rods 660 (see, e.g., FIGS. 131-132). The rods 660 are spaced apart so that they support opposite sides of the sample tube cylindrical body without the tube falling therethrough when the sample tubes 202 are loaded into the carriage 332 of the unloading apparatus 340 by the decapper 545 mechanism. This reduces weight and eliminates cleanout of a chute.

EXAMPLES

The following are non limiting examples.

Example 1—a sample unloading system comprising: a sample staging rack comprising at least one inclined feed ramp configured for receiving an elongated sample tube configured for holding the sample, the sample tube including a first end cap and a second end cap; an unloading apparatus coupled to the staging rack, the unloading apparatus configured to receive the sample tube from the staging rack; and a transfer mechanism operable to transfer the sample tube from the staging rack to the unloading apparatus.

Example 2—the system according to any one of Examples 1, wherein the unloading apparatus comprises a rotatable carriage configured to hold and rotate the sample tube in opposing directions.

Example 3—the system according to Example 2, wherein the unloading apparatus comprises a loading mechanism operable to load the sample tube into the carriage.

Example 4—the system according to any one of Examples 2 or 3, wherein the carriage is operable to rotate the sample tube between an upright vertical position and an inverted vertical position.

Example 5—the system according to Example 4, wherein the carriage is operable to rotate the sample tube: 90 degrees in a first direction to the upright vertical position; and 180 degrees therefrom in an opposite second direction to the inverted vertical position.

Example 6—the system according to Example 4, wherein the first end cap is detachably coupled to a first end of the sample tube, and the second end cap is slideably movable inside the sample tube towards and away from the first end cap.

Example 7—the system according to Example 6, wherein the unloading apparatus further comprises a decapper operable to remove the first end cap from the sample tube when in a horizontal position.

Example 8—the system according to Example 7, wherein the unloading apparatus comprises a sample ejector configured to eject the sample from the sample tube when in its inverted vertical position when the first end cap is removed.

Example 9—the system according to Example 8, wherein the sample ejector comprises a vertically movable plunger which engages and slideably pushes the second end cap inside the sample tube to eject the sample.

Example 10—the system according to Example 9, wherein the plunger is configured to releasably lockingly engage the second cap such that the plunger is further operable to both push the second end cap in a first direction to eject the sample and pull the second end cap back in an opposite second direction inside the sample tube.

Example 11—the system according to any one of Examples 1-10, wherein the staging rack comprises a plurality of inclined feed ramps arranged in parallel relationship to each other.

Example 12—the system according to Example 11, wherein the transfer mechanism comprises a rotary feed gate configured to grasp the sample tube on the staging rack and pass the sample tube towards the unloading apparatus.

Example 13—the system according to Example 12, wherein the rotary feed gate is positioned at a proximal end of the inclined feed ramp adjacent to the unloading apparatus.

Example 14—the system according to Examples 13, wherein the transfer mechanism comprises a tube elevator comprising a movable chain with a lifting member configured to engage and load the sample tube into the unloading apparatus from the staging rack.

Example 15—the system according to Example 3, wherein the loading mechanism comprises a ramrod operable to push the sample tube into a receptacle of the carriage.

Example 16—the system according to Example 15, wherein the unloading mechanism comprises an unloading plunger operable to push the sample tube out of the receptacle of the carriage.

Example 17—the system according to Examples 15 or 16, wherein the unloading mechanism comprises a feed chute pivotably coupled to the unloading apparatus.

Example 18—the system according to any one of Examples 1-17, further comprising a programmable controller operably coupled to and configured to control operation of the unloading apparatus and transfer mechanism.

Example 19—the system according to any one of Examples 1-18, wherein the sample is a soil sample.

Example 20—a method for unloading a sample container comprising: inserting a capped sample tube containing a sample into an unloading apparatus; uncapping the sample tube which creates an open top end; rotating the sample tube to an inverted vertical position; and ejecting the sample from the sample tube.

Example 21—the method according to Example 20, wherein the unloading apparatus comprises a movable carriage including an elongated receptacle into which the sample tube is inserted.

Example 22—the method according to Example 20, wherein the ejecting step comprises inserting a sample ejector piston-plunger through the sample tube in a downward stroke.

Example 23—the method according to Example 22, wherein the sample ejector piston-plunger lockingly engages a push cap slideably disposed inside the sample tube and moves the push cap downwards towards the open top end of the sample tube to eject the sample.

Example 24—the method according to Example 23, further comprising after the ejecting step, a step of moving the sample ejector piston-plunger in an upward stroke which draws the push cap back upwards in the sample tube.

Example 25—the method according to Example 21, wherein the uncapping step includes engaging a decapper with a snap-fit cap on the top end of the sample tube.

Example 26—the method according to Example 21, further comprising after the ejecting steps of rotating the sample tube a third time to a horizontal position, and removing the sample tube out of the unloading apparatus with the moveable carriage.

Example 27—the method according to Example 26, wherein the sample tube is both inserted into the unloading apparatus and pushed out of the unloading apparatus in opposing linear directions along a common feed axis.

Example 28—the method according to any one of Examples 20-21, further comprising a programmable controller operably coupled to the unloading apparatus and configured to control operation of the unloading apparatus.

Example 29—a sample container comprising: an elongated tubular body defining a longitudinal axis, a top end, a bottom end, and an internal cavity extending between the ends configured for holding the sample; a first cap detachably coupled to the top end; and a second cap slideably disposed in the cavity, the second cap being movable in opposing directions between the first and second ends.

Example 30—the sample container according to Example 29, wherein the second cap comprises a base and a plurality of longitudinally-extending retention protrusions extending downwards from the base.

Example 31—the sample container according to Examples 29 or 30, wherein the body further comprises a plurality of circumferentially spaced apart retention slots configured to lockingly engage the retention protrusions.

Example 32—the sample container according to Example 31, wherein the retention protrusions are outwardly flared and form outward protruding locking tabs which engage the retention slots.

Example 33—the sample container according to Examples 31 or 32, wherein retention slots are located proximate to the bottom end of the tubular body.

Example 34—the sample container according to Example 32, wherein the retention protrusions each further comprise an inward projecting tab disposed opposite the outward protruding locking tabs.

Example 35—the sample container according to Example 29, wherein the tubular body defines a pair of longitudinally spaced apart circumferential grooves formed in an exterior surface of the tubular body.

Example 36—the sample container according to Example 29, wherein the first cap comprises an external circumference groove.

Example 37—the sample container according to Example 36, wherein the first cap is snap-fit to top end of the tubular body via an inwardly projecting annular snap protrusion engageable with a circumferentially-extending snap groove formed in the tubular body.

Example 38—the sample container according to Example 29, wherein the tubular body is cylindrical with a circular cross-sectional shape.

Example 39—a sample unloading system comprising: a wash-down enclosure defining an inner chamber; a rotatable carriage disposed in the inner chamber, the carriage configured to receive a sample tube containing an agricultural material and rotate the sample tube between a plurality of rotational positions; a tube gripper mechanism disposed on the carriage, the tube gripper mechanism configured to selectively engage the sample tube when positioned in the carriage; wherein the tube gripper mechanism retains the sample tube in the carriage when the sample tube is in an inverted position.

Example 40—the system according to Example 39, wherein the tube gripper mechanism comprises a spring-biased gripper actuator operably coupled to a pair of collapsible and spreadable gripping arm linkages configured to selectively engage and disengage the sample tube.

Example 41—the system according to Example 40, wherein the gripping arm linkages are engageable with a circumferential retention groove formed on an exterior surface of sample tube.

Example 42—the system according to Example 40 or 41, further comprising a piston-plunger linearly movable to engage the gripper actuator which actuates the tube gripper mechanism.

Example 43—the system according to Example 42, wherein the piston-plunger is further operable to enter an end of the sample tube to push the agricultural material out of the sample tube.

Example 44—the system according to Example 39, further comprising a plurality of spray nozzles coupled to the carriage.

Example 45—the system according to Example 44, wherein the spray nozzles are operable to wash down the inner chamber of the wash-down enclose while the carriage is rotated.

While the foregoing description and drawings represent some example systems, it will be understood that various additions, modifications and substitutions may be made therein without departing from the spirit and scope and range of equivalents of the accompanying claims. In particular, it will be clear to those skilled in the art that embodiments of the present disclosure may be embodied in other forms, structures, arrangements, proportions, sizes, and with other elements, materials, and components, without departing from the spirit or essential characteristics thereof. In addition, numerous variations in the methods/processes described herein may be made. One skilled in the art will further appreciate that the embodiments of the present disclosure may be used with many modifications of structure, arrangement, proportions, sizes, materials, and components and otherwise, used in the practice of the embodiments of the present disclosure, which are particularly adapted to specific environments and operative requirements without departing from the principles of the present embodiments of the present disclosure. The presently disclosed embodiments are therefore to be considered in all respects as illustrative and not restrictive, the scope of the embodiments of the present disclosure being defined by the appended claims and equivalents thereof, and not limited to the foregoing description or embodiments. Rather, the appended claims should be construed broadly, to include other variants and embodiments, which may be made by those skilled in the art without departing from the scope and range of equivalents of the embodiments of the present disclosure.

What is claimed is:

1. A method for unloading a sample container comprising:

inserting a capped sample tube containing a sample into an unloading apparatus comprising a moveable carriage including an elongated receptacle into which the sample tube is inserted and at least one spray nozzle;

uncapping the sample tube which creates an opening at a top end of the sample tube;

rotating the sample tube to an inverted vertical position;

ejecting the sample from the sample tube; and washing an interior surface of the unloading apparatus by spraying water with the at least one spray nozzle.

2. The method according to claim 1, wherein the ejecting step comprises inserting a sample ejector piston-plunger through the sample tube in a downward stroke.

3. The method according to claim 2, wherein the sample ejector piston-plunger lockingly engages a push cap slideably disposed inside the sample tube and moves the push cap downwards towards the opening at the top end of the sample tube to eject the sample.

4. The method according to claim 3, further comprising after the ejecting step, a step of moving the sample ejector piston-plunger in an upward stroke which draws the push cap back upwards in the sample tube.

5. The method according to claim 1, further comprising after the ejecting step, rotating the sample tube to a horizontal position, and removing the sample tube out of the unloading apparatus with the moveable carriage.

6. The method according to claim 5, wherein the sample tube is both inserted into the unloading apparatus and pushed out of the unloading apparatus in opposing linear directions along a common feed axis.

7. The method according to claim 1, further comprising a programmable controller operably coupled to the unloading apparatus and configured to control operation of the unloading apparatus.

8. The method according to claim 1, wherein during the washing step the movable carriage rotates 360 degrees to fully wash the interior surface of the unloading apparatus.

9. The method according to claim 1, wherein a fixed nozzle is mounted on the unloading apparatus which sprays water during the washing step to wash the movable carriage.

10. The method according to claim 1 wherein the sample is a soil sample.

11. A method for unloading a sample container comprising:

inserting a capped sample tube containing a sample into an unloading apparatus;

uncapping the sample tube which creates an opening at a top end of the sample tube;

rotating the sample tube to an inverted vertical position;

ejecting the sample from the sample tube; and wherein the uncapping step includes engaging a decapper with a snap-fit cap on the top end of the sample tube.

12. A method for unloading a sample container comprising:

inserting a sample tube comprising a top end and containing a sample into a rotatable carriage disposed within an unloading apparatus;

gripping the sample tube with a tube gripper mechanism comprising a gripper actuator, the tube gripper mechanism disposed on the rotatable carriage;

rotating the sample tube to an inverted vertical position;

inserting a piston-plunger through the sample tube in a downward stroke to engage a push cap disposed inside the sample tube;

moving the piston-plunger and the push cap downwards towards the top end to extract the sample from the sample tube;

retracting the piston-plunger in an upward stroke and disengaging the push cap;

rotating the rotatable carriage into a horizontal position;

moving the piston-plunger in a downward stroke to engage the gripper actuator to ungrip the sample tube.

13. The method according to claim 12, wherein the gripper actuator is a spring biased gripper actuator operably coupled to a pair of gripping arm linkages which grip the sample tube during the gripping step.

14. The method according to claim 13, wherein the gripping arm linkages grip the sample tube through retention grooves in an exterior surface of the rotatable carriage.

15. The method according to claim 12 wherein the sample is a soil sample.

16. A method for unloading a sample container comprising:

horizontally inserting a capped sample tube containing a sample into an unloading apparatus;

uncapping the sample tube which creates an opening at a top end of the sample tube;

rotating the sample tube to an inverted vertical position;

ejecting the sample from the sample tube;

rotating the sample tube to a horizontal position; and removing the sample tube out of the unloading apparatus.

17. The method according to claim 16, wherein the sample tube is both inserted into the unloading apparatus and pushed out of the unloading apparatus in opposing linear directions along a common feed axis.

18. The method according to claim 16, wherein the sample is a soil sample.

* * * * *